(12) United States Patent
Simmons et al.

(10) Patent No.: US 7,855,327 B2
(45) Date of Patent: Dec. 21, 2010

(54) DEFENSIN POLYNUCLEOTIDES AND METHODS OF USE

(75) Inventors: Carl R. Simmons, Des Moines, IA (US); Pedro A. Navarro Acevedo, Ames, IA (US); Leslie Harvell, Newark, DE (US); Rebecca Cahoon, Webster Groves, MO (US); Billy Fred McCutchen, College Station, TX (US); Albert L. Lu, Newark, DE (US); Rafael Herrmann, Wilmington, DE (US); James F. H. Wong, Johnston, IA (US)

(73) Assignees: Pioneer Hi-Bred International, Inc., Des Moines, IA (US); E.I. du Pont de Nemours and Company, Wilmington, DE (US)

( * ) Notice: Subject to any disclaimer, the term of this patent is extended or adjusted under 35 U.S.C. 154(b) by 387 days.

(21) Appl. No.: 12/132,442

(22) Filed: Jun. 3, 2008

(65) Prior Publication Data

US 2009/0031448 A1   Jan. 29, 2009

Related U.S. Application Data

(62) Division of application No. 11/123,896, filed on May 6, 2005, now Pat. No. 7,396,980, which is a division of application No. 10/178,213, filed on Jun. 21, 2002, now Pat. No. 6,911,577.

(60) Provisional application No. 60/300,152, filed on Jun. 22, 2001, provisional application No. 60/300,241, filed on Jun. 22, 2001.

(51) Int. Cl.
*A01H 5/00* (2006.01)
*A01H 5/10* (2006.01)
*C12N 15/82* (2006.01)
*C12N 15/29* (2006.01)

(52) U.S. Cl. .................. 800/301; 536/23.6; 424/93.2; 435/418; 800/279

(58) Field of Classification Search .................. None
See application file for complete search history.

(56) References Cited

U.S. PATENT DOCUMENTS

| 4,945,050 | A | 7/1990 | Sanford et al. |
| 5,421,839 | A | 6/1995 | Ulbrich et al. |
| 5,538,525 | A | 7/1996 | Broekaert et al. |
| 5,689,043 | A | 11/1997 | Broekaert et al. |
| 5,750,504 | A | 5/1998 | Broekaert et al. |
| 5,773,694 | A | 6/1998 | Broekaert et al. |
| 5,824,869 | A | 10/1998 | Broekaert et al. |
| 5,837,458 | A | 11/1998 | Minshull et al. |
| 5,847,047 | A | 12/1998 | Haynie |
| 5,861,480 | A | 1/1999 | Attenborough et al. |
| 5,919,918 | A | 7/1999 | Broekaert et al. |
| 6,150,588 | A | 11/2000 | Attenborough et al. |
| 6,187,904 | B1 | 2/2001 | Broekaert et al. |
| 6,215,048 | B1 | 4/2001 | Liang et al. |
| 6,911,577 | B2 | 6/2005 | Simmons et al. |
| 2001/0014732 | A1 | 8/2001 | Broekaert et al. |
| 2001/0051335 | A1 | 12/2001 | Lalgudi et al. |
| 2005/0273881 | A1 | 12/2005 | Simmons et al. |

FOREIGN PATENT DOCUMENTS

| WO | WO 93/05153 A1 | 3/1993 |
| WO | WO 94/16076 A1 | 7/1994 |
| WO | WO 97/21814 A1 | 6/1997 |
| WO | WO 97/21815 A2 | 6/1997 |
| WO | WO 97/37024 A2 | 10/1997 |
| WO | WO 98/00023 A2 | 1/1998 |
| WO | WO 99/02038 A1 | 1/1999 |
| WO | WO 00/11196 A1 | 3/2000 |
| WO | WO 00/68405 A2 | 11/2000 |
| WO | WO 00/78983 A2 | 12/2000 |
| WO | WO 02/09738 A1 | 2/2002 |
| WO | WO 02/063011 A1 | 8/2002 |

OTHER PUBLICATIONS

Cushman et al (1999, GenBank Accession No. U12150).*
Broekaert, et al., "Plant Defensins: Novel Antimicrobial Peptides ans Components of the Host Defense System, " *Plant Phys.*, 1995, pp. 1353-1358, vol. 108.
Chih-Ching, C., et al., "Establishment of an Efficient Medium for Anther Culture of Rice Through Comparative Experiments on the Nitrogen Sources," *Sci. Sin. Peking*, 1975, pp. 659-668, vol. 18(5).
De Lucca, A., et al., "Fungicidal and Binding Properties of the Natural Peptides Cecropin B and Dermaseptin," *Medical Mycology*, Oct. 1998, pp. 291-298, vol. 36(5), ISHAM.
De Lucca, A., et al., "Fungicidal Properties, Sterol Binding, and Proteolytic Resistance of the Synthetic Peptide D4E1," *Can. J. Microbiol.*, 1998, pp. 514-520, vol. 44, NRC Canada.
Doyle, J., et al., "The Glycosylated Seed Storage Proteins of *Glycine max* and *Phaseolus vulgaris*," *Journ. of Biol. Chem.*, 1986, pp. 9228-9238, vol. 261(20), The American Society of Biological Chemists, Inc., USA.
Ezaki, B., et al., "Cloning and Sequencing of the cDNAs Induced by Aluminum Treatment and $P_i$ Starvation in Cultured Tobacco Cells," *Physiologia Plantarum*, 1995, pp. 11-18, vol. 93.
Fromm, M., et al., "Inheritance and Expression of Chimeric Genes in the Progeny of Transgenic Maize Plants," *Bio/Technology*, 1990, pp. 833-839, vol. 8.
Garcia-Olmedo, F., et al., "Plant Defense Peptides," *Biopolymers* (*Peptide Science*), 1998, pp. 479-491, vol. 47, John Wiley & Sons, Inc., USA.

(Continued)

*Primary Examiner*—Anne Kubelik
(74) *Attorney, Agent, or Firm*—Alston & Bird LLP

(57) ABSTRACT

Methods and compositions for modulating development and defense responses are provided. Nucleotide sequences encoding defensin proteins are provided. The sequences can be used in expression cassettes for modulating development, developmental pathways, and defense responses. Transformed plants, plant cells, tissues, and seed are also provided.

29 Claims, 1 Drawing Sheet

OTHER PUBLICATIONS

Gritz, L., and J. Davies, "Plasmid-Encoded Hygromycin B Resistance: The Sequence of Hygromycin B Phosphotransferase Gene and Its Expression in *Escherichia coli* and *Saccharomyces cerevisiae*," *Gene*, 1983, pp. 179-188, vol. 25, Elsevier Science Publishers.

Guo, H.H., et al., "Protein Tolerance to Random Amino Acid Change," *Proc. Natl. Acad. Sci.*, Jun. 22, 2004, pp. 9205-9210, vol. 101, No. 25.

Higgins, D., and P. Sharp, "Fast and Sensitive Multiple Sequence Alignments on a Microcomputer," *Cabios Comm.*, 1989, pp. 151-153, vol. 5(2).

Jia-Qi, C., et al., "The Important Role of Historical Flood Data in the Estimation of Spillway Design Floods," *Sci. Sin. Peking*, 1975, pp. 657-658, vol. 18(5).

Klein, T., et al., "High-Velocity Microprojectiles for Delivering Nucleic Acids into Living Cells," *Nature*, 1987, pp. 70-73, vol. 327.

Maitra, N., et al., "Characterization of a Drought-Induced Soybean cDNA Encoding a Plant Defensin," *Plant Phys.*, 1998, p. 1536, vol. 118.

Manners, J., et al., "The Promoter of the Plant Defensin Gene *PDF1.2* from *Arabidopsis* is Systemically Activated by Fungal Pathogens and Responds to Methyl Jasmonate But Not to Salicylic Acid," *Plant Mol. Biol.*, 1998, pp. 1071-1080, vol. 38, Kluwer Academic Publishers, Netherlands.

Odell, J., et al., "Identification of DNA Sequences Required for Activity of the Cauliflower Mosaic Virus 35S Promoter," *Nature*, 1985, pp. 810-812, vol. 313.

Osborn, R., et al., "Isolation and Characterisation of Plant Defensins from Seeds of Asteraceae, Fabaceae, Hippocastanaceae and Saxifragaceae," FEBS Letters, 1995, pp. 257-262, vol. 368, FEBS.

Pelegrini, P.B., and O. L. Franco, "Plant γ-thionins. Novel Insights on the Mechanism of Action of a Multi-functional Class of Defense Proteins," *The International Journal of Biochemistry & Cell Biology*, 2005, pp. 2239-2253, vol. 37.

Rosenberg, A., et al., "Vectors for Selective Expression of Cloned DNAs by T7 RNA Polymerase," *Gene*, 1987, pp. 125-135, vol. 56, Elsevier Science Publishers, BV.

Studier, F., and B. Moffatt, "Use of Bacteriophage T7 RNA Polymerase to Direct Selective High-Level Expression of Cloned Genes," *J. Mol. Biol.*, 1986, pp. 113-130, vol. 189.

Terras, F., et al., "Evidence that the Role of Plant Defensins in Radish Defense Responses is Independent of Salicylic Acid," *Planta*, 1998, pp. 117-124, vol. 206, Springer-Verlag.

Terras, F., et al., "Small Cysteine-Rich Antifungal Proteins from Radish: Their Role in Host Defense," *The Plant Cell*, May 1995, pp. 573-588, vol. 7, American Society of Plant Physiologists, USA.

Thevissen, K., et al., "Fungal Membrane Responses Induced by Plant Defensins and Thionins," *J. of Biol. Chem.*, 1996, pp. 15018-15025, vol. 271(25), The American Society of Biochemistry and Molecular Biology, Inc., USA.

Thomma, B.P.H.J., et al., "Plant Defensins," *Planta*, 2002, pp. 193-202, vol. 216.

Urwin, P.E., et al., "Resistance to Both Cyst and Root-Knot Nematodes Conferred by Transgenic *Arabidopsis* Expressing a Modified Plant Cystatin," *The Plant Journal*, 1998, pp. 455-461, vol. 12(2).

Yamada, S., et al., "cDNA Cloning of γ-Thionin from *Nicotiana excelsion*," *Plant Phys.*, 1997, p. 314, vol. 115.

GenBank Report for Accession No. Z13956, Direct Submission Jun. 25, 1992.

GenBank Report for Accession No. Z18359, Direct Submission Nov. 12, 1992.

GenBank Report for Accession No. BAA06149, Direct Submission on Mar. 28, 1994.

GenBank Report for Accession No. U12150, Direct Submission Jul. 11, 1994.

GenBank Report for Accession No. L27173, Apr. 4, 1995.

GenBank Report for Accession No. S66221, Direct Submission on Mar. 19, 1997.

GenBank Report for Accession No. AF044059, Direct Submission Jan. 22, 1998.

GenBank Report for Accession No. AF178634, Direct Submission Aug. 17, 1999.

GenBank Report for Accession No. AB034956, Direct Submission Nov. 14, 1999.

GenBank Report for Accession No. AI665330, Feb. 2, 2000.

GenBank Report for Accession No. BE025241, Jun. 7, 2000.

GenBank Report for Accession No. S11156, Jun. 9, 2000.

GenBank Report for Accession No. AF293407, Direct Submission Aug. 4, 2000.

GenSeq Report for Accession No. ABN20963, Dec. 6, 2001.

GenBank Report for Accession No. BE050465, Mar. 18, 2002.

GenBank Report for Accession No. BJ227949, Sep. 17, 2002.

GenBank Report for Accession No. BQ590762, Dec. 6, 2002.

\* cited by examiner

```
              1                                                  50
Zm-PDF1    (1) --------------ATGTGGACGATCAGGAAGGTGGCGACGCCGCAGGTG
Zm-PDF2    (1) ------ATGGAGCTCATCAAGTCCAGGGCGACCGTGTGCGCGCTCCTCCTG
Zm-PDF3    (1) ATGGCCCTGTCGTCTCGCCGTAT-GGCCGCCGCACCATTCTTCGTCGTCG
Zm-PDF4    (1) --------------ATGGAGTCG-TCACGCATG-----TTCGAGCCGGC-
Zm-PDF5    (1) --------------ATGGAGCTC-TCTCGCAAGCTC-TTGACGGCCGTCC
Zm-PDF6    (1) --------------ATGGAGTCG-TCACGCAGG-----TTCCAGCCGGC-
Zm-PDF13   (1) ATGGCGCTGTC---TCGACGTAT-GGCGGCTCC------CGTCCTCGTCC
Consensus  (1)               ATG AGTC  TC CGCA G      TC C-GCCG C 51                                                100
Zm-PDF1   (37) GCCGTCCTCCTGCTGCTCCTCATCGTCGTTGCGCAGGAGGCGGCGCCCGTT
Zm-PDF2   (46) GCGCTGCTCCTGCTCTCACACTACGACGGCGGGACGACGACGACGGATGGT
Zm-PDF3   (50) TCC-TTCTCGTCCTCGTGGCGGCAGAGAGGACGATGGGCAGGGTGG---T
Zm-PDF4   (30) -CA-TCATCCTGCTTCTC---CTGCTCATTGTGACCACCGATGTGGCGCA
Zm-PDF5   (35) TCC-TCGTCATGCTGCTGCTGCTGTCCGCAGAGGTCGGGCCGGTGGCCGT
Zm-PDF6   (30) -CG-TCATCCTGCTTCTC---CTGCTCATTGTGTCCACCGATATGCCACA
Zm-PDF13  (41) TCA-TGCTCCTCCTCGTCGCCACAGAGCTGGGGACGACCAAGGTGG---C
Consensus (51)    C  TCCTCCTGCT CTC      T G C T G  GACGACC    GGTGGCG  T 101                                               150
Zm-PDF1   (87) GGCCGGAGGCGCGCCGTGTGCCGGCGCCGGAGCCGCGGGCTTCAAGGGGGTCT
Zm-PDF2   (96) GGCGGAGGCGCCCGGGTGTGCATGGGCAAGAGCCAGCACCACTCGTTCCCCT
Zm-PDF3   (96) GGTGGAAGAGACGCTCGTGCCTGTCGCAGAGCCATGCCTTCAAAGGCGTGT
Zm-PDF4   (75) GGCGGG----CGAGGGAATGCGAGAAGGACGCGAGCGATTCCTTGGGGCAT
Zm-PDF5   (84) GGCGGAGGCGCGCAGACGTGCCACTCGCAGAGCCACAGGTTCCGGGCCCCT
Zm-PDF6   (75) GGC-------AAGGGAATGCGAGAAGTACAGTGAGCGATTTGTTGGGGCAT
Zm-PDF13  (87) GGAGG----CGAGGCACTGCCTGTCGCAGAGCCACCGGTTCAAGGGCCTGT
Consensus(101)  GGCGGA GCGAGGG  TGCC G   GCAGAGCCAGCG  TTC  GGGCGC T 151                                               200
Zm-PDF1  (137) GCATGTCCGACCACAACTGCGCGCAGGTGTGCTTGCAGGAG--GGCTACG
Zm-PDF2  (146) GCATCTCCGACCGCCTCTGCAGCAACGAGTGCGTCAAGGAG--GACGGCG
Zm-PDF3  (146) GCCTCAGCAACACCAACTGCGACAACGTATGCAAGACGGAG--AAGTTCA
Zm-PDF4  (122) GCATGGCCGTCGGACAACTGCGCCAACGTGTGCCG--CGGTGAGGGCTTCT
Zm-PDF5  (134) GCCTCCGCCGGTCCAACTGCGCCAACGTCTGCAGGACCGAG--GGGTTCC
Zm-PDF6  (119) GCATGATCGCAGACAACTGCGCCAATGTGTGCCG--CGGTGAGGGCTTCT
Zm-PDF13 (134) GCATGAGCAGCAACAACTGCGCCAACGTGTGCAGACCGAG--AACTTCC
Consensus(151) GCATG  C  C ACAACTGCGCCAACGTGTGC  GACGGAG  GGCTTC 201                                               250
Zm-PDF1  (185) GCGGCGGCAACTGCGACGGCA--------TCATGCGCCAGTGCAAGTGCAT
Zm-PDF2  (194) GGTGGACCGCCGGCTACTGCC---------ACCTCCGCTACTGCAGGTGCCA
Zm-PDF3  (194) CAGGCCGCGAGTGCAAGATGG-ACGGCGTCATGCGCAAGTGCTACTGCAA
Zm-PDF4  (170) CCGGCGGCAGGTGCAGCACCTTCCG---CCGC-CGC---TGCATCTGCAC
Zm-PDF5  (182) CCGGCGGCAGGTGCCGCGGCTTCCG---CCGC-CGC---TGCTTCTGCAC
Zm-PDF6  (167) TGGCCGGCAGGTGCAGCACCTTCCG---CCGC-CGC---TGCATCTGCAC
Zm-PDF13 (182) CCGGCGGCGAGTGCAAGGCGG-AGGGCGCCACGCGCAAGTGCTTTTGCAA
Consensus(201)   CCGGCGGCA GTGCAAC  C   CG   CC C  CGC A TGCATCTGCA 251       266
Zm-PDF1  (228) CAGGGAGTGCTAG---
Zm-PDF2  (237) GAAGGCGTGCTAA---
Zm-PDF3  (243) GAAGGTCTTGCTAG---
Zm-PDF4  (213) TAAGCCGTGCTAA---
Zm-PDF5  (225) CACGCACTGCCACTGA
Zm-PDF6  (210) TAGGCAGTGCTAA---
Zm-PDF13 (231) GAAGATATGCTAG---
Consensus(251)   AAG  GTGCTA
```

DEFENSIN POLYNUCLEOTIDES AND METHODS OF USE

CROSS-REFERENCE TO RELATED APPLICATIONS

This application is a divisional of U.S. patent application Ser. No. 11/123,896, filed May 6, 2005, which is a divisional of U.S. patent application Ser. No. 10/178,213, filed Jun. 21, 2002, now U.S. Pat. No. 6,911,577, which claims the benefit of U.S. Provisional Application No. 60/300,152, filed Jun. 22, 2001 and U.S. Provisional Application No. 60/300,241, filed Jun. 22, 2001, all of which are hereby incorporated in their entirety by reference herein.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 343768SequenceListing.txt, a creation date of May 6, 2005, and a size of 419 KB. The sequence listing filed via EFS-Web is part of the specification and is hereby incorporated in its entirety by reference herein.

FIELD OF INVENTION

The invention relates to the field of the genetic manipulation of plants, particularly the modulation of gene activity and development in plants and increased disease resistance.

BACKGROUND OF THE INVENTION

Disease in plants is caused by biotic and abiotic causes. Biotic causes include fungi, viruses, bacteria, and nematodes. An example of the importance of plant disease is illustrated by phytopathogenic fungi, which cause significant annual crop yield losses as well as devastating epidemics. Plant disease outbreaks have resulted in catastrophic crop failures that have triggered famines and caused major social change. All of the approximately 300,000 species of flowering plants are attacked by pathogenic fungi; however, a single plant species can be host to only a few fungal species, and similarly, most fungi usually have a limited host range. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Molecular methods of crop protection have the potential to implement novel mechanisms for disease resistance and can also be implemented more quickly than traditional breeding methods. Accordingly, molecular methods are needed to supplement traditional breeding methods to protect plants from pathogen attack.

A host of cellular processes enable plants to defend themselves against diseases caused by pathogenic agents. These defense mechanisms are activated by initial pathogen infection in a process known as elicitation. In elicitation, the host plant recognizes a pathogen-derived compound known as an elicitor; the plant then activates disease gene expression to limit further spread of the invading organism. It is generally believed that to overcome these plant defense mechanisms, plant pathogens must find a way to suppress elicitation as well as to overcome more physically-based barriers to infection, such as reinforcement and/or rearrangement of the actin filament networks near the cell's plasma membrane.

Thus, the present invention solves needs for enhancement of the plant's defensive elicitation response via a molecularly based mechanism which can be quickly incorporated into commercial crops.

SUMMARY OF THE INVENTION

Compositions and methods relating to disease resistance are provided. Particularly, isolated nucleic acid molecules having nucleotide and amino acid sequences for defensins from plants are provided. The nucleotide sequences of the invention encode small cysteine-rich proteins and are variously annotated or described as defensins, defensin-like proteins, antimicrobial peptides, anti-pathogenic peptides, thionins, antifungal peptides, protease inhibitors, amylase inhibitors, scorpion toxin-like proteins and small cysteine-rich peptides. They are referred to herein as defensins as they exhibit similarity in primary structure to insect defensins. Transformed plants can be obtained having altered metabolic states with respect to the defense response.

The defensin genes of the present invention may find use in enhancing the plant pathogen defense system. The compositions and methods of the invention can be used for enhancing resistance to plant pathogens including fungal pathogens, plant viruses, microorganisms, nematodes, insects, and the like. The method involves stably transforming a plant with a nucleotide sequence capable of modulating the plant pathogen defense system operably linked with a promoter capable of driving expression of a gene in a plant cell. The defensin genes additionally find use in manipulating these processes in transformed plants and plant cells.

Transformed plants, plant cells, and seeds, as well as methods for making such plants, plant cells, and seeds are additionally provided. It is recognized that a variety of promoters will be useful in the invention, the choice of which will depend in part upon the desired level of expression of the disclosed genes. It is recognized that the levels of expression can be controlled to modulate the levels of expression in the plant cell.

BRIEF DESCRIPTION OF THE DRAWINGS

FIG. 1 depicts an alignment of several defensin genes and a consensus defensin sequence (SEQ ID NO:469). Zm-PDF1 is set forth in SEQ ID NO:465; Zm-PDF2 is set forth in SEQ ID NO:463; Zm-PDF3 is set forth in SEQ ID NO:235; Zm-PDF4 is set forth in SEQ ID NO:1; Zm-PDF6 is set forth in SEQ ID NO:4; and Zm-PDF13 is set forth in SEQ ID NO:10.

DETAILED DESCRIPTION OF THE INVENTION

Overview

The present invention provides, inter alia, compositions and methods for modulating the total level of polypeptides of the present invention and/or altering their ratios in a plant. By "modulation" an increase or decrease in a particular character, quality, substance, or response is intended.

The compositions comprise nucleotide and amino acid sequences from numerous plant species. Particularly, the nucleotide and amino acid sequences for 85 groups of defensins are provided. By "plant defensin genes" is intended genes that are structurally related to plant defensins, and include thionins, small cysteine-rich peptides, proteinase inhibitors, amylase inhibitors, and the like. They are called defensin genes after a structural classification of proteins (SCOP) classification system. Defensins play a role in defense, more specifically plant defense against pathogens, and they share similarity in primary and secondary structure with insect defensins. Defensins of the invention are classified in the superfamily of Scorpion toxin-like proteins and in the Plant Defensin family. While not bound by any mechanism of action, expression of the sequences and related genes around disease induced lesions may control symptom development, as in a hypersensitive response (HR), by controlling the protease mediated cell death mechanism. The compositions may also function directly as antipathogenic proteins by inhibiting proteases produced by pathogens or by binding cell wall components of pathogens. Thirdly, they may also act as amphipathic proteins that perturb membrane function, leading to cellular toxicity of the pathogens. The defensins are generally small cysteine-rich peptides and demonstrate antimicrobial activity. By "antimicrobial" or "antimicrobial activity" antibacterial, antiviral, nematocidal, insecticidal, or and antifungal activity is intended. Accordingly, the polypeptides of the invention may enhance resistance to insects and nematodes. Any one defensin exhibits a spectrum of antimicrobial activity that may involve one or more antibacterial, antifungal, antiviral, insecticidal, nematocidal, or antipathogenic activities. They may also be useful in regulating seed storage protein turnover and metabolism.

Plant defensins generally comprise about 45-54 amino acids with four disulfide bridges (Broekaert et al. (1995) *Plant Physiol.* (Bethesda) 108:1353-1358). The defensins of the invention inhibit the growth of a broad range of pathogens, including but not limited to fungi, nematocides, bacteria, insects, and viruses at micromolar concentrations. Thus, by "defensin-like activity" it is intended that the peptides inhibit pathogen growth or damage caused by a variety of pathogens, including but not limited to, fungi, insects, nematodes, viruses and bacteria. Defensins inhibit pathogen damage through a variety of mechanisms including, but not limited to, alteration of membrane ion permeability and induction of hyphal branching in fungal targets (Garcia-Olmeda et al. (1998) *Biopolymers, Peptide Science* 47:479-491, herein incorporated by reference).

The compositions of the invention can be used in a variety of methods whereby the protein products can be expressed in crop plants to function as antimicrobial proteins. Expression will result in alterations or modulation of the level, tissue, or timing of expression to achieve enhanced disease, insect, nematode, viral, fungal, or stress resistance. The compositions of the invention may be expressed in the native species including, but not limited to *Arachis hypogaea, Vitis vinifera, Licania michauxii, Cyamopsis tetragonoloba, Parthenium argentatum, Nicotiana benthamiana, Eucalyptus grandis, Tropaeolum majus, Ricinus communis, Vernonia mespilifolia, Chrysobalanus icaco, Glycine max, Triticum aestivum, Oryza sativa, Zea mays, Brassica napus, Tulipa gesneriana, Beta vulgaris, Allium porrum, Amaranthus retroflexus, Hedera helix, Picramnia pentandra, Taraxacum kok-saghyz., Tulipa fosteriana, Momordica charantia,* or alternatively, can be heterologously expressed in any plant of interest. In this manner, the coding sequence for the defensin can be used in combination with a promoter that is introduced into a crop plant. In one embodiment, a high-level expressing constitutive promoter may be utilized and would result in high levels of expression of the defensin. In other embodiments, the coding sequence may be operably linked to a tissue-preferred promoter to direct the expression to a plant tissue known to be susceptible to a pathogen. Likewise, manipulation of the timing of expression may be utilized. For example, by judicious choice of promoter, expression can be enhanced early in plant growth to prime the plant to be responsive to pathogen attack. Likewise, pathogen inducible promoters can be used wherein expression of the defensin is turned on in the presence of the pathogen.

If desired, a transit peptide can be utilized to direct cellular localization of the protein product. In this manner, the native transit peptide or a heterologous transit peptide can be used. However, it is recognized that both extracellular expression and intracellular expression are encompassed by the methods of the invention.

Sequences of the invention, as discussed in more detail below, encompass coding sequences, antisense sequences, and fragments and variants thereof. Expression of the sequences of the invention can be used to modulate or regulate the expression of corresponding defensin proteins.

The defensin genes of the present invention additionally find use in enhancing the plant pathogen defense system. The compositions and methods of the invention can be used for enhancing resistance to plant pathogens including fungal pathogens, plant viruses, insect pathogens, bacterial pathogens, nematodes, and the like. The method involves stably transforming a plant with a nucleotide sequence capable of modulating the plant pathogen defense system operably linked with a promoter capable of driving expression of a gene in a plant cell. By "enhancing resistance" increasing the tolerance of the plant to pathogens is intended. That is, the defensin may slow or prevent pathogen infection and/or spread.

Compositions

Compositions of the invention include nucleotide sequences that have been identified as defensins. Defensins are involved in defense response and development. In particular, the present invention provides for isolated nucleic acid molecules comprising nucleotide sequences encoding the amino acid sequences shown in SEQ ID NO:2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 75, 77, 78, 80, 81, 83, 84, 86, 87, 89, 90, 92, 93, 95, 96, 98, 99, 101, 102, 104, 105, 107, 108, 110, 111, 113, 114, 116, 117, 119, 120, 122, 123, 125, 126, 128, 129, 131, 132, 134, 135, 137, 138, 140, 141, 143, 144, 146, 147, 149, 150, 152, 153, 155, 156, 158, 159, 161, 162, 164, 165, 167, 168, 170, 171, 173, 174, 176, 177, 179, 180, 182, 183, 185, 186, 188, 189, 191, 192, 194, 195, 197, 198, 200, 201, 203, 204, 206, 207, 209, 210, 212, 213, 215, 216, 218, 219, 221, 222, 224, 225, 227, 228, 230, 231, 233, 234, 236, 237, 239, 240, 242, 243, 245, 246, 248, 249, 251, 252, 254, 255, 257, 258, 260, 261, 263, 264, 266, 267, 269, 270, 272, 273, 275, 276, 278, 279, 281, 282, 284, 285, 287, 288, 290, 291, 293, 294, 296, 297, 299, 300, 302, 303, 305, 306, 308, 309, 311, 312, 314, 315, 317, 318, 320, 321, 323, 324, 326, 327, 329, 330, 332, 333, 335, 336, 338, 339, 341, 342, 344, 345, 347, 348, 350, 351, 353, 354, 356, 357, 359, 360, 362, 363, 365, 366, 368, 369, 371, 372, 374, 375, 377, 378, 380, 381, 383, 384, 386, 387, 389, 390, 392, 393, 395, 396, 398, 399, 401, 402, 404, 405, 407, 408, 410, 411, 413, 414, 416, 417, 419, 420, 422, 423, 425, 426, 428, 429, 431, 432, 434, 435, 437, 438, 440, 441, 443, 444, 446, 447, 449, 450, 452, 453, 455, 456, 458, 459, 461, 462, 464, 466, or 468. In particular the invention provides the mature polypeptides having the amino acid sequences set forth in SEQ ID NO:3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 171, 174, 177, 180, 183, 186, 189, 192, 195, 198, 201, 204, 207, 210, 213, 216, 219, 222, 225, 228, 231, 234, 237, 240, 243, 246, 249, 252, 255, 258, 261, 264, 267, 270, 273, 276, 279, 282, 285, 288, 291, 294, 297, 300, 303, 306, 309, 312, 315, 318, 321, 324, 327, 330, 333, 336, 339, 342, 345, 348, 351, 354, 357, 360, 363, 366, 369, 372, 375, 378, 381, 384, 387, 390, 393, 396, 399, 402, 405, 408, 411, 414, 417, 420, 423, 426, 429, 432, 435, 438, 441, 444, 447, 450, 453, 456, 459, or 462. Further provided are polypeptides having an amino acid sequence encoded by a nucleic acid molecule described herein, for example those set forth in SEQ ID NO: 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148, 151, 154, 157, 160, 163, 166, 169, 172, 175, 178, 181, 184, 187, 190, 193, 196, 199, 202, 205, 208, 211, 214, 217, 220, 223, 226, 229, 232, 235, 238, 241, 244, 247, 250, 253, 256, 259, 262, 265, 268, 271, 274, 277, 280, 283, 286, 289, 292, 295, 298, 301, 304, 307, 310, 313, 316, 319, 322, 325, 328, 331, 334, 337, 340, 343, 346, 349, 352, 355, 358, 361, 364, 367, 370, 373, 376, 379, 382, 385, 388, 391, 394, 397, 400, 403, 406, 409, 412, 415, 418, 421, 424, 427, 430, 433, 436, 439, 442, 445, 448, 451, 454, 457, 460, 463, 465, or 467.

The nucleotide sequences of the invention are sequences comprising a protein superfamily including defensins, thionins, protease inhibitors, amylase inhibitors, scorpion toxin-like proteins, and small cysteine-rich peptides. The claimed sequences are members of the plant defensin class of genes and polypeptides. The plant defensins are identified herein as "CS" followed by a three-digit number. The defensins of the invention fall into 85 groups based on sequence homology. As indicated elsewhere herein, some of the maize plant defensins are identified as "Zm-PDF" for Zea mays plant defensins and designated as numbers ZmPDF or PDF (e.g. Zm-PDF1 or PDF1). The Zm-PDF and PDF nomenclature has been described previously in U.S. Patent Application Nos. 60/300,152, and 60/300,241, both filed Jun. 22, 2001, and herein incorporated by reference in their entirety.

The defensins of the invention are aligned to a diverse set of mostly plant, some non-plant and some animal, proteinase-inhibitors, thionins, especially gamma-thionins, and defensins, and antifungal proteins. A consensus sequence (SEQ ID NO:469) for some of the maize nucleotide sequences of the invention can be seen in FIG. 1. There are homologs to these sequences in soybeans, rice, wheat, and other crops. They represent a diverse and conserved super-gene family in plants.

Group 1 comprises three nucleotide sequences, of which CS004 (SEQ ID NO:1, PDF4) is the representative sequence. The CS004 polypeptide (SEQ ID NOS:2 and 3), encoded by the nucleotide sequence set forth in SEQ ID NO:1, is expressed in a tassel-preferred pattern. The full-length CS004 polypeptide (SEQ ID NO:2) appears to include a signal peptide, which when processed yields a mature polypeptide having the amino acid sequence set forth in SEQ ID NO:3. CS004 is extracellular. CS006 (SEQ ID NO:4, PDF6) appears to be preferentially expressed in the tassel. The full length CS006 polypeptide (SEQ ID NO:5) appears to include a signal peptide, which when processed yields a mature polypeptide having the amino acid sequence set forth in SEQ ID NO:6. CS006 is extracellular. The CS031 nucleotide sequence (SEQ ID NO:7) was obtained from Oryza sativa. The full length CS031 polypeptide (SEQ ID NO:8) appears to include a signal peptide, which when processed yields a mature polypeptide having the amino acid sequence set forth in SEQ ID NO:9.

Group 2 comprises CS013 (SEQ ID NO:10, PDF13), a maize gene. PDF13 is widely expressed. The full length CS013 polypeptide (SEQ ID NO:11) is expected to have a signal peptide, thus the mature protein (SEQ ID NO:12) would be extracellular.

Group 3 comprises two maize sequences, of which CS017 (SEQ ID NO:13, PDF17) is the representative sequence. The CS017 sequence appears to be preferentially expressed in kernels. The full length CS017 (SEQ ID NO:14) appears to include a signal peptide, which when processed yields a mature polypeptide having the amino acid sequence set forth in SEQ ID NO:15. Thus, the predicted CS017 polypeptide would be extracellular. CS018 (SEQ ID NO:16, PDF18) is expressed in the kernel endosperm and may be expressed elsewhere. The full length polypeptide (SEQ ID NO:17) appears to include a signal peptide, which when processed yields a mature polypeptide having the amino acid sequence set forth in SEQ ID NO:18.

Group 4 comprises 13 sequences of which CS065 (SEQ ID NO:43) is the representative sequence. CS065, having the nucleotide sequence set forth in SEQ ID NO:43 and encoding the polypeptides set forth in SEQ ID NOS:44 and 45, was isolated from Triticum aestivum. The nucleotide sequences for CS040 (SEQ ID NO:25), CS041 (SEQ ID NO:28), CS051 (SEQ ID NO:31), CS057 (SEQ ID NO:34), CS059 (SEQ ID NO:37), CS062 (SEQ ID NO:40), CS066 (SEQ ID NO:46), CS069 (SEQ ID NO:49), CS070 (SEQ ID NO:52), and CS073 (SEQ ID NO:55) were isolated from Triticum aestivum also. These nucleotide sequences encode full length polypeptides having the amino acid sequences set forth in SEQ ID NOS:26, 29, 32, 35, 38, 41, 47, 50, 53, and 56, which when processed yield mature polypeptides having the amino acid sequences set forth in SEQ ID NOS:27, 30, 33, 36, 39, 42, 48, 51, 54, and 57, respectively. The nucleotide sequences for CS028 (SEQ ID NO:19) and CS029 (SEQ ID NO:22) were isolated from Oryzae sativa. These nucleotide sequences encode full length polypeptides having the amino acid sequences set forth in SEQ ID NOS:20 and 23, which when processed yield mature polypeptides having the amino acid sequences set forth in SEQ ID NOS:21 and 24, respectively.

Group 5 comprises four sequences of which CS032 (SEQ ID NO:58) is the representative sequence. CS032, having the nucleotide sequence set forth in SEQ ID NO:58 and encoding the full-length and mature polypeptides set forth in SEQ ID NOS:59 and 60, was isolated from Glycine max. The nucleotide sequences for CS034 (SEQ ID NO:61) and CS035 (SEQ ID NO:64) were isolated from Glycine max also. These nucleotide sequences encode full length polypeptides having the amino acid sequences set forth in SEQ ID NOS:62 and 65, which when processed yield mature polypeptides having the amino acid sequences set forth in SEQ ID NOS:63 and 66, respectively. The nucleotide sequences for CS052 (SEQ ID NO:67) was isolated from Triticum aestivum. This nucleotide sequence encodes a full length polypeptide having the amino acid sequence set forth in SEQ ID NO:68, which when processed yields a mature polypeptide having the amino acid sequences set forth in SEQ ID NO:69.

Group 6 comprises two Triticum aestivum sequences of which CS044 (SEQ ID NO:70) is the representative sequence. CS044 (SEQ ID NO:70) and CS050 (SEQ ID NO:73) encode full length polypeptides having the amino acid sequences set forth in SEQ ID NOS:71 and 74, which when processed yield mature polypeptides having the amino acid sequences set forth in SEQ ID NOS:72 and 75, respectively.

Group 7 comprises two *Triticum aestivum* sequences of which CS074 (SEQ ID NO:79) is the representative sequence. CS063 (SEQ ID NO:76) and CS074 (SEQ ID NO:79) encode full length polypeptides having the amino acid sequences set forth in SEQ ID NOS:77 and 80, which when processed yield mature polypeptides having the amino acid sequences set forth in SEQ ID NOS:78 and 81, respectively.

Group 8 comprises two *Beta vulgaris* sequences of which CS078 (SEQ ID NO:85) is the representative sequence. CS079 (SEQ ID NO:82) and CS078 (SEQ ID NO:85) encode full length polypeptides having the amino acid sequences set forth in SEQ ID NOS:83 and 86, which when processed yield mature polypeptides having the amino acid sequences set forth in SEQ ID NOS:84 and 87, respectively.

Group 9 comprises CS084 (SEQ ID NO:88), a *Hedera helix* sequence. This nucleotide sequence encodes a full length polypeptide having the amino acid sequence set forth in SEQ ID NO:89, which when processed yields a mature polypeptide having the amino acid sequence set forth in SEQ ID NO:90.

Group 10 comprises two sequences of which CS091 (SEQ ID NO:91) is the representative sequence. CS091 (SEQ ID NO:91) and CS098 (SEQ ID NO:94) encode full length polypeptides having the amino acid sequences set forth in SEQ ID NOS:92 and 95, which when processed yield mature polypeptides having the amino acid sequences set forth in SEQ ID NOS:93 and 96, respectively. CS091 was isolated from *Tulipa fosteriana*, and CS098 was isolated from *Tulipa gesneriana*.

Group 11 comprises four sequences of which CS092 (SEQ ID NO:100) is the representative sequence. CS092, having the nucleotide sequence set forth in SEQ ID NO:100 and encoding the full-length and mature polypeptides set forth in SEQ ID NOS:101 and 102, was isolated from *Tulipa fosteriana*. CS094 (SEQ ID NO:97), CS093 (SEQ ID NO:103), and CS099 (SEQ ID NO:106) encode full length polypeptides having the amino acid sequences set forth in SEQ ID NOS:98, 104, and 107, which when processed yield mature polypeptides having the amino acid sequences set forth in SEQ ID NOS:99, 105, and 108, respectively.

Group 12 comprises two *Tulipa gesneriana* sequences of which CS097 (SEQ ID NO:112) is the representative sequence. CS102 (SEQ ID NO:109) and CS097 (SEQ ID NO:112) encode full length polypeptides having the amino acid sequences set forth in SEQ ID NOS:110 and 113, which when processed yield mature polypeptides having the amino acid sequences set forth in SEQ ID NOS:111 and 114, respectively.

Group 13 comprises two *Tulipa gesneriana* sequences of which CS101 (SEQ ID NO:115) is the representative sequence. CS101 (SEQ ID NO:115) and CS154 (SEQ ID NO:118) encode full length polypeptides having the amino acid sequences set forth in SEQ ID NOS:116 and 119, which when processed yield mature polypeptides having the amino acid sequences set forth in SEQ ID NOS:117 and 120, respectively.

Group 14 comprises two *Momordica charantia* sequences of which CS 104 (SEQ ID NO:121) is the representative sequence. CS104 (SEQ ID NO:121) and CS105 (SEQ ID NO:124) encode full length polypeptides having the amino acid sequences set forth in SEQ ID NOS:122 and 125, which when processed yield mature polypeptides having the amino acid sequences set forth in SEQ ID NOS:123 and 126, respectively.

Group 15 comprises two *Nicotiana benthamiana* sequences of which CS112 (SEQ ID NO:127) is the representative sequence. CS112 (SEQ ID NO:127) and CS166 (SEQ ID NO:130) encode full length polypeptides having the amino acid sequences set forth in SEQ ID NOS:128 and 131, which when processed yield mature polypeptides having the amino acid sequences set forth in SEQ ID NOS:129 and 132, respectively.

Group 16 comprises two sequences of which CS128 (SEQ ID NO:133) is the representative sequence. CS128 (SEQ ID NO:133) and CS153 (SEQ ID NO:136) encode full length polypeptides having the amino acid sequences set forth in SEQ ID NOS:134 and 137, which when processed yield mature polypeptides having the amino acid sequences set forth in SEQ ID NOS:135 and 138, respectively. CS128 was isolated from *Tulipa fosteriana*, and CS153 was isolated from *Tulipa gesneriana*.

Group 17 comprises 24 *Taraxacum kok-saghyz* sequences of which CS130 (SEQ ID NO:142) is the representative sequence. CS129 (SEQ ID NO:139), CS130 (SEQ ID NO:142), CS131 (SEQ ID NO:145), CS132 (SEQ ID NO:148), CS133 (SEQ ID NO:151), CS134 (SEQ ID NO:154), CS135 (SEQ ID NO:157), CS136 (SEQ ID NO:160), CS137 (SEQ ID NO:163), CS138 (SEQ ID NO:166), CS139 (SEQ ID NO:169), CS140 (SEQ ID NO:172), CS141 (SEQ ID NO:175), CS142 (SEQ ID NO:178), CS143 (SEQ ID NO:181), CS144 (SEQ ID NO:184), CS145 (SEQ ID NO:187), CS146 (SEQ ID NO:190), CS147 (SEQ ID NO:193), CS148 (SEQ ID NO:196), CS149 (SEQ ID NO:199), CS150 (SEQ ID NO:202), CS151 (SEQ ID NO:205), and CS152 (SEQ ID NO:208) encode full length polypeptides having the amino acid sequences set forth in SEQ ID NOS:140, 143, 146, 149, 152, 155, 158, 161, 164, 167, 170, 173, 176, 179, 182, 185, 188, 191, 194, 197, 200, 203, 206, and 209, which when processed yield mature polypeptides having the amino acid sequences set forth in SEQ ID NOS:141, 144, 147, 150, 153, 156, 159, 162, 165, 168, 171, 174, 177, 180, 183, 186, 189, 192, 195, 198, 201, 204, 207, and 210, respectively.

Group 18 comprises five *Picramnia pentandra* sequences of which CS161 (SEQ ID NO:211) is the representative sequence. CS161 (SEQ ID NO:211), CS164 (SEQ ID NO:214), CS160 (SEQ ID NO:217), CS162 (SEQ ID NO:220), and CS163 (SEQ ID NO:223) encode full length polypeptides having the amino acid sequences set forth in SEQ ID NOS:212, 215, 218, 221, and 224, which when processed yield mature polypeptides having the amino acid sequences set forth in SEQ ID NOS:213, 216, 219, 222, and 225, respectively.

Group 19 comprises three *Nicotiana benthamiana* sequences of which CS165 (SEQ ID NO:226) is the representative sequence. CS165 (SEQ ID NO:226), CS168 (SEQ ID NO:229), and CS169 (SEQ ID NO:232) encode full length polypeptides having the amino acid sequences set forth in SEQ ID NOS:227, 230, and 233, which when processed yield mature polypeptides having the amino acid sequences set forth in SEQ ID NOS:228, 231, and 234, respectively.

Group 20 comprises CS003 (SEQ ID NO:235, PDF3), a maize gene. The full length CS003 polypeptide (SEQ ID NO:236) is expected to have a signal peptide, thus the mature protein (SEQ ID NO:237) is likely to be secreted or extracellular.

Group 21 comprises CS007 (SEQ ID NO:238, PDF7), a maize gene. PDF7 is likely to be expressed in a kernel-specific or kernel-preferred expression pattern. The full length CS007 polypeptide (SEQ ID NO:239) is expected to have a signal peptide, thus the mature protein (SEQ ID NO:240) would be extracellular.

Group 22 comprises CS008 (SEQ ID NO:241, PDF8), a maize gene. PDF8 is expressed in a kernel-preferred expression pattern. The full length CS008 polypeptide (SEQ ID NO:242) is expected to have a signal peptide, thus the mature protein (SEQ ID NO:243) would be extracellular. PDF8 may be secreted.

Group 23 comprises CS009 (SEQ ID NO:244, PDF9), a maize gene. PDF9 is expressed in a kernel-preferred pattern, particularly an endosperm- and pericarp-preferred expression pattern. The full length CS009 polypeptide (SEQ ID NO:245) includes a predicted transit peptide, thus the mature protein (SEQ ID NO:246) would be extracellular.

Group 24 comprises CS010 (SEQ ID NO:247, PDF10), a maize gene. The full length CS010 polypeptide (SEQ ID NO:248) is expected to have a signal peptide, thus the mature protein (SEQ ID NO:249) is likely to be secreted or extracellular. Expression appears to be kernel-specific or kernel-preferred.

Group 25 comprises CS014 (SEQ ID NO:250, PDF14), a maize gene. PDF14 is expressed in a tassel-preferred manner. The full length CS014 polypeptide (SEQ ID NO:251) appears to include a signal peptide, thus the mature protein (SEQ ID NO:252) would be secreted.

Group 26 comprises CS016 (SEQ ID NO:253, PDF16), a maize gene. The PDF16 nucleotide sequence appears to be expressed preferentially in the kernel, particularly in the endosperm and scutellum. The full length CS016 polypeptide (SEQ ID NO:254) is predicted to have a signal peptide ending at amino acid position 22, thus the mature protein (SEQ ID NO:255) is likely to be an extracellular polypeptide.

Group 27 comprises CS019 (SEQ ID NO:256, PDF19), a maize gene. Expression of the sequence appears to be kernel-preferred. The protein is likely extracellular as the full length CS019 polypeptide (SEQ ID NO:257) contains a signal peptide, thus the mature protein (SEQ ID NO:258) appears to be secreted or extracellular.

Group 28 comprises CS020 (SEQ ID NO:259, PDF20), a maize gene. Expression of PDF20 appears to be kernel-preferred. The predicted protein appears to be extracellular as it has a predicted signal peptide. The full length CS020 polypeptide (SEQ ID NO:260) is expected to have a signal peptide, thus the mature protein (SEQ ID NO:261) is likely to be secreted or extracellular.

Group 29 comprises CS043 (SEQ ID NO:262), a *Triticum aestivum* sequence. This nucleotide sequence encodes a full length polypeptide having the amino acid sequence set forth in SEQ ID NO:263, which when processed yields a mature polypeptide having the amino acid sequence set forth in SEQ ID NO:264.

Group 30 comprises CS045 (SEQ ID NO:265), a *Triticum aestivum* sequence. This nucleotide sequence encodes a full length polypeptide having the amino acid sequence set forth in SEQ ID NO:266, which when processed yields a mature polypeptide having the amino acid sequence set forth in SEQ ID NO:267.

Group 31 comprises CS046 (SEQ ID NO:268), a *Triticum aestivum* sequence. This nucleotide sequence encodes a full length polypeptide having the amino acid sequence set forth in SEQ ID NO:269, which when processed yields a mature polypeptide having the amino acid sequence set forth in SEQ ID NO:270.

Group 32 comprises CS048 (SEQ ID NO:271), a *Triticum aestivum* sequence. This nucleotide sequence encodes a full length polypeptide having the amino acid sequence set forth in SEQ ID NO:272, which when processed yields a mature polypeptide having the amino acid sequence set forth in SEQ ID NO:273.

Group 33 comprises CS049 (SEQ ID NO:274), a *Triticum aestivum* sequence. This nucleotide sequence encodes a full length polypeptide having the amino acid sequence set forth in SEQ ID NO:275, which when processed yields a mature polypeptide having the amino acid sequence set forth in SEQ ID NO:276.

Group 34 comprises CS060 (SEQ ID NO:277), a *Triticum aestivum* sequence. This nucleotide sequence encodes a full length polypeptide having the amino acid sequence set forth in SEQ ID NO:278, which when processed yields a mature polypeptide having the amino acid sequence set forth in SEQ ID NO:279.

Group 35 comprises CS061 (SEQ ID NO:280), a *Triticum aestivum* sequence. This nucleotide sequence encodes a full length polypeptide having the amino acid sequence set forth in SEQ ID NO:281, which when processed yields a mature polypeptide having the amino acid sequence set forth in SEQ ID NO:282.

Group 36 comprises CS068 (SEQ ID NO:283), a *Triticum aestivum* sequence. This nucleotide sequence encodes a full length polypeptide having the amino acid sequence set forth in SEQ ID NO:284, which when processed yields a mature polypeptide having the amino acid sequence set forth in SEQ ID NO:285.

Group 37 comprises CS071 (SEQ ID NO:286), a *Triticum aestivum* sequence. This nucleotide sequence encodes a full length polypeptide having the amino acid sequence set forth in SEQ ID NO:287, which when processed yields a mature polypeptide having the amino acid sequence set forth in SEQ ID NO:288.

Group 38 comprises CS072 (SEQ ID NO:289), a *Triticum aestivum* sequence. This nucleotide sequence encodes a full length polypeptide having the amino acid sequence set forth in SEQ ID NO:290, which when processed yields a mature polypeptide having the amino acid sequence set forth in SEQ ID NO:291.

Group 39 comprises CS076 (SEQ ID NO:292), a *Beta vulgaris* sequence. This nucleotide sequence encodes a full length polypeptide having the amino acid sequence set forth in SEQ ID NO:293, which when processed yields a mature polypeptide having the amino acid sequence set forth in SEQ ID NO:294.

Group 40 comprises CS085 (SEQ ID NO:295), a *Hedera helix* sequence. This nucleotide sequence encodes a full length polypeptide having the amino acid sequence set forth in SEQ ID NO:296, which when processed yields a mature polypeptide having the amino acid sequence set forth in SEQ ID NO:297.

Group 41 comprises CS103 (SEQ ID NO:298), a *Tulipa gesneriana* sequence. This nucleotide sequence encodes a full length polypeptide having the amino acid sequence set forth in SEQ ID NO:299, which when processed yields a mature polypeptide having the amino acid sequence set forth in SEQ ID NO:300.

Group 42 comprises CS124 (SEQ ID NO:301), an *Amaranthus retroflexus* sequence. This nucleotide sequence encodes a full length polypeptide having the amino acid sequence set forth in SEQ ID NO:302, which when processed yields a mature polypeptide having the amino acid sequence set forth in SEQ ID NO:303.

Group 43 comprises CS159 (SEQ ID NO:304), an *Allium porrum* sequence. This nucleotide sequence encodes a full length polypeptide having the amino acid sequence set forth in SEQ ID NO:305, which when processed yields a mature polypeptide having the amino acid sequence set forth in SEQ ID NO:306.

Group 44 comprises CS113 (SEQ ID NO:307), a *Nicotiana benthamiana* sequence. This nucleotide sequence encodes a full length polypeptide having the amino acid sequence set forth in SEQ ID NO:308, which when processed yields a mature polypeptide having the amino acid sequence set forth in SEQ ID NO:309.

Group 45 comprises CS095 (SEQ ID NO:310), a *Tulipa gesneriana* sequence. This nucleotide sequence encodes a full length polypeptide having the amino acid sequence set forth in SEQ ID NO:311, which when processed yields a mature polypeptide having the amino acid sequence set forth in SEQ ID NO:312.

Group 46 comprises CS077 (SEQ ID NO:313), a *Beta vulgaris* sequence. This nucleotide sequence encodes a full length polypeptide having the amino acid sequence set forth in SEQ ID NO:314, which when processed yields a mature polypeptide having the amino acid sequence set forth in SEQ ID NO:315.

Group 47 comprises three *Cyamopsis tetragonoloba* sequences of which CS108 (SEQ ID NO:316) is the representative sequence. CS108 (SEQ ID NO:316), CS156 (SEQ ID NO:319), and CS157 (SEQ ID NO:322) encode full length polypeptides having the amino acid sequences set forth in SEQ ID NOS:317, 320, and 323, which when processed yield mature polypeptides having the amino acid sequences set forth in SEQ ID NOS:318, 321, and 324, respectively.

Group 48 comprises three sequences of which CS005 (SEQ ID NO:325, PDF5) is the representative sequence. CS005 was isolated from *Zea mays*. The PDF5 expression pattern suggests fairly wide-distribution of expression. However, there is strong representation of CS005 in endosperms and embryos of kernels. The mature peptide appears to be extracellular, as a signal peptide is included in the sequence. CS005 (SEQ ID NO:325), CS042 (SEQ ID NO:328) and CS067 (SEQ ID NO:331) encode full length polypeptides having the amino acid sequences set forth in SEQ ID NOS: 326, 329, and 332, which when processed yield mature polypeptides having the amino acid sequences set forth in SEQ ID NOS:327, 330, and 333, respectively. CS042 and CS067 were isolated from *Triticum aestivum*.

Group 49 comprises four sequences of which CS053 (SEQ ID NO:337) is the representative sequence. CS100 (SEQ ID NO:334), CS053 (SEQ ID NO:337), CS064 (SEQ ID NO:340), and CS096 (SEQ ID NO:343) encode full length polypeptides having the amino acid sequences set forth in SEQ ID NOS:335, 338, 341, and 344, which when processed yield mature polypeptides having the amino acid sequences set forth in SEQ ID NOS:336, 339, 342, and 345, respectively. CS100 and CS096 were isolated from *Tulipa gesneriana*. CS053 and CS064 were isolated from *Triticum aestivum*.

Group 50 comprises CS036 (SEQ ID NO:346), a *Glycine max* sequence. This nucleotide sequence encodes a full length polypeptide having the amino acid sequence set forth in SEQ ID NO:347, which when processed yields a mature polypeptide having the amino acid sequence set forth in SEQ ID NO:348.

Group 51 comprises CS125 (SEQ ID NO:349), a *Brassica napus* sequence. This nucleotide sequence encodes a full length polypeptide having the amino acid sequence set forth in SEQ ID NO:350, which when processed yields a mature polypeptide having the amino acid sequence set forth in SEQ ID NO:351.

Group 52 comprises CS056 (SEQ ID NO:352), a *Triticum aestivum* sequence. This nucleotide sequence encodes a full length polypeptide having the amino acid sequence set forth in SEQ ID NO:353, which when processed yields a mature polypeptide having the amino acid sequence set forth in SEQ ID NO:354.

Group 53 comprises CS047 (SEQ ID NO:355), a *Triticum aestivum* sequence. This nucleotide sequence encodes a full length polypeptide having the amino acid sequence set forth in SEQ ID NO:356, which when processed yields a mature polypeptide having the amino acid sequence set forth in SEQ ID NO:357.

Group 54 comprises CS021 (SEQ ID NO:358, PDF21), a *Zea mays* sequence. PDF21 may be predominately expressed in the kernel. The sequence appears to be extracellular as it includes a signal peptide. This nucleotide sequence encodes a full length polypeptide having the amino acid sequence set forth in SEQ ID NO:359, which when processed yields a mature polypeptide having the amino acid sequence set forth in SEQ ID NO:360.

Group 55 comprises CS122 (SEQ ID NO:361), a *Vernonia mespilifolia* sequence. This nucleotide sequence encodes a full length polypeptide having the amino acid sequence set forth in SEQ ID NO:362, which when processed yields a mature polypeptide having the amino acid sequence set forth in SEQ ID NO:363.

Group 56 comprises CS111 (SEQ ID NO:364), a *Picramnia pentandra* sequence. This nucleotide sequence encodes a full length polypeptide having the amino acid sequence set forth in SEQ ID NO:365, which when processed yields a mature polypeptide having the amino acid sequence set forth in SEQ ID NO:366.

Group 57 comprises CS171 (SEQ ID NO:367), a *Vernonia mespilifolia* sequence. This nucleotide sequence encodes a full length polypeptide having the amino acid sequence set forth in SEQ ID NO:368, which when processed yields a mature polypeptide having the amino acid sequence set forth in SEQ ID NO:369.

Group 58 comprises CS172 (SEQ ID NO:370), a *Vernonia mespilifolia* sequence. This nucleotide sequence encodes a full length polypeptide having the amino acid sequence set forth in SEQ ID NO:371, which when processed yields a mature polypeptide having the amino acid sequence set forth in SEQ ID NO:372.

Group 59 comprises CS030 (SEQ ID NO:373), an *Oryza sativa* sequence. This nucleotide sequence encodes a full length polypeptide having the amino acid sequence set forth in SEQ ID NO:374, which when processed yields a mature polypeptide having the amino acid sequence set forth in SEQ ID NO:375.

Group 60 comprises CS088 (SEQ ID NO:376), a *Parthenium argentatum* sequence. This nucleotide sequence encodes a full length polypeptide having the amino acid sequence set forth in SEQ ID NO:377, which when processed yields a mature polypeptide having the amino acid sequence set forth in SEQ ID NO:378.

Group 61 comprises CS107 (SEQ ID NO:379), a *Cyamopsis tetragonoloba* sequence. This nucleotide sequence encodes a full length polypeptide having the amino acid sequence set forth in SEQ ID NO:380, which when processed yields a mature polypeptide having the amino acid sequence set forth in SEQ ID NO:381.

Group 62 comprises CS058 (SEQ ID NO:382), a *Triticum aestivum* sequence. This nucleotide sequence encodes a full length polypeptide having the amino acid sequence set forth in SEQ ID NO:383, which when processed yields a mature polypeptide having the amino acid sequence set forth in SEQ ID NO:384.

Group 63 comprises CS037 (SEQ ID NO:385), a *Glycine max* sequence. This nucleotide sequence encodes a full length polypeptide having the amino acid sequence set forth in SEQ ID NO:386, which when processed yields a mature polypeptide having the amino acid sequence set forth in SEQ ID NO:387.

Group 64 comprises two sequences of which CS082 (SEQ ID NO:391) is the representative sequence. CS086 (SEQ ID NO:388) and CS082 (SEQ ID NO:391) encode full length polypeptides having the amino acid sequences set forth in SEQ ID NOS:389 and 392, which when processed yield mature polypeptides having the amino acid sequences set forth in SEQ ID NOS:390 and 393, respectively. CS086 was isolated from *Licania michauxii*, and CS082 was isolated from *Chrysobalanus icaco*.

Group 65 comprises CS081 (SEQ ID NO:394), a *Ricinus communis* sequence. This nucleotide sequence encodes a full length polypeptide having the amino acid sequence set forth in SEQ ID NO:395, which when processed yields a mature polypeptide having the amino acid sequence set forth in SEQ ID NO:396.

Group 66 comprises two *Vernonia mespilifolia* sequences of which CS121 (SEQ ID NO:400) is the representative sequence. CS123 (SEQ ID NO:397) and CS121 (SEQ ID NO:400) encode full length polypeptides having the amino acid sequences set forth in SEQ ID NOS:398 and 401, which when processed yield mature polypeptides having the amino acid sequences set forth in SEQ ID NOS:399 and 402, respectively.

Group 67 comprises CS080 (SEQ ID NO:403), a *Ricinus communis* sequence. This nucleotide sequence encodes a full length polypeptide having the amino acid sequence set forth in SEQ ID NO:404, which when processed yields a mature polypeptide having the amino acid sequence set forth in SEQ ID NO:405.

Group 68 comprises two sequences of which CS083 (SEQ ID NO:406) is the representative sequence. CS083 (SEQ ID NO:406) and CS087 (SEQ ID NO:409) encode full length polypeptides having the amino acid sequences set forth in SEQ ID NOS:407 and 410, which when processed yield mature polypeptides having the amino acid sequences set forth in SEQ ID NOS:408 and 411, respectively. CS083 was isolated from *Eucalyptus grandis*, and CS087 was isolated from *Tropaeolum majus*.

Group 69 comprises CS155 (SEQ ID NO:412), a *Cyamopsis tetragonoloba* sequence. This nucleotide sequence encodes a full length polypeptide having the amino acid sequence set forth in SEQ ID NO:413, which when processed yields a mature polypeptide having the amino acid sequence set forth in SEQ ID NO:414.

Group 70 comprises three *Vitis vinifera* sequences of which CS117 (SEQ ID NO:421) is the representative sequence. CS119 (SEQ ID NO:415), CS116 (SEQ ID NO:418), and CS117 (SEQ ID NO:421) encode full length polypeptides having the amino acid sequences set forth in SEQ ID NOS: 416, 419, and 422, which when processed yield mature polypeptides having the amino acid sequences set forth in SEQ ID NOS:417, 420, and 423, respectively.

Group 71 comprises CS126 (SEQ ID NO:424), a *Eucalyptus grandis* sequence. This nucleotide sequence encodes a full length polypeptide having the amino acid sequence set forth in SEQ ID NO:425, which when processed yields a mature polypeptide having the amino acid sequence set forth in SEQ ID NO:426.

Group 72 comprises CS109 (SEQ ID NO:427), a *Cyamopsis tetragonoloba* sequence. This nucleotide sequence encodes a full length polypeptide having the amino acid sequence set forth in SEQ ID NO:428, which when processed yields a mature polypeptide having the amino acid sequence set forth in SEQ ID NO:429.

Group 73 comprises CS115 (SEQ ID NO:430), a *Nicotiana benthamiana* sequence. This nucleotide sequence encodes a full length polypeptide having the amino acid sequence set forth in SEQ ID NO:431, which when processed yields a mature polypeptide having the amino acid sequence set forth in SEQ ID NO:432.

Group 74 comprises CS089 (SEQ ID NO:433), a *Parthenium argentatum* sequence. This nucleotide sequence encodes a full length polypeptide having the amino acid sequence set forth in SEQ ID NO:434, which when processed yields a mature polypeptide having the amino acid sequence set forth in SEQ ID NO:435.

Group 75 comprises CS110 (SEQ ID NO:436), a *Cyamopsis tetragonoloba* sequence. This nucleotide sequence encodes a full length polypeptide having the amino acid sequence set forth in SEQ ID NO:437, which when processed yields a mature polypeptide having the amino acid sequence set forth in SEQ ID NO:438.

Group 76 comprises CS158 (SEQ ID NO:439), a *Cyamopsis tetragonoloba* sequence. This nucleotide sequence encodes a full length polypeptide having the amino acid sequence set forth in SEQ ID NO:440, which when processed yields a mature polypeptide having the amino acid sequence set forth in SEQ ID NO:441.

Group 77 comprises CS127 (SEQ ID NO:442), a *Licania michauxii* sequence. This nucleotide sequence encodes a full length polypeptide having the amino acid sequence set forth in SEQ ID NO:443, which when processed yields a mature polypeptide having the amino acid sequence set forth in SEQ ID NO:444.

Group 78 comprises two *Vitis vinifera*. sequences of which CS118 (SEQ ID NO:445) is the representative sequence. CS118 (SEQ ID NO:445) and CS170 (SEQ ID NO:448) encode full length polypeptides having the amino acid sequences set forth in SEQ ID NOS:446 and 449, which when processed yield mature polypeptides having the amino acid sequences set forth in SEQ ID NOS:447 and 450, respectively.

Group 79 comprises CS090 (SEQ ID NO:451), an *Arachis hypogaea* sequence. This nucleotide sequence encodes a full length polypeptide having the amino acid sequence set forth in SEQ ID NO:452, which when processed yields a mature polypeptide having the amino acid sequence set forth in SEQ ID NO:453.

Group 80 comprises CS075 (SEQ ID NO:454), a *Brassica napus*. sequence. This nucleotide sequence encodes a full length polypeptide having the amino acid sequence set forth in SEQ ID NO:455, which when processed yields a mature polypeptide having the amino acid sequence set forth in SEQ ID NO:456.

Group 81 comprises CS011 (SEQ ID NO:457, PDF11), a *Zea mays* sequence. This nucleotide sequence encodes a full length polypeptide having the amino acid sequence set forth in SEQ ID NO:458, which when processed yields a mature polypeptide having the amino acid sequence set forth in SEQ ID NO:459. PDF11 expression seems to be tassel-preferred. The mature peptide may be secreted or extracellular as the sequence includes a signal peptide.

Group 82 comprises CS012 (SEQ ID NO:460, PDF12), a *Zea mays* sequence. This nucleotide sequence encodes a full length polypeptide having the amino acid sequence set forth in SEQ ID NO:461, which when processed yields a mature polypeptide having the amino acid sequence set forth in SEQ ID NO:462. The sequence may be preferentially expressed in kernels. PDF12 encodes a signal peptide, and thus would be secreted.

Group 83 comprises CS002 (SEQ ID NO:463, PDF2), a *Zea mays* sequence. This nucleotide sequence encodes a full-length polypeptide having the amino acid sequence set forth in SEQ ID NO:464. PDF2 is expressed in a kernel-preferred pattern.

Group 84 comprises CS015 (SEQ ID NO:465, PDF15), a *Zea mays* sequence. This nucleotide sequence encodes a full-length polypeptide having the amino acid sequence set forth in SEQ ID NO:466. PDF15 is preferentially expressed in kernels. The Zm-PDF15 sequence differs from Zm-ES-4 (Cordts et al. (2001) *Plant J.* 25:103-114) by one amino acid residue. The gene appears to encode an extracellularly localized protein as there is a signal peptide.

Group 85 comprises CS001 (SEQ ID NO:467, PDF1), a *Zea mays* sequence. This nucleotide sequence encodes a full-length polypeptide having the amino acid sequence set forth in SEQ ID NO:468. Zm-PDF1 is predicted to be an extracellular protein.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence have defensin-like activity and thereby affect development, developmental pathways, and defense responses. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a defensin nucleotide sequence that encodes a biologically active portion of a defensin protein of the invention will encode at least 15, 25, 30, 50, 100, 150, 153, 200, 250, 300 contiguous amino acids, or up to the total number of amino acids present in a full-length protein of the invention. Fragments of a defensin nucleotide sequence that are useful as hybridization probes for PCR primers generally need not encode a biologically active portion of a defensin protein.

Thus, a fragment of a defensin nucleotide sequence may encode a biologically active portion of a defensin protein, or it may be a fragment that can be used as a hybridization probe or PCR primer using methods disclosed below. A biologically active portion of a defensin protein can be prepared by isolating a portion of one of the defensin nucleotide sequences of the invention, expressing the encoded portion of the defensin protein (e.g., by recombinant expression in vitro), and assessing the activity of the encoded portion of the defensin protein. Nucleic acid molecules that are fragments of a defensin nucleotide sequence comprise at least 16, 20, 50, 75, 100, 150, 200, 250, 300, 350, 400, 450, 500, 550, 600, 650, 683, 700, 800, or 900 nucleotides, or up to the number of nucleotides present in a full-length defensin nucleotide sequence disclosed herein By "variants" substantially similar sequences are intended. For nucleotide sequences, conservative variants include those sequences that, because of the degeneracy of the genetic code, encode the amino acid sequence of one of the defensin polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a defensin protein of the invention. Generally, variants of a particular nucleotide sequence of the invention will have at least about 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they continue to possess the desired biological activity of the native protein, that is, defensin-like activity as described herein. Such variants may result from, for example, genetic polymorphism or from human manipulation. Biologically active variants of a native defensin protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

Biological activity of the defensin polypeptides (i.e., influencing the plant defense response and various developmental pathways, including, for example, influencing cell division) can be assayed by any method known in the art. Biological activity of the polypeptides of the present invention can be assayed by any method known in the art (see for example, U.S. Pat. No. 5,614,395; Thomma et al. (1998) *Plant Biology* 95:15107-15111; Liu et al. (1994) *Plant Biology* 91:1888-1892; Hu et al. (1997) *Plant Mol. Biol.* 34:949-959; Cammue et al. (1992) *J. Biol. Chem.* 267:2228-2233; and Thevissen et al. (1996) *J. Biol. Chem.* 271:15018-15025, all of which are herein incorporated by reference). Furthermore, assays to detect defensin-like activity include, for example, assessing antifungal and/or antimicrobial activity (Terras et al. (1992) *J. Biol. Chem.* 267:14301-15309; Terras et al. (1993) *Plant Physiol* (Bethesda) 103:1311-1319; Terras et al. (1995) *Plant Cell* 7:573-588, Moreno et al. (1994) *Eur. J. Biochem.* 223: 135-139; and Osborn et al. (1995) *FEBS Lett.* 368:257-262, all of which are herein incorporated by reference).

The polypeptides of the invention may be altered in various ways including amino acid substitutions, deletions, truncations, and insertions. Novel proteins having properties of interest may be created by combining elements and fragments of proteins of the present invention as well as other proteins. Methods for such manipulations are generally known in the art. For example, amino acid sequence variants of the defensin proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (Macmillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired developmental activity, or defense response activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by defensin activity assays. See, for example, Lancaster et al. (1994) *J. Biol. Chem.* 14:1137-1142 and Terras et al. (1995) *Plant Cell* 7:537-588, herein incorporated by reference. Additionally, differences in the expression of specific genes between uninfected and infected plants can be determined using gene expression profiling. RNA was analyzed using the gene expression profiling process (GeneCalling®) as described in U.S. Pat. No. 5,871,697, herein incorporated by reference.

Variant nucleotide sequences and proteins also encompass sequences and proteins derived from a mutagenic and recombinogenic procedure such as DNA shuffling. With such a procedure, one or more different defensin coding sequences can be manipulated to create a new defensin protein possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire defensin sequences set forth herein or to fragments thereof are encompassed by the present invention. Such sequences include sequences that are orthologs of the disclosed sequences. By "orthologs" genes derived from a common ancestral gene and which are found in different species as a result of speciation is intended. Genes found in different species are considered orthologs when their nucleotide sequences and/or their encoded protein sequences share substantial identity as defined elsewhere herein. Functions of orthologs are often highly conserved among species. Thus, isolated sequences that encode a defensin and which hybridize under stringent conditions to the defensin sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the defensin sequences of the invention. Methods for preparation of probes for hybridization and for construction of cDNA and genomic libraries are generally known in the art and are disclosed in Sambrook et al. (1989)

*Molecular Cloning: A Laboratory Manual* (2d ed., Cold Spring Harbor Laboratory Press, Plainview, N.Y.).

For example, an entire defensin sequence disclosed herein, or one or more portions thereof, may be used as a probe capable of specifically hybridizing to corresponding defensin sequences and messenger RNAs. To achieve specific hybridization under a variety of conditions, such probes include sequences that are unique among defensin sequences and are preferably at least about 10 nucleotides in length, and most preferably at least about 20 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" conditions under which a probe will hybridize to its target sequence to a detectably greater degree than to other sequences (e.g., at least 2-fold over background) is intended. Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode a defensin polypeptide and which hybridize under stringent conditions to the defensin sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.*

85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.hlm.nih.gov. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e) (ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Disease and Pests

Compositions and methods for controlling pathogenic agents are provided. The anti-pathogenic compositions comprise plant defensin nucleotide and amino acid sequences. Particularly, the plant nucleic acid and amino acid sequences and fragments and variants thereof set forth herein possess anti-pathogenic activity. Accordingly, the compositions and methods are useful in protecting plants against fungal pathogens, viruses, nematodes, insects, and the like. Additionally provided are transformed plants, plant cells, plant tissues and seeds thereof.

By "plant pathogen" or "plant pest" any organism that can cause harm to a plant, by inhibiting or slowing the growth of a plant, by damaging the tissues of a plant, by weakening the immune system of a plant, reducing the resistance of a plant to abiotic stresses, and/or by causing the premature death of the plant, etc. is intended. Plant pathogens and plant pests include insects, nematodes, and organisms such as fungi, viruses, and bacteria.

By "disease resistance" or "pathogen resistance" it is intended that the organisms avoid the disease symptoms which are the outcome of organism-pathogen interactions. That is, pathogens are prevented from causing diseases and the associated disease symptoms, or alternatively, the disease symptoms caused by the pathogen is minimized or lessened.

By "anti-pathogenic compositions" is intended that the compositions of the invention are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

An "antimicrobial agent," a "pesticidal agent," a "defensin," an "antiviral agent," and "insecticidal agent," and/or a "fungicidal agent" will act similarly to suppress, control, and/or kill the invading pathogen.

A defensive agent will possess defensive activity. By "defensive activity" an antipathogenic, antimicrobial, antiviral, insecticidal, or antifungal activity is intended.

By "antipathogenic compositions" it is intended that the compositions of the invention have activity against pathogens; including fungi, microorganisms, viruses, insects and nematodes, and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect organisms, particularly plants, from disease, particularly those diseases that are caused by invading pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) *J. Biol. Chem.* 267:2228-2233, both of which are herein incorporated by reference).

In specific embodiments, methods for increasing pathogen resistance in a plant comprise stably transforming a plant with a DNA construct comprising an anti-pathogenic nucleotide sequence of the invention operably linked to promoter that drives expression in a plant. Such methods find use in agriculture particularly in limiting the impact of plant pathogens on crop plants. While the choice of promoter will depend on the desired timing and location of expression of the anti-pathogenic nucleotide sequences, preferred promoters include constitutive and pathogen-inducible promoters.

It is understood in the art that plant DNA viruses and fungal pathogens remodel the control of the host replication and gene expression machinery to accomplish their own replication and effective infection. The present invention may be useful in preventing such corruption of the cell.

The defensin sequences find use in disrupting cellular function of plant pathogens or insect pests as well as altering the defense mechanisms of a host plant to enhance resistance to disease or insect pests. While the invention is not bound by any particular mechanism of action to enhance disease resistance, the gene products of the defensin sequences function to inhibit or prevent diseases in a plant.

The methods of the invention can be used with other methods available in the art for enhancing disease resistance in plants. For example, any one of a variety of second nucleotide sequences may be utilized, embodiments of the invention encompass those second nucleotide sequences that, when expressed in a plant, help to increase the resistance of a plant to pathogens. It is recognized that such second nucleotide sequences may be used in either the sense or antisense orientation depending on the desired outcome. Other plant defense proteins include those described in PCT patent publications WO 99/43823 and WO 99/43821, both of which are herein incorporated by reference.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* f.sp. *glycinea, Macrophomina phaseolina, Rhizoctonia solani, Sclerotinia sclerotiorum, Fusarium oxysporum, Diaporthe phaseolorum* var. *sojae (Phomopsis sojae), Diaporthe phaseolorum* var. *caulivora, Sclerotium rolfsii, Cercospora kikuchii, Cercospora sojina, Peronospora manshurica, Colletotrichum dematium (Colletotrichum truncatum), Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines, Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibacter* Michigan's subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium* spp., *Xanthomonas campestris* p.v. *alfalfae, Aphanomyces euteiches, Stemphylium herbarum, Stemphylium alfalfae;* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* fsp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Tilletia indica, Pythium gramicola,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *carotovora, Cephalosporium acremonium, Phytophthora cryptogea, Albugo tragopogonis;* Corn: *Fusarium moniliforme* var. *subglutinans, Erwinia stewartii, Fusarium moniliforme, Gibberella zeae (Fusarium graminearum), Stenocarpella maydis (Diplodia maydis), Pythium irregulare, Pythium debaryanum, Pythium graminicola, Pythium splendens, Pythium ultimum, Pythium aphanidermatum, Aspergillus flavus, Bipolaris maydis* O, T *(Cochliobolus heterostrophus), Helminthosporium carbonum* I, II & III *(Cochliobolus carbonum), Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudomonas avenae, Erwinia chrysanthemi* p.v. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora saccharin, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Periconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchairn, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium*

*strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, and lesion nematodes, including *Heterodera* and *Globodera* spp.; particularly *Globodera rostochiensis* and *Globodera pailida* (potato cyst nematodes); *Heterodera glycines* (soybean cyst nematode); *Heterodera schachtii* (beet cyst nematode); and *Heterodera avenae* (cereal cyst nematode). Additional nematodes include: *Heterodera cajani; Heterodera trifolii; Heterodera oryzae; Globodera tabacum; Meloidogyne incognita; Meloidogyne javonica; Meloidogyne hapla; Meloidogyne arenaria; Meloidogyne naasi; Meloidogyne exigua; Xiphinema index; Xiphinema italiae; Xiphinema americanum; Xiphinema diversicaudatum; Pratylenchus penetrans; Pratylenchus brachyurus; Pratylenchus zeae; Pratylenchus coffeae; Pratylenchus thornei; Pratylenchus scribneri; Pratylenchus vulnus; Pratylenchus curvitatus; Radopholus similis; Radopholus citrophilus; Ditylenchus dipsaci; Helicotylenchus multicintus; Rotylenchulus reniformis; Belonolaimus* spp.; *Paratrichodorus anemones; Trichodorus* spp.; *Primitivus* spp.; *Anguina tritici; Bider avenae; Subanguina radicicola; Tylenchorhynchus* spp.; *Haplolaimus seinhorsti; Tylenchulus semipenetrans; Hemicycliophora arenaria; Belonolaimus langicaudatus; Paratrichodorus xiphinema; Paratrichodorus christiei; Rhadinaphelenchus cocophilus; Paratrichodorus minor; Hoplolaimus galeatus; Hoplolaimus columbus; Criconemella* spp.; *Paratylenchus* spp.; *Nacoabbus aberrans; Aphelenchoides besseyi; Ditylenchus angustus; Hirchmaniella* spp.; *Scutellonema* spp.; *Hemicriconemoides kanayaensis; Tylenchorynchus claytoni*; and *Cacopaurus pestis*.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, sugarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blotch leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* spp., Root maggots.

Expression of Sequences

The nucleic acid sequences of the present invention can be expressed in a host cell such as bacterial, fungal, yeast, insect, mammalian, or preferably plant cells. It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

By "host cell" a cell, which comprises a heterologous nucleic acid sequence of the invention is meant. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The defensin sequences of the invention are provided in expression cassettes or DNA constructs for expression in the plant of interest. The cassette will include 5' and 3' regulatory sequences operably linked to a defensin sequence of the invention. By "operably linked" a functional linkage between a promoter and a second sequence, wherein the promoter sequence initiates and mediates transcription of the DNA sequence corresponding to the second sequence is intended. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the defensin sequence to be under the transcriptional regulation of the regulatory regions. The expression cassette may additionally contain selectable marker genes.

The expression cassette will include in the 5'-3' direction of transcription, a transcriptional and translational initiation region, a defensin DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of defensin in the host cell (i.e., plant or plant cell). Thus, the phenotype of the host cell (i.e., plant or plant cell) is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126-6130); potyvirus leaders, for example, TEV leader (Tobacco Etch Virus) (Allison et al. (1986); MDMV leader (Maize Dwarf Mosaic Virus); *Virology* 154:9-20), and human immunoglobulin heavy-chain binding protein (BiP), (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611, herein incorporated by reference.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819 published Sep. 9, 1999, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2): 141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced defensin expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol Gen Genet.* 254(3):337-343; Russell et al. (1997) *Transgenic Res.* 6(2): 157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-specific promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10: 108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see WO 00/11177, herein incorporated by reference). Gamma-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The present invention may be used for transformation of any plant species, including, but not limited to, monocots and dicots. Examples of plants of interest include, but are not limited to, corn (*Zea mays*), Brassica sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp., *Pisum* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Hydrangea macrophylla*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived PL promoter and N-gene ribosome binding site (Simatake and Rosenberg (1981) *Nature* 292:128). Examples of selection markers for *E. coli* include, for example, genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229-235 and Mosbach et al. (1983) *Nature* 302:543-545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention. Such antimicrobial proteins can be used for any application including coating surfaces to target microbes as described further infra.

Synthesis of heterologous nucleotide sequences in yeast is well known. Sherman, F., et al. (1982) *Methods in Yeast Genetics*, Cold Spring Harbor Laboratory is a well recognized work describing the various methods available to produce proteins in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like, as desired.

A protein of the present invention, once expressed, can be isolated from yeast by lysing the cells and applying standard protein isolation techniques to the lysates. The monitoring of the purification process can be accomplished by using Western blot techniques, radioimmunoassay, or other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, army worm, moth and *Drosophila* cell lines such as a Schneider cell line (See, Schneider (1987) *J. Embyol. Exp. Morphol.* 27:353-365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP 1 intron from SV40 (Sprague, et al. (1983) *J. Virol.* 45:773-781). Additionally, gene sequences to control replication in the host cell may be incorporated into the vector such as those found in bovine papilloma virus type-vectors. Saveria-Campo, M., (1985) Bovine Papilloma Virus DNA a Eukaryotic Cloning Vector in *DNA Cloning Vol. II a Practical Approach*, D. M. Glover, Ed., IRL Press, Arlington, Va. pp. 213-238.

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art. Kuchler, R. J. (1997) *Biochemical Methods in Cell Culture and Virology*, Dowden, Hutchinson and Ross, Inc.

It is recognized that with these nucleotide sequences, antisense constructions, complementary to at least a portion of the messenger RNA (mRNA) for the defensin sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See U.S. Pat. Nos. 5,283,184 and 5,034,323; herein incorporated by reference.

In some embodiments, the content and/or composition of polypeptides of the present invention in a plant may be modulated by altering, in vivo or in vitro, the promoter of the nucleotide sequence to up- or down-regulate expression. For instance, an isolated nucleic acid comprising a promoter sequence operably linked to a polynucleotide of the present invention is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra. Detection of expression of a polypeptide of the invention occurs through any method known to one of skill in the art including, but not limited to, immunolocalization.

In general, concentration or composition of the polypeptides of the invention is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds, which activate expression from these promoters, are well known in the art. In various embodiments, the polypeptides of the present invention are modulated in crop plants, particularly maize, wheat, soybean, alfalfa, barley, oats, and rice.

The methods of the invention can be used with other methods available in the art for enhancing disease resistance in plants. Similarly, the antimicrobial compositions described herein may be used alone or in combination with other nucleotide sequences, polypeptides, or agents to protect against plant diseases and pathogens. Although any one of a variety of second nucleotide sequences may be utilized, specific embodiments of the invention encompass those second nucleotide sequences that, when expressed in a plant, help to increase the resistance of a plant to pathogens.

Proteins, peptides, and lysozymes that naturally occur in insects (Jaynes et al. (1987) *Bioassays* 6:263-270), plants (Broekaert et al. (1997) *Critical Reviews in Plant Sciences* 16:297-323), animals (Vunnam et al. (1997) *J. Peptide Res.* 49:59-66), and humans (Mitra and Zang (1994) *Plant Physiol.* 106:977-981; Nakajima et al. (1997) *Plant Cell Reports* 16:674-679) are also a potential source of plant disease resistance. Examples of such plant resistance-conferring sequences include those encoding sunflower rhoGTPase-Activating Protein (rhoGAP), lipoxygenase (LOX), Alcohol Dehydrogenase (ADH), and *Sclerotinia*-Inducible Protein-I (SCIP-1) described in U.S. application Ser. No. 09/714,767, herein incorporated by reference. These nucleotide sequences enhance plant disease resistance through the modulation of development, developmental pathways, and the plant pathogen defense system. Other plant defense proteins include those described in WO 99/43823 and WO 99/43821, all of which are herein incorporated by reference. It is recognized that such second nucleotide sequences may be used in either the sense or antisense orientation depending on the desired outcome.

In another embodiment, the defensins comprise isolated polypeptides of the invention. The defensins of the invention find use in the decontamination of plant pathogens during the processing of grain for animal or human food consumption; during the processing of feedstuffs, and during the processing of plant material for silage. In this embodiment, the defensins of the invention are presented to grain, plant material for silage, or a contaminated food crop, or during an appropriate stage of the processing procedure, in amounts effective for antimicrobial activity. The compositions can be applied to the environment of a plant pathogen by, for example, spraying, atomizing, dusting, scattering, coating or pouring, introducing into or on the soil, introducing into irrigation water, by seed treatment, or dusting at a time when the plant pathogen has begun to appear or before the appearance of pests as a protective measure. It is recognized that any means that bring the defensive agent polypeptides in contact with the plant pathogen can be used in the practice of the invention.

Additionally, the compositions can be used in formulations used for their antimicrobial activities. Methods are provided for controlling plant pathogens comprising applying a decontaminating amount of a polypeptide or composition of the invention to the environment of the plant pathogen. The polypeptides of the invention can be formulated with an acceptable carrier into a composition(s) that is, for example, a suspension, a solution, an emulsion, a dusting powder, a dispersible granule, a wettable powder, an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors or other preparations that influence plant growth. One or more agrochemicals including, but not limited to, herbicides, insecticides, fungicides, bacteriocides, nematocides, molluscicides, acaracides, plant growth regulators, harvest aids, and fertilizers, can be combined with carriers, surfactants, or adjuvants customarily employed in the art of formulation or other components to facilitate product handling and application for particular target mycotoxins. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area or plant to be treated, simultaneously or in succession, with other compounds. In some embodiments, methods of applying an active ingredient of the present invention or an agrochemical composition of the present invention (which contains at least one of the proteins of the present invention) are foliar application, seed coating, and soil application.

Suitable surface-active agents include, but are not limited to, anionic compounds such as a carboxylate of, for example, a metal; a carboxylate of a long chain fatty acid; an N-acyl-sarcosinate; mono or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g. polyoxyethylene sorbitar fatty acid esters, block copolymers of ethylene oxide and propylene oxide, acetylenic glycols such as 2, 4, 7, 9-tetraethyl-5-decyn-4,7-diol, or ethoxylated acetylenic glycols. Examples of a cationic surface-active agent include, for instance, an aliphatic mono-, di-, or polyamine such as an acetate, naphthenate, or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as concentrate of primary composition, which requires dilution with a suitable quantity of water or other diluent before application. The decontaminating concentration will vary depending upon the nature of the particular formulation, specifically, whether it is a concentrate or to be used directly.

In a further embodiment, the compositions, as well as the polypeptides of the present invention can be treated prior to formulation to prolong the activity when applied to the environment of a plant pathogen as long as the pretreatment is not deleterious to the activity. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W. H. Freeman and Co.)).

In an embodiment of the invention, the compositions of the invention comprise a microbe having stably integrated the nucleotide sequence of a defensive agent. The resulting microbes can be processed and used as a microbial spray. Any suitable microorganism can be used for this purpose. See, for example, Gaertner et al. (1993) in *Advanced Engineered Pesticides*, Kim (Ed.). In one embodiment, the nucleotide sequences of the invention are introduced into microorganisms that multiply on plants (epiphytes) to deliver the defensins to potential target crops. Epiphytes can be, for example, gram-positive or gram-negative bacteria.

It is further recognized that whole, i.e., unlysed, cells of the transformed microorganism can be treated with reagents that prolong the activity of the polypeptide produced in the microorganism when the microorganism is applied to the environment of a target plant. A secretion signal sequence may be used in combination with the gene of interest such that the resulting enzyme is secreted outside the microorganism for presentation to the target plant.

In this manner, a gene encoding a defensive agent of the invention may be introduced via a suitable vector into a microbial host, and said transformed host applied to the environment, plants, or animals. Microorganism hosts that are known to occupy the "phytosphere" (phylloplane, phyllosphere, rhizosphere, and/or rhizoplane) of one or more crops of interest may be selected for transformation. These microorganisms are selected so as to be capable of successfully competing in the particular environment with the wild-type microorganisms, to provide for stable maintenance and expression of the gene expressing the detoxifying polypeptide, and for improved protection of the proteins of the invention from environmental degradation and inactivation.

Such microorganisms include bacteria, algae, and fungi. Illustrative prokaryotes, both Gram-negative and -positive, include *Enterobacteriaceae*, such as *Escherichia, Erwinia, Shigella, Salmonella*, and *Proteus; Bacillaceae; Rhizobiaceae*, such as *Rhizobium; Spirillaceae*, such as photobacterium, *Zymomonas, Serratia, Aeromonas, Vibrio, Desulfovibrio, Spirillum; Lactobacillaceae; Pseudomonadaceae*, such as *Pseudomonas* and *Acetobacter; Azotobacteraceae*; and *Nitrobacteraceae*. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like. Of particular interest are microorganisms, such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*; fungi, particularly yeast, e.g., *Saccharomyces, Pichia, Cryptococcus, Kluyveromyces, Sporobolomyces, Rhodotorula, Aureobasidium*, and *Gliocladium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pullulans*.

In an embodiment of the invention, the defensins of the invention may be used as a pharmaceutical compound for treatment of fungal and microbial pathogens in humans and other animals. Diseases and disorders caused by fungal and microbial pathogens include but are not limited to fungal meningoencephalitis, superficial fungal infections, ringworm, Athlete's foot, histoplasmosis, candidiasis, thrush, coccidioidoma, pulmonary cryptococcus, trichosporonosis, piedra, tinea nigra, fungal keratitis, onychomycosis, tinea capitis, chromomycosis, aspergillosis, endobronchial pulmonary aspergillosis, mucormycosis, chromoblastomycosis, dermatophytosis, tinea, fusariosis, pityriasis, mycetoma, pseudallescheriasis, and sporotrichosis.

In particular, the compositions of the invention may be used as pharmaceutical compounds to provide treatment for diseases and disorders associated with, but not limited to, the following fungal pathogens: *Histoplasma capsulatum, Candida* spp. (*C. albicans, C. tropicalis, C. parapsilosis, C. guilliermondii, C. glabrata/Torulopsis glabrata, C. krusei, C. lusitaniae*), *Aspergillus fumigatus, A. flavus, A. niger, Rhizopus* spp., *Rhizomucor* spp., *Cunninghamella* spp., *Apophyso-*

*myces* spp., *Saksenaee* spp., *Mucor* spp., and *Absidia* spp. Efficacy of the compositions of the invention as anti-fungal treatments may be determined through anti-fungal assays known to one in the art.

The defensins may be administered to a patient through numerous means. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of active compound is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" comprises, but is not limited to, the small molecules, peptides, antibodies, and antisense oligonucleotides of the invention.

The defensins of the invention can be used for any application including coating surfaces to target microbes. In this manner, target microbes include human pathogens or microorganisms. Surfaces that might be coated with the defensins of the invention include carpets and sterile medical facilities. Polymer bound polypeptides of the invention may be used to coat surfaces. Methods for incorporating compositions with antimicrobial properties into polymers are known in the art. See U.S. Pat. No. 5,847,047 herein incorporated by reference.

An isolated polypeptide of the invention can be used as an immunogen to generate antibodies that bind defensins using standard techniques for polyclonal and monoclonal antibody preparation. The full-length defensins can be used or, alternatively, the invention provides antigenic peptide fragments of defensins for use as immunogens. The antigenic peptide of a defensive agent comprises at least 8, preferably 10, 15, 20, or amino acid residues of the amino acid sequence shown in SEQ ID NO: 2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 75, 77, 78, 80, 81, 83, 84, 86, 87, 89, 90, 92, 93, 95, 96, 98, 99, 101, 102, 104, 105, 107, 108, 110, 111, 113, 114, 116, 117, 119, 120, 122, 123, 125, 126, 128, 129, 131, 132, 134, 135, 137, 138, 140, 141, 143, 144, 146, 147, 149, 150, 152, 153, 155, 156, 158, 159, 161, 162, 164, 165, 167, 168, 170, 171, 173, 174, 176, 177, 179, 180, 182, 183, 185, 186, 188, 189, 191, 192, 194, 195, 197, 198, 200, 201, 203, 204, 206, 207, 209, 210, 212, 213, 215, 216, 218, 219, 221, 222, 224, 225, 227, 228, 230, 231, 233, 234, 236, 237, 239, 240, 242, 243, 245, 246, 248, 249, 251, 252, 254, 255, 257, 258, 260, 261, 263, 264, 266, 267, 269, 270, 272, 273, 275, 276, 278, 279, 281, 282, 284, 285, 287, 288, 290, 291, 293, 294, 296, 297, 299, 300, 302, 303, 305, 306, 308, 309, 311, 312, 314, 315, 317, 318, 320, 321, 323, 324, 326, 327, 329, 330, 332, 333, 335, 336, 338, 339, 341, 342, 344, 345, 347, 348, 350, 351, 353, 354, 356, 357, 359, 360, 362, 363, 365, 366, 368, 369, 371, 372, 374, 375, 377, 378, 380, 381, 383, 384, 386, 387, 389, 390, 392, 393, 395, 396, 398, 399, 401, 402, 404, 405, 407, 408, 410, 411, 413, 414, 416, 417, 419, 420, 422, 423, 425, 426, 428, 429, 431, 432, 434, 435, 437, 438, 440, 441, 443, 444, 446, 447, 449, 450, 452, 453, 455, 456, 458, 459, 461, 462, 464, 466, or 468 and encompasses an epitope of a defensin such that an antibody raised against the peptide forms a specific immune complex with the antimicrobial polypeptides. Epitopes encompassed by the antigenic peptide are regions of defensins that are located on the surface of the protein, e.g., hydrophilic regions, which are readily ascertainable by those of skill in the art.

Accordingly, another aspect of the invention pertains to anti-defensin polyclonal and monoclonal antibodies that bind a defensin. Polyclonal defensin-like antibodies can be prepared by immunizing a suitable subject (e.g., rabbit, goat, mouse, or other mammal) with an defensive agent immunogen. The anti-defensin antibody titer in the immunized subject can be monitored over time by standard techniques, such as with an enzyme linked immunosorbent assay (ELISA) using immobilized antimicrobial polypeptides. At an appropriate time after immunization, e.g., when the anti-defensive agent antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387-402).

Alternative to preparing monoclonal antibody-secreting hybridomas, a monoclonal anti-defensin-like antibody can be identified and isolated by screening a recombinant combinatorial immunoglobulin library (e.g., an antibody phage display library) with a defensin to thereby isolate immunoglobulin library members that bind the defensive agent. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening an antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734. The antibodies can be used to identify homologs of the defensins of the invention.

The following examples are offered by way of illustration and not by way of limitation.

EXPERIMENTAL

Example 1

Transformation and Regeneration of Transgenic Plants in Maize

Immature maize embryos from greenhouse donor plants are bombarded with a plasmid containing a defensin nucleotide sequence of the invention operably linked to a ubiquitin promoter and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a defensin nucleotide sequence of the invention operably linked to a ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288 J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for altered defense response defensin activity, insect resistance, nematode resistance, viral resistance, or fungal resistance.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l Bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l Bialaphos (added after sterilizing the medium and cooling to 60° C.). Hormone-free medium (272V) comprises 4.3 g/l MS salts (GIBCO 11117-074), 5.0 ml/i MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 2

Agrobacterium-Mediated Transformation in Maize

For Agrobacterium-mediated transformation of maize with a defensin nucleotide sequence of the invention operably linked to a ubiquitin promoter, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the DNA construct containing the defensin nucleotide sequence to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 3

Soybean Embryo Transformation

Soybean embryos are bombarded with a plasmid containing the defensin nucleotide sequences operably linked to a ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) Nature (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) Nature 313:810-812), the hygromycin phosphotransferase gene from plasmid pJR225 (from E. coli; Gritz et al. (1983) Gene 25:179-188), and the 3' region of the nopaline synthase gene from the T-DNA of the Ti plasmid of Agrobacterium tumefaciens. The expression cassette comprising the defensin nucleotide sequence operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 4

Sunflower Meristem Tissue Transformation

Sunflower meristem tissues are transformed with an expression cassette containing the defensin sequence operably linked to a ubiquitin promoter as follows (see also European Patent Number EP 0 486233, herein incorporated by reference, and Malone-Schoneberg et al. (1994) Plant Science 103:199-207). Mature sunflower seed (Helianthus annuus L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9: 55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.,* 15: 473-497), Shepard's vitamin additions (Shepard (1980) in *Emergent Techniques for the Genetic Improvement of Crops* University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney et al. (1992) *Plant Mol. Biol.* 18: 301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS1000® particle acceleration device.

Disarmed *Agrobacterium tumefaciens* strain EHA105 is used in all transformation experiments. A binary plasmid vector comprising the expression cassette that contains the defensin gene operably linked to the ubiquitin promoter is introduced into *Agrobacterium* strain EHA105 via freeze-thawing as described by Holsters et al. (1978) *Mol. Gen. Genet.* 163:181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for defensin-like activity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by defensin-like activity analysis of leaf extracts while transgenic seeds harvested from NPTII-positive $T_0$ plants are identified by defensin-like activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it are dropped on the center of the surface of macrocarrier. Each plate is bombarded twice with 650 PSI rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for defensin-like activity using assays known in the art. After positive (i.e., for defensin expression) explants are identified, those shoots that fail to exhibit defensin-like activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate defensin-like protein activity assay. At this time, the positive shoots recovered from a single node will generally have been enriched in the transgenic sector detected in the initial assay prior to nodal culture.

Recovered shoots positive for defensin-like activity expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 5

Assaying Defensin-Like Activity

The polypeptides described herein may be produced using any number of methods known to those skilled in the art. Such methods include, but are not limited to, expression in bacteria, eukaryotic cell cultures, in planta, and viral expression systems in suitably infected organisms or cell lines. The instant polypeptides may be expressed either as full-length polypeptides, mature forms, or as fusion proteins by covalent attachment to a variety of enzymes, proteins, or affinity tags. Common fusion protein partners include, but are not limited to, glutathione-S-transferase, thioredoxin, maltose binding protein, hexahistidine polypeptides, and chitin binding protein. The fusion proteins may be engineered with a protease recognition site at the fusion point so that fusion partners can be separated by protease digestion to yield intact mature peptides. Examples of such proteases include, but are not limited to, thrombin, enterokinase, and factor Xa. Indeed, any protease which specifically cleaves the peptide connecting the fusion protein and polypeptide of the invention can be used.

Purification of the polypeptides of the invention may utilize any number of separation technologies known to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography, and affinity chromatography. When the polypeptides of the invention are expressed as fusion proteins, the purification protocol may include the use of an affinity resin specific for the fusion protein partner or for the polypeptide of interest. Additional suitable affinity resins may be synthesized by linking the appropriate ligands to a suitable resin such as Sepharose-4B.

Crude, partially purified, or purified polypeptides of the invention, either alone or as a fusion protein, may be utilized in assays to verify expression levels of functional plant defensins in host cells and transgenic plants. Assays may be conducted under well known experimental conditions which permit optimal enzymatic activity. See, for example, assays for plant defensin activities presented by Thevissen, K et al. (1996) *J. Biol. Chem.* 271:15018-15025 and WO 00/68405, herein incorporated by reference.

Example 6

Bioassay Testing the Pesticidal Activity of Polypeptides Against Southern Corn Rootworm (SCRW) and Western Corn Rootworm (WCRW)

Bio-Serv diet (catalog number F9800B, from: BIOSERV, Entomology Division, One $8^{th}$ Street, Suite 1, Frenchtown, N.J. 08825) is dispensed in 128-well CD International Bioassay trays (catalog number BIO-BA-128 from CD International, Pitman, N.J. 08071).

Protein samples are applied topically to the diet surface. Enough sample material is supplied to provide for replicate observations per sample. The trays are allowed to dry. Rootworms are dispensed into the wells of the bioassay trays. A lid (catalog number BIO-CV-16, CD International, Pitman, N.J., 08071) is placed on each tray, and the trays are placed in an incubator at 26° C. for 4 to 7 days.

For the evaluation of pesticidal activity against SCRW and WCRW, insects are exposed to a solution comprising either buffer (50 mM carbonate buffer (pH 10)) or a solution of protein sample at selected doses, for example, 50 or 5.0 µg/cm$^2$.

The bioassays are then scored by counting "live" versus "dead" larvae. Mortality is calculated as a percentage of dead larvae out of the total number of larvae tested.

Example 7

Bioassay Testing Pesticidal Activity of Polypeptides Against the Colorado Potato Beetle (*Leptinotarsa decemlineata*)

Briefly, bioassay parameters are as follows: Bio-Serv diet (catalog number F9800B, from: BIOSERV, Entomology Division, One 8th Street, Suite 1, Frenchtown, N.J. 08825) is dispensed in a 96 well microtiter plate (catalog number 353918, Becton Dickinson, Franklin Lakes, N.J. 07417-1886) having a surface area of 0.33 cm$^2$ Protein samples of the invention are applied topically to the diet surface. Enough sample material is supplied to provide for 8 observations/sample. After the samples dry, 1 Colorado potato beetle neonate is added to each well providing for a total of 8 larvae/sample. A Mylar® lid (Clear Lam Packaging, Inc., 1950 Pratt Blvd., Elk Grove Village, Ill. 60007-5993) is affixed to each tray. Bioassay trays are placed in an incubator at 25° C. The test is scored for mortality on the 7th day following live infesting.

Example 8

Bioassay Testing Pesticidal Activity of Polypeptides Against Lepidopterans

Neonate larvae are reared according to standard protocols, such as those published by Czapla and Lang, *J. Economic Entomology* 83:2480-2485 (1990). Test compounds are either applied topically to the diet or incorporated into the larvae diet (see Czapla and Lang, *J. Economic Entomology* 83:2480-2485 (1990)). The larvae diet is dispensed to bioassay trays. One larva is applied per well of the bioassay tray. Weight and mortality are recorded 7 days following the start of the test.

Example 9

Homopteran Membrane Feeding Bioassay for Screening Proteins

This assay can be used for a variety of homopterans. The assay involves trapping the sample protein between two layers of maximally stretched parafilm which act as a sachet on top of a small vessel containing the insect of choice.

The assay is prepared as follows: 1 cm diameter polystyrene tubing is cut into 15 mm lengths. One end of the tube is then capped with a fine mesh screen. Five insects are then added to the chamber after which the first layer of parafilm is stretched over the remaining open end. 25 µl of sample (polypeptide in a 5% sucrose solution containing McCormick green food coloring) is then placed on top of the stretched parafilm. A second layer of parafilm is then stretched by hand and placed over the sample. The sample is spread between the two layers of parafilm to make a continuous sachet on which the insects feed. The sachet is then covered tightly with saran wrap to prevent evaporation and produce a slightly pressurized sample. The assay tubes are monitored for insect reproduction and death on a 24 hour basis and compared to the 5% sucrose control.

Example 10

SCN Bioassay of Transgenic T0 Events

Soybean Cyst Nematodes (SCN) are used to infest transgenic T0 soybean plants in soil. SCN egg inoculum is acquired by harvesting cysts from plants infested 4-6 weeks earlier. Briefly, the soil is rinsed from the roots and passed through nested 20 mesh and 60 mesh screens. The material retained by the 20 mesh screen is discarded but the material retained by the 60 mesh screen is washed thoroughly and the creamy white cysts are recovered (older brown cysts are ignored). Similarly, the plant's root system is scrubbed against the 20 mesh screen nested over the 60 mesh screen. Cysts are harvested from the debris on the 60 mesh screen. Eggs are released from the cysts by means of a dounce homogenizer in the presence of 0.5% Clorox for 2.5 minutes. Following this treatment the eggs are washed with sterile water from the homogenizer onto the surface of a 200 mesh screen. The eggs are then rinsed in water for an additional 5 minutes. Eggs are transferred to a 50 ml conical tube and counted. The eggs are diluted to 5000 eggs/ml. Plants grown in 15 cm conical tubes are inoculated with about 5000 eggs. Plants are maintained in a 26° C. growth chamber with 12:12 light:dark cycle for 1 month prior to harvest and counting of cysts.

Example 11

Bioactivity of Polypeptides Against Fungal Pathogens

The proteins of the invention are suspended in $dH_2O$ to a final concentration of about 4 µg/µl. 12 µg of purified protein is added to 200 µl of ½ strength potato dextrose broth (PDB) containing a spore suspension of the fungal pathogen to be tested. The spore suspension contains approximately 2500 spores/ml. This results in a stock solution with a starting concentration of 10 µM. A 0.5× dilution series for the protein sample to be tested from 10 µM through to about 0.05 µM is prepared by removing 100 µl of the 10 µM stock and adding it to 100 µl of spore suspension (2500 spores/ml), mixing thoroughly to achieve a 5 µM protein sample concentration, transferring 100 µl of the 5 µM suspension to a fresh 100 µl spore suspension etc., until about 0.005 µM is reached. Two replicates per pathogen are performed. The fungal assay plate is scored for inhibition of fungal growth after a 48 hour incubation at 28° C. Inhibition of fungal growth is defined as little to no spore germination without detectable hyphae growth.

All publications, patents and patent applications mentioned in the specification are indicative of the level of those skilled in the art to which this invention pertains. All publications, patents and patent applications are herein incorporated by reference to the same extent as if each individual publication, patent, or patent application was specifically and individually indicated to be incorporated by reference.

Although the foregoing invention has been described in some detail by way of illustration and example, for purposes of clarity of understanding, it will be obvious that certain changes and modifications may be practiced within the scope of the appended claims.

That which is claimed:

1. An isolated nucleic acid molecule comprising a nucleotide sequence that encodes a polypeptide that has defensin-like activity, wherein said polypeptide comprises an amino acid sequence that has at least 95 percent sequence identity to the amino acid sequence set forth in SEQ ID NO:27.

2. The isolated nucleic acid molecule of claim 1, wherein said nucleotide sequence comprises nucleotides 193-339 of SEQ ID NO:25.

3. The isolated nucleic acid molecule of claim 1, wherein said nucleotide sequence comprises SEQ ID NO:25.

4. The isolated nucleic acid molecule of claim 2, wherein said nucleotide sequence encodes a polypeptide comprising the amino acid sequence set forth in SEQ ID NO:27.

5. The isolated nucleic acid molecule of claim 1, wherein said nucleotide sequence encodes a polypeptide comprising SEQ ID NO:26.

6. A method for enhancing disease resistance in a plant, said method comprising transforming said plant with at least one nucleotide construct comprising a nucleotide sequence encoding a polypeptide having at least 95% sequence identity to the sequence set forth in SEQ ID NO:27 operably linked to a promoter that drives expression in a plant, and regenerating said transformed plant.

7. The isolated nucleic acid molecule of claim 1, wherein said nucleotide sequence comprises nucleotides 88-336 of SEQ ID NO:52.

8. The isolated nucleic acid molecule of claim 1, wherein said nucleotide sequence comprises SEQ ID NO:52.

9. The isolated nucleic acid molecule of claim 1, wherein said nucleotide sequence encodes a polypeptide comprising SEQ ID NO:53.

10. The isolated nucleic acid molecule of claim 1, wherein said nucleotide sequence encodes a polypeptide comprising SEQ ID NO:54.

11. A DNA construct comprising the nucleic acid molecule of claim 1, wherein said nucleotide sequence is operably linked to a promoter that drives expression in a host cell.

12. A transformed host cell comprising in its genome at least one stably incorporated DNA construct of claim 11.

13. The host cell of claim 12, wherein said host cell is a plant cell.

14. A plant comprising the host cell of claim 12.

15. Transformed seed of the plant of claim 14, wherein said seed comprises said DNA construct.

16. The plant of claim 14, wherein said plant has enhanced resistance to a disease caused by a fungal pathogen.

17. The plant of claim 16, wherein said fungal pathogen is selected from the group consisting of *Colletotrichum graminicola, Diplodia maydis, Fusarium graminearum*, and *Fusarium moniliforme*.

18. The plant of claim 16, wherein said plant is selected from the group consisting of soybean, canola, alfalfa, wheat, sunflower, corn, and sorghum.

19. The method of claim 6, wherein said nucleotide sequence comprises nucleotides 193-339 of SEQ ID NO:25.

20. The method of claim 6, wherein said disease resistance is resistance to a disease caused by a fungal pathogen.

21. The method of claim 20, wherein said fungal pathogen is selected from the group consisting of *Colletotrichum graminicola, Diplodia maydis, Fusarium graminearum*, and *Fusarium moniliforme*.

22. The method of claim 6, wherein said nucleotide sequence is the sequence set forth in SEQ ID NO:25.

23. The method of claim 6, wherein said nucleotide sequence encodes SEQ ID NO:27.

24. The method of claim 6, wherein said nucleotide sequence encodes SEQ ID NO:26.

25. The method of claim 6, wherein said nucleotide sequence comprises nucleotides 88-336 of SEQ ID NO:52.

26. The method of claim 6, wherein said nucleotide sequence comprises SEQ ID NO:52.

27. The method of claim 6, wherein said nucleotide sequence comprises encodes SEQ ID NO:53.

28. The method of claim 6, wherein said nucleotide sequence encodes SEQ ID NO:54.

29. The method of claim 6, wherein said plant is selected from the group consisting of soybean, canola, alfalfa, wheat, sunflower, corn, and sorghum.

* * * * *

SEQUENCE LISTING

```
<160> NUMBER OF SEQ ID NOS: 469

<210> SEQ ID NO 1
<211> LENGTH: 559
<212> TYPE: DNA
<213> ORGANISM: Zea mays
<220> FEATURE:
<221> NAME/KEY: CDS
<222> LOCATION: (79)...(303)
<220> FEATURE:
<221> NAME/KEY: mat_peptide
<222> LOCATION: (160)...(300)

<400> SEQUENCE: 1
gaagagccat atttgaaaca gttaagaatt catatataag agtgcatata tatatataat        60
tctgccaaga caaaggta atg gag tcg tca cgc atg ttc cag ccg gcc atc        111
                    Met Glu Ser Ser Arg Met Phe Gln Pro Ala Ile
                     1               5                  10
```

```
atc ctg ctt ctc ctg ctc att gtg acc acc gat gtg gcg cag gcg gcg      159
Ile Leu Leu Leu Leu Leu Ile Val Thr Thr Asp Val Ala Gln Ala Ala
            15                  20                  25 agg gaa tgc gag aag gac agc gag cga ttc ctt ggg gca tgc atg gcg      207
Arg Glu Cys Glu Lys Asp Ser Glu Arg Phe Leu Gly Ala Cys Met Ala
    30                  35                  40 tcg gac aac tgc gcc aac gtg tgc cgc ggt gag ggc ttc tcc ggc ggc      255
Ser Asp Asn Cys Ala Asn Val Cys Arg Gly Glu Gly Phe Ser Gly Gly
45                  50                  55 agg tgc agc acc ttc cgc cgc cgc tgc atc tgc act aag ccg tgc taa      303
Arg Cys Ser Thr Phe Arg Arg Arg Cys Ile Cys Thr Lys Pro Cys *
60                  65                  70 attaacctac tcccggcagt tcgatggtgg acgtttattc tatttattgg cttacttgat    363
ttttttcccc ctaacaataa gaaaacgcac gtgctggcat gtacgttgtg ttgtatatgc    423
ttttcttgct ggcttcattt gctgattact gatgagttgt aaggtccctg cacgatccat    483
ttcacatgga tatgatgctt aattgtattc ctgcttatat ggtatgtata tttaattaat    543
taaaaaaaaa aaaaaa                                                    559

<210> SEQ ID NO 2
<211> LENGTH: 74
<212> TYPE: PRT
<213> ORGANISM: Zea mays

<400> SEQUENCE: 2

Met Glu Ser Ser Arg Met Phe Gln Pro Ala Ile Ile Leu Leu Leu Leu
1               5                   10                  15

Leu Ile Val Thr Thr Asp Val Ala Gln Ala Ala Arg Glu Cys Glu Lys
            20                  25                  30

Asp Ser Glu Arg Phe Leu Gly Ala Cys Met Ala Ser Asp Asn Cys Ala
        35                  40                  45

Asn Val Cys Arg Gly Glu Gly Phe Ser Gly Gly Arg Cys Ser Thr Phe
    50                  55                  60

Arg Arg Arg Cys Ile Cys Thr Lys Pro Cys
65                  70

<210> SEQ ID NO 3
<211> LENGTH: 47
<212> TYPE: PRT
<213> ORGANISM: Zea mays

<400> SEQUENCE: 3

Arg Glu Cys Glu Lys Asp Ser Glu Arg Phe Leu Gly Ala Cys Met Ala
1               5                   10                  15

Ser Asp Asn Cys Ala Asn Val Cys Arg Gly Glu Gly Phe Ser Gly Gly
            20                  25                  30

Arg Cys Ser Thr Phe Arg Arg Arg Cys Ile Cys Thr Lys Pro Cys
        35                  40                  45

<210> SEQ ID NO 4
<211> LENGTH: 524
<212> TYPE: DNA
<213> ORGANISM: Zea mays
<220> FEATURE:
<221> NAME/KEY: CDS
<222> LOCATION: (80)...(301)
<220> FEATURE:
<221> NAME/KEY: mat_peptide
<222> LOCATION: (158)...(298)

<400> SEQUENCE: 4
```

```
gtgatttgaa ataattggga ataaatagtt cgtgaatccc tgaagcgtgc atatatatat         60
tcctgccaag ataaaggta atg gag tcg tca cgc agg ttc cag ccg gcc gtc         112
                    Met Glu Ser Ser Arg Arg Phe Gln Pro Ala Val
                     1               5                  10 atc ctg ctt ctc ctg ctc att gtg tcc acc gat atg gca cag gca agg         160
Ile Leu Leu Leu Leu Leu Ile Val Ser Thr Asp Met Ala Gln Ala Arg
             15                  20                  25 gaa tgc gag aag tac agt gag cga ttt gtt ggg gca tgc atg atc gca         208
Glu Cys Glu Lys Tyr Ser Glu Arg Phe Val Gly Ala Cys Met Ile Ala
         30                  35                  40 gac aac tgc gcc aat gtg tgc cgc ggt gag ggc ttc ttg gcc ggc agg         256
Asp Asn Cys Ala Asn Val Cys Arg Gly Glu Gly Phe Leu Ala Gly Arg
     45                  50                  55 tgc agc acc ttc cgc cgc cgc tgc atc tgc act agg cag tgc taa             301
Cys Ser Thr Phe Arg Arg Arg Cys Ile Cys Thr Arg Gln Cys  *
 60                  65                  70 acaagatcgc tcgatcgttc gccatgcatc gacaacctat tcttaataac gttcattatc        361
tcgttcttat ttatgacgaa tgtcatgtat gttctggtga ctgtcatgta tattctgatg        421
actgtcatgt atcttgttca tgtatgctca aggttcatta tcttgttcat gtattaagta        481
tgttatgaat aactcaatat ttattaaaaa aaaaaaaaa aaa                           524
```

```
<210> SEQ ID NO 5
<211> LENGTH: 73
<212> TYPE: PRT
<213> ORGANISM: Zea mays

<400> SEQUENCE: 5

Met Glu Ser Ser Arg Arg Phe Gln Pro Ala Val Ile Leu Leu Leu Leu
 1               5                  10                  15

Leu Ile Val Ser Thr Asp Met Ala Gln Ala Arg Glu Cys Glu Lys Tyr
             20                  25                  30

Ser Glu Arg Phe Val Gly Ala Cys Met Ile Ala Asp Asn Cys Ala Asn
         35                  40                  45

Val Cys Arg Gly Glu Gly Phe Leu Ala Gly Arg Cys Ser Thr Phe Arg
     50                  55                  60

Arg Arg Cys Ile Cys Thr Arg Gln Cys
 65                  70

<210> SEQ ID NO 6
<211> LENGTH: 47
<212> TYPE: PRT
<213> ORGANISM: Zea mays

<400> SEQUENCE: 6

Arg Glu Cys Glu Lys Tyr Ser Glu Arg Phe Val Gly Ala Cys Met Ile
 1               5                  10                  15

Ala Asp Asn Cys Ala Asn Val Cys Arg Gly Glu Gly Phe Leu Ala Gly
             20                  25                  30

Arg Cys Ser Thr Phe Arg Arg Arg Cys Ile Cys Thr Arg Gln Cys
         35                  40                  45

<210> SEQ ID NO 7
<211> LENGTH: 463
<212> TYPE: DNA
<213> ORGANISM: Oryza sativa
<220> FEATURE:
<221> NAME/KEY: CDS
<222> LOCATION: (73)...(294)
```

```
<220> FEATURE:
<221> NAME/KEY: mat_peptide
<222> LOCATION: (151)...(291)
<220> FEATURE:
<221> NAME/KEY: misc_feature
<222> LOCATION: 363, 374, 382, 393, 402, 404, 410, 413, 423, 435, 442,
      451
<223> OTHER INFORMATION: n = A,T,C or G

<400> SEQUENCE: 7
aaataattgg gaataaatag ttcgtgaaat ccctgaagcg tgcatatata tattcctgcc     60
aagataaagg ta atg gag tcg tca cgc agg ttc cag ccg gcc gtc atc ctg   111
           Met Glu Ser Ser Arg Arg Phe Gln Pro Ala Val Ile Leu
             1               5                  10 ctt ctc ctg ctc att gtg tcc acc ggt atg gca cag gca agg gaa tgc   159
Leu Leu Leu Leu Ile Val Ser Thr Gly Met Ala Gln Ala Arg Glu Cys
         15                  20                  25 gag aag ttc agt gag cga ttt gtt ggg gca tgc atg atc gca gac aac   207
Glu Lys Phe Ser Glu Arg Phe Val Gly Ala Cys Met Ile Ala Asp Asn
 30              35                  40                  45 tgc gcc aat gtg tgc cgc ggt gag ggc ttc ttg gcc ggc agg tgc agc   255
Cys Ala Asn Val Cys Arg Gly Glu Gly Phe Leu Ala Gly Arg Cys Ser
             50                  55                  60 acc ttc cgc cgc cgc tgc atc tgc act agg cag tgc taa acaaggtcgc    304
Thr Phe Arg Arg Arg Cys Ile Cys Thr Arg Gln Cys  *
         65                  70 tcgatcgttc gccatgcatc ggcaacctat tcttaattac gttccttatc tcgttcttnt    364
ttttggcggn tgtctgtntg ttctggtgnc tgtctgtntn ttctgntgnc tgtcctgtnt    424
cttgttctgt ntgctccngg gtccttntct tgttcctgt                            463

<210> SEQ ID NO 8
<211> LENGTH: 73
<212> TYPE: PRT
<213> ORGANISM: Oryza sativa

<400> SEQUENCE: 8

Met Glu Ser Ser Arg Arg Phe Gln Pro Ala Val Ile Leu Leu Leu Leu
  1               5                  10                  15

Leu Ile Val Ser Thr Gly Met Ala Gln Ala Arg Glu Cys Glu Lys Phe
             20                  25                  30

Ser Glu Arg Phe Val Gly Ala Cys Met Ile Ala Asp Asn Cys Ala Asn
         35                  40                  45

Val Cys Arg Gly Glu Gly Phe Leu Ala Gly Arg Cys Ser Thr Phe Arg
     50                  55                  60

Arg Arg Cys Ile Cys Thr Arg Gln Cys
 65                  70

<210> SEQ ID NO 9
<211> LENGTH: 47
<212> TYPE: PRT
<213> ORGANISM: Oryza sativa

<400> SEQUENCE: 9

Arg Glu Cys Glu Lys Phe Ser Glu Arg Phe Val Gly Ala Cys Met Ile
  1               5                  10                  15

Ala Asp Asn Cys Ala Asn Val Cys Arg Gly Glu Gly Phe Leu Ala Gly
             20                  25                  30

Arg Cys Ser Thr Phe Arg Arg Arg Cys Ile Cys Thr Arg Gln Cys
         35                  40                  45
```

<210> SEQ ID NO 10
<211> LENGTH: 504
<212> TYPE: DNA
<213> ORGANISM: Zea mays
<220> FEATURE:
<221> NAME/KEY: CDS
<222> LOCATION: (120)...(359)
<220> FEATURE:
<221> NAME/KEY: mat_peptide
<222> LOCATION: (213)...(359)
<220> FEATURE:
<221> NAME/KEY: misc_feature
<222> LOCATION: 11, 14, 454, 462, 477, 494, 502
<223> OTHER INFORMATION: n = A,T,C or G

<400> SEQUENCE: 10

```
cgtccaccat nctngtcgtt aggacgtaag gtaagacacc caggggcgag ccagtgagta      60
cagagagtag ccttacgtag cgaagctcag agcaagcgag ggtacggtca agggggggtg     119 atg gcg ctg tct cga cgt atg gcg gct ccc gtc ctc gtc ctc atg ctc      167
Met Ala Leu Ser Arg Arg Met Ala Ala Pro Val Leu Val Leu Met Leu
 1               5                  10                  15 ctc ctc gtc gcc aca gag ctg ggg acg acc aag gtg gcg gag gcg agg      215
Leu Leu Val Ala Thr Glu Leu Gly Thr Thr Lys Val Ala Glu Ala Arg
             20                  25                  30 cac tgc ctg tcg cag agc cac cgg ttc aag ggc ctg tgc atg agc agc      263
His Cys Leu Ser Gln Ser His Arg Phe Lys Gly Leu Cys Met Ser Ser
         35                  40                  45 aac aac tgc gcc aac gtg tgc cag acc gag aac ttc ccc ggc ggc gag      311
Asn Asn Cys Ala Asn Val Cys Gln Thr Glu Asn Phe Pro Gly Gly Glu
     50                  55                  60 tgc aag gcg gag ggc gcc acg cgc aag tgc ttt tgc aag aag ata tgc      359
Cys Lys Ala Glu Gly Ala Thr Arg Lys Cys Phe Cys Lys Lys Ile Cys
 65                  70                  75                  80 tag tagtagcctc ggctttgctg gcgttgggcg gcacaggcag gtcgtcggca            412
cgaaacgcaa ttcaagcata tatatcggtc ctcctcctgc gntgcgctgn ctaactcgat     472
cccgntttct ctttcgatcg anttcattgn tt                                   504
```

<210> SEQ ID NO 11
<211> LENGTH: 80
<212> TYPE: PRT
<213> ORGANISM: Zea mays

<400> SEQUENCE: 11

```
Met Ala Leu Ser Arg Arg Met Ala Ala Pro Val Leu Val Leu Met Leu
 1               5                  10                  15

Leu Leu Val Ala Thr Glu Leu Gly Thr Thr Lys Val Ala Glu Ala Arg
             20                  25                  30

His Cys Leu Ser Gln Ser His Arg Phe Lys Gly Leu Cys Met Ser Ser
         35                  40                  45

Asn Asn Cys Ala Asn Val Cys Gln Thr Glu Asn Phe Pro Gly Gly Glu
     50                  55                  60

Cys Lys Ala Glu Gly Ala Thr Arg Lys Cys Phe Cys Lys Lys Ile Cys
 65                  70                  75                  80
```

<210> SEQ ID NO 12
<211> LENGTH: 49
<212> TYPE: PRT
<213> ORGANISM: Zea mays

<400> SEQUENCE: 12

```
Arg His Cys Leu Ser Gln Ser His Arg Phe Lys Gly Leu Cys Met Ser
 1               5                  10                  15

Ser Asn Asn Cys Ala Asn Val Cys Gln Thr Glu Asn Phe Pro Gly Gly
            20                  25                  30

Glu Cys Lys Ala Glu Gly Ala Thr Arg Lys Cys Phe Cys Lys Lys Ile
            35                  40                  45

Cys

<210> SEQ ID NO 13
<211> LENGTH: 510
<212> TYPE: DNA
<213> ORGANISM: Zea mays
<220> FEATURE:
<221> NAME/KEY: CDS
<222> LOCATION: (13)...(402)
<220> FEATURE:
<221> NAME/KEY: mat_peptide
<222> LOCATION: (79)...(213)

<400> SEQUENCE: 13
caatgctcag cc atg aag aga aat gag atc gca gca gca gcc atg gtt ttg        51
              Met Lys Arg Asn Glu Ile Ala Ala Ala Ala Met Val Leu
               1               5                  10 ctc ttg ttg acg ttg ggc gct gag gcc cag atc tgt tac tcg cgg agc        99
Leu Leu Leu Thr Leu Gly Ala Glu Ala Gln Ile Cys Tyr Ser Arg Ser
        15                  20                  25 aag acc ttc aag ggg tgg tgc tac cac agc acc aac tgc atc tcc gtt        147
Lys Thr Phe Lys Gly Trp Cys Tyr His Ser Thr Asn Cys Ile Ser Val
 30              35                  40                  45 tgc atc acc gag ggg gag att agc ggg ttc tgc cag cat gga att tgc        195
Cys Ile Thr Glu Gly Glu Ile Ser Gly Phe Cys Gln His Gly Ile Cys
                50                  55                  60 atg tgc acc tat gag tgt ctc acg ggt aac gaa gct agc ctg cct ggt        243
Met Cys Thr Tyr Glu Cys Leu Thr Gly Asn Glu Ala Ser Leu Pro Gly
            65                  70                  75 ggt ggt ggt ggt ggt gaa gac cca cag tta tta cac gtc gcc acg cca        291
Gly Gly Gly Gly Gly Glu Asp Pro Gln Leu Leu His Val Ala Thr Pro
        80                  85                  90 aac ggt gat ggg gct aga cca ctg tca ctt gag gat gac aag aaa gag        339
Asn Gly Asp Gly Ala Arg Pro Leu Ser Leu Glu Asp Asp Lys Lys Glu
 95                 100                 105 aca tcg aca gag acg gct atg agg ggc gcc aag agc cat agt ccg cgc        387
Thr Ser Thr Glu Thr Ala Met Arg Gly Ala Lys Ser His Ser Pro Arg
110                 115                 120                 125 tac atg agg agg tag ctgacagtag agcggctggt tcgtgggat ggtgctactc        442
Tyr Met Arg Arg * tcttctacat gctaattgag ttgatgaata ataaattggt tgtgtttact taaaaaaaaa      502
aaaaaaaa                                                                510

<210> SEQ ID NO 14
<211> LENGTH: 129
<212> TYPE: PRT
<213> ORGANISM: Zea mays

<400> SEQUENCE: 14

Met Lys Arg Asn Glu Ile Ala Ala Ala Ala Met Val Leu Leu Leu Leu
 1               5                  10                  15

Thr Leu Gly Ala Glu Ala Gln Ile Cys Tyr Ser Arg Ser Lys Thr Phe
            20                  25                  30

Lys Gly Trp Cys Tyr His Ser Thr Asn Cys Ile Ser Val Cys Ile Thr
```

-continued

```
                 35                  40                  45
Glu Gly Glu Ile Ser Gly Phe Cys Gln His Gly Ile Cys Met Cys Thr
         50                  55                  60
Tyr Glu Cys Leu Thr Gly Asn Glu Ala Ser Leu Pro Gly Gly Gly Gly
 65                  70                  75                  80
Gly Gly Glu Asp Pro Gln Leu Leu His Val Ala Thr Pro Asn Gly Asp
                 85                  90                  95
Gly Ala Arg Pro Leu Ser Leu Glu Asp Asp Lys Lys Glu Thr Ser Thr
            100                 105                 110
Glu Thr Ala Met Arg Gly Ala Lys Ser His Ser Pro Arg Tyr Met Arg
        115                 120                 125
Arg
```

<210> SEQ ID NO 15
<211> LENGTH: 45
<212> TYPE: PRT
<213> ORGANISM: Zea mays

<400> SEQUENCE: 15

```
Gln Ile Cys Tyr Ser Arg Ser Lys Thr Phe Lys Gly Trp Cys Tyr His
  1               5                  10                  15
Ser Thr Asn Cys Ile Ser Val Cys Ile Thr Glu Gly Glu Ile Ser Gly
             20                  25                  30
Phe Cys Gln His Gly Ile Cys Met Cys Thr Tyr Glu Cys
         35                  40                  45
```

<210> SEQ ID NO 16
<211> LENGTH: 483
<212> TYPE: DNA
<213> ORGANISM: Zea mays
<220> FEATURE:
<221> NAME/KEY: CDS
<222> LOCATION: (50)...(355)
<220> FEATURE:
<221> NAME/KEY: mat_peptide
<222> LOCATION: (113)...(247)

<400> SEQUENCE: 16

```
ccagtcgtcc tagccaacaa aattcaattg agggttcttc agttcagcc atg aag ctt        58
                                                    Met Lys Leu
                                                      1 gag atg aca gca gcg gcc atg gtc ttg ctc ctg ctg acc tcg ggc gcc         106
Glu Met Thr Ala Ala Ala Met Val Leu Leu Leu Leu Thr Ser Gly Ala
      5                  10                  15 gag gcc aag gtg tgc tac tcg cgt agc agg acc ttc aag ggg tgg tgc         154
Glu Ala Lys Val Cys Tyr Ser Arg Ser Arg Thr Phe Lys Gly Trp Cys
 20                  25                  30                  35 tac cac agc atc aac tgc atc gcc atc tgc atc acc gag ggc gac acc         202
Tyr His Ser Ile Asn Cys Ile Ala Ile Cys Ile Thr Glu Gly Asp Thr
                 40                  45                  50 agc ggg ttc tgc cag gcc ggg gcc tgc atg tgc act tat gag tgt ctc         250
Ser Gly Phe Cys Gln Ala Gly Ala Cys Met Cys Thr Tyr Glu Cys Leu
             55                  60                  65 aat ggt gtc gtc gcc ggt ggc ggc ggt ggc ggc gga cag cat cca tcg         298
Asn Gly Val Val Ala Gly Gly Gly Gly Gly Gly Gln His Pro Ser
         70                  75                  80 gtt ggc tca tcg cta cgt ggt ggt gct gag gct aaa gca gcc gtc ccg         346
Val Gly Ser Ser Leu Arg Gly Gly Ala Glu Ala Lys Ala Ala Val Pro
 85                  90                  95 tca gtg tag agcttctgat tctggcgggg tgatggcaga tggcgcacta                 395
Ser Val *
```

```
Ser Val  *
       100 ctactctcct gtgtgcacat gccaactcaa gatttcgagt tgatgaataa cacaaatggt       455 tcttttactt aaaaaaaaaa aaaaaaaa                                          483
```

<210> SEQ ID NO 17
<211> LENGTH: 101
<212> TYPE: PRT
<213> ORGANISM: Zea mays

<400> SEQUENCE: 17

```
Met Lys Leu Glu Met Thr Ala Ala Met Val Leu Leu Leu Thr
 1               5                  10                  15

Ser Gly Ala Glu Ala Lys Val Cys Tyr Ser Arg Ser Arg Thr Phe Lys
             20                  25                  30

Gly Trp Cys Tyr His Ser Ile Asn Cys Ile Ala Ile Cys Ile Thr Glu
         35                  40                  45

Gly Asp Thr Ser Gly Phe Cys Gln Ala Gly Ala Cys Met Cys Thr Tyr
     50                  55                  60

Glu Cys Leu Asn Gly Val Val Ala Gly Gly Gly Gly Gly Gly Gly Gln
 65                  70                  75                  80

His Pro Ser Val Gly Ser Ser Leu Arg Gly Gly Ala Glu Ala Lys Ala
                 85                  90                  95

Ala Val Pro Ser Val
            100
```

<210> SEQ ID NO 18
<211> LENGTH: 45
<212> TYPE: PRT
<213> ORGANISM: Zea mays

<400> SEQUENCE: 18

```
Lys Val Cys Tyr Ser Arg Ser Arg Thr Phe Lys Gly Trp Cys Tyr His
 1               5                  10                  15

Ser Ile Asn Cys Ile Ala Ile Cys Ile Thr Glu Gly Asp Thr Ser Gly
             20                  25                  30

Phe Cys Gln Ala Gly Ala Cys Met Cys Thr Tyr Glu Cys
         35                  40                  45
```

<210> SEQ ID NO 19
<211> LENGTH: 515
<212> TYPE: DNA
<213> ORGANISM: Oryza sativa
<220> FEATURE:
<221> NAME/KEY: CDS
<222> LOCATION: (43)...(285)
<220> FEATURE:
<221> NAME/KEY: mat_peptide
<222> LOCATION: (136)...(282)

<400> SEQUENCE: 19

```
ctcatcactc atcagtgagc gcagttcgag tcgccggtac ag atg gct ccg tct         54
                                              Met Ala Pro Ser
                                               1 cgt cgc atg gtc gcg tcc gcc ttc ctc ctc ctg gcc atc ctc gtc gcc       102
Arg Arg Met Val Ala Ser Ala Phe Leu Leu Leu Ala Ile Leu Val Ala
 5                  10                  15                  20 aca gag atg ggg acg acc aag gtg gcg gag gcg agg cac tgc ctg tcg       150
Thr Glu Met Gly Thr Thr Lys Val Ala Glu Ala Arg His Cys Leu Ser
             25                  30                  35
```

```
cag agc cac agg ttc aag ggc atg tgc gtg agc agc aac aac tgc gcc      198
Gln Ser His Arg Phe Lys Gly Met Cys Val Ser Ser Asn Asn Cys Ala
             40                  45                  50 aac gtg tgc agg acg gag agc ttc ccc gac ggc gag tgc aag tcg cac      246
Asn Val Cys Arg Thr Glu Ser Phe Pro Asp Gly Glu Cys Lys Ser His
     55                  60                  65 ggc ctc gag cgc aag tgc ttc tgc aag aag gtc tgc tag tgcatgctag       295
Gly Leu Glu Arg Lys Cys Phe Cys Lys Lys Val Cys *
 70                  75                  80 ccccgctgtc tctgcagtcg cattgctcgt cggctgtgta tctgcagaga ttgtagtcgc    355
gtgttctcct ttgtctgttg ttcatgacga gcttctgttc ttggcttaca ggctagttga    415
gttgctttcg attatccttg cttagaataa gtaataagta cgcgctggat acatgctcca    475
gcttagttag ttgttgggta tttgcaagct gctgtcatgt                          515

<210> SEQ ID NO 20
<211> LENGTH: 80
<212> TYPE: PRT
<213> ORGANISM: Oryza sativa

<400> SEQUENCE: 20

Met Ala Pro Ser Arg Arg Met Val Ala Ser Ala Phe Leu Leu Leu Ala
 1               5                   10                  15

Ile Leu Val Ala Thr Glu Met Gly Thr Thr Lys Val Ala Glu Ala Arg
             20                  25                  30

His Cys Leu Ser Gln Ser His Arg Phe Lys Gly Met Cys Val Ser Ser
         35                  40                  45

Asn Asn Cys Ala Asn Val Cys Arg Thr Glu Ser Phe Pro Asp Gly Glu
     50                  55                  60

Cys Lys Ser His Gly Leu Glu Arg Lys Cys Phe Cys Lys Lys Val Cys
 65                  70                  75                  80

<210> SEQ ID NO 21
<211> LENGTH: 49
<212> TYPE: PRT
<213> ORGANISM: Oryza sativa

<400> SEQUENCE: 21

Arg His Cys Leu Ser Gln Ser His Arg Phe Lys Gly Met Cys Val Ser
 1               5                   10                  15

Ser Asn Asn Cys Ala Asn Val Cys Arg Thr Glu Ser Phe Pro Asp Gly
             20                  25                  30

Glu Cys Lys Ser His Gly Leu Glu Arg Lys Cys Phe Cys Lys Lys Val
         35                  40                  45

Cys

<210> SEQ ID NO 22
<211> LENGTH: 573
<212> TYPE: DNA
<213> ORGANISM: Oryza sativa
<220> FEATURE:
<221> NAME/KEY: CDS
<222> LOCATION: (55)...(297)
<220> FEATURE:
<221> NAME/KEY: mat_peptide
<222> LOCATION: (148)...(294)

<400> SEQUENCE: 22
gcacgaggca gcctcatcac tcatcagtga gcgcagttcg agtcgccggt acag atg     57
                                                             Met
                                                              1
```

```
gct ccg tct cgt cgc atg gtc gcg tcc gcc ttc ctc ctc ctg gcc atc      105
Ala Pro Ser Arg Arg Met Val Ala Ser Ala Phe Leu Leu Leu Ala Ile
        5                  10                  15 ctc gtc gcc aca gag atg ggg acg acc aag gtg gcg gag gcg agg cac      153
Leu Val Ala Thr Glu Met Gly Thr Thr Lys Val Ala Glu Ala Arg His
     20                  25                  30 tgc ctg tcg cag agc cac agg ttc aag ggc atg tgc gtg agc agc aac      201
Cys Leu Ser Gln Ser His Arg Phe Lys Gly Met Cys Val Ser Ser Asn
 35                  40                  45 aac tgc gcc aac gtg tgc agg acg gag agc ttc ccc gac ggc gag tgc      249
Asn Cys Ala Asn Val Cys Arg Thr Glu Ser Phe Pro Asp Gly Glu Cys
 50                  55                  60                  65 aag tcg cac ggc ctc gag cgc aag tgc ttc tgc aag aag gtc tgc tag      297
Lys Ser His Gly Leu Glu Arg Lys Cys Phe Cys Lys Lys Val Cys  *
         70                  75                  80 tgcatgctag ccccgctgtc tctgcagtcg cattgctcgt cggctgtgta tctgcagaga    357
ttgtagtcgc gtgttctcct tgtctgttg ttcatgacga gcttctgttc ttggcttaca    417
ggctagttga gttgctttcg attatccttg cttagaataa gtaataagta cgcgctggat    477
acatgctcca gcttagttag ttgttgggta tttgcaagct gctgtcatgt aaggttccac    537
atttcagcat taatgaattg catacgtga tgaaaa                               573
```

<210> SEQ ID NO 23
<211> LENGTH: 80
<212> TYPE: PRT
<213> ORGANISM: Oryza sativa
<400> SEQUENCE: 23

```
Met Ala Pro Ser Arg Arg Met Val Ala Ser Ala Phe Leu Leu Leu Ala
 1               5                  10                  15

Ile Leu Val Ala Thr Glu Met Gly Thr Thr Lys Val Ala Glu Ala Arg
             20                  25                  30

His Cys Leu Ser Gln Ser His Arg Phe Lys Gly Met Cys Val Ser Ser
         35                  40                  45

Asn Asn Cys Ala Asn Val Cys Arg Thr Glu Ser Phe Pro Asp Gly Glu
     50                  55                  60

Cys Lys Ser His Gly Leu Glu Arg Lys Cys Phe Cys Lys Lys Val Cys
 65                  70                  75                  80
```

<210> SEQ ID NO 24
<211> LENGTH: 49
<212> TYPE: PRT
<213> ORGANISM: Oryza sativa
<400> SEQUENCE: 24

```
Arg His Cys Leu Ser Gln Ser His Arg Phe Lys Gly Met Cys Val Ser
 1               5                  10                  15

Ser Asn Asn Cys Ala Asn Val Cys Arg Thr Glu Ser Phe Pro Asp Gly
             20                  25                  30

Glu Cys Lys Ser His Gly Leu Glu Arg Lys Cys Phe Cys Lys Lys Val
         35                  40                  45

Cys
```

<210> SEQ ID NO 25
<211> LENGTH: 662
<212> TYPE: DNA
<213> ORGANISM: Triticum aestivum
<220> FEATURE:

```
<221> NAME/KEY: CDS
<222> LOCATION: (94)...(342)
<220> FEATURE:
<221> NAME/KEY: mat_peptide
<222> LOCATION: (193)...(339)

<400> SEQUENCE: 25
ccacgcgtcc gcttctccat tcgctttgct aacacagtcc ccagtagcag cagcagcagg       60
acagctcagt ctcgggtgaa gctgagcaga tcg atg gcg ctc tct cgt cgc atg      114
                                    Met Ala Leu Ser Arg Arg Met
                                      1               5 gct gcg tcc gcc ctc ctg ctg ctg gtc ctc ctc gtc gcc aca gag atg       162
Ala Ala Ser Ala Leu Leu Leu Leu Val Leu Leu Val Ala Thr Glu Met
         10                  15                  20 ggg gcg acg acg gtc aag ctg gct gag gcg cgg gac tgc ctg tcc cag       210
Gly Ala Thr Thr Val Lys Leu Ala Glu Ala Arg Asp Cys Leu Ser Gln
     25                  30                  35 agc cac aag ttc aag ggc gcc tgc ctc agc agc agc aac tgc gcc gcc       258
Ser His Lys Phe Lys Gly Ala Cys Leu Ser Ser Ser Asn Cys Ala Ala
 40                  45                  50                  55 gtc tgc cgc acc gag aac ttc ccc gac ggg gag tgc cac acg cac aac       306
Val Cys Arg Thr Glu Asn Phe Pro Asp Gly Glu Cys His Thr His Asn
                 60                  65                  70 ttc gcc cgc aag tgc ttc tgc aag agg gcc tgc tag cccgcctgct            352
Phe Ala Arg Lys Cys Phe Cys Lys Arg Ala Cys  *
             75                  80 cgatcgcccc ggccgccctg ccggccagcg ccgccacgtc cgatgctagc tagctgttag      412
atcgtccgtg ccttttggta gatctgttcg tcagtccgtt cccgttcgtc actagtagct      472
gttcgtgtgg ctgtctcccg taataaagta cgaaatcaac cggggtctcg gtagtttggt      532
tcgcagcacg tcgtgtttgt cgctgctttg tgtggtaatg taatatggtc cttgtttcag      592
tatggacgga cgtgtgcact gcatctaaat ctgaggatgg tttcatactt aaaccatact      652
tgaaccaaaa                                                             662

<210> SEQ ID NO 26
<211> LENGTH: 82
<212> TYPE: PRT
<213> ORGANISM: Triticum aestivum

<400> SEQUENCE: 26

Met Ala Leu Ser Arg Arg Met Ala Ala Ser Ala Leu Leu Leu Leu Val
 1               5                  10                  15

Leu Leu Val Ala Thr Glu Met Gly Ala Thr Thr Val Lys Leu Ala Glu
             20                  25                  30

Ala Arg Asp Cys Leu Ser Gln Ser His Lys Phe Lys Gly Ala Cys Leu
         35                  40                  45

Ser Ser Ser Asn Cys Ala Ala Val Cys Arg Thr Glu Asn Phe Pro Asp
     50                  55                  60

Gly Glu Cys His Thr His Asn Phe Ala Arg Lys Cys Phe Cys Lys Arg
 65                  70                  75                  80

Ala Cys

<210> SEQ ID NO 27
<211> LENGTH: 49
<212> TYPE: PRT
<213> ORGANISM: Triticum aestivum

<400> SEQUENCE: 27
```

```
Arg Asp Cys Leu Ser Gln Ser His Lys Phe Lys Gly Ala Cys Leu Ser
1               5                   10                  15

Ser Ser Asn Cys Ala Ala Val Cys Arg Thr Glu Asn Phe Pro Asp Gly
            20                  25                  30

Glu Cys His Thr His Asn Phe Ala Arg Lys Cys Phe Cys Lys Arg Ala
        35                  40                  45

Cys

<210> SEQ ID NO 28
<211> LENGTH: 557
<212> TYPE: DNA
<213> ORGANISM: Triticum aestivum
<220> FEATURE:
<221> NAME/KEY: CDS
<222> LOCATION: (36)...(293)
<220> FEATURE:
<221> NAME/KEY: mat_peptide
<222> LOCATION: (147)...(293)

<400> SEQUENCE: 28
ctcgggtgaa gcaagagagc aagtacagaa gagag atg gca tcc cct cgc cgc         53
                                      Met Ala Ser Pro Arg Arg
                                      1               5 atc gcc gcc gcg ccc gcc gcc gcg ccc gcc acc ctc ctc atc ctg ctc       101
Ile Ala Ala Ala Pro Ala Ala Ala Pro Ala Thr Leu Leu Ile Leu Leu
            10                  15                  20 ctc ctc gtc gcc acg gag atg ggg acg acg aag gtg gcg gag gcc cgg       149
Leu Leu Val Ala Thr Glu Met Gly Thr Thr Lys Val Ala Glu Ala Arg
        25                  30                  35 acg tgc gag tcg cag agc cac aat ttc aag ggc gct tgc ttc agc gac       197
Thr Cys Glu Ser Gln Ser His Asn Phe Lys Gly Ala Cys Phe Ser Asp
    40                  45                  50 acc aac tgc gcc agc gtg tgc cgc acc gag aac ttc ccc cgc ggg cag       245
Thr Asn Cys Ala Ser Val Cys Arg Thr Glu Asn Phe Pro Arg Gly Gln
55                  60                  65                  70 tgc cac cag cac cac ctc gag cgc aag tgc tac tgc gag cgg gac tgc       293
Cys His Gln His His Leu Glu Arg Lys Cys Tyr Cys Glu Arg Asp Cys
                75                  80                  85 tga gcttaggatg accagaaata aagtagctcc atcggttttg cctcttcatc            346
ttcatgcatg catccatgca tgttgtttag gtgaagattg gtcctggctc cggcgtgttt     406
gcggcttcaa ttagtctgtg aggttaatgt atactaataa cgatgcatgc cactgatgca     466
tgtggcttct ctgtgttgtg atgcgttgtg ttggattcag tcagtttgca gttagttggc     526
ttgtcttttt cttcaaaaag attatgttca a                                    557

<210> SEQ ID NO 29
<211> LENGTH: 86
<212> TYPE: PRT
<213> ORGANISM: Triticum aestivum

<400> SEQUENCE: 29

Met Ala Ser Pro Arg Arg Ile Ala Ala Ala Pro Ala Ala Ala Pro Ala
1               5                   10                  15

Thr Leu Leu Ile Leu Leu Leu Leu Val Ala Thr Glu Met Gly Thr Thr
            20                  25                  30

Lys Val Ala Glu Ala Arg Thr Cys Glu Ser Gln Ser His Asn Phe Lys
        35                  40                  45

Gly Ala Cys Phe Ser Asp Thr Asn Cys Ala Ser Val Cys Arg Thr Glu
    50                  55                  60
```

```
Asn Phe Pro Arg Gly Gln Cys His Gln His His Leu Glu Arg Lys Cys
 65                  70                  75                  80

Tyr Cys Glu Arg Asp Cys
                85

<210> SEQ ID NO 30
<211> LENGTH: 49
<212> TYPE: PRT
<213> ORGANISM: Triticum aestivum

<400> SEQUENCE: 30

Arg Thr Cys Glu Ser Gln Ser His Asn Phe Lys Gly Ala Cys Phe Ser
  1               5                  10                  15

Asp Thr Asn Cys Ala Ser Val Cys Arg Thr Glu Asn Phe Pro Arg Gly
            20                  25                  30

Gln Cys His Gln His His Leu Glu Arg Lys Cys Tyr Cys Glu Arg Asp
        35                  40                  45

Cys

<210> SEQ ID NO 31
<211> LENGTH: 681
<212> TYPE: DNA
<213> ORGANISM: Triticum aestivum
<220> FEATURE:
<221> NAME/KEY: CDS
<222> LOCATION: (83)...(331)
<220> FEATURE:
<221> NAME/KEY: mat_peptide
<222> LOCATION: (182)...(328)

<400> SEQUENCE: 31
gcacgaggct tgctacgta gcagcagcag ggtagctcct cagtccaata cgtcgtctcg        60
agtgaagaag atcagcagct cg atg gcg ctc tct cgt cgc agc gcc gca tcc      112
                         Met Ala Leu Ser Arg Arg Ser Ala Ala Ser
                           1               5                  10 gcc ctc ctg ctt ctc gtg ctc ctc gtg gcc aca gag atg ggg acg acg       160
Ala Leu Leu Leu Leu Val Leu Leu Val Ala Thr Glu Met Gly Thr Thr
                 15                  20                  25 acg acc aag ctg gcg gag gcg cgg gac tgc ctg tcg cag agt cac aac       208
Thr Thr Lys Leu Ala Glu Ala Arg Asp Cys Leu Ser Gln Ser His Asn
             30                  35                  40 ttc aag ggc gcc tgc ctc agc agc agc aac tgc gcc ggc gtc tgc cac       256
Phe Lys Gly Ala Cys Leu Ser Ser Ser Asn Cys Ala Gly Val Cys His
         45                  50                  55 acc gag agc ttc ccc ggc ggc gag tgc cac acg cag cac ttc gag cgc       304
Thr Glu Ser Phe Pro Gly Gly Glu Cys His Thr Gln His Phe Glu Arg
     60                  65                  70 aag tgc ttc tgc aag agg gtc tgc tag cccgcctgct cgccccggcc              351
Lys Cys Phe Cys Lys Arg Val Cys *
 75                  80 gccctgccgg ccagcgccga gacgtccgat catccgtgcc gtgcctccac gttcgtcagt      411
agtagtattt ctgttccgtg acgttagata gttcatccgt gccgttagct acttttgttc      471
tgttcgtccg tgtgtccctc ttagtataga atagaactat aataaagtag aaaaccaatc      531
ggggtctcgg ttgtttagtt cgctgtacgc ctgtttgtgc ctgatttgtg tgtggtgatg      591
tactaaatat ggatcgttat ttcagcatgc aggacatgtc aatgcagtcc ccctctctct      651
caaggcgtta acatgactag taacaaagag                                      681

<210> SEQ ID NO 32
```

-continued

```
<211> LENGTH: 82
<212> TYPE: PRT
<213> ORGANISM: Triticum aestivum

<400> SEQUENCE: 32

Met Ala Leu Ser Arg Arg Ser Ala Ala Ser Ala Leu Leu Leu Leu Val
1               5                   10                  15

Leu Leu Val Ala Thr Glu Met Gly Thr Thr Thr Lys Leu Ala Glu
            20                  25                  30

Ala Arg Asp Cys Leu Ser Gln Ser His Asn Phe Lys Gly Ala Cys Leu
        35                  40                  45

Ser Ser Ser Asn Cys Ala Gly Val Cys His Thr Glu Ser Phe Pro Gly
    50                  55                  60

Gly Glu Cys His Thr Gln His Phe Glu Arg Lys Cys Phe Cys Lys Arg
65                  70                  75                  80

Val Cys

<210> SEQ ID NO 33
<211> LENGTH: 49
<212> TYPE: PRT
<213> ORGANISM: Triticum aestivum

<400> SEQUENCE: 33

Arg Asp Cys Leu Ser Gln Ser His Asn Phe Lys Gly Ala Cys Leu Ser
1               5                   10                  15

Ser Ser Asn Cys Ala Gly Val Cys His Thr Glu Ser Phe Pro Gly Gly
            20                  25                  30

Glu Cys His Thr Gln His Phe Glu Arg Lys Cys Phe Cys Lys Arg Val
        35                  40                  45

Cys

<210> SEQ ID NO 34
<211> LENGTH: 465
<212> TYPE: DNA
<213> ORGANISM: Triticum aestivum
<220> FEATURE:
<221> NAME/KEY: CDS
<222> LOCATION: (49)...(297)
<220> FEATURE:
<221> NAME/KEY: mat_peptide
<222> LOCATION: (148)...(294)
<220> FEATURE:
<221> NAME/KEY: misc_feature
<222> LOCATION: 11
<223> OTHER INFORMATION: n = A,T,C or G

<400> SEQUENCE: 34
gcacggccta ncatctccgg tgaggcaggc aagcaagagc agagagtg atg gcg tcc       57
                                                    Met Ala Ser
                                                    1 ccc cgt ccc atg gcc gcc gcg ccc gcc gtc ctc ctc ctc gtc ctg ctc     105
Pro Arg Pro Met Ala Ala Ala Pro Ala Val Leu Leu Leu Val Leu Leu
    5                   10                  15 ctc gtc gcc aca gag atg ggg acg atg aag acg gcg gag gcc cgg acg     153
Leu Val Ala Thr Glu Met Gly Thr Met Lys Thr Ala Glu Ala Arg Thr
20                  25                  30                  35 tgc cag tcg cag agc cac aag ttc aag ggc gcc tgc ttc agc gac acc     201
Cys Gln Ser Gln Ser His Lys Phe Lys Gly Ala Cys Phe Ser Asp Thr
                40                  45                  50 aac tgc gcc agc gtg tgc cgc acc gag aag ttc ccc cgc ggc cag tgc     249
Asn Cys Ala Ser Val Cys Arg Thr Glu Lys Phe Pro Arg Gly Gln Cys
            55                  60                  65
```

```
aac acg cac tac gtc gag cgc aag tgc tac tgc gag cgg gac tgc tga        297
Asn Thr His Tyr Val Glu Arg Lys Cys Tyr Cys Glu Arg Asp Cys *
        70                  75                  80 gcttccgcct ccgtcggcgc ctgttcgttc gtgtcttccg tgccggtcga tcttaggatt     357
gaccagaaat aaaaggagct ccatcgatgt tgcctcttca tctgcatgca tgcacgcatg     417
catccatgca tgtggtttgg gtgaagatcg gtcgtggctc cggcgtgt                  465

<210> SEQ ID NO 35
<211> LENGTH: 82
<212> TYPE: PRT
<213> ORGANISM: Triticum aestivum

<400> SEQUENCE: 35

Met Ala Ser Pro Arg Pro Met Ala Ala Pro Ala Val Leu Leu Leu
 1               5                  10                  15

Val Leu Leu Val Ala Thr Glu Met Gly Thr Met Lys Thr Ala Glu
            20                  25                  30

Ala Arg Thr Cys Gln Ser Gln Ser His Lys Phe Lys Gly Ala Cys Phe
        35                  40                  45

Ser Asp Thr Asn Cys Ala Ser Val Cys Arg Thr Glu Lys Phe Pro Arg
    50                  55                  60

Gly Gln Cys Asn Thr His Tyr Val Glu Arg Lys Cys Tyr Cys Glu Arg
65                  70                  75                  80

Asp Cys

<210> SEQ ID NO 36
<211> LENGTH: 49
<212> TYPE: PRT
<213> ORGANISM: Triticum aestivum

<400> SEQUENCE: 36

Arg Thr Cys Gln Ser Gln Ser His Lys Phe Lys Gly Ala Cys Phe Ser
 1               5                  10                  15

Asp Thr Asn Cys Ala Ser Val Cys Arg Thr Glu Lys Phe Pro Arg Gly
            20                  25                  30

Gln Cys Asn Thr His Tyr Val Glu Arg Lys Cys Tyr Cys Glu Arg Asp
        35                  40                  45

Cys

<210> SEQ ID NO 37
<211> LENGTH: 635
<212> TYPE: DNA
<213> ORGANISM: Triticum aestivum
<220> FEATURE:
<221> NAME/KEY: CDS
<222> LOCATION: (149)...(403)
<220> FEATURE:
<221> NAME/KEY: mat_peptide
<222> LOCATION: (254)...(400)

<400> SEQUENCE: 37
tgatctctct ctctctctcc ctgcctatat aaactccttc tcttttgctt cgttaattaa      60
cacacccagg ccacgctgca gcagcagcag cagcagagag ctcggattta acactcgggt     120
gaagcaagag agcaagtgca gagagag atg gca tcc cct cgt cgc atg ggc          172
                                Met Ala Ser Pro Arg Arg Met Gly
                                 1               5 atg gcc gcc gta ccg gcc gtc ctc ctc atc ctg ctc ctc ctc gtc gcc       220
Met Ala Ala Val Pro Ala Val Leu Leu Ile Leu Leu Leu Leu Val Ala
```

```
                   10               15                20
aca gag atg ggg acg acg aag acc gcg gag gcc cgg acg tgc gag tcg      268
Thr Glu Met Gly Thr Thr Lys Thr Ala Glu Ala Arg Thr Cys Glu Ser
 25              30                  35                  40 cag agc cac aag ttc aag ggc ccc tgc ttc agc gac agc aac tgc gca      316
Gln Ser His Lys Phe Lys Gly Pro Cys Phe Ser Asp Ser Asn Cys Ala
                 45                  50                  55 acc gtg tgc cgc acc gag aac ttt ccc cgc ggc cag tgc aac acg cac      364
Thr Val Cys Arg Thr Glu Asn Phe Pro Arg Gly Gln Cys Asn Thr His
                     60                  65                  70 cac gtc gag cgc aag tgc tac tgc gag cgg gac tgc tga gctttcttct      413
His Val Glu Arg Lys Cys Tyr Cys Glu Arg Asp Cys *
                 75                  80 ttgtgccttc cgtgttgatc tgcggatgac cagaaataaa gttgcttcgt gtctgaggtg    473
aagatcggtc ctgggcctac tgcagcgatt cgtcgccgtg tttgcggctt caattagttt    533
gcgcggttaa tgtatacgag tactactgta ctagtaataa cgataccact gaccactgat    593
gtatgtggct tctctccaaa aaaaaaaaaa aaaaaaaaa aa                        635

<210> SEQ ID NO 38
<211> LENGTH: 84
<212> TYPE: PRT
<213> ORGANISM: Triticum aestivum

<400> SEQUENCE: 38

Met Ala Ser Pro Arg Met Gly Met Ala Ala Val Pro Ala Val Leu
 1               5                  10                  15

Leu Ile Leu Leu Leu Val Ala Thr Glu Met Gly Thr Thr Lys Thr
                 20                  25                  30

Ala Glu Ala Arg Thr Cys Glu Ser Gln Ser His Lys Phe Lys Gly Pro
             35                  40                  45

Cys Phe Ser Asp Ser Asn Cys Ala Thr Val Cys Arg Thr Glu Asn Phe
 50                  55                  60

Pro Arg Gly Gln Cys Asn Thr His His Val Glu Arg Lys Cys Tyr Cys
65                   70                  75                  80

Glu Arg Asp Cys

<210> SEQ ID NO 39
<211> LENGTH: 49
<212> TYPE: PRT
<213> ORGANISM: Triticum aestivum

<400> SEQUENCE: 39

Arg Thr Cys Glu Ser Gln Ser His Lys Phe Lys Gly Pro Cys Phe Ser
 1               5                  10                  15

Asp Ser Asn Cys Ala Thr Val Cys Arg Thr Glu Asn Phe Pro Arg Gly
                 20                  25                  30

Gln Cys Asn Thr His His Val Glu Arg Lys Cys Tyr Cys Glu Arg Asp
             35                  40                  45

Cys

<210> SEQ ID NO 40
<211> LENGTH: 632
<212> TYPE: DNA
<213> ORGANISM: Triticum aestivum
<220> FEATURE:
<221> NAME/KEY: CDS
<222> LOCATION: (134)...(382)
<220> FEATURE:
```

```
<221> NAME/KEY: mat_peptide
<222> LOCATION: (233)...(379)

<400> SEQUENCE: 40
gcacgagggc ccattctcct ccattcgctt tgctagctag ctaacagagt cccccgtcgc      60
agcagcaaca tcaggatagc tttgctagct agctcggtcc agtacgtcgt ctcgggtgag     120
ccagagcaga tcg atg gcg ctc tct cgt cgc atg gcc gcg tcc gcc ctc       169
            Met Ala Leu Ser Arg Arg Met Ala Ala Ser Ala Leu
            1               5                   10 ctc ctg ctg gtc ctc ctc gtc gcc aca gag atg ggg acg acg acg acc      217
Leu Leu Leu Val Leu Leu Val Ala Thr Glu Met Gly Thr Thr Thr Thr
                15                  20                  25 aag gtg gcg gag gcg cgg gac tgc ctg tcg cag agc ttc aag ttc aag      265
Lys Val Ala Glu Ala Arg Asp Cys Leu Ser Gln Ser Phe Lys Phe Lys
        30                  35                  40 ggt gcg tgt ctc agc agc agc aac tgc gcc gcc gtc tgc cgc acc gag      313
Gly Ala Cys Leu Ser Ser Ser Asn Cys Ala Ala Val Cys Arg Thr Glu
45                  50                  55                  60 aag ttc cct gac ggc gag tgc cac agg cag cac ttg gag cgc aag tgc      361
Lys Phe Pro Asp Gly Glu Cys His Arg Gln His Leu Glu Arg Lys Cys
                65                  70                  75 ttc tgc aag agg ccc tgc tag ttcgcccgcg cgccggcccc gccctgccgg         412
Phe Cys Lys Arg Pro Cys *
                80 ccagcaccga gacgtccat gctagctcga tcatccgtgc cgttagctta tatttgttcc     472 gttcgccact gcgtccacgt tcgtcgctac ttgttcgtgt gtcccgctcg gctcggtaga    532 actaataaag tagagaacca atcggggtct cgctagttta gttcgctgtg cgtcctgttc    592 gttgtcacct gatttgtgcg tggcgatgta ctccattcaa                          632

<210> SEQ ID NO 41
<211> LENGTH: 82
<212> TYPE: PRT
<213> ORGANISM: Triticum aestivum

<400> SEQUENCE: 41

Met Ala Leu Ser Arg Arg Met Ala Ala Ser Ala Leu Leu Leu Leu Val
1               5                   10                  15

Leu Leu Val Ala Thr Glu Met Gly Thr Thr Thr Thr Lys Val Ala Glu
            20                  25                  30

Ala Arg Asp Cys Leu Ser Gln Ser Phe Lys Phe Lys Gly Ala Cys Leu
        35                  40                  45

Ser Ser Ser Asn Cys Ala Ala Val Cys Arg Thr Glu Lys Phe Pro Asp
    50                  55                  60

Gly Glu Cys His Arg Gln His Leu Glu Arg Lys Cys Phe Cys Lys Arg
65                  70                  75                  80

Pro Cys

<210> SEQ ID NO 42
<211> LENGTH: 49
<212> TYPE: PRT
<213> ORGANISM: Triticum aestivum

<400> SEQUENCE: 42

Arg Asp Cys Leu Ser Gln Ser Phe Lys Phe Lys Gly Ala Cys Leu Ser
1               5                   10                  15

Ser Ser Asn Cys Ala Ala Val Cys Arg Thr Glu Lys Phe Pro Asp Gly
            20                  25                  30
```

```
Glu Cys His Arg Gln His Leu Glu Arg Lys Cys Phe Cys Lys Arg Pro
        35                  40                  45

Cys

<210> SEQ ID NO 43
<211> LENGTH: 635
<212> TYPE: DNA
<213> ORGANISM: Triticum aestivum
<220> FEATURE:
<221> NAME/KEY: CDS
<222> LOCATION: (102)...(350)
<220> FEATURE:
<221> NAME/KEY: mat_peptide
<222> LOCATION: (201)...(347)

<400> SEQUENCE: 43
gcacgagtca gtttgctagc cagctaacac agtccccccgt atgtagcagc agcagaatag      60
ctcggtccag tacgtcgtct cgggtgaagc agagcagatc g atg gcg ctc tct cgt     116
                                              Met Ala Leu Ser Arg
                                                1               5 cgc atg gcc gcg tcc acc ctc ctg ctc gtc ctc ctc gtc gcc act            164
Arg Met Ala Ala Ser Thr Leu Leu Leu Val Leu Leu Val Ala Thr
            10                  15                  20 gag atg ggg gcg acg acg acc aag acg gcg gag gcg cgg gac tgc ctg        212
Glu Met Gly Ala Thr Thr Thr Lys Thr Ala Glu Ala Arg Asp Cys Leu
                25                  30                  35 tcg cag agc cac aag ttc aat ggc gcg tgc ctc agc agc agc aac tgc        260
Ser Gln Ser His Lys Phe Asn Gly Ala Cys Leu Ser Ser Ser Asn Cys
            40                  45                  50 gcc ggc gtg tgc cgc acc gag aac ttc ccc gac ggc gag tgc cac acg        308
Ala Gly Val Cys Arg Thr Glu Asn Phe Pro Asp Gly Glu Cys His Thr
        55                  60                  65 cag cac ttc gag cgc aag tgc ttc tgc aag agg gtc tgc tag                350
Gln His Phe Glu Arg Lys Cys Phe Cys Lys Arg Val Cys  *
    70                  75                  80 ccgccctgcc ggccagcgcc gccacgtccc atggtagcta gctagctgct agatcgtccg     410
tgccttttgc tagatctgtt cgtcagtgcg ttcgcattcg tcagtagttg ttcgtgtgag     470
ttgactctgt atcccataat aaagtaggaa atcaaccggg gactcggtag tttggttggc     530
cgcacgtagt gtttgtggct gctttgtgtc gtaaagtgta ataaggtcgt aatttcagca     590
tggacggacg tgtgcactgc atcccctctt tctatacatc agcat                     635

<210> SEQ ID NO 44
<211> LENGTH: 82
<212> TYPE: PRT
<213> ORGANISM: Triticum aestivum

<400> SEQUENCE: 44

Met Ala Leu Ser Arg Arg Met Ala Ala Ser Thr Leu Leu Leu Val
  1               5                  10                  15

Leu Leu Val Ala Thr Glu Met Gly Ala Thr Thr Thr Lys Thr Ala Glu
                20                  25                  30

Ala Arg Asp Cys Leu Ser Gln Ser His Lys Phe Asn Gly Ala Cys Leu
            35                  40                  45

Ser Ser Ser Asn Cys Ala Gly Val Cys Arg Thr Glu Asn Phe Pro Asp
        50                  55                  60

Gly Glu Cys His Thr Gln His Phe Glu Arg Lys Cys Phe Cys Lys Arg
 65                 70                  75                  80
```

-continued

Val Cys

<210> SEQ ID NO 45
<211> LENGTH: 49
<212> TYPE: PRT
<213> ORGANISM: Triticum aestivum

<400> SEQUENCE: 45

Arg Asp Cys Leu Ser Gln Ser His Lys Phe Asn Gly Ala Cys Leu Ser
1               5                   10                  15

Ser Ser Asn Cys Ala Gly Val Cys Arg Thr Glu Asn Phe Pro Asp Gly
            20                  25                  30

Glu Cys His Thr Gln His Phe Glu Arg Lys Cys Phe Cys Lys Arg Val
        35                  40                  45

Cys

<210> SEQ ID NO 46
<211> LENGTH: 629
<212> TYPE: DNA
<213> ORGANISM: Triticum aestivum
<220> FEATURE:
<221> NAME/KEY: CDS
<222> LOCATION: (108)...(356)
<220> FEATURE:
<221> NAME/KEY: mat_peptide
<222> LOCATION: (210)...(356)

<400> SEQUENCE: 46
gcacgaggct agacaggaca gcctatattg acgtagacgc agcaggagca gcagcagcga      60
actctgtcag ttctctagca tctccggtga agcaagcaag cagagag atg gcg tcc      116
                                                    Met Ala Ser
                                                     1 cct cgt cgc atg gcc gcc gcg ccc gcc gtc ctc ctc ctc gtc ctg ctc      164
Pro Arg Arg Met Ala Ala Ala Pro Ala Val Leu Leu Leu Val Leu Leu
    5                   10                  15 ctc ctc gtc gcc acg gag atg ggg acg atg aag acg gcg gag gcc cgg      212
Leu Leu Val Ala Thr Glu Met Gly Thr Met Lys Thr Ala Glu Ala Arg
 20                  25                  30                  35 acg tgc ctg tcg cag agc cac aag ttc aag ggc acc tgc ctc agc aac      260
Thr Cys Leu Ser Gln Ser His Lys Phe Lys Gly Thr Cys Leu Ser Asn
                40                  45                  50 agc aac tgc gcc ggc gtg tgc cgc acc gag aac ttc ccc gac ggc gag      308
Ser Asn Cys Ala Gly Val Cys Arg Thr Glu Asn Phe Pro Asp Gly Glu
        55                  60                  65 tgc aac tcc cac cgc ctc gag cgc aag tgc ttc tgc aag cgc acc tgc      356
Cys Asn Ser His Arg Leu Glu Arg Lys Cys Phe Cys Lys Arg Thr Cys
    70                  75                  80 taa gcaagcccag tccgcgctac tggctctggc tagctagact gctagatcag           409
cagccatgcc gtcagttaga tctgttcgtc cctactttg tttccgtttg ctttacgttg      469
ctcttgggga tgactgaaaa taagtagct acctacatcc tctgcattgg ctgttccact      529
gcatgttgtc taagtgtttc tggctttagt ttgtgctgtt gatgtaataa cgatgccact      589
aacaatttgg cttctatgtg ttgtgttgaa acttggaatc                            629

<210> SEQ ID NO 47
<211> LENGTH: 83
<212> TYPE: PRT
<213> ORGANISM: Triticum aestivum

<400> SEQUENCE: 47

```
Met Ala Ser Pro Arg Met Ala Ala Ala Pro Ala Val Leu Leu Leu
1               5                   10                  15

Val Leu Leu Leu Leu Val Ala Thr Glu Met Gly Thr Met Lys Thr Ala
            20                  25                  30

Glu Ala Arg Thr Cys Leu Ser Gln Ser His Lys Phe Lys Gly Thr Cys
        35                  40                  45

Leu Ser Asn Ser Asn Cys Ala Gly Val Cys Arg Thr Glu Asn Phe Pro
    50                  55                  60

Asp Gly Glu Cys Asn Ser His Arg Leu Glu Arg Lys Cys Phe Cys Lys
65                  70                  75                  80

Arg Thr Cys

<210> SEQ ID NO 48
<211> LENGTH: 49
<212> TYPE: PRT
<213> ORGANISM: Triticum aestivum

<400> SEQUENCE: 48

Arg Thr Cys Leu Ser Gln Ser His Lys Phe Lys Gly Thr Cys Leu Ser
1               5                   10                  15

Asn Ser Asn Cys Ala Gly Val Cys Arg Thr Glu Asn Phe Pro Asp Gly
            20                  25                  30

Glu Cys Asn Ser His Arg Leu Glu Arg Lys Cys Phe Cys Lys Arg Thr
        35                  40                  45

Cys

<210> SEQ ID NO 49
<211> LENGTH: 628
<212> TYPE: DNA
<213> ORGANISM: Triticum aestivum
<220> FEATURE:
<221> NAME/KEY: CDS
<222> LOCATION: (127)...(369)
<220> FEATURE:
<221> NAME/KEY: mat_peptide
<222> LOCATION: (220)...(366)

<400> SEQUENCE: 49
gcacgagcgt ccaccagcct cgtcgttagg acgtaaggta agacacccag gggcgagcca        60
gtgagtacag agagtagcct tacgtagcga agctcagagc aagcgagggt acggtcaagg       120 gggggtg atg gcg ctg tct cga cgc atg gcg gct ccc gtc ctc gtc ctc        168
        Met Ala Leu Ser Arg Arg Met Ala Ala Pro Val Leu Val Leu
        1               5                   10 atg ctc ctc ctc gtc gcc aca gag ctg ggg acg acc aag gtg gcg gag        216
Met Leu Leu Leu Val Ala Thr Glu Leu Gly Thr Thr Lys Val Ala Glu
15                  20                  25                  30 gcg agg cac tgc ctg tcg cag agc cac cgg ttc aag ggc ctg tgc atg        264
Ala Arg His Cys Leu Ser Gln Ser His Arg Phe Lys Gly Leu Cys Met
                35                  40                  45 agc agc aac aac tgc gcc aac gtg tgc cag acc gag aac ttc ccc ggc        312
Ser Ser Asn Asn Cys Ala Asn Val Cys Gln Thr Glu Asn Phe Pro Gly
            50                  55                  60 ggc gag tgt aag gcg gag ggc gcc acg cgc aag tgc ttc tgc aag aag        360
Gly Glu Cys Lys Ala Glu Gly Ala Thr Arg Lys Cys Phe Cys Lys Lys
        65                  70                  75 ata tgc tag tagtagcctc ggctttgctg gcacaagcag gtcgtcggca                 409
Ile Cys *
        80 cgcaacgcaa ttcaagcatc atatcggtcc tcctcccgcg ttgctgtcta ctcgaccccg       469
```

```
tttctcttt cgatcgattt cgttgtttcc tgttgctctc ttcttttccc gcgaataata      529
tgctccatgg gatctcactg ttgtactttc tgcatccgtt ggtagtcagg acgatccttc      589
ttcccgctgt cacgtgtgat tcaaaatgga tgtactaat                            628
```

```
<210> SEQ ID NO 50
<211> LENGTH: 80
<212> TYPE: PRT
<213> ORGANISM: Triticum aestivum

<400> SEQUENCE: 50
```

Met Ala Leu Ser Arg Met Ala Ala Pro Val Leu Val Leu Met Leu
1               5                   10                  15

Leu Leu Val Ala Thr Glu Leu Gly Thr Thr Lys Val Ala Glu Ala Arg
            20                  25                  30

His Cys Leu Ser Gln Ser His Arg Phe Lys Gly Leu Cys Met Ser Ser
        35                  40                  45

Asn Asn Cys Ala Asn Val Cys Gln Thr Glu Asn Phe Pro Gly Gly Glu
    50                  55                  60

Cys Lys Ala Glu Gly Ala Thr Arg Lys Cys Phe Cys Lys Lys Ile Cys
65                  70                  75                  80

```
<210> SEQ ID NO 51
<211> LENGTH: 49
<212> TYPE: PRT
<213> ORGANISM: Triticum aestivum

<400> SEQUENCE: 51
```

Arg His Cys Leu Ser Gln Ser His Arg Phe Lys Gly Leu Cys Met Ser
1               5                   10                  15

Ser Asn Asn Cys Ala Asn Val Cys Gln Thr Glu Asn Phe Pro Gly Gly
            20                  25                  30

Glu Cys Lys Ala Glu Gly Ala Thr Arg Lys Cys Phe Cys Lys Lys Ile
        35                  40                  45

Cys

```
<210> SEQ ID NO 52
<211> LENGTH: 637
<212> TYPE: DNA
<213> ORGANISM: Triticum aestivum
<220> FEATURE:
<221> NAME/KEY: CDS
<222> LOCATION: (88)...(336)
<220> FEATURE:
<221> NAME/KEY: mat_peptide
<222> LOCATION: (187)...(333)
<220> FEATURE:
<221> NAME/KEY: misc_feature
<222> LOCATION: 629
<223> OTHER INFORMATION: n = A,T,C or G

<400> SEQUENCE: 52
```

```
tttcctatct aacctaacac aggcccccgt tgcagcagca gagcagatcg atccagtacg      60
tctcgggtga accagctgag cagatcg atg gcg ctc act cgt cgc atg gcc gca    114
                                Met Ala Leu Thr Arg Arg Met Ala Ala
                                                    1               5 tcc gcc ctc ctg ctg ctc ctc ctc gtc gcc aca gag atg ggg acg         162
Ser Ala Leu Leu Leu Leu Leu Leu Val Ala Thr Glu Met Gly Thr
        10                  15                  20                  25 acg agg acc aag acg gcg gag gcg cgg gac tgc ctg tcg cag agc cac     210
Thr Arg Thr Lys Thr Ala Glu Ala Arg Asp Cys Leu Ser Gln Ser His
```

```
                    30              35              40
aag ttc aag ggc gcc tgc ctc agc agc agc aac tgc gcc ggc gtc tgc    258
Lys Phe Lys Gly Ala Cys Leu Ser Ser Ser Asn Cys Ala Gly Val Cys
             45                  50                  55 cgc acc gag aac ttc ccc gac ggc gag tgc cac acg cac aac ttc gcc    306
Arg Thr Glu Asn Phe Pro Asp Gly Glu Cys His Thr His Asn Phe Ala
         60                  65                  70 cgc aag tgc ttc tgc aag agg gcc tgc tag ccggcctgct cgccccggcc      356
Arg Lys Cys Phe Cys Lys Arg Ala Cys *
     75                  80 gccctgccgg ccagcgccga gacgtccgat ctgttcgtca gtgctgtctg ctagatctgt  416
tcttcagtgc gttcgcgttc gtcggcagta gctgttcgtg tgacgactgt gtcccgtaat  476
aaagtaggaa atcaaccggg ctcttggtag tttggttcgc cttctgctag taggtcgtgt  536
ttgttgctgc tttgtgtggt gaacttgtga tgtagtaata aggtcgttgt ttcagcaaaa  596
aaaaaaaaaa aaaaaaaaaa aactcgaggg ggnggcccgg t                      637
```

<210> SEQ ID NO 53
<211> LENGTH: 82
<212> TYPE: PRT
<213> ORGANISM: Triticum aestivum

<400> SEQUENCE: 53

Met Ala Leu Thr Arg Met Ala Ala Ser Ala Leu Leu Leu Leu Leu Leu
1               5                   10                  15

Leu Leu Val Ala Thr Glu Met Gly Thr Thr Arg Thr Lys Thr Ala Glu
            20                  25                  30

Ala Arg Asp Cys Leu Ser Gln Ser His Lys Phe Lys Gly Ala Cys Leu
        35                  40                  45

Ser Ser Ser Asn Cys Ala Gly Val Cys Arg Thr Glu Asn Phe Pro Asp
    50                  55                  60

Gly Glu Cys His Thr His Asn Phe Ala Arg Lys Cys Phe Cys Lys Arg
65                  70                  75                  80

Ala Cys

<210> SEQ ID NO 54
<211> LENGTH: 49
<212> TYPE: PRT
<213> ORGANISM: Triticum aestivum

<400> SEQUENCE: 54

Arg Asp Cys Leu Ser Gln Ser His Lys Phe Lys Gly Ala Cys Leu Ser
1               5                   10                  15

Ser Ser Asn Cys Ala Gly Val Cys Arg Thr Glu Asn Phe Pro Asp Gly
            20                  25                  30

Glu Cys His Thr His Asn Phe Ala Arg Lys Cys Phe Cys Lys Arg Ala
        35                  40                  45

Cys

<210> SEQ ID NO 55
<211> LENGTH: 631
<212> TYPE: DNA
<213> ORGANISM: Triticum aestivum
<220> FEATURE:
<221> NAME/KEY: CDS
<222> LOCATION: (57)...(305)
<220> FEATURE:
<221> NAME/KEY: mat_peptide
<222> LOCATION: (156)...(302)

```
<400> SEQUENCE: 55
gcacgaggct agacaagaca gactccaagt ctccggtgaa gcgagcaagc agagag atg      59
                                                                Met
                                                                1 gcg tcc cca agt cgc acg gcc gcc acg ccc gcc gtc ctc ctc ctc ctg       107
Ala Ser Pro Ser Arg Thr Ala Ala Thr Pro Ala Val Leu Leu Leu Leu
                5                   10                  15 ctc ctg ctt gtc gcc aca gag atg ggg acg acc aag gtg gtg gag gcc       155
Leu Leu Leu Val Ala Thr Glu Met Gly Thr Thr Lys Val Val Glu Ala
            20                  25                  30 cgg acg tgc ctg tcg cag agc cac aag ttc aag ggc acc tgc ctc agc       203
Arg Thr Cys Leu Ser Gln Ser His Lys Phe Lys Gly Thr Cys Leu Ser
        35                  40                  45 gac agc aac tgc gcc ggc gtg tgc cgc acc gag aac ttc ccc gac ggc       251
Asp Ser Asn Cys Ala Gly Val Cys Arg Thr Glu Asn Phe Pro Asp Gly
50                  55                  60                  65 gag tgc aac tcc cac cgc ctc gag cgc aag tgc ttc tgc aag cgg acc       299
Glu Cys Asn Ser His Arg Leu Glu Arg Lys Cys Phe Cys Lys Arg Thr
                70                  75                  80 tgc taa gcaagaagtc atccgatgga tgctacgtat cagagcatcc atgcgtgtgc        355
Cys * cggccagtta gatctgatcg tccctgcatt tgtttcacgt ccgtcagtag tttcttcgtg     415
tgtttcgttt acaataatgg ttcatctcca tgcatccgga ggtacgcact ttaggtgaca     475
atcggtcggc gtttcggtgg tgtagttagt tcgccggccg ccgtgtggtg atgtaatatg     535
gtcatgggat ccctatggtc attgcgttgt ttcagccttt cagcatggac ggacacccat     595
atgcaatgaa tccgttcgtg gctttaattt gaataa                              631

<210> SEQ ID NO 56
<211> LENGTH: 82
<212> TYPE: PRT
<213> ORGANISM: Triticum aestivum

<400> SEQUENCE: 56

Met Ala Ser Pro Ser Arg Thr Ala Ala Thr Pro Ala Val Leu Leu Leu
1               5                   10                  15

Leu Leu Leu Val Ala Thr Glu Met Gly Thr Thr Lys Val Val Glu
            20                  25                  30

Ala Arg Thr Cys Leu Ser Gln Ser His Lys Phe Lys Gly Thr Cys Leu
        35                  40                  45

Ser Asp Ser Asn Cys Ala Gly Val Cys Arg Thr Glu Asn Phe Pro Asp
    50                  55                  60

Gly Glu Cys Asn Ser His Arg Leu Glu Arg Lys Cys Phe Cys Lys Arg
65                  70                  75                  80

Thr Cys

<210> SEQ ID NO 57
<211> LENGTH: 49
<212> TYPE: PRT
<213> ORGANISM: Triticum aestivum

<400> SEQUENCE: 57

Arg Thr Cys Leu Ser Gln Ser His Lys Phe Lys Gly Thr Cys Leu Ser
1               5                   10                  15

Asp Ser Asn Cys Ala Gly Val Cys Arg Thr Glu Asn Phe Pro Asp Gly
            20                  25                  30
```

```
Glu Cys Asn Ser His Arg Leu Glu Arg Lys Cys Phe Cys Lys Arg Thr
        35                  40                  45

Cys

<210> SEQ ID NO 58
<211> LENGTH: 486
<212> TYPE: DNA
<213> ORGANISM: Glycine max
<220> FEATURE:
<221> NAME/KEY: CDS
<222> LOCATION: (30)...(254)
<220> FEATURE:
<221> NAME/KEY: mat_peptide
<222> LOCATION: (111)...(251)

<400> SEQUENCE: 58
gaaacaattc aattcaatct gcctcgatc atg gag agg aaa aca ttt ggg ttt         53
                                Met Glu Arg Lys Thr Phe Gly Phe
                                  1               5 ttg ttc ttg ctc ctc ctt gtc tta gct tct gat gtg acg gtg aag aga       101
Leu Phe Leu Leu Leu Leu Val Leu Ala Ser Asp Val Thr Val Lys Arg
     10                  15                  20 gca gag gcg aaa gat tgc ttg aca agg agg cac ggg ttc cag ggt aga       149
Ala Glu Ala Lys Asp Cys Leu Thr Arg Arg His Gly Phe Gln Gly Arg
 25                  30                  35                  40 tgc tta ttc gac agg caa tgt gca cat gtg tgc agg agc gat ggt ttc       197
Cys Leu Phe Asp Arg Gln Cys Ala His Val Cys Arg Ser Asp Gly Phe
                 45                  50                  55 atc ggt ggt cag tgc cga ggc cct ctt cgc aaa tgc ttt tgc agc agg       245
Ile Gly Gly Gln Cys Arg Gly Pro Leu Arg Lys Cys Phe Cys Ser Arg
             60                  65                  70 cca tgt tga tcgaaattac tactgccaaa gaggccatga aataaacaaa                294
Pro Cys * caaacaaata aataaatagc tttaaccgac acatatgtac ttagtgtcgg taggtacgtg      354
tgtcttttgt tatcgatcct agtttggtgg agcaagtatg gcatcatgat ctagttatat      414
atatgtcgtg atcatcttgc tctgttcagc aataaattat aatggaaatt aataaattag      474
ttatgccttt tc                                                          486

<210> SEQ ID NO 59
<211> LENGTH: 74
<212> TYPE: PRT
<213> ORGANISM: Glycine max

<400> SEQUENCE: 59

Met Glu Arg Lys Thr Phe Gly Phe Leu Phe Leu Leu Leu Val Leu
  1               5                  10                  15

Ala Ser Asp Val Thr Val Lys Arg Ala Glu Ala Lys Asp Cys Leu Thr
                 20                  25                  30

Arg Arg His Gly Phe Gln Gly Arg Cys Leu Phe Asp Arg Gln Cys Ala
             35                  40                  45

His Val Cys Arg Ser Asp Gly Phe Ile Gly Gly Gln Cys Arg Gly Pro
         50                  55                  60

Leu Arg Lys Cys Phe Cys Ser Arg Pro Cys
 65                  70

<210> SEQ ID NO 60
<211> LENGTH: 47
<212> TYPE: PRT
<213> ORGANISM: Glycine max
```

<400> SEQUENCE: 60

```
Lys Asp Cys Leu Thr Arg Arg His Gly Phe Gln Gly Arg Cys Leu Phe
1               5                   10                  15
Asp Arg Gln Cys Ala His Val Cys Arg Ser Asp Gly Phe Ile Gly Gly
            20                  25                  30
Gln Cys Arg Gly Pro Leu Arg Lys Cys Phe Cys Ser Arg Pro Cys
        35                  40                  45
```

<210> SEQ ID NO 61
<211> LENGTH: 519
<212> TYPE: DNA
<213> ORGANISM: Glycine max
<220> FEATURE:
<221> NAME/KEY: CDS
<222> LOCATION: (49)...(273)
<220> FEATURE:
<221> NAME/KEY: mat_peptide
<222> LOCATION: (130)...(270)

<400> SEQUENCE: 61

```
ttcggcacga gctcgtgccg aaacaattca attcaatctg cctcgatc atg gag agg         57
                                                    Met Glu Arg
                                                      1 aaa aca ttt ggg ttt ttg ttc ttg ctc ctc ctt gtc tta gct tct gat         105
Lys Thr Phe Gly Phe Leu Phe Leu Leu Leu Leu Val Leu Ala Ser Asp
  5                  10                  15 gtg acg gtg aag aga gca gag gcg aaa gat tgc ttg aca agg agg cac         153
Val Thr Val Lys Arg Ala Glu Ala Lys Asp Cys Leu Thr Arg Arg His
 20                  25                  30                  35 ggg ttc cag ggt aga tgc tta ttc gac agg caa tgt gca cat gtg tgc         201
Gly Phe Gln Gly Arg Cys Leu Phe Asp Arg Gln Cys Ala His Val Cys
             40                  45                  50 agg agc gat ggt ttc atc ggt ggt cag tgc cga ggc cct ctt cgc aaa         249
Arg Ser Asp Gly Phe Ile Gly Gly Gln Cys Arg Gly Pro Leu Arg Lys
         55                  60                  65 tgc ttt tgc agc agg cca tgt tga tcgaaattac tactgccaaa gaggccatga        303
Cys Phe Cys Ser Arg Pro Cys  *
         70 aataaacaaa caaacaaata aataaatagc tttaaccgac acatatgtac ttagtgtcgg       363 taggtacgtg tgtcttttgt tatcgatcct agtttggtgg agcaagtatg gcatcatgat       423 ctagttatat atatgtcgtg atcatcttgc tctgttcagc aataaattat aatggaaatt       483 aataaattag ttatgccaaa aaaaaaaaaa aaaaaa                                 519
```

<210> SEQ ID NO 62
<211> LENGTH: 74
<212> TYPE: PRT
<213> ORGANISM: Glycine max

<400> SEQUENCE: 62

```
Met Glu Arg Lys Thr Phe Gly Phe Leu Phe Leu Leu Leu Leu Val Leu
1               5                   10                  15
Ala Ser Asp Val Thr Val Lys Arg Ala Glu Ala Lys Asp Cys Leu Thr
            20                  25                  30
Arg Arg His Gly Phe Gln Gly Arg Cys Leu Phe Asp Arg Gln Cys Ala
        35                  40                  45
His Val Cys Arg Ser Asp Gly Phe Ile Gly Gly Gln Cys Arg Gly Pro
    50                  55                  60
Leu Arg Lys Cys Phe Cys Ser Arg Pro Cys
65                  70
```

<210> SEQ ID NO 63
<211> LENGTH: 47
<212> TYPE: PRT
<213> ORGANISM: Glycine max

<400> SEQUENCE: 63

```
Lys Asp Cys Leu Thr Arg Arg His Gly Phe Gln Gly Arg Cys Leu Phe
  1               5                  10                  15

Asp Arg Gln Cys Ala His Val Cys Arg Ser Asp Gly Phe Ile Gly Gly
             20                  25                  30

Gln Cys Arg Gly Pro Leu Arg Lys Cys Phe Cys Ser Arg Pro Cys
         35                  40                  45
```

<210> SEQ ID NO 64
<211> LENGTH: 530
<212> TYPE: DNA
<213> ORGANISM: Glycine max
<220> FEATURE:
<221> NAME/KEY: CDS
<222> LOCATION: (37)...(261)
<220> FEATURE:
<221> NAME/KEY: mat_peptide
<222> LOCATION: (118)...(258)

<400> SEQUENCE: 64

```
gcacgaggaa acaattcaat tcaatctgcc tcgatc atg gag agg aaa aca ttt          54
                                        Met Glu Arg Lys Thr Phe
                                          1               5 ggg ttt ttg ttc ttg ctc ctc ctt gtc tta gct tct gat gtg acg gtg         102
Gly Phe Leu Phe Leu Leu Leu Leu Val Leu Ala Ser Asp Val Thr Val
             10                  15                  20 aag aga gca gag gcg aaa gat tgc ttg aca agg agg cac ggg ttc cag         150
Lys Arg Ala Glu Ala Lys Asp Cys Leu Thr Arg Arg His Gly Phe Gln
         25                  30                  35 ggt aga tgc tta ttc gac agg caa tgt gca cac gtg tgc agg agc gat         198
Gly Arg Cys Leu Phe Asp Arg Gln Cys Ala His Val Cys Arg Ser Asp
     40                  45                  50 ggt ttc atc ggt ggt cag tgc cga ggc cct ctt cgc aaa tgc ttt tgc         246
Gly Phe Ile Gly Gly Gln Cys Arg Gly Pro Leu Arg Lys Cys Phe Cys
 55                  60                  65                  70 agc agg cca tgt tga tcgaaattac tactgccaaa gaggccatga ataaacaaa          301
Ser Arg Pro Cys * caaacaaata aataaatagc tttaaccgac acatatgtac ttagtgtcgg taggtacgtg       361
tgtcttttgt tatcgatcct agtttggtgg agcaagtatg gcatcatcat gatctagtat       421
tatatatatg tcgtgatcat cttgctctgt tcagcaataa attataatgg aaattaataa       481
attagttatg cctttcaaa aaaaaaaaaa aaaaaaaaaa aaaaaaaaa                    530
```

<210> SEQ ID NO 65
<211> LENGTH: 74
<212> TYPE: PRT
<213> ORGANISM: Glycine max

<400> SEQUENCE: 65

```
Met Glu Arg Lys Thr Phe Gly Phe Leu Phe Leu Leu Leu Val Leu
  1               5                  10                  15

Ala Ser Asp Val Thr Val Lys Arg Ala Glu Ala Lys Asp Cys Leu Thr
             20                  25                  30

Arg Arg His Gly Phe Gln Gly Arg Cys Leu Phe Asp Arg Gln Cys Ala
         35                  40                  45
```

His Val Cys Arg Ser Asp Gly Phe Ile Gly Gly Gln Cys Arg Gly Pro
         50                  55                  60
Leu Arg Lys Cys Phe Cys Ser Arg Pro Cys
 65                  70

<210> SEQ ID NO 66
<211> LENGTH: 47
<212> TYPE: PRT
<213> ORGANISM: Glycine max

<400> SEQUENCE: 66

Lys Asp Cys Leu Thr Arg Arg His Gly Phe Gln Gly Arg Cys Leu Phe
 1               5                  10                  15
Asp Arg Gln Cys Ala His Val Cys Arg Ser Asp Gly Phe Ile Gly Gly
             20                  25                  30
Gln Cys Arg Gly Pro Leu Arg Lys Cys Phe Cys Ser Arg Pro Cys
         35                  40                  45

<210> SEQ ID NO 67
<211> LENGTH: 435
<212> TYPE: DNA
<213> ORGANISM: Triticum aestivum
<220> FEATURE:
<221> NAME/KEY: CDS
<222> LOCATION: (30)...(254)
<220> FEATURE:
<221> NAME/KEY: mat_peptide
<222> LOCATION: (111)...(251)

<400> SEQUENCE: 67
gcacgagttc aattcaatct gcctcgatc atg gag agg aaa aca ttt ggg ttt       53
                                Met Glu Arg Lys Thr Phe Gly Phe
                                 1               5 ttg ttc ttg ctc ctc ctt gtc tta gct tct gat gtg acg gtg aag aga      101
Leu Phe Leu Leu Leu Leu Val Leu Ala Ser Asp Val Thr Val Lys Arg
     10                  15                  20 gca gag gcg aaa gat tgc ttg aca agg agg cac ggg ttc cag ggt aga      149
Ala Glu Ala Lys Asp Cys Leu Thr Arg Arg His Gly Phe Gln Gly Arg
 25                  30                  35                  40 tgc tta ttc gac agg caa tgt gca cat gtg tgc agg agc gat ggt ttc      197
Cys Leu Phe Asp Arg Gln Cys Ala His Val Cys Arg Ser Asp Gly Phe
                 45                  50                  55 atc ggt ggt cag tgc cga ggc cct ctt cgc aaa tgc ttt tgc agc agg      245
Ile Gly Gly Gln Cys Arg Gly Pro Leu Arg Lys Cys Phe Cys Ser Arg
             60                  65                  70 cca tgt tga tcgaaattac tactgccaaa gaggccatga aataaacaaa              294
Pro Cys * caaacaaata aataaatagc tttaaccgac acatatgtac ttagtgtcgg taggtacgtg    354
tgtcttttgt tatcgatcct agtttggtgg agcaagtatg gcatcatgat ctagttatat    414
atatgtcgtg atcatcttgc t                                              435

<210> SEQ ID NO 68
<211> LENGTH: 74
<212> TYPE: PRT
<213> ORGANISM: Triticum aestivum

<400> SEQUENCE: 68

Met Glu Arg Lys Thr Phe Gly Phe Leu Phe Leu Leu Leu Leu Val Leu
 1               5                  10                  15
Ala Ser Asp Val Thr Val Lys Arg Ala Glu Ala Lys Asp Cys Leu Thr

```
            20                  25                  30
Arg Arg His Gly Phe Gln Gly Arg Cys Leu Phe Asp Arg Gln Cys Ala
         35                  40                  45

His Val Cys Arg Ser Asp Gly Phe Ile Gly Gly Gln Cys Arg Gly Pro
 50                  55                  60

Leu Arg Lys Cys Phe Cys Ser Arg Pro Cys
 65                  70

<210> SEQ ID NO 69
<211> LENGTH: 47
<212> TYPE: PRT
<213> ORGANISM: Triticum aestivum

<400> SEQUENCE: 69

Lys Asp Cys Leu Thr Arg Arg His Gly Phe Gln Gly Arg Cys Leu Phe
  1               5                  10                  15

Asp Arg Gln Cys Ala His Val Cys Arg Ser Asp Gly Phe Ile Gly Gly
             20                  25                  30

Gln Cys Arg Gly Pro Leu Arg Lys Cys Phe Cys Ser Arg Pro Cys
         35                  40                  45

<210> SEQ ID NO 70
<211> LENGTH: 507
<212> TYPE: DNA
<213> ORGANISM: Triticum aestivum
<220> FEATURE:
<221> NAME/KEY: CDS
<222> LOCATION: (58)...(285)
<220> FEATURE:
<221> NAME/KEY: mat_peptide
<222> LOCATION: (148)...(282)

<400> SEQUENCE: 70
gcacgaggct ttcacattct accatacaat cctcttcatc cttcacaagc aaccgcc atg    60
                                                                Met
                                                                 1 ggt ctg tcc gca aag gtc ttc gtg gtc ctc ctg ctg ctc gtt gcc           108
Gly Leu Ser Ala Lys Val Phe Val Val Leu Leu Leu Leu Val Ala
         5                  10                  15 acg gag gag cag ggg ggt tcc gtg cag gtg gct ctg gcg agg gat tgc       156
Thr Glu Glu Gln Gly Gly Ser Val Gln Val Ala Leu Ala Arg Asp Cys
             20                  25                  30 aag tcg gat agc cac aag ttc cat ggg gcg tgc ttc agc gac acc aac       204
Lys Ser Asp Ser His Lys Phe His Gly Ala Cys Phe Ser Asp Thr Asn
         35                  40                  45 tgc gcg aac gtc tgc cag acc gag ggc ttc acc ggc ggc aag tgc gac       252
Cys Ala Asn Val Cys Gln Thr Glu Gly Phe Thr Gly Gly Lys Cys Asp
 50                  55                  60                  65 ggc atc cac tgc cac tgc acc aag gac tgc tag atgcctagat ggccttggct     305
Gly Ile His Cys His Cys Thr Lys Asp Cys *
             70                  75 agtttgttct cgcgtactag atgcatgatt ccatgtgatg ttagctgaac gatggtagat     365
ctattatatg tctatgtatg tgcgcgcgtt gatctgcgag tgctggtcct cggagattgc     425
atgaatgaat aagggaatc acatcatctt gtgagtgaga tctgttccct gctttgtgag      485
atcaaaaaaa aaaaaaaaaa aa                                              507

<210> SEQ ID NO 71
<211> LENGTH: 75
<212> TYPE: PRT
<213> ORGANISM: Triticum aestivum
```

<400> SEQUENCE: 71

Met Gly Leu Ser Ala Lys Val Phe Val Val Leu Leu Leu Leu Val
1               5                   10                  15

Ala Thr Glu Glu Gln Gly Gly Ser Val Gln Val Ala Leu Ala Arg Asp
            20                  25                  30

Cys Lys Ser Asp Ser His Lys Phe His Gly Ala Cys Phe Ser Asp Thr
        35                  40                  45

Asn Cys Ala Asn Val Cys Gln Thr Glu Gly Phe Thr Gly Gly Lys Cys
    50                  55                  60

Asp Gly Ile His Cys His Cys Thr Lys Asp Cys
65                  70                  75

<210> SEQ ID NO 72
<211> LENGTH: 45
<212> TYPE: PRT
<213> ORGANISM: Triticum aestivum

<400> SEQUENCE: 72

Arg Asp Cys Lys Ser Asp Ser His Lys Phe His Gly Ala Cys Phe Ser
1               5                   10                  15

Asp Thr Asn Cys Ala Asn Val Cys Gln Thr Glu Gly Phe Thr Gly Gly
            20                  25                  30

Lys Cys Asp Gly Ile His Cys His Cys Thr Lys Asp Cys
        35                  40                  45

<210> SEQ ID NO 73
<211> LENGTH: 500
<212> TYPE: DNA
<213> ORGANISM: Triticum aestivum
<220> FEATURE:
<221> NAME/KEY: CDS
<222> LOCATION: (70)...(303)
<220> FEATURE:
<221> NAME/KEY: mat_peptide
<222> LOCATION: (160)...(300)

<400> SEQUENCE: 73
gcacgagccc agctccaagg ctttcacatt ctaccataca atcctcttca tccttcacaa    60 ggaaccgcc atg ggt ctg tcc gcg aag gtc ttc gtg gtc ctc ctg ctg ctt   111
           Met Gly Leu Ser Ala Lys Val Phe Val Val Leu Leu Leu Leu
           1               5                   10 ctc gtc gcc acg gag gag cag ggg gga tcg gtg cag gtg gct ctg gcg   159
Leu Val Ala Thr Glu Glu Gln Gly Gly Ser Val Gln Val Ala Leu Ala
 15              20                  25                  30 agg gat tgc gag tcg gat agc cac aag ttc cat ggg gcg tgc ttc agc   207
Arg Asp Cys Glu Ser Asp Ser His Lys Phe His Gly Ala Cys Phe Ser
            35                  40                  45 gac acc aac tgt gcg tac gtc tgc cag acc gag ggc ttc acc gcc ggc   255
Asp Thr Asn Cys Ala Tyr Val Cys Gln Thr Glu Gly Phe Thr Ala Gly
        50                  55                  60 aag tgc gtc ggc gtc cag cgc cac tgc cac tgc acc aag gac tgc tag   303
Lys Cys Val Gly Val Gln Arg His Cys His Cys Thr Lys Asp Cys *
    65                  70                  75 atgccttgcc tagatggccc tggctacttt gttctcgcgt actggatgca tgattccctg   363
tgtgtgatat tacctgaacg atagtagatc tatatatcta tgtgtgtatg cgtgtgttga   423
tttgcgagcg ctactcgtca gagatttcat gaatgaataa agggaatcgc atcatcttaa   483
aaaaaaaaaa aaaaaa                                                   500

<210> SEQ ID NO 74
<211> LENGTH: 77
<212> TYPE: PRT
<213> ORGANISM: Triticum aestivum

<400> SEQUENCE: 74

```
Met Gly Leu Ser Ala Lys Val Phe Val Val Leu Leu Leu Leu Val
1               5                   10                  15

Ala Thr Glu Glu Gln Gly Gly Ser Val Gln Val Ala Leu Ala Arg Asp
                20                  25                  30

Cys Glu Ser Asp Ser His Lys Phe His Gly Ala Cys Phe Ser Asp Thr
            35                  40                  45

Asn Cys Ala Tyr Val Cys Gln Thr Glu Gly Phe Thr Ala Gly Lys Cys
        50                  55                  60

Val Gly Val Gln Arg His Cys His Cys Thr Lys Asp Cys
65                  70                  75
```

<210> SEQ ID NO 75
<211> LENGTH: 47
<212> TYPE: PRT
<213> ORGANISM: Triticum aestivum

<400> SEQUENCE: 75

```
Arg Asp Cys Glu Ser Asp Ser His Lys Phe His Gly Ala Cys Phe Ser
1               5                   10                  15

Asp Thr Asn Cys Ala Tyr Val Cys Gln Thr Glu Gly Phe Thr Ala Gly
                20                  25                  30

Lys Cys Val Gly Val Gln Arg His Cys His Cys Thr Lys Asp Cys
            35                  40                  45
```

<210> SEQ ID NO 76
<211> LENGTH: 512
<212> TYPE: DNA
<213> ORGANISM: Triticum aestivum
<220> FEATURE:
<221> NAME/KEY: CDS
<222> LOCATION: (85)...(342)
<220> FEATURE:
<221> NAME/KEY: mat_peptide
<222> LOCATION: (193)...(339)
<220> FEATURE:
<221> NAME/KEY: misc_feature
<222> LOCATION: 483, 491
<223> OTHER INFORMATION: n = A,T,C or G

<400> SEQUENCE: 76

```
atcactgtaa ccttaagttg gactacagca tccgttgcga aaccaccaga atcataaggt        60
agacattcta cgcaagcaga gcaa atg gcg tcg acc tct cgc cgt atg gtt         111
                          Met Ala Ser Thr Ser Arg Arg Met Val
                            1               5 gcg tcc gtc ctc ttg gtc ctt ctt ctc ctc gtc gcc aca gag atg ggg         159
Ala Ser Val Leu Leu Val Leu Leu Leu Leu Val Ala Thr Glu Met Gly
 10                  15                  20                  25 acg atg agg gtg gcg gag gcg agg cac ggg cac agg cac tgc gag tcg         207
Thr Met Arg Val Ala Glu Ala Arg His Gly His Arg His Cys Glu Ser
                30                  35                  40 caa agc cac agg tac cgc gga gcg tgc tgg agg gac gac aac tgc gaa         255
Gln Ser His Arg Tyr Arg Gly Ala Cys Trp Arg Asp Asp Asn Cys Glu
            45                  50                  55 cac gtc tgc aac acc gag ggc ttc cct tgg ggc aag tgc aag ttc cac         303
His Val Cys Asn Thr Glu Gly Phe Pro Trp Gly Lys Cys Lys Phe His
        60                  65                  70
```

-continued

```
gac ttc gaa agg aag tgc ttc tgc aag aaa ccg tgc tag ccacttcatc      352
Asp Phe Glu Arg Lys Cys Phe Cys Lys Lys Pro Cys  *
         75                  80                  85 gaccgatgga tcagctggct agttagccgc gcaccacgac caccctcgtg atcttcgtag    412
tgctcctctc ctgtttcgtg taccgctttc cttaatccta atctagtaag gtctacatgc    472
gttgtgcatg ncaattccnt ggtacaagta attttgctcc                          512
```

<210> SEQ ID NO 77
<211> LENGTH: 85
<212> TYPE: PRT
<213> ORGANISM: Triticum aestivum

<400> SEQUENCE: 77

```
Met Ala Ser Thr Ser Arg Arg Met Val Ala Ser Val Leu Leu Val Leu
 1               5                  10                  15

Leu Leu Leu Val Ala Thr Glu Met Gly Thr Met Arg Val Ala Glu Ala
             20                  25                  30

Arg His Gly His Arg His Cys Glu Ser Gln Ser His Arg Tyr Arg Gly
         35                  40                  45

Ala Cys Trp Arg Asp Asp Asn Cys Glu His Val Cys Asn Thr Glu Gly
     50                  55                  60

Phe Pro Trp Gly Lys Cys Lys Phe His Asp Phe Glu Arg Lys Cys Phe
65                  70                  75                  80

Cys Lys Lys Pro Cys
                 85
```

<210> SEQ ID NO 78
<211> LENGTH: 49
<212> TYPE: PRT
<213> ORGANISM: Triticum aestivum

<400> SEQUENCE: 78

```
Arg His Cys Glu Ser Gln Ser His Arg Tyr Arg Gly Ala Cys Trp Arg
 1               5                  10                  15

Asp Asp Asn Cys Glu His Val Cys Asn Thr Glu Gly Phe Pro Trp Gly
             20                  25                  30

Lys Cys Lys Phe His Asp Phe Glu Arg Lys Cys Phe Cys Lys Lys Pro
         35                  40                  45

Cys
```

<210> SEQ ID NO 79
<211> LENGTH: 587
<212> TYPE: DNA
<213> ORGANISM: Triticum aestivum
<220> FEATURE:
<221> NAME/KEY: CDS
<222> LOCATION: (74)...(328)
<220> FEATURE:
<221> NAME/KEY: mat_peptide
<222> LOCATION: (176)...(322)

<400> SEQUENCE: 79

```
gcacgaggta accttaagtt ggagtacatc gcccctcct agcaaaacca ccagcatcac     60
gcaagcagag caa atg gag tcg acc tct cgc cat atg gtt gcg tcc gtc      109
                Met Glu Ser Thr Ser Arg His Met Val Ala Ser Val
                 1               5                  10 ctc ttg gtc ctt ctc ctc ctc gtc gcc aca gag atg ggg acg acg agg    157
Leu Leu Val Leu Leu Leu Leu Val Ala Thr Glu Met Gly Thr Thr Arg
             15                  20                  25
```

```
gtg gcg gag gcg agg cac agg cac tgc gag tcg cag agc cac agg tac    205
Val Ala Glu Ala Arg His Arg His Cys Glu Ser Gln Ser His Arg Tyr
     30                  35                  40 cgc gga gcg tgc tgg agg gac gac aac tgc aag cac gtc tgc aac acc    253
Arg Gly Ala Cys Trp Arg Asp Asp Asn Cys Lys His Val Cys Asn Thr
 45                  50                  55                  60 gag ggc ttc ccc tcg ggc aag tgc aag ttc cac ggc ttc gaa agc aag    301
Glu Gly Phe Pro Ser Gly Lys Cys Lys Phe His Gly Phe Glu Ser Lys
                 65                  70                  75 tgc gtc tgc acg aaa ccc tgc cag tag ccacctcatc gaccgacgga          348
Cys Val Cys Thr Lys Pro Cys Gln *
                 80 tcacatagct agctagccgc gcaccacgac cgccctcgtg tcttcagagt gttcctcccc   408 tgttcgtgta ccgctttcct tattccgaat ctagtaaggt ctacatgcgt tgtgcatgcc   468 attttccttg ttacaagtgt tttgcttcct acggtgtaat ctagcttggg tgctaataaa   528 aattggtcgt cggtgtgctt gggcgtcttt tatcaaaaaa aaaaaaaaaa aaaaaaaa     587
```

<210> SEQ ID NO 80
<211> LENGTH: 84
<212> TYPE: PRT
<213> ORGANISM: Triticum aestivum

<400> SEQUENCE: 80

```
Met Glu Ser Thr Ser Arg His Met Val Ala Ser Val Leu Leu Val Leu
 1               5                  10                  15

Leu Leu Leu Val Ala Thr Glu Met Gly Thr Thr Arg Val Ala Glu Ala
                 20                  25                  30

Arg His Arg His Cys Glu Ser Gln Ser His Arg Tyr Arg Gly Ala Cys
             35                  40                  45

Trp Arg Asp Asp Asn Cys Lys His Val Cys Asn Thr Glu Gly Phe Pro
 50                  55                  60

Ser Gly Lys Cys Lys Phe His Gly Phe Glu Ser Lys Cys Val Cys Thr
65                  70                  75                  80

Lys Pro Cys Gln
```

<210> SEQ ID NO 81
<211> LENGTH: 49
<212> TYPE: PRT
<213> ORGANISM: Triticum aestivum

<400> SEQUENCE: 81

```
Arg His Cys Glu Ser Gln Ser His Arg Tyr Arg Gly Ala Cys Trp Arg
 1               5                  10                  15

Asp Asp Asn Cys Lys His Val Cys Asn Thr Glu Gly Phe Pro Ser Gly
                 20                  25                  30

Lys Cys Lys Phe His Gly Phe Glu Ser Lys Cys Val Cys Thr Lys Pro
             35                  40                  45

Cys
```

<210> SEQ ID NO 82
<211> LENGTH: 516
<212> TYPE: DNA
<213> ORGANISM: Beta vulgaris
<220> FEATURE:
<221> NAME/KEY: CDS
<222> LOCATION: (31)...(267)
<220> FEATURE:
<221> NAME/KEY: mat_peptide

<222> LOCATION: (121)...(261)

<400> SEQUENCE: 82

```
gcacgagggt taaagttcat tgcgcataat atg aaa cag tca atg aag ccc gtt          54
                                 Met Lys Gln Ser Met Lys Pro Val
                                  1               5 gtt gct ttt ttc ctt gtg ttc ttg att gtc ctg aca aca gat gtt ggc         102
Val Ala Phe Phe Leu Val Phe Leu Ile Val Leu Thr Thr Asp Val Gly
     10                  15                  20 aca aga gta gct gaa gca agg aca tgt atg act cca agt cac cag ttc         150
Thr Arg Val Ala Glu Ala Arg Thr Cys Met Thr Pro Ser His Gln Phe
 25                  30                  35                  40 agg gga ata tgc gtt agt agt aga aat tgt gaa tct gct tgc cac act         198
Arg Gly Ile Cys Val Ser Ser Arg Asn Cys Glu Ser Ala Cys His Thr
                 45                  50                  55 gag aga ttt cct gga gga acg tgt caa ggc ttt cgt aga aga tgc atg         246
Glu Arg Phe Pro Gly Gly Thr Cys Gln Gly Phe Arg Arg Arg Cys Met
             60                  65                  70 tgc act aag cct tgc gca tag gtggttcgac ttatctacgt caagccttgc            297
Cys Thr Lys Pro Cys Ala  *
         75 gcataagtgg tttaatttgc cttctcaagt tttagcataa aataaatgtt tctagacaca       357 atgtgaagta cctaatgctc aatcactatg ctacaatata tatttataat gtacgctagt       417 gattttatat gttgttaatt aggtgtaatt gaagtgtatg gtgtgaaact ctaatgtata       477 gcaccttgct atacatctat ataagtttat gtttgtgaa                              516
```

<210> SEQ ID NO 83
<211> LENGTH: 78
<212> TYPE: PRT
<213> ORGANISM: Beta vulgaris

<400> SEQUENCE: 83

```
Met Lys Gln Ser Met Lys Pro Val Val Ala Phe Phe Leu Val Phe Leu
 1               5                  10                  15

Ile Val Leu Thr Thr Asp Val Gly Thr Arg Val Ala Glu Ala Arg Thr
             20                  25                  30

Cys Met Thr Pro Ser His Gln Phe Arg Gly Ile Cys Val Ser Ser Arg
         35                  40                  45

Asn Cys Glu Ser Ala Cys His Thr Glu Arg Phe Pro Gly Gly Thr Cys
     50                  55                  60

Gln Gly Phe Arg Arg Arg Cys Met Cys Thr Lys Pro Cys Ala
 65                  70                  75
```

<210> SEQ ID NO 84
<211> LENGTH: 47
<212> TYPE: PRT
<213> ORGANISM: Beta vulgaris

<400> SEQUENCE: 84

```
Arg Thr Cys Met Thr Pro Ser His Gln Phe Arg Gly Ile Cys Val Ser
 1               5                  10                  15

Ser Arg Asn Cys Glu Ser Ala Cys His Thr Glu Arg Phe Pro Gly Gly
             20                  25                  30

Thr Cys Gln Gly Phe Arg Arg Arg Cys Met Cys Thr Lys Pro Cys
         35                  40                  45
```

<210> SEQ ID NO 85
<211> LENGTH: 508

```
<212> TYPE: DNA
<213> ORGANISM: Beta vulgaris
<220> FEATURE:
<221> NAME/KEY: CDS
<222> LOCATION: (31)...(267)
<220> FEATURE:
<221> NAME/KEY: mat_peptide
<222> LOCATION: (121)...(261)

<400> SEQUENCE: 85
tttaattagt taaagctcat tgcgcataat atg aaa cag tca atg aag ccc gtt        54
                                 Met Lys Gln Ser Met Lys Pro Val
                                  1               5 gtt gct ttt ttc ctt gtg ttc ttg att gtc ctg aca aca gat gtt ggc       102
Val Ala Phe Phe Leu Val Phe Leu Ile Val Leu Thr Thr Asp Val Gly
         10                  15                  20 aca aga gta gct gaa gca agg aca tgt atg act cca agt cac cag ttc       150
Thr Arg Val Ala Glu Ala Arg Thr Cys Met Thr Pro Ser His Gln Phe
 25                  30                  35                  40 agg gga ata tgc gtt agt agt aga aat tgt gaa tct gct tgc cac act       198
Arg Gly Ile Cys Val Ser Ser Arg Asn Cys Glu Ser Ala Cys His Thr
                 45                  50                  55 gag aga ttt cct gga gga acg tgt caa ggc ttt cgt aga aga tgc atg       246
Glu Arg Phe Pro Gly Gly Thr Cys Gln Gly Phe Arg Arg Arg Cys Met
             60                  65                  70 tgc act agg cct tgc gca tag gtggttcgac ttatctacgt caagccttgc          297
Cys Thr Arg Pro Cys Ala  *
                 75 gcatataagt ggtttaattt gccttctcaa gttttagcat aaaataaatg tttctagaca     357 caatgtgaag tgcggcaagt acctaatgct caatcactat gctacaatat atatttataa     417 tgtacgctag tgatttata tgttgttaat taggtgcaat tgaagtgtat ggtgtgaaac      477 tctaatgtat agcaccttgc tatacatcta t                                    508

<210> SEQ ID NO 86
<211> LENGTH: 78
<212> TYPE: PRT
<213> ORGANISM: Beta vulgaris

<400> SEQUENCE: 86

Met Lys Gln Ser Met Lys Pro Val Val Ala Phe Phe Leu Val Phe Leu
 1               5                  10                  15

Ile Val Leu Thr Thr Asp Val Gly Thr Arg Val Ala Glu Ala Arg Thr
             20                  25                  30

Cys Met Thr Pro Ser His Gln Phe Arg Gly Ile Cys Val Ser Ser Arg
         35                  40                  45

Asn Cys Glu Ser Ala Cys His Thr Glu Arg Phe Pro Gly Gly Thr Cys
 50                  55                  60

Gln Gly Phe Arg Arg Arg Cys Met Cys Thr Arg Pro Cys Ala
65                  70                  75

<210> SEQ ID NO 87
<211> LENGTH: 47
<212> TYPE: PRT
<213> ORGANISM: Beta vulgaris

<400> SEQUENCE: 87

Arg Thr Cys Met Thr Pro Ser His Gln Phe Arg Gly Ile Cys Val Ser
 1               5                  10                  15

Ser Arg Asn Cys Glu Ser Ala Cys His Thr Glu Arg Phe Pro Gly Gly
             20                  25                  30
```

```
Thr Cys Gln Gly Phe Arg Arg Arg Cys Met Cys Thr Arg Pro Cys
         35                  40                  45

<210> SEQ ID NO 88
<211> LENGTH: 470
<212> TYPE: DNA
<213> ORGANISM: Hedera helix
<220> FEATURE:
<221> NAME/KEY: CDS
<222> LOCATION: (20)...(262)
<220> FEATURE:
<221> NAME/KEY: mat_peptide
<222> LOCATION: (113)...(259)

<400> SEQUENCE: 88
gcacgaggga agattaaat atg gca gga aaa ttt agc cca act agc ttt ctt       52
                    Met Ala Gly Lys Phe Ser Pro Thr Ser Phe Leu
                     1               5                  10 gca atc tct ctc gtt ttt ttc ctt ctc gct aac acg gaa aca att ata      100
Ala Ile Ser Leu Val Phe Phe Leu Leu Ala Asn Thr Glu Thr Ile Ile
             15                  20                  25 ggt gtt gag gga aaa tta tgt gaa aaa cca agc ttg aca tgg tcc ggg      148
Gly Val Glu Gly Lys Leu Cys Glu Lys Pro Ser Leu Thr Trp Ser Gly
         30                  35                  40 aaa tgc gga aac aca cag aac tgt gat aag caa tgc cag act tgg gaa      196
Lys Cys Gly Asn Thr Gln Asn Cys Asp Lys Gln Cys Gln Thr Trp Glu
     45                  50                  55 tct gca aaa cat gga gca tgt cac aaa cga ggc aat tgg aaa tgc ttc      244
Ser Ala Lys His Gly Ala Cys His Lys Arg Gly Asn Trp Lys Cys Phe
 60                  65                  70                  75 tgt tac ttt gac tgt tga tccaactcca aggaatattt aagaatctta             292
Cys Tyr Phe Asp Cys *
                 80 aaccatgcat gcataaaaat gcatgcgtat gagttaattt cctttgttat tattagtact    352 gcaatcttaa taaataaaag gaaatgcttc ttagctggcg caaaaaaaaa aaaaaaaaa     412 aaaaaaaaaa aaaaaaaaaa tttaaaaaaa aaaaaaaaaa aaaaaaaaaa aaaaaaa       470

<210> SEQ ID NO 89
<211> LENGTH: 80
<212> TYPE: PRT
<213> ORGANISM: Hedera helix

<400> SEQUENCE: 89

Met Ala Gly Lys Phe Ser Pro Thr Ser Phe Leu Ala Ile Ser Leu Val
 1               5                  10                  15

Phe Phe Leu Leu Ala Asn Thr Glu Thr Ile Ile Gly Val Glu Gly Lys
             20                  25                  30

Leu Cys Glu Lys Pro Ser Leu Thr Trp Ser Gly Lys Cys Gly Asn Thr
         35                  40                  45

Gln Asn Cys Asp Lys Gln Cys Gln Thr Trp Glu Ser Ala Lys His Gly
     50                  55                  60

Ala Cys His Lys Arg Gly Asn Trp Lys Cys Phe Cys Tyr Phe Asp Cys
 65                  70                  75                  80

<210> SEQ ID NO 90
<211> LENGTH: 49
<212> TYPE: PRT
<213> ORGANISM: Hedera helix

<400> SEQUENCE: 90
```

```
Lys Leu Cys Glu Lys Pro Ser Leu Thr Trp Ser Gly Lys Cys Gly Asn
 1               5                  10                  15

Thr Gln Asn Cys Asp Lys Gln Cys Gln Thr Trp Glu Ser Ala Lys His
            20                  25                  30

Gly Ala Cys His Lys Arg Gly Asn Trp Lys Cys Phe Cys Tyr Phe Asp
            35                  40                  45

Cys

<210> SEQ ID NO 91
<211> LENGTH: 469
<212> TYPE: DNA
<213> ORGANISM: Tulipa fosteriana
<220> FEATURE:
<221> NAME/KEY: CDS
<222> LOCATION: (3)...(233)
<220> FEATURE:
<221> NAME/KEY: mat_peptide
<222> LOCATION: (84)...(230)
<220> FEATURE:
<221> NAME/KEY: misc_feature
<222> LOCATION: 329, 390, 432, 457, 459, 463
<223> OTHER INFORMATION: n = A,T,C or G

<400> SEQUENCE: 91 tg aag ctc aac ata gct ctc ctc tgc tct ttc ttc ttc gct ctc ctc         47
   Lys Leu Asn Ile Ala Leu Leu Cys Ser Phe Phe Phe Ala Leu Leu
    1               5                  10                  15 tta ctg ctg gct tct ggg cct gga gtt gaa gct ggt ctc ctc tgc cga        95
Leu Leu Leu Ala Ser Gly Pro Gly Val Glu Ala Gly Leu Leu Cys Arg
            20                  25                  30 agg gtt tcg agc aat ggg ttc aaa gga ctg tgc ttc agc agc gac aag       143
Arg Val Ser Ser Asn Gly Phe Lys Gly Leu Cys Phe Ser Ser Asp Lys
            35                  40                  45 tgt gcc aag gtt tgc atg agc gag ggc aac cgc agg ggc ggt tct tgc       191
Cys Ala Lys Val Cys Met Ser Glu Gly Asn Arg Arg Gly Gly Ser Cys
        50                  55                  60 gat ggc att cgc cgt cgc tgc atg tgt aag cca aac tgc tga               233
Asp Gly Ile Arg Arg Arg Cys Met Cys Lys Pro Asn Cys  *
        65                  70                  75 accaccggcc ttcgagacac tgctgtatca gaatctgcta gccctctat ctgtactacg      293 ttcaagtatg tatgttttgt gaccaaaata aagaanaaaa agctcatgat cttgtgggcc     353
ggctcttcat gtcttgaata tttatgctag agaatantaa cctcaagtta ctcatgttta     413
aattacgact taatatgang ttaaataagt tgatgcctat agcncncaan ccccta         469

<210> SEQ ID NO 92
<211> LENGTH: 76
<212> TYPE: PRT
<213> ORGANISM: Tulipa fosteriana

<400> SEQUENCE: 92

Lys Leu Asn Ile Ala Leu Leu Cys Ser Phe Phe Phe Ala Leu Leu Leu
 1               5                  10                  15

Leu Leu Ala Ser Gly Pro Gly Val Glu Ala Gly Leu Leu Cys Arg Arg
            20                  25                  30

Val Ser Ser Asn Gly Phe Lys Gly Leu Cys Phe Ser Ser Asp Lys Cys
            35                  40                  45

Ala Lys Val Cys Met Ser Glu Gly Asn Arg Arg Gly Gly Ser Cys Asp
        50                  55                  60

Gly Ile Arg Arg Arg Cys Met Cys Lys Pro Asn Cys
65                  70                  75
```

<210> SEQ ID NO 93
<211> LENGTH: 49
<212> TYPE: PRT
<213> ORGANISM: Tulipa fosteriana

<400> SEQUENCE: 93

```
Leu Leu Cys Arg Arg Val Ser Ser Asn Gly Phe Lys Gly Leu Cys Phe
 1               5                  10                  15

Ser Ser Asp Lys Cys Ala Lys Val Cys Met Ser Glu Gly Asn Arg Arg
            20                  25                  30

Gly Gly Ser Cys Asp Gly Ile Arg Arg Cys Met Cys Lys Pro Asn
        35                  40                  45

Cys
```

<210> SEQ ID NO 94
<211> LENGTH: 416
<212> TYPE: DNA
<213> ORGANISM: Tulipa gesneriana
<220> FEATURE:
<221> NAME/KEY: CDS
<222> LOCATION: (3)...(233)
<220> FEATURE:
<221> NAME/KEY: mat_peptide
<222> LOCATION: (84)...(230)
<220> FEATURE:
<221> NAME/KEY: misc_feature
<222> LOCATION: 355, 380, 385, 396, 405
<223> OTHER INFORMATION: n = A,T,C or G

<400> SEQUENCE: 94

```
gg aag ctc agc ata gct ctc ctc tgc tct ttc ttc ttc gct ctc ttc        47
   Lys Leu Ser Ile Ala Leu Leu Cys Ser Phe Phe Phe Ala Leu Phe
    1               5                  10                  15 tta ctg ctg gct tct ggg cct gga gtg gaa gct agt ctc ctc tgc cga       95
Leu Leu Leu Ala Ser Gly Pro Gly Val Glu Ala Ser Leu Leu Cys Arg
            20                  25                  30 agg gtt tcg agc aat ggg ttc aaa gga ctg tgc ttc agc agc gac aag      143
Arg Val Ser Ser Asn Gly Phe Lys Gly Leu Cys Phe Ser Ser Asp Lys
                35                  40                  45 tgt gcc aag gtt tgc atg agc gag ggc aac cgc agt ggt ggt tct tgc      191
Cys Ala Lys Val Cys Met Ser Glu Gly Asn Arg Ser Gly Gly Ser Cys
        50                  55                  60 gat ggc gtt cgc cgt cgg tgc atg tgt aag cca aac tgc tga              233
Asp Gly Val Arg Arg Arg Cys Met Cys Lys Pro Asn Cys *
        65                  70                  75 accacaggcc tccgagaaac ggctgtatct gtagctgcta agttactcta tctgtagtac    293
gttgagtatg tatgttttgt gaccaaaata aaagaagaaa aggctcatga tcttgttggc    353
cngctcctcg tgtcttgaat atttaangtt angagaaaaa gtnactcagt tnccccaggt    413
gtt                                                                  416
```

<210> SEQ ID NO 95
<211> LENGTH: 76
<212> TYPE: PRT
<213> ORGANISM: Tulipa gesneriana

<400> SEQUENCE: 95

```
Lys Leu Ser Ile Ala Leu Leu Cys Ser Phe Phe Phe Ala Leu Phe Leu
 1               5                  10                  15

Leu Leu Ala Ser Gly Pro Gly Val Glu Ala Ser Leu Leu Cys Arg Arg
            20                  25                  30
```

```
Val Ser Ser Asn Gly Phe Lys Gly Leu Cys Phe Ser Ser Asp Lys Cys
         35                  40                  45

Ala Lys Val Cys Met Ser Glu Gly Asn Arg Ser Gly Gly Ser Cys Asp
     50                  55                  60

Gly Val Arg Arg Arg Cys Met Cys Lys Pro Asn Cys
 65                  70                  75

<210> SEQ ID NO 96
<211> LENGTH: 49
<212> TYPE: PRT
<213> ORGANISM: Tulipa gesneriana

<400> SEQUENCE: 96

Leu Leu Cys Arg Arg Val Ser Ser Asn Gly Phe Lys Gly Leu Cys Phe
 1               5                  10                  15

Ser Ser Asp Lys Cys Ala Lys Val Cys Met Ser Glu Gly Asn Arg Ser
             20                  25                  30

Gly Gly Ser Cys Asp Gly Val Arg Arg Arg Cys Met Cys Lys Pro Asn
         35                  40                  45

Cys

<210> SEQ ID NO 97
<211> LENGTH: 468
<212> TYPE: DNA
<213> ORGANISM: Tulipa gesneriana
<220> FEATURE:
<221> NAME/KEY: CDS
<222> LOCATION: (13)...(186)
<220> FEATURE:
<221> NAME/KEY: mat_peptide
<222> LOCATION: (49)...(183)
<220> FEATURE:
<221> NAME/KEY: misc_feature
<222> LOCATION: 467, 468
<223> OTHER INFORMATION: n = A,T,C or G

<400> SEQUENCE: 97
gcacgaggca ct cct cta cct tca gaa atg ggg aca acg acg gtg gag gcg    51
                            Pro Leu Pro Ser Glu Met Gly Thr Thr Thr Val Glu Ala
                             1               5                  10 gat tgc tac aga ccg agc ggg agt tac cac ggc ccc tgc ttt agt tcg    99
Asp Cys Tyr Arg Pro Ser Gly Ser Tyr His Gly Pro Cys Phe Ser Ser
         15                  20                  25 agc ggc tgc gat aat acc tgc aag att cag gac ggg cac cca gga gga   147
Ser Gly Cys Asp Asn Thr Cys Lys Ile Gln Asp Gly His Pro Gly Gly
     30                  35                  40                  45 ggg tct tgc agc ggc ttt aag tgc tac tgc agg tgt tga tgatgcttta   196
Gly Ser Cys Ser Gly Phe Lys Cys Tyr Cys Arg Cys *
                 50                  55 tgcttcgagt ctattcggag aagagtggta gagcctttcg atgggtctat taagtgtctt   256
gatatgaata atatggacct tagtgtgctt cacctaggtc catgaatttc ctgcttaagt   316
gtgtagtagc ttgtgtgagc tccacgtctg tgttatgtag tatggagcct gttatatagt   376
aatcacaagt tcataactgt tgtgatgcat gggcatctta taaaatatgt aatttgttac   436
cacataagta taatatatat gagatttgct nn                                 468

<210> SEQ ID NO 98
<211> LENGTH: 57
<212> TYPE: PRT
<213> ORGANISM: Tulipa gesneriana
```

```
<400> SEQUENCE: 98

Pro Leu Pro Ser Glu Met Gly Thr Thr Thr Val Glu Ala Asp Cys Tyr
  1               5                  10                  15

Arg Pro Ser Gly Ser Tyr His Gly Pro Cys Phe Ser Ser Ser Gly Cys
             20                  25                  30

Asp Asn Thr Cys Lys Ile Gln Asp Gly His Pro Gly Gly Gly Ser Cys
         35                  40                  45

Ser Gly Phe Lys Cys Tyr Cys Arg Cys
     50                  55

<210> SEQ ID NO 99
<211> LENGTH: 45
<212> TYPE: PRT
<213> ORGANISM: Tulipa gesneriana

<400> SEQUENCE: 99

Ala Asp Cys Tyr Arg Pro Ser Gly Ser Tyr His Gly Pro Cys Phe Ser
  1               5                  10                  15

Ser Ser Gly Cys Asp Asn Thr Cys Lys Ile Gln Asp Gly His Pro Gly
             20                  25                  30

Gly Gly Ser Cys Ser Gly Phe Lys Cys Tyr Cys Arg Cys
         35                  40                  45

<210> SEQ ID NO 100
<211> LENGTH: 471
<212> TYPE: DNA
<213> ORGANISM: Tulipa fosteriana
<220> FEATURE:
<221> NAME/KEY: CDS
<222> LOCATION: (16)...(225)
<220> FEATURE:
<221> NAME/KEY: mat_peptide
<222> LOCATION: (91)...(222)
<220> FEATURE:
<221> NAME/KEY: misc_feature
<222> LOCATION: 147, 366, 371, 392, 396, 398, 415, 432, 438, 447, 453,
      455, 458
<223> OTHER INFORMATION: n = A,T,C or G

<400> SEQUENCE: 100
cctctgcctt cagat atg gcg aaa att ccg acc ctc cta ctg ctg ctc gtc        51
                Met Ala Lys Ile Pro Thr Leu Leu Leu Leu Val
                  1               5                  10 ctc gtt gtc gcc tct gaa atg ggg aca acg acg gtg gag gca gat tgc        99
Leu Val Val Ala Ser Glu Met Gly Thr Thr Thr Val Glu Ala Asp Cys
         15                  20                  25 tac aga ccg agc ggg agt tac cac ggc ccc tgc ttt agt tcg agc ggn        147
Tyr Arg Pro Ser Gly Ser Tyr His Gly Pro Cys Phe Ser Ser Ser Gly
         30                  35                  40 tgc gat agt acc tgc aag att cag gac ggg ctc tca gga ggg tct tgc        195
Cys Asp Ser Thr Cys Lys Ile Gln Asp Gly Leu Ser Gly Gly Ser Cys
 45                  50                  55                  60 agc ggc ttc aag tgc tac tgc agg tgt tga tgatgattca tgcttcgaat          245
Ser Gly Phe Lys Cys Tyr Cys Arg Cys *
                 65 ctattcggag tgtggtagaa gccttgtggt gctctatttc atgggtatta agtgtcttga      305 tatgaataaa tatggacctt agtgtgcttc acctaggtcc gtgcatttcc tgcttaagtg      365 ngttantagc cttgtgagag ctccacntcc ngngttacgt tagtttgggn cgcccaaaag      425 taaccantgt ttncaaaaaa tnttgtgnan gtntggggta ttgtac                    471
```

```
<210> SEQ ID NO 101
<211> LENGTH: 69
<212> TYPE: PRT
<213> ORGANISM: Tulipa fosteriana

<400> SEQUENCE: 101

Met Ala Lys Ile Pro Thr Leu Leu Leu Leu Val Leu Val Val Ala
1               5                   10                  15

Ser Glu Met Gly Thr Thr Thr Val Glu Ala Asp Cys Tyr Arg Pro Ser
            20                  25                  30

Gly Ser Tyr His Gly Pro Cys Phe Ser Ser Gly Cys Asp Ser Thr
        35                  40                  45

Cys Lys Ile Gln Asp Gly Leu Ser Gly Gly Ser Cys Ser Gly Phe Lys
    50                  55                  60

Cys Tyr Cys Arg Cys
65

<210> SEQ ID NO 102
<211> LENGTH: 44
<212> TYPE: PRT
<213> ORGANISM: Tulipa fosteriana

<400> SEQUENCE: 102

Ala Asp Cys Tyr Arg Pro Ser Gly Ser Tyr His Gly Pro Cys Phe Ser
1               5                   10                  15

Ser Ser Gly Cys Asp Ser Thr Cys Lys Ile Gln Asp Gly Leu Ser Gly
            20                  25                  30

Gly Ser Cys Ser Gly Phe Lys Cys Tyr Cys Arg Cys
        35                  40

<210> SEQ ID NO 103
<211> LENGTH: 534
<212> TYPE: DNA
<213> ORGANISM: Tulipa gesneriana
<220> FEATURE:
<221> NAME/KEY: CDS
<222> LOCATION: (21)...(233)
<220> FEATURE:
<221> NAME/KEY: mat_peptide
<222> LOCATION: (96)...(230)
<220> FEATURE:
<221> NAME/KEY: misc_feature
<222> LOCATION: 533
<223> OTHER INFORMATION: n = A,T,C or G

<400> SEQUENCE: 103
gcacgaggct accttcagat atg gcg aaa att ccg acc ctc cta ctg ctt ctc        53
                     Met Ala Lys Ile Pro Thr Leu Leu Leu Leu Leu
                     1               5                   10 gtc ctc gtt gtc gcc tct gaa atg ggg aca acg acg gtg gag gcg gat        101
Val Leu Val Val Ala Ser Glu Met Gly Thr Thr Thr Val Glu Ala Asp
            15                  20                  25 tgc tac aga ccg agc ggg agt tac cac ggc ccc tgc ttt agt tcg agc        149
Cys Tyr Arg Pro Ser Gly Ser Tyr His Gly Pro Cys Phe Ser Ser Ser
        30                  35                  40 ggc tgc gat aat acc tgc aag att cag gac ggg ctc cca ggt gga ggg        197
Gly Cys Asp Asn Thr Cys Lys Ile Gln Asp Gly Leu Pro Gly Gly Gly
    45                  50                  55 tct tgc agc ggc ttc aag tgc tac tgc agg tgt tga tgatgcttta             243
Ser Cys Ser Gly Phe Lys Cys Tyr Cys Arg Cys *
60                  65                  70 tggttcaaat ctattctgag aagtgtgcta gagccttgtg gtgctctatt tcatgggtct      303
```

```
attaagtgtc ttgatatgaa taatatggac cttagtgtgc ttcacctagg tccgtgcatt      363
tcctgcttaa gtgtgtagta gcttgtgaga gctccacgtc tgtgttatgt agtttggagc      423
ctgttatata gtaatcactg tttcataaat gttgtgatgt attggtattg tataaaatat      483
gtaatttgtt accacgtgaa tataatacat atgagtgttg ctagtctgtn a              534
```

```
<210> SEQ ID NO 104
<211> LENGTH: 70
<212> TYPE: PRT
<213> ORGANISM: Tulipa gesneriana

<400> SEQUENCE: 104
```

```
Met Ala Lys Ile Pro Thr Leu Leu Leu Leu Val Leu Val Val Ala
 1               5                  10                  15

Ser Glu Met Gly Thr Thr Thr Val Glu Ala Asp Cys Tyr Arg Pro Ser
            20                  25                  30

Gly Ser Tyr His Gly Pro Cys Phe Ser Ser Gly Cys Asp Asn Thr
        35                  40                  45

Cys Lys Ile Gln Asp Gly Leu Pro Gly Gly Gly Ser Cys Ser Gly Phe
 50                  55                  60

Lys Cys Tyr Cys Arg Cys
 65                  70
```

```
<210> SEQ ID NO 105
<211> LENGTH: 45
<212> TYPE: PRT
<213> ORGANISM: Tulipa gesneriana

<400> SEQUENCE: 105
```

```
Ala Asp Cys Tyr Arg Pro Ser Gly Ser Tyr His Gly Pro Cys Phe Ser
 1               5                  10                  15

Ser Ser Gly Cys Asp Asn Thr Cys Lys Ile Gln Asp Gly Leu Pro Gly
            20                  25                  30

Gly Gly Ser Cys Ser Gly Phe Lys Cys Tyr Cys Arg Cys
        35                  40                  45
```

```
<210> SEQ ID NO 106
<211> LENGTH: 441
<212> TYPE: DNA
<213> ORGANISM: Tulipa gesneriana
<220> FEATURE:
<221> NAME/KEY: CDS
<222> LOCATION: (44)...(253)
<220> FEATURE:
<221> NAME/KEY: mat_peptide
<222> LOCATION: (119)...(250)
<220> FEATURE:
<221> NAME/KEY: misc_feature
<222> LOCATION: 24, 270, 294, 423
<223> OTHER INFORMATION: n = A,T,C or G

<400> SEQUENCE: 106
```

```
gacctcacca agctagtctt ccancacgcc tctgccttca gat atg tcg aaa att       55
                                             Met Ser Lys Ile
                                              1 ccg acc ctc cta ctg ctg ctc gtc ctc gtt gtc gcc tca gaa atg ggg      103
Pro Thr Leu Leu Leu Leu Leu Val Leu Val Val Ala Ser Glu Met Gly
 5                  10                  15                  20 aca acg acg gtg gag gcg gat tgc tac aga ccg agc ggg agt tac cac      151
Thr Thr Thr Val Glu Ala Asp Cys Tyr Arg Pro Ser Gly Ser Tyr His
                25                  30                  35 ggc ccc tgc ttt gat tcg gac ggc tgc gat agt acc tgc aag att cag      199
```

```
Gly Pro Cys Phe Asp Ser Asp Gly Cys Asp Ser Thr Cys Lys Ile Gln
            40                  45                  50 gac ggg aaa cca gga ggg act tgc agc ggc ttc cgc tgc ttc tgc aac    247
Asp Gly Lys Pro Gly Gly Thr Cys Ser Gly Phe Arg Cys Phe Cys Asn
            55                  60                  65 tgt tga tgatgcttca agcttcnaat ctattcggag aaatgtggta naaccttgtg     303
Cys * gtgctctatt tcaagggttt aataaagtgt cttcatatta aaaaaatggg ccttaagtgt   363
gcttcaccta aggttcaatg cttttcctgc ttaaatgtgt tgtagcttgt gtgagcttcn   423
acgtccgtgt caagttgg                                                 441

<210> SEQ ID NO 107
<211> LENGTH: 69
<212> TYPE: PRT
<213> ORGANISM: Tulipa gesneriana

<400> SEQUENCE: 107

Met Ser Lys Ile Pro Thr Leu Leu Leu Leu Val Leu Val Val Ala
 1               5                  10                  15

Ser Glu Met Gly Thr Thr Thr Val Glu Ala Asp Cys Tyr Arg Pro Ser
            20                  25                  30

Gly Ser Tyr His Gly Pro Cys Phe Asp Ser Asp Gly Cys Asp Ser Thr
            35                  40                  45

Cys Lys Ile Gln Asp Gly Lys Pro Gly Gly Thr Cys Ser Gly Phe Arg
        50                  55                  60

Cys Phe Cys Asn Cys
65

<210> SEQ ID NO 108
<211> LENGTH: 44
<212> TYPE: PRT
<213> ORGANISM: Tulipa gesneriana

<400> SEQUENCE: 108

Ala Asp Cys Tyr Arg Pro Ser Gly Ser Tyr His Gly Pro Cys Phe Asp
 1               5                  10                  15

Ser Asp Gly Cys Asp Ser Thr Cys Lys Ile Gln Asp Gly Lys Pro Gly
            20                  25                  30

Gly Thr Cys Ser Gly Phe Arg Cys Phe Cys Asn Cys
            35                  40

<210> SEQ ID NO 109
<211> LENGTH: 427
<212> TYPE: DNA
<213> ORGANISM: Tulipa gesneriana
<220> FEATURE:
<221> NAME/KEY: CDS
<222> LOCATION: (4)...(276)
<220> FEATURE:
<221> NAME/KEY: mat_peptide
<222> LOCATION: (82)...(249)
<220> FEATURE:
<221> NAME/KEY: misc_feature
<222> LOCATION: 398
<223> OTHER INFORMATION: n = A,T,C or G

<400> SEQUENCE: 109 gca atg gag agg aag aat gta cca agt ggc ttc atc ttg gtg atg ctg    48
    Met Glu Arg Lys Asn Val Pro Ser Gly Phe Ile Leu Val Met Leu
     1               5                  10                  15 atc gtc ttg gaa tta gaa gtg atg gtg gtg aat ggg att tgc acg gag    96
```

```
Ile Val Leu Glu Leu Glu Val Met Val Val Asn Gly Ile Cys Thr Glu
         20                  25                  30 aag agc aag aat tgg aag ggc gtg tgc ttt gtg tca gag cac tgt gag    144
Lys Ser Lys Asn Trp Lys Gly Val Cys Phe Val Ser Glu His Cys Glu
             35                  40                  45 ctg aca tgc atg gct gaa ggt tcg gtc tac ggt tgg tgc gat tcc acg    192
Leu Thr Cys Met Ala Glu Gly Ser Val Tyr Gly Trp Cys Asp Ser Thr
         50                  55                  60 gat gca tcg tgg gct ata ttt aca aca tac tgc ttg tgt ttc aag ctc    240
Asp Ala Ser Trp Ala Ile Phe Thr Thr Tyr Cys Leu Cys Phe Lys Leu
 65                  70                  75 acc tca tgc ggg tca agt atg gaa aaa ggc aat tag aagtaacgac         286
Thr Ser Cys Gly Ser Ser Met Glu Lys Gly Asn  *
 80                  85                  90 aagccatggt gtcaattata actgtaatgg ctgatctctt aatacgcaca tctatctcta  346
taataatgtg gtgagcgaac ctatgatccg ggcattgttg ctgcctgatt antggatctt  406
aaaagttcaa ataaaattgt t                                            427
```

<210> SEQ ID NO 110
<211> LENGTH: 90
<212> TYPE: PRT
<213> ORGANISM: Tulipa gesneriana

<400> SEQUENCE: 110

```
Met Glu Arg Lys Asn Val Pro Ser Gly Phe Ile Leu Val Met Leu Ile
 1               5                  10                  15

Val Leu Glu Leu Glu Val Met Val Val Asn Gly Ile Cys Thr Glu Lys
             20                  25                  30

Ser Lys Asn Trp Lys Gly Val Cys Phe Val Ser Glu His Cys Glu Leu
         35                  40                  45

Thr Cys Met Ala Glu Gly Ser Val Tyr Gly Trp Cys Asp Ser Thr Asp
     50                  55                  60

Ala Ser Trp Ala Ile Phe Thr Thr Tyr Cys Leu Cys Phe Lys Leu Thr
 65                  70                  75                  80

Ser Cys Gly Ser Ser Met Glu Lys Gly Asn
                 85                  90
```

<210> SEQ ID NO 111
<211> LENGTH: 56
<212> TYPE: PRT
<213> ORGANISM: Tulipa gesneriana

<400> SEQUENCE: 111

```
Gly Ile Cys Thr Glu Lys Ser Lys Asn Trp Lys Gly Val Cys Phe Val
 1               5                  10                  15

Ser Glu His Cys Glu Leu Thr Cys Met Ala Glu Gly Ser Val Tyr Gly
             20                  25                  30

Trp Cys Asp Ser Thr Asp Ala Ser Trp Ala Ile Phe Thr Thr Tyr Cys
         35                  40                  45

Leu Cys Phe Lys Leu Thr Ser Cys
     50                  55
```

<210> SEQ ID NO 112
<211> LENGTH: 468
<212> TYPE: DNA
<213> ORGANISM: Tulipa gesneriana
<220> FEATURE:
<221> NAME/KEY: CDS
<222> LOCATION: (9)...(284)

```
<220> FEATURE:
<221> NAME/KEY: mat_peptide
<222> LOCATION: (90)...(257)
<220> FEATURE:
<221> NAME/KEY: misc_feature
<222> LOCATION: 321, 380, 386, 414, 432, 436, 441, 452, 462, 467
<223> OTHER INFORMATION: n = A,T,C or G

<400> SEQUENCE: 112 ggaaatca atg gag agg aag aat gta cca agt ggc ttc atc ttg gtg atg       50
        Met Glu Arg Lys Asn Val Pro Ser Gly Phe Ile Leu Val Met
        1               5                   10 ctg atc gtc ttg gca tta gca gaa gtg gtg gtg aat ggg gtt tgc            98
Leu Ile Val Leu Ala Leu Ala Glu Val Val Val Asn Gly Val Cys
 15                  20                  25                  30 acg gag aag agc aag aat tgg aag ggc gtg tgc ttt gtg tca gag cac       146
Thr Glu Lys Ser Lys Asn Trp Lys Gly Val Cys Phe Val Ser Glu His
                 35                  40                  45 tgt gag ctg aca tgc att gct gaa ggt tcg gtc tac ggt tgg tgc gat       194
Cys Glu Leu Thr Cys Ile Ala Glu Gly Ser Val Tyr Gly Trp Cys Asp
             50                  55                  60 tcc acg gat gca tcg tgg gct ata ttt aca aca tac tgc ttg tgt ttc       242
Ser Thr Asp Ala Ser Trp Ala Ile Phe Thr Thr Tyr Cys Leu Cys Phe
         65                  70                  75 aag ctc acc tca tgc ggg tca agt atg gaa aaa ggc aat tag               284
Lys Leu Thr Ser Cys Gly Ser Ser Met Glu Lys Gly Asn *
     80                  85                  90 aagtaacgac aagccatggg tgtcaattat aactgtnatg gctggatctc ttaatacgca    344
caatctatct ctataataat ctgggtgaag ccgaanccta tngattccgg ggctttgttg    404
cctgctaaan ttattgggat tcttaaangc tncaaantaa atttgttnaa tggtaatnat    464 ccng                                                                  468

<210> SEQ ID NO 113
<211> LENGTH: 91
<212> TYPE: PRT
<213> ORGANISM: Tulipa gesneriana

<400> SEQUENCE: 113

Met Glu Arg Lys Asn Val Pro Ser Gly Phe Ile Leu Val Met Leu Ile
1               5                   10                  15

Val Leu Ala Leu Ala Glu Val Val Val Asn Gly Val Cys Thr Glu
            20                  25                  30

Lys Ser Lys Asn Trp Lys Gly Val Cys Phe Val Ser Glu His Cys Glu
         35                  40                  45

Leu Thr Cys Ile Ala Glu Gly Ser Val Tyr Gly Trp Cys Asp Ser Thr
     50                  55                  60

Asp Ala Ser Trp Ala Ile Phe Thr Thr Tyr Cys Leu Cys Phe Lys Leu
65                  70                  75                  80

Thr Ser Cys Gly Ser Ser Met Glu Lys Gly Asn
                 85                  90

<210> SEQ ID NO 114
<211> LENGTH: 56
<212> TYPE: PRT
<213> ORGANISM: Tulipa gesneriana

<400> SEQUENCE: 114

Gly Val Cys Thr Glu Lys Ser Lys Asn Trp Lys Gly Val Cys Phe Val
1               5                   10                  15
```

```
Ser Glu His Cys Glu Leu Thr Cys Ile Ala Glu Gly Ser Val Tyr Gly
         20                  25                  30

Trp Cys Asp Ser Thr Asp Ala Ser Trp Ala Ile Phe Thr Thr Tyr Cys
         35                  40                  45

Leu Cys Phe Lys Leu Thr Ser Cys
     50                  55

<210> SEQ ID NO 115
<211> LENGTH: 416
<212> TYPE: DNA
<213> ORGANISM: Tulipa gesneriana
<220> FEATURE:
<221> NAME/KEY: CDS
<222> LOCATION: (36)...(263)
<220> FEATURE:
<221> NAME/KEY: mat_peptide
<222> LOCATION: (57)...(248)
<220> FEATURE:
<221> NAME/KEY: misc_feature
<222> LOCATION: 318, 403, 408
<223> OTHER INFORMATION: n = A,T,C or G

<400> SEQUENCE: 115
gcttttattg tagagcatcg acattaagct gaacc atg gag ctt ggg aag aga      53
                                       Met Glu Leu Gly Lys Arg
                                         1               5 att gtt tgt tgt gtg atg cta cta ctg ctt gtg ctg gcc tat gac ggg   101
Ile Val Cys Cys Val Met Leu Leu Leu Leu Val Leu Ala Tyr Asp Gly
         10                  15                  20 atg cag tcg act tat gca gca act act gat tca atg acg ttg aaa ccg   149
Met Gln Ser Thr Tyr Ala Ala Thr Thr Asp Ser Met Thr Leu Lys Pro
     25                  30                  35 tgc aat tct gat atc atg tgc gac cag ttt tgc aag aaa aat ggt gca   197
Cys Asn Ser Asp Ile Met Cys Asp Gln Phe Cys Lys Lys Asn Gly Ala
 40                  45                  50 tac gca aat ggt tac tgc cgt gtg atg ctc ctc agc ccg tta tgt gtt   245
Tyr Ala Asn Gly Tyr Cys Arg Val Met Leu Leu Ser Pro Leu Cys Val
 55                  60                  65                  70 tgc acc aaa aca agt tga agatatccgt atcaaataat tctagctcac           293
Cys Thr Lys Thr Ser  *
                 75 tccaacaagg aattggtctg agggntttaa aataataat taaataacaa tcaagtttaa   353 taaagaggct ccgtccgggc ttcaattatc tacaaaagtt gattgtcaan ttggnatctg   413 tgg                                                                416

<210> SEQ ID NO 116
<211> LENGTH: 75
<212> TYPE: PRT
<213> ORGANISM: Tulipa gesneriana

<400> SEQUENCE: 116

Met Glu Leu Gly Lys Arg Ile Val Cys Cys Val Met Leu Leu Leu Leu
 1               5                  10                  15

Val Leu Ala Tyr Asp Gly Met Gln Ser Thr Tyr Ala Ala Thr Thr Asp
             20                  25                  30

Ser Met Thr Leu Lys Pro Cys Asn Ser Asp Ile Met Cys Asp Gln Phe
         35                  40                  45

Cys Lys Lys Asn Gly Ala Tyr Ala Asn Gly Tyr Cys Arg Val Met Leu
     50                  55                  60

Leu Ser Pro Leu Cys Val Cys Thr Lys Thr Ser
 65                  70                  75
```

<210> SEQ ID NO 117
<211> LENGTH: 64
<212> TYPE: PRT
<213> ORGANISM: Tulipa gesneriana

<400> SEQUENCE: 117

```
Val Cys Cys Val Met Leu Leu Leu Val Leu Ala Tyr Asp Gly Met
  1               5                  10                  15

Gln Ser Thr Tyr Ala Ala Thr Thr Asp Ser Met Thr Leu Lys Pro Cys
             20                  25                  30

Asn Ser Asp Ile Met Cys Asp Gln Phe Cys Lys Lys Asn Gly Ala Tyr
         35                  40                  45

Ala Asn Gly Tyr Cys Arg Val Met Leu Leu Ser Pro Leu Cys Val Cys
     50                  55                  60
```

<210> SEQ ID NO 118
<211> LENGTH: 416
<212> TYPE: DNA
<213> ORGANISM: Tulipa gesneriana
<220> FEATURE:
<221> NAME/KEY: CDS
<222> LOCATION: (36)...(263)
<220> FEATURE:
<221> NAME/KEY: mat_peptide
<222> LOCATION: (57)...(248)
<220> FEATURE:
<221> NAME/KEY: misc_feature
<222> LOCATION: 318, 403, 408
<223> OTHER INFORMATION: n = A,T,C or G

<400> SEQUENCE: 118

```
gcttttattg tagagcatcg acattaagct gaacc atg gag ctt ggg aag aga        53
                                      Met Glu Leu Gly Lys Arg
                                        1               5 att gtt tgt tgt gtg atg cta cta ctg ctt gtt ctg gcc tat gac ggg      101
Ile Val Cys Cys Val Met Leu Leu Leu Leu Val Leu Ala Tyr Asp Gly
         10                  15                  20 atg cag tcg act tat gca gca act act gat tca atg acg ttg aaa ccg     149
Met Gln Ser Thr Tyr Ala Ala Thr Thr Asp Ser Met Thr Leu Lys Pro
             25                  30                  35 tgc aat tct gat atc atg tgc gac cag ttt tgc aag aaa aat ggt gca     197
Cys Asn Ser Asp Ile Met Cys Asp Gln Phe Cys Lys Lys Asn Gly Ala
         40                  45                  50 tac gca aat ggt tac tgc cgt gtg atg ctc ctc agc ccg tta tgt gtt     245
Tyr Ala Asn Gly Tyr Cys Arg Val Met Leu Leu Ser Pro Leu Cys Val
 55                  60                  65                  70 tgc acc aaa aca agt tga agatatccgt atcaaataat tctagctcac            293
Cys Thr Lys Thr Ser  *
                 75 tccaacaagg aattggtctg agggntttaa aataataat taaataacaa tcaagtttaa    353 taaagaggct ccgtccgggc ttcaattatc tacaaaagtt gattgtcaan ttggnatctg   413 tgg                                                                  416
```

<210> SEQ ID NO 119
<211> LENGTH: 75
<212> TYPE: PRT
<213> ORGANISM: Tulipa gesneriana

<400> SEQUENCE: 119

```
Met Glu Leu Gly Lys Arg Ile Val Cys Cys Val Met Leu Leu Leu Leu
  1               5                  10                  15
```

```
Val Leu Ala Tyr Asp Gly Met Gln Ser Thr Tyr Ala Ala Thr Thr Asp
        20                  25                  30

Ser Met Thr Leu Lys Pro Cys Asn Ser Asp Ile Met Cys Asp Gln Phe
        35                  40                  45

Cys Lys Lys Asn Gly Ala Tyr Ala Asn Gly Tyr Cys Arg Val Met Leu
50                  55                  60

Leu Ser Pro Leu Cys Val Cys Thr Lys Thr Ser
65                  70                  75

<210> SEQ ID NO 120
<211> LENGTH: 64
<212> TYPE: PRT
<213> ORGANISM: Tulipa gesneriana

<400> SEQUENCE: 120

Val Cys Cys Val Met Leu Leu Leu Val Leu Ala Tyr Asp Gly Met
 1               5                  10                  15

Gln Ser Thr Tyr Ala Ala Thr Thr Asp Ser Met Thr Leu Lys Pro Cys
            20                  25                  30

Asn Ser Asp Ile Met Cys Asp Gln Phe Cys Lys Lys Asn Gly Ala Tyr
            35                  40                  45

Ala Asn Gly Tyr Cys Arg Val Met Leu Leu Ser Pro Leu Cys Val Cys
50                  55                  60

<210> SEQ ID NO 121
<211> LENGTH: 367
<212> TYPE: DNA
<213> ORGANISM: Momordica charantia
<220> FEATURE:
<221> NAME/KEY: CDS
<222> LOCATION: (71)...(265)
<220> FEATURE:
<221> NAME/KEY: mat_peptide
<222> LOCATION: (107)...(262)

<400> SEQUENCE: 121
gaattcggca cgagaaagaa ataaaatgag aaactcttat tcttcatctt catcccatgc      60
tgtgttcttg atg ctc ctc ctt ctc ctt gcc atg agg gag atg gcg agg       109
            Met Leu Leu Leu Leu Leu Ala Met Arg Glu Met Ala Arg
             1               5                  10 cca tgt gag ggg agg aca tgc cag tcg aag agc cat cgg ttc cat gga      157
Pro Cys Glu Gly Arg Thr Cys Gln Ser Lys Ser His Arg Phe His Gly
        15                  20                  25 cca tgc att aat gac cac aac tgt gca gag act tgt cga aac gaa gcc      205
Pro Cys Ile Asn Asp His Asn Cys Ala Glu Thr Cys Arg Asn Glu Ala
 30                  35                  40                  45 tat acc ggt ggc cac tgc gaa gga ttt cgc cgt cgc tgt ttc tgc act      253
Tyr Thr Gly Gly His Cys Glu Gly Phe Arg Arg Arg Cys Phe Cys Thr
                50                  55                  60 aaa gcc tgt tag ctagctgtct tgaatgtcaa tgtcaatgca aatatcgatg          305
Lys Ala Cys * caactttttt atgaaaatct atataaaata tatcatattt ctcaccgttg aggatgaaaa     365
aa                                                                    367

<210> SEQ ID NO 122
<211> LENGTH: 64
<212> TYPE: PRT
<213> ORGANISM: Momordica charantia

<400> SEQUENCE: 122
```

```
Met Leu Leu Leu Leu Leu Ala Met Arg Glu Met Ala Arg Pro Cys Glu
 1               5                  10                  15

Gly Arg Thr Cys Gln Ser Lys Ser His Arg Phe His Gly Pro Cys Ile
            20                  25                  30

Asn Asp His Asn Cys Ala Glu Thr Cys Arg Asn Glu Ala Tyr Thr Gly
        35                  40                  45

Gly His Cys Glu Gly Phe Arg Arg Arg Cys Phe Cys Thr Lys Ala Cys
    50                  55                  60
```

<210> SEQ ID NO 123
<211> LENGTH: 52
<212> TYPE: PRT
<213> ORGANISM: Momordica charantia

<400> SEQUENCE: 123

```
Arg Pro Cys Glu Gly Arg Thr Cys Gln Ser Lys Ser His Arg Phe His
 1               5                  10                  15

Gly Pro Cys Ile Asn Asp His Asn Cys Ala Glu Thr Cys Arg Asn Glu
            20                  25                  30

Ala Tyr Thr Gly Gly His Cys Glu Gly Phe Arg Arg Arg Cys Phe Cys
        35                  40                  45

Thr Lys Ala Cys
    50
```

<210> SEQ ID NO 124
<211> LENGTH: 363
<212> TYPE: DNA
<213> ORGANISM: Momordica charantia
<220> FEATURE:
<221> NAME/KEY: CDS
<222> LOCATION: (15)...(254)
<220> FEATURE:
<221> NAME/KEY: mat_peptide
<222> LOCATION: (96)...(251)

<400> SEQUENCE: 124

```
gcacgaggaa taaa atg aga aac tct tat tct tca tct tca tcc cat gct        50
             Met Arg Asn Ser Tyr Ser Ser Ser Ser His Ala
              1               5                  10 gtg ttc ttg atg ctc ctc ctt ctc ctt gcc atg agg gag atg gcg agg        98
Val Phe Leu Met Leu Leu Leu Leu Leu Ala Met Arg Glu Met Ala Arg
         15                  20                  25 cca tgt gag ggg agg aca tgc cag tcg aag agc cat cgg ttc cat gga       146
Pro Cys Glu Gly Arg Thr Cys Gln Ser Lys Ser His Arg Phe His Gly
 30                  35                  40 cca tgc att aat gac cac aac tgt gca gag act tgt cga aac gaa gcc       194
Pro Cys Ile Asn Asp His Asn Cys Ala Glu Thr Cys Arg Asn Glu Ala
 45                  50                  55                  60 tat acc ggt ggc cac tgc gaa gga ttt cgc cgt cgc tgt ttc tgc act       242
Tyr Thr Gly Gly His Cys Glu Gly Phe Arg Arg Arg Cys Phe Cys Thr
                 65                  70                  75 aaa gcc tgt tag ctagctgtct tgaatgtcaa tgtcaatgca aatatcgatg           294
Lys Ala Cys * caactttttt atgaaaatct atataaaata tatcatattt ctcaccgttg aggatgagaa     354
tatagtatc                                                             363
```

<210> SEQ ID NO 125
<211> LENGTH: 79
<212> TYPE: PRT
<213> ORGANISM: Momordica charantia

```
<400> SEQUENCE: 125

Met Arg Asn Ser Tyr Ser Ser Ser Ser His Ala Val Phe Leu Met
1               5                   10                  15

Leu Leu Leu Leu Leu Ala Met Arg Glu Met Ala Arg Pro Cys Glu Gly
                20                  25                  30

Arg Thr Cys Gln Ser Lys Ser His Arg Phe His Gly Pro Cys Ile Asn
            35                  40                  45

Asp His Asn Cys Ala Glu Thr Cys Arg Asn Glu Ala Tyr Thr Gly Gly
        50                  55                  60

His Cys Glu Gly Phe Arg Arg Arg Cys Phe Cys Thr Lys Ala Cys
65                  70                  75

<210> SEQ ID NO 126
<211> LENGTH: 52
<212> TYPE: PRT
<213> ORGANISM: Momordica charantia

<400> SEQUENCE: 126

Arg Pro Cys Glu Gly Arg Thr Cys Gln Ser Lys Ser His Arg Phe His
1               5                   10                  15

Gly Pro Cys Ile Asn Asp His Asn Cys Ala Glu Thr Cys Arg Asn Glu
                20                  25                  30

Ala Tyr Thr Gly Gly His Cys Glu Gly Phe Arg Arg Arg Cys Phe Cys
            35                  40                  45

Thr Lys Ala Cys
    50

<210> SEQ ID NO 127
<211> LENGTH: 476
<212> TYPE: DNA
<213> ORGANISM: Nicotiana benthamiana
<220> FEATURE:
<221> NAME/KEY: CDS
<222> LOCATION: (15)...(242)
<220> FEATURE:
<221> NAME/KEY: mat_peptide
<222> LOCATION: (108)...(242)
<220> FEATURE:
<221> NAME/KEY: misc_feature
<222> LOCATION: 296, 307, 322, 345, 380, 398, 416, 427, 430, 436
<223> OTHER INFORMATION: n = A,T,C or G

<400> SEQUENCE: 127
aaaagattta agaa atg gct caa cct aaa gtt agc aaa ata agt ata tgt      50
              Met Ala Gln Pro Lys Val Ser Lys Ile Ser Ile Cys
              1               5                   10 gtt gtc ctc ttt tgc ttt ctt ctc atg ttt gct tct gag gtg caa ata      98
Val Val Leu Phe Cys Phe Leu Leu Met Phe Ala Ser Glu Val Gln Ile
        15                  20                  25 aca gaa gca aaa cac tgt ggg aag cct agc aaa agc tgg aac ggg aag     146
Thr Glu Ala Lys His Cys Gly Lys Pro Ser Lys Ser Trp Asn Gly Lys
    30                  35                  40 tgt ttt ccc agg aag tgt aac cat tgg tgc aag aac aag gat gat gca     194
Cys Phe Pro Arg Lys Cys Asn His Trp Cys Lys Asn Lys Asp Asp Ala
45                  50                  55                  60 gat tat ggc aat tgc aac cat gga gat tgc tat tgc tat tac cat tgc     242
Asp Tyr Gly Asn Cys Asn His Gly Asp Cys Tyr Cys Tyr Tyr His Cys
                65                  70                  75 taa aaataaacgg atctgaatct attaccattt catatataaa tggcactaac         295
ngtcctaatg tnataaataa cctatanata aataaatgct ggcaattacn agggtaatgc  355
```

```
aaccttgggc aataatccaa aaggnccaac ctaaagtccc cgnttaactg gaggtggtaa    415
nggtgaaata cnaangtgca ngtgtttggg gaaaaaaaag gggggcccgg ttaccaaatc    475
t                                                                   476
```

<210> SEQ ID NO 128
<211> LENGTH: 76
<212> TYPE: PRT
<213> ORGANISM: Nicotiana benthamiana

<400> SEQUENCE: 128

```
Met Ala Gln Pro Lys Val Ser Lys Ile Ser Ile Cys Val Val Leu Phe
1               5                   10                  15

Cys Phe Leu Leu Met Phe Ala Ser Glu Val Gln Ile Thr Glu Ala Lys
            20                  25                  30

His Cys Gly Lys Pro Ser Lys Ser Trp Asn Gly Lys Cys Phe Pro Arg
        35                  40                  45

Lys Cys Asn His Trp Cys Lys Asn Lys Asp Asp Ala Asp Tyr Gly Asn
    50                  55                  60

Cys Asn His Gly Asp Cys Tyr Cys Tyr Tyr His Cys
65                  70                  75
```

<210> SEQ ID NO 129
<211> LENGTH: 45
<212> TYPE: PRT
<213> ORGANISM: Nicotiana benthamiana

<400> SEQUENCE: 129

```
Lys His Cys Gly Lys Pro Ser Lys Ser Trp Asn Gly Lys Cys Phe Pro
1               5                   10                  15

Arg Lys Cys Asn His Trp Cys Lys Asn Lys Asp Asp Ala Asp Tyr Gly
            20                  25                  30

Asn Cys Asn His Gly Asp Cys Tyr Cys Tyr Tyr His Cys
        35                  40                  45
```

<210> SEQ ID NO 130
<211> LENGTH: 476
<212> TYPE: DNA
<213> ORGANISM: Nicotiana benthamiana
<220> FEATURE:
<221> NAME/KEY: CDS
<222> LOCATION: (15)...(242)
<220> FEATURE:
<221> NAME/KEY: mat_peptide
<222> LOCATION: (108)...(242)
<220> FEATURE:
<221> NAME/KEY: misc_feature
<222> LOCATION: 296, 307, 322, 345, 380, 398, 416, 427, 430, 436
<223> OTHER INFORMATION: n = A,T,C or G

<400> SEQUENCE: 130

```
aaaagattta agaa atg gct caa cct aaa gtt agc aaa ata agt ata tgt    50
              Met Ala Gln Pro Lys Val Ser Lys Ile Ser Ile Cys
              1               5                   10 gtt gtc ctc ttt tgc ttt ctt ctc atg ttt gct tct gag gtg caa ata    98
Val Val Leu Phe Cys Phe Leu Leu Met Phe Ala Ser Glu Val Gln Ile
        15                  20                  25 aca gaa gca aaa cac tgt ggg aag cct agc aaa agc tgg aac ggg aag   146
Thr Glu Ala Lys His Cys Gly Lys Pro Ser Lys Ser Trp Asn Gly Lys
    30                  35                  40 tgt ttt ccc agg aag tgt aac cat tgg tgc aag aac aag gat gat gca   194
Cys Phe Pro Arg Lys Cys Asn His Trp Cys Lys Asn Lys Asp Asp Ala
```

```
             45                  50                  55                  60
gat tat ggc aat tgc aac cat gga gat tgc tat tgc tac tac cat tgc            242
Asp Tyr Gly Asn Cys Asn His Gly Asp Cys Tyr Cys Tyr Tyr His Cys
                 65                  70                  75 taa aaataaacgg atctgaatct attaccattt catatataaa tggcactaac                  295
ngtcctaatg tnataaataa cctatanata aataaatgct ggcaattacn agggtaatgc           355
aaccttgggc aataatccaa aaggnccaac ctaaagtccc cgnttaactg gaggtggtaa           415
nggtgaaata cnaangtgca ngtgtttggg gaaaaaaaag ggggggcccgg ttaccaaatc          475 t                                                                          476
```

<210> SEQ ID NO 131
<211> LENGTH: 76
<212> TYPE: PRT
<213> ORGANISM: Nicotiana benthamiana

<400> SEQUENCE: 131

```
Met Ala Gln Pro Lys Val Ser Lys Ile Ser Ile Cys Val Val Leu Phe
1               5                   10                  15

Cys Phe Leu Leu Met Phe Ala Ser Glu Val Gln Ile Thr Glu Ala Lys
            20                  25                  30

His Cys Gly Lys Pro Ser Lys Ser Trp Asn Gly Lys Cys Phe Pro Arg
        35                  40                  45

Lys Cys Asn His Trp Cys Lys Asn Lys Asp Asp Ala Asp Tyr Gly Asn
    50                  55                  60

Cys Asn His Gly Asp Cys Tyr Cys Tyr Tyr His Cys
65                  70                  75
```

<210> SEQ ID NO 132
<211> LENGTH: 45
<212> TYPE: PRT
<213> ORGANISM: Nicotiana benthamiana

<400> SEQUENCE: 132

```
Lys His Cys Gly Lys Pro Ser Lys Ser Trp Asn Gly Lys Cys Phe Pro
1               5                   10                  15

Arg Lys Cys Asn His Trp Cys Lys Asn Lys Asp Asp Ala Asp Tyr Gly
            20                  25                  30

Asn Cys Asn His Gly Asp Cys Tyr Cys Tyr Tyr His Cys
        35                  40                  45
```

<210> SEQ ID NO 133
<211> LENGTH: 424
<212> TYPE: DNA
<213> ORGANISM: Tulip fosteriana
<220> FEATURE:
<221> NAME/KEY: CDS
<222> LOCATION: (2)...(241)
<220> FEATURE:
<221> NAME/KEY: mat_peptide
<222> LOCATION: (95)...(238)
<220> FEATURE:
<221> NAME/KEY: misc_feature
<222> LOCATION: 283, 320, 424
<223> OTHER INFORMATION: n = A,T,C or G

<400> SEQUENCE: 133

```
c ttc gcc atg aag ttc aac aaa gca ttc atc agc ttt ttc ttc ttc gct          49
  Phe Ala Met Lys Phe Asn Lys Ala Phe Ile Ser Phe Phe Phe Phe Ala
  1               5                   10                  15 ctc ctc tta ctg ttg gct tcg ggg ccg aga gtg aaa gct cgt agt ttc            97
```

```
Leu Leu Leu Leu Leu Ala Ser Gly Pro Arg Val Glu Ala Arg Ser Phe
             20                  25                  30 ttc tgc cat aag gtt aag agc cat cgg ttc cac gga ctg tgc ttc agc       145
Phe Cys His Lys Val Lys Ser His Arg Phe His Gly Leu Cys Phe Ser
         35                  40                  45 agc gtc aat tgt ggc cag act tgc gtc agc gag ggc tac agg ggt ggt       193
Ser Val Asn Cys Gly Gln Thr Cys Val Ser Glu Gly Tyr Arg Gly Gly
     50                  55                  60 tat tgc cat ggc ctt cgc cat cgg tgc atg tgt agg aaa aac tgc tga       241
Tyr Cys His Gly Leu Arg His Arg Cys Met Cys Arg Lys Asn Cys  *
 65                  70                  75 accacaagcc ttccaggaac ttctgtatga gaaatggact anctactatc tactctatct     301
gtaccaagtt gagtatgtna gttacgtggt gaaataaaa gaagaaagct catggatctt      361
cctggggtgg gttttcaact ccctgcgtgg tttatgtaag aagaataata actcaattac     421 ccn                                                                    424

<210> SEQ ID NO 134
<211> LENGTH: 79
<212> TYPE: PRT
<213> ORGANISM: Tulip fosteriana

<400> SEQUENCE: 134

Phe Ala Met Lys Phe Asn Lys Ala Phe Ile Ser Phe Phe Phe Ala
 1               5                  10                  15

Leu Leu Leu Leu Leu Ala Ser Gly Pro Arg Val Glu Ala Arg Ser Phe
             20                  25                  30

Phe Cys His Lys Val Lys Ser His Arg Phe His Gly Leu Cys Phe Ser
         35                  40                  45

Ser Val Asn Cys Gly Gln Thr Cys Val Ser Glu Gly Tyr Arg Gly Gly
     50                  55                  60

Tyr Cys His Gly Leu Arg His Arg Cys Met Cys Arg Lys Asn Cys
 65                  70                  75

<210> SEQ ID NO 135
<211> LENGTH: 48
<212> TYPE: PRT
<213> ORGANISM: Tulip fosteriana

<400> SEQUENCE: 135

Phe Phe Cys His Lys Val Lys Ser His Arg Phe His Gly Leu Cys Phe
 1               5                  10                  15

Ser Ser Val Asn Cys Gly Gln Thr Cys Val Ser Glu Gly Tyr Arg Gly
             20                  25                  30

Gly Tyr Cys His Gly Leu Arg His Arg Cys Met Cys Arg Lys Asn Cys
         35                  40                  45

<210> SEQ ID NO 136
<211> LENGTH: 447
<212> TYPE: DNA
<213> ORGANISM: Tulipa gesneriana
<220> FEATURE:
<221> NAME/KEY: CDS
<222> LOCATION: (1)...(303)
<220> FEATURE:
<221> NAME/KEY: mat_peptide
<222> LOCATION: (157)...(300)

<400> SEQUENCE: 136 ggt tca aca aag cat tca tca gct ttt tct tct tcg ctc ttc tct tac        48
Gly Ser Thr Lys His Ser Ser Ala Phe Ser Ser Ser Leu Phe Ser Tyr
```

```
                1               5                    10                   15
tgt tgg cct ccg gta aac gtt tcc ctt tcc ctc aaa gat ttc ctc tgt              96
Cys Trp Pro Pro Val Asn Val Ser Leu Ser Leu Lys Asp Phe Leu Cys
             20                  25                  30 tct atc ttc ttc gct cgc ctc gta ttg ctg ggt tct ggg cct gga gtg             144
Ser Ile Phe Phe Ala Arg Leu Val Leu Leu Gly Ser Gly Pro Gly Val
         35                  40                  45 gaa gct cgt cat ttc ttc tgc cat aag gtt aag agc cat cgg ttc cac             192
Glu Ala Arg His Phe Phe Cys His Lys Val Lys Ser His Arg Phe His
 50                  55                  60 gga ctt tgc ttc agc agc gtc aat tgt ggc cag act tgc gtc agc gag             240
Gly Leu Cys Phe Ser Ser Val Asn Cys Gly Gln Thr Cys Val Ser Glu
 65                  70                  75                  80 ggc tac agg ggt ggt tat tgc cat ggc ctt cgc cgt cgg tgc atg tgt             288
Gly Tyr Arg Gly Gly Tyr Cys His Gly Leu Arg Arg Arg Cys Met Cys
                 85                  90                  95 agg aaa aac tgc tga actacaagcc ttccaggagc tgctgtttga gaaatggact             343
Arg Lys Asn Cys  *
            100 agctgctagc tactatctgt actaagctga gtacgtaagt tatgtgatca aaataaggaa           403 gaaaaagcca ttatcttgtg ggctggctct taagctccgg cttt                            447

<210> SEQ ID NO 137
<211> LENGTH: 100
<212> TYPE: PRT
<213> ORGANISM: Tulipa gesneriana

<400> SEQUENCE: 137

Gly Ser Thr Lys His Ser Ser Ala Phe Ser Ser Leu Phe Ser Tyr
1               5                   10                  15

Cys Trp Pro Pro Val Asn Val Ser Leu Ser Leu Lys Asp Phe Leu Cys
            20                  25                  30

Ser Ile Phe Phe Ala Arg Leu Val Leu Leu Gly Ser Gly Pro Gly Val
        35                  40                  45

Glu Ala Arg His Phe Phe Cys His Lys Val Lys Ser His Arg Phe His
 50                 55                  60

Gly Leu Cys Phe Ser Ser Val Asn Cys Gly Gln Thr Cys Val Ser Glu
65                  70                  75                  80

Gly Tyr Arg Gly Gly Tyr Cys His Gly Leu Arg Arg Arg Cys Met Cys
                85                  90                  95

Arg Lys Asn Cys
            100

<210> SEQ ID NO 138
<211> LENGTH: 48
<212> TYPE: PRT
<213> ORGANISM: Tulipa gesneriana

<400> SEQUENCE: 138

Phe Phe Cys His Lys Val Lys Ser His Arg Phe His Gly Leu Cys Phe
1               5                   10                  15

Ser Ser Val Asn Cys Gly Gln Thr Cys Val Ser Glu Gly Tyr Arg Gly
            20                  25                  30

Gly Tyr Cys His Gly Leu Arg Arg Arg Cys Met Cys Arg Lys Asn Cys
        35                  40                  45

<210> SEQ ID NO 139
<211> LENGTH: 387
```

-continued

```
<212> TYPE: DNA
<213> ORGANISM: Taraxacum kok-saghyz
<220> FEATURE:
<221> NAME/KEY: CDS
<222> LOCATION: (51)...(269)
<220> FEATURE:
<221> NAME/KEY: mat_peptide
<222> LOCATION: (132)...(266)
<220> FEATURE:
<221> NAME/KEY: misc_feature
<222> LOCATION: 304, 344, 351, 357, 365, 373, 375, 378
<223> OTHER INFORMATION: n = A,T,C or G

<400> SEQUENCE: 139
aattcggcca ttatggccgg ggattgtttt tctgtgcatc ataattcaaa atg gga          56
                                                        Met Gly
                                                          1 aaa agc ctg ttt gtg ttc atg ttg ctg ctt gct ctc ttt gct act gat        104
Lys Ser Leu Phe Val Phe Met Leu Leu Leu Ala Leu Phe Ala Thr Asp
          5                  10                  15 aag act ttg gtg agt gtg acc gaa gca aag atg tgt caa acg acg agc        152
Lys Thr Leu Val Ser Val Thr Glu Ala Lys Met Cys Gln Thr Thr Ser
 20                  25                  30 cat gca ttt agt tgt gtg aac gac tcg ggt tgc agt ggc tcc tgc gaa        200
His Ala Phe Ser Cys Val Asn Asp Ser Gly Cys Ser Gly Ser Cys Glu
 35                  40                  45                  50 aag cga gga ttt gct agc ggc aaa tgt gat gga gta cgt cgt cgt tgt        248
Lys Arg Gly Phe Ala Ser Gly Lys Cys Asp Gly Val Arg Arg Arg Cys
                 55                  60                  65 acg tgt tac aag aag tgt tga gcatatatat gctctttatt aaaactatgt           299
Thr Cys Tyr Lys Lys Cys  *
             70 aaacnagtca cgtggtgact ttctcctgta ccatctttgg tatcngatgg tnatattnaa      359 ataaangttg accncntgnt ccccttag                                         387

<210> SEQ ID NO 140
<211> LENGTH: 72
<212> TYPE: PRT
<213> ORGANISM: Taraxacum kok-saghyz

<400> SEQUENCE: 140

Met Gly Lys Ser Leu Phe Val Phe Met Leu Leu Leu Ala Leu Phe Ala
  1               5                  10                  15

Thr Asp Lys Thr Leu Val Ser Val Thr Glu Ala Lys Met Cys Gln Thr
             20                  25                  30

Thr Ser His Ala Phe Ser Cys Val Asn Asp Ser Gly Cys Ser Gly Ser
         35                  40                  45

Cys Glu Lys Arg Gly Phe Ala Ser Gly Lys Cys Asp Gly Val Arg Arg
     50                  55                  60

Arg Cys Thr Cys Tyr Lys Lys Cys
 65                  70

<210> SEQ ID NO 141
<211> LENGTH: 45
<212> TYPE: PRT
<213> ORGANISM: Taraxacum kok-saghyz

<400> SEQUENCE: 141

Lys Met Cys Gln Thr Thr Ser His Ala Phe Ser Cys Val Asn Asp Ser
  1               5                  10                  15

Gly Cys Ser Gly Ser Cys Glu Lys Arg Gly Phe Ala Ser Gly Lys Cys
             20                  25                  30
```

```
Asp Gly Val Arg Arg Arg Cys Thr Cys Tyr Lys Lys Cys
        35                  40                  45

<210> SEQ ID NO 142
<211> LENGTH: 380
<212> TYPE: DNA
<213> ORGANISM: Taraxacum kok-saghyz
<220> FEATURE:
<221> NAME/KEY: CDS
<222> LOCATION: (51)...(269)
<220> FEATURE:
<221> NAME/KEY: mat_peptide
<222> LOCATION: (132)...(266)

<400> SEQUENCE: 142
aattcggcca ttatggccgg ggattgtttt tctgtgcatc ataattcaaa atg gga      56
                                                          Met Gly
                                                            1 aaa agc ctg ttt gtg ttc atg ttg ctt gtt ctc ttt gct act gat       104
Lys Ser Leu Phe Val Phe Met Leu Leu Val Leu Phe Ala Thr Asp
        5                  10                  15 aag act ttg gtg agt gtg acc gaa gca aag atg tgt caa acg acg agc   152
Lys Thr Leu Val Ser Val Thr Glu Ala Lys Met Cys Gln Thr Thr Ser
    20                  25                  30 cat gca ttt agt tgt gtg aac gac tcg ggt tgc agt ggc tcc tgc gaa   200
His Ala Phe Ser Cys Val Asn Asp Ser Gly Cys Ser Gly Ser Cys Glu
 35                  40                  45                  50 aag caa gga ttt gct agc ggc aaa tgt gat gga gta cgt cgt cgt tgt   248
Lys Gln Gly Phe Ala Ser Gly Lys Cys Asp Gly Val Arg Arg Arg Cys
            55                  60                  65 acg tgt tac aag aag tgt tga gcatatatat gctctttatt aaaactatgt      299
Thr Cys Tyr Lys Lys Cys  *
            70 aaactagtca cgtggtgact ttctcctgta ccatctttag tatctgatgg tatgttaaat  359 aaaagtttga cgtttgtagc a                                            380

<210> SEQ ID NO 143
<211> LENGTH: 72
<212> TYPE: PRT
<213> ORGANISM: Taraxacum kok-saghyz

<400> SEQUENCE: 143

Met Gly Lys Ser Leu Phe Val Phe Met Leu Leu Val Leu Phe Ala
 1               5                  10                  15

Thr Asp Lys Thr Leu Val Ser Val Thr Glu Ala Lys Met Cys Gln Thr
            20                  25                  30

Thr Ser His Ala Phe Ser Cys Val Asn Asp Ser Gly Cys Ser Gly Ser
        35                  40                  45

Cys Glu Lys Gln Gly Phe Ala Ser Gly Lys Cys Asp Gly Val Arg Arg
    50                  55                  60

Arg Cys Thr Cys Tyr Lys Lys Cys
 65                  70

<210> SEQ ID NO 144
<211> LENGTH: 45
<212> TYPE: PRT
<213> ORGANISM: Taraxacum kok-saghyz

<400> SEQUENCE: 144

Lys Met Cys Gln Thr Thr Ser His Ala Phe Ser Cys Val Asn Asp Ser
 1               5                  10                  15
```

```
Gly Cys Ser Gly Ser Cys Glu Lys Gln Gly Phe Ala Ser Gly Lys Cys
            20                  25                  30

Asp Gly Val Arg Arg Cys Thr Cys Tyr Lys Lys Cys
        35                  40                  45

<210> SEQ ID NO 145
<211> LENGTH: 417
<212> TYPE: DNA
<213> ORGANISM: Taraxacum kok-saghyz
<220> FEATURE:
<221> NAME/KEY: CDS
<222> LOCATION: (71)...(286)
<220> FEATURE:
<221> NAME/KEY: mat_peptide
<222> LOCATION: (152)...(283)
<220> FEATURE:
<221> NAME/KEY: misc_feature
<222> LOCATION: 7, 9, 378, 396, 397
<223> OTHER INFORMATION: n = A,T,C or G

<400> SEQUENCE: 145
cattgangnt ggtacccggg aattcggcca ttatggccgg ggattgtttt tctgtgcatc       60
ataattcaaa atg gga aaa agc ctg ttt gtg ttc atg ttg ctg ctt gct      109
           Met Gly Lys Ser Leu Phe Val Phe Met Leu Leu Leu Ala
             1               5                  10 ctc ttt gct act gat aag act ttg gtg agt gtg acc gaa gca aag atg    157
Leu Phe Ala Thr Asp Lys Thr Leu Val Ser Val Thr Glu Ala Lys Met
     15                  20                  25 tgt caa acg acg agc cat gca ttt agt tgt gtg aac gac tcg ggt tgc    205
Cys Gln Thr Thr Ser His Ala Phe Ser Cys Val Asn Asp Ser Gly Cys
 30                  35                  40                  45 agt ggc tcc tgc gaa agg caa gga ttt gct agc ggc aaa tgt gat gga    253
Ser Gly Ser Cys Glu Arg Gln Gly Phe Ala Ser Gly Lys Cys Asp Gly
             50                  55                  60 gta cgt cgt tgt acg tgt tac aag aag tgt tga gcatatatat gctctttatt   306
Val Arg Arg Cys Thr Cys Tyr Lys Lys Cys *
         65                  70 aaaactatgt aaactaagtc acgtggtgac tttctcctgt accatctttg ggtatctgat   366
ggtatattaa anaaagtttg acgttttgtn ngcaagctgg ttaaatgagg a            417

<210> SEQ ID NO 146
<211> LENGTH: 71
<212> TYPE: PRT
<213> ORGANISM: Taraxacum kok-saghyz

<400> SEQUENCE: 146

Met Gly Lys Ser Leu Phe Val Phe Met Leu Leu Leu Ala Leu Phe Ala
  1               5                  10                  15

Thr Asp Lys Thr Leu Val Ser Val Thr Glu Ala Lys Met Cys Gln Thr
             20                  25                  30

Thr Ser His Ala Phe Ser Cys Val Asn Asp Ser Gly Cys Ser Gly Ser
         35                  40                  45

Cys Glu Arg Gln Gly Phe Ala Ser Gly Lys Cys Asp Gly Val Arg Arg
     50                  55                  60

Cys Thr Cys Tyr Lys Lys Cys
 65                  70

<210> SEQ ID NO 147
<211> LENGTH: 44
<212> TYPE: PRT
<213> ORGANISM: Taraxacum kok-saghyz
```

<400> SEQUENCE: 147

Lys Met Cys Gln Thr Thr Ser His Ala Phe Ser Cys Val Asn Asp Ser
1               5                   10                  15

Gly Cys Ser Gly Ser Cys Glu Arg Gln Gly Phe Ala Ser Gly Lys Cys
            20                  25                  30

Asp Gly Val Arg Arg Cys Thr Cys Tyr Lys Lys Cys
        35                  40

<210> SEQ ID NO 148
<211> LENGTH: 410
<212> TYPE: DNA
<213> ORGANISM: Taraxacum kok-saghyz
<220> FEATURE:
<221> NAME/KEY: CDS
<222> LOCATION: (79)...(297)
<220> FEATURE:
<221> NAME/KEY: mat_peptide
<222> LOCATION: (160)...(294)
<220> FEATURE:
<221> NAME/KEY: misc_feature
<222> LOCATION: 1, 328, 401
<223> OTHER INFORMATION: n = A,T,C or G

<400> SEQUENCE: 148 nccccgcgcca ttgtataagg tacccgggaa ttcggccatt atggccgggg attgtttttc        60
tgtgcatcat aattcaaa atg gga aaa agc ctg ttt gtg ttc atg ttg ctg         111
                    Met Gly Lys Ser Leu Phe Val Phe Met Leu Leu
                     1               5                   10 ctt gct ctc ttt gct act gat aag act ttg gtg agt gtg acc gaa gca         159
Leu Ala Leu Phe Ala Thr Asp Lys Thr Leu Val Ser Val Thr Glu Ala
            15                  20                  25 aag atg tgt caa acg acg agc cat gca ttt agt tgt gtg aac gac tcg         207
Lys Met Cys Gln Thr Thr Ser His Ala Phe Ser Cys Val Asn Asp Ser
        30                  35                  40 ggt tgc agt ggc tcc tgc gaa aag caa gga ttt gct agc ggc aaa tgt         255
Gly Cys Ser Gly Ser Cys Glu Lys Gln Gly Phe Ala Ser Gly Lys Cys
    45                  50                  55 gat gga gta cgt cgt cgt tgt acg tgt tgc aag aag tgt tga                 297
Asp Gly Val Arg Arg Arg Cys Thr Cys Cys Lys Lys Cys *
60                  65                  70 gcatatatat gctctttatt aaaactatgt naactagtca cgtggtgact ttctccctgt        357
accatctttg ggtatctgac ggtatattaa ataaaagttt gacntttgtc gaa              410

<210> SEQ ID NO 149
<211> LENGTH: 72
<212> TYPE: PRT
<213> ORGANISM: Taraxacum kok-saghyz

<400> SEQUENCE: 149

Met Gly Lys Ser Leu Phe Val Phe Met Leu Leu Ala Leu Phe Ala
1               5                   10                  15

Thr Asp Lys Thr Leu Val Ser Val Thr Glu Ala Lys Met Cys Gln Thr
            20                  25                  30

Thr Ser His Ala Phe Ser Cys Val Asn Asp Ser Gly Cys Ser Gly Ser
        35                  40                  45

Cys Glu Lys Gln Gly Phe Ala Ser Gly Lys Cys Asp Gly Val Arg Arg
    50                  55                  60

Arg Cys Thr Cys Cys Lys Lys Cys
65                  70

```
<210> SEQ ID NO 150
<211> LENGTH: 45
<212> TYPE: PRT
<213> ORGANISM: Taraxacum kok-saghyz

<400> SEQUENCE: 150

Lys Met Cys Gln Thr Thr Ser His Ala Phe Ser Cys Val Asn Asp Ser
1               5                   10                  15

Gly Cys Ser Gly Ser Cys Glu Lys Gln Gly Phe Ala Ser Gly Lys Cys
            20                  25                  30

Asp Gly Val Arg Arg Arg Cys Thr Cys Cys Lys Lys Cys
        35                  40                  45

<210> SEQ ID NO 151
<211> LENGTH: 385
<212> TYPE: DNA
<213> ORGANISM: Taraxacum kok-saghyz
<220> FEATURE:
<221> NAME/KEY: CDS
<222> LOCATION: (51)...(269)
<220> FEATURE:
<221> NAME/KEY: mat_peptide
<222> LOCATION: (132)...(266)
<220> FEATURE:
<221> NAME/KEY: misc_feature
<222> LOCATION: 380
<223> OTHER INFORMATION: n = A,T,C or G

<400> SEQUENCE: 151
aattcggcca ttatggccgg ggattgtttt tctgtgcatc ataattcaaa atg gga         56
                                                         Met Gly
                                                         1 aaa agc ctg ttt gtg ttc atg ttg ctg ctt gct ctc att gct act gat      104
Lys Ser Leu Phe Val Phe Met Leu Leu Leu Ala Leu Ile Ala Thr Asp
    5                   10                  15 aag act ttg gtg agt gtg acc gaa gca aag atg tgt caa acg acg agc      152
Lys Thr Leu Val Ser Val Thr Glu Ala Lys Met Cys Gln Thr Thr Ser
    20                  25                  30 cat gca ttt agt tgt gtg aac gac tcg ggt tgc agt ggc tcc tgc gaa      200
His Ala Phe Ser Cys Val Asn Asp Ser Gly Cys Ser Gly Ser Cys Glu
35                  40                  45                  50 aag caa gga ttt gct agc ggc aaa tgt gat gga gta cgt cgt cgt tgt      248
Lys Gln Gly Phe Ala Ser Gly Lys Cys Asp Gly Val Arg Arg Arg Cys
            55                  60                  65 acg tgt tac aag aag tgt tga gcatatatat gctctttatt aaaactatgt         299
Thr Cys Tyr Lys Lys Cys *
            70 aaactagtca cgtggtgact ttctcctgta ccatctttgg tatctgatgg tatattaaat    359 aaagtttgac gtttgtacca naaaac                                         385

<210> SEQ ID NO 152
<211> LENGTH: 72
<212> TYPE: PRT
<213> ORGANISM: Taraxacum kok-saghyz
<220> FEATURE:
<221> NAME/KEY: VARIANT
<222> LOCATION: 50
<223> OTHER INFORMATION: Xaa = Any Amino Acid

<400> SEQUENCE: 152

Met Gly Lys Ser Leu Phe Val Phe Met Leu Leu Leu Ala Leu Ile Ala
1               5                   10                  15

Thr Asp Lys Thr Leu Val Ser Val Thr Glu Ala Lys Met Cys Gln Thr
```

20                  25                  30
Thr Ser His Ala Phe Ser Cys Val Asn Asp Ser Gly Cys Ser Gly Ser
            35                  40                  45

Cys Xaa Lys Gln Gly Phe Ala Ser Gly Lys Cys Asp Gly Val Arg Arg
 50                  55                  60

Arg Cys Thr Cys Tyr Lys Lys Cys
65                  70

<210> SEQ ID NO 153
<211> LENGTH: 45
<212> TYPE: PRT
<213> ORGANISM: Taraxacum kok-saghyz
<220> FEATURE:
<221> NAME/KEY: VARIANT
<222> LOCATION: 23
<223> OTHER INFORMATION: Xaa = Any Amino Acid

<400> SEQUENCE: 153

Lys Met Cys Gln Thr Thr Ser His Ala Phe Ser Cys Val Asn Asp Ser
 1               5                  10                  15

Gly Cys Ser Gly Ser Cys Xaa Lys Gln Gly Phe Ala Ser Gly Lys Cys
            20                  25                  30

Asp Gly Val Arg Arg Arg Cys Thr Cys Tyr Lys Lys Cys
            35                  40                  45

<210> SEQ ID NO 154
<211> LENGTH: 408
<212> TYPE: DNA
<213> ORGANISM: Taraxacum kok-saghyz
<220> FEATURE:
<221> NAME/KEY: CDS
<222> LOCATION: (72)...(290)
<220> FEATURE:
<221> NAME/KEY: mat_peptide
<222> LOCATION: (153)...(287)
<220> FEATURE:
<221> NAME/KEY: misc_feature
<222> LOCATION: 8, 11, 333, 368, 374, 404
<223> OTHER INFORMATION: n = A,T,C or G

<400> SEQUENCE: 154
ccattgangt nggtacccgg gaattcggcc attatggccg gggattgttt ttctgtgcat      60
cataattcaa a atg gga aaa agc ctg ttt gtg ttc atg ttg ctg ctt gct     110
            Met Gly Lys Ser Leu Phe Val Phe Met Leu Leu Leu Ala
             1               5                  10 ctc ttt gct act gat aag act ttg gtg agt gtg acc gaa gca aag atg     158
Leu Phe Ala Thr Asp Lys Thr Leu Val Ser Val Thr Glu Ala Lys Met
 15                  20                  25 tgt caa acg acg agc cat gca ttt agt tgt gtg aac gac tcg ggt cgc     206
Cys Gln Thr Thr Ser His Ala Phe Ser Cys Val Asn Asp Ser Gly Arg
 30                  35                  40                  45 agt ggc tcc tgc gaa aag caa gga ttt gct agc ggc aaa tgt gat gga     254
Ser Gly Ser Cys Glu Lys Gln Gly Phe Ala Ser Gly Lys Cys Asp Gly
             50                  55                  60 gta cgt cgt cgt tgt acg tgt tac aag aag tgt tga gcatatatat          300
Val Arg Arg Arg Cys Thr Cys Tyr Lys Lys Cys *
             65                  70 gctctttatt aaaactatgt aaactagtca cgnggtgact ttctcctgta ccatctttgg   360
tatctgangg tacnttaaat aaagtttggc ctttgttctc accncagt               408

<210> SEQ ID NO 155
<211> LENGTH: 72

```
<212> TYPE: PRT
<213> ORGANISM: Taraxacum kok-saghyz

<400> SEQUENCE: 155

Met Gly Lys Ser Leu Phe Val Phe Met Leu Leu Ala Leu Phe Ala
 1               5                  10                  15

Thr Asp Lys Thr Leu Val Ser Val Thr Glu Ala Lys Met Cys Gln Thr
                20                  25                  30

Thr Ser His Ala Phe Ser Cys Val Asn Asp Ser Gly Arg Ser Gly Ser
            35                  40                  45

Cys Glu Lys Gln Gly Phe Ala Ser Gly Lys Cys Asp Gly Val Arg Arg
50                  55                  60

Arg Cys Thr Cys Tyr Lys Lys Cys
65                  70

<210> SEQ ID NO 156
<211> LENGTH: 45
<212> TYPE: PRT
<213> ORGANISM: Taraxacum kok-saghyz

<400> SEQUENCE: 156

Lys Met Cys Gln Thr Thr Ser His Ala Phe Ser Cys Val Asn Asp Ser
 1               5                  10                  15

Gly Arg Ser Gly Ser Cys Glu Lys Gln Gly Phe Ala Ser Gly Lys Cys
                20                  25                  30

Asp Gly Val Arg Arg Arg Cys Thr Cys Tyr Lys Lys Cys
            35                  40                  45

<210> SEQ ID NO 157
<211> LENGTH: 398
<212> TYPE: DNA
<213> ORGANISM: Taraxacum kok-saghyz
<220> FEATURE:
<221> NAME/KEY: CDS
<222> LOCATION: (70)...(264)
<220> FEATURE:
<221> NAME/KEY: mat_peptide
<222> LOCATION: (127)...(261)
<220> FEATURE:
<221> NAME/KEY: misc_feature
<222> LOCATION: 340, 341, 342, 372, 373, 374, 375, 379, 380, 381, 382,
      383, 384, 387, 388, 391, 392, 393, 394, 398
<223> OTHER INFORMATION: n = A,T,C or G

<400> SEQUENCE: 157
ggccattatg gccggggatt gtttttctgt gcatcataat tcaaagtggg aaaaagcctg    60 tttgtgttc atg ttg ctg cct gct ctc ttt gct act gat aag act ttg gtg   111
        Met Leu Leu Pro Ala Leu Phe Ala Thr Asp Lys Thr Leu Val
         1               5                  10 agt gtg acc gaa gca aag atg tgt caa acg acg agc cat gca ttt agt    159
Ser Val Thr Glu Ala Lys Met Cys Gln Thr Thr Ser His Ala Phe Ser
 15                  20                  25                  30 tgt gtg aac gac tcg ggt tgc agt ggc tcc tgc gaa aag caa gga ttt    207
Cys Val Asn Asp Ser Gly Cys Ser Gly Ser Cys Glu Lys Gln Gly Phe
                35                  40                  45 gct agc ggc aaa tgt gat gga gta cgt cgt cgt tgt acg tgt tac aag    255
Ala Ser Gly Lys Cys Asp Gly Val Arg Arg Arg Cys Thr Cys Tyr Lys
                50                  55                  60 aag tgt tga gcatatatat gctctttatt aaaactatgt aaactagtca             304
Lys Cys * cgtggtgact ttctcctgta ccatctttgg tatctnnggg tatattaaat aaagtttgac   364
```

```
gtttgtcnnn naaannnnnn ccnnccnnnn aatn                                        398
```

<210> SEQ ID NO 158
<211> LENGTH: 64
<212> TYPE: PRT
<213> ORGANISM: Taraxacum kok-saghyz

<400> SEQUENCE: 158

```
Met Leu Leu Pro Ala Leu Phe Ala Thr Asp Lys Thr Leu Val Ser Val
 1               5                  10                  15

Thr Glu Ala Lys Met Cys Gln Thr Thr Ser His Ala Phe Ser Cys Val
            20                  25                  30

Asn Asp Ser Gly Cys Ser Gly Ser Cys Glu Lys Gln Gly Phe Ala Ser
        35                  40                  45

Gly Lys Cys Asp Gly Val Arg Arg Arg Cys Thr Cys Tyr Lys Lys Cys
    50                  55                  60
```

<210> SEQ ID NO 159
<211> LENGTH: 45
<212> TYPE: PRT
<213> ORGANISM: Taraxacum kok-saghyz

<400> SEQUENCE: 159

```
Lys Met Cys Gln Thr Thr Ser His Ala Phe Ser Cys Val Asn Asp Ser
 1               5                  10                  15

Gly Cys Ser Gly Ser Cys Glu Lys Gln Gly Phe Ala Ser Gly Lys Cys
            20                  25                  30

Asp Gly Val Arg Arg Arg Cys Thr Cys Tyr Lys Lys Cys
        35                  40                  45
```

<210> SEQ ID NO 160
<211> LENGTH: 398
<212> TYPE: DNA
<213> ORGANISM: Taraxacum kok-saghyz
<220> FEATURE:
<221> NAME/KEY: CDS
<222> LOCATION: (46)...(264)
<220> FEATURE:
<221> NAME/KEY: mat_peptide
<222> LOCATION: (127)...(261)
<220> FEATURE:
<221> NAME/KEY: misc_feature
<222> LOCATION: 371, 372, 373, 374, 375, 376, 377, 378, 379, 380, 381,
      382, 383, 384, 385, 386, 387, 388, 389, 390, 391, 392, 393, 394,
      395, 396, 397, 398
<223> OTHER INFORMATION: n = A,T,C or G

<400> SEQUENCE: 160

```
ggccattatg gccggggatt gttttctgt gcatcataat tcaaa atg gga aaa agc      57
                                              Met Gly Lys Ser
                                               1 ctg ttt gtg ttc atg ttg ctg ctt gct ctc ttt gct act gat aag act     105
Leu Phe Val Phe Met Leu Leu Leu Ala Leu Phe Ala Thr Asp Lys Thr
 5                  10                  15                  20 ttg gtg agt gtg acc gaa gca aag atg tgt caa acg acg agc cat gca     153
Leu Val Ser Val Thr Glu Ala Lys Met Cys Gln Thr Thr Ser His Ala
            25                  30                  35 ttt agt tgt gtg aac gac tcg ggt tgc agt ggc tcc tgc gaa aag caa     201
Phe Ser Cys Val Asn Asp Ser Gly Cys Ser Gly Ser Cys Glu Lys Gln
        40                  45                  50 gga ttt gct agc ggc aaa tgt gat gga gta cgt cgt cgt tgt acg tgt     249
Gly Phe Ala Ser Gly Lys Cys Asp Gly Val Arg Arg Arg Cys Thr Cys
    55                  60                  65
```

```
tac aag aag tgt tga gcatatatat gctctttatt aaaactatgt aaactagtca      304
Tyr Lys Lys Cys *
        70 cgtggtgact ttctcctgta ccatctttgg tatctgatgg tatattaaat aaagtttgac    364 gtttgcnnnn nnnnnnnnnn nnnnnnnnnn nnnn                                398

<210> SEQ ID NO 161
<211> LENGTH: 72
<212> TYPE: PRT
<213> ORGANISM: Taraxacum kok-saghyz

<400> SEQUENCE: 161

Met Gly Lys Ser Leu Phe Val Phe Met Leu Leu Ala Leu Phe Ala
 1               5                  10                  15

Thr Asp Lys Thr Leu Val Ser Val Thr Glu Ala Lys Met Cys Gln Thr
                20                  25                  30

Thr Ser His Ala Phe Ser Cys Val Asn Asp Ser Gly Cys Ser Gly Ser
            35                  40                  45

Cys Glu Lys Gln Gly Phe Ala Ser Gly Lys Cys Asp Gly Val Arg Arg
        50                  55                  60

Arg Cys Thr Cys Tyr Lys Lys Cys
65                  70

<210> SEQ ID NO 162
<211> LENGTH: 45
<212> TYPE: PRT
<213> ORGANISM: Taraxacum kok-saghyz

<400> SEQUENCE: 162

Lys Met Cys Gln Thr Thr Ser His Ala Phe Ser Cys Val Asn Asp Ser
 1               5                  10                  15

Gly Cys Ser Gly Ser Cys Glu Lys Gln Gly Phe Ala Ser Gly Lys Cys
                20                  25                  30

Asp Gly Val Arg Arg Arg Cys Thr Cys Tyr Lys Lys Cys
            35                  40                  45

<210> SEQ ID NO 163
<211> LENGTH: 355
<212> TYPE: DNA
<213> ORGANISM: Taraxacum kok-saghyz
<220> FEATURE:
<221> NAME/KEY: CDS
<222> LOCATION: (46)...(264)
<220> FEATURE:
<221> NAME/KEY: mat_peptide
<222> LOCATION: (127)...(261)
<220> FEATURE:
<221> NAME/KEY: misc_feature
<222> LOCATION: 276, 277, 278, 325, 326, 327, 328, 329, 330, 331, 332,
      333, 334, 335, 336, 337, 338, 347, 348, 355
<223> OTHER INFORMATION: n = A,T,C or G

<400> SEQUENCE: 163
ggccattatg gccggggatt gttttttctgt gcatcataat tcaaa atg gga aaa agc    57
                                                 Met Gly Lys Ser
                                                  1 ctg tct gtg ttc atg ttg ctg ctt gct ctc ttt gct act gat aag act     105
Leu Ser Val Phe Met Leu Leu Leu Ala Leu Phe Ala Thr Asp Lys Thr
  5                  10                  15                  20 ttg gtg agt gtg acc gaa gca aag atg tgt caa acg acg agc cat gca     153
Leu Val Ser Val Thr Glu Ala Lys Met Cys Gln Thr Thr Ser His Ala
                25                  30                  35
```

```
ttt act tgt gtg aac gac tcg ggt tgc tgt ggc tcc tgc gaa aag caa      201
Phe Thr Cys Val Asn Asp Ser Gly Cys Cys Gly Ser Cys Glu Lys Gln
             40                  45                  50 gga ttt gct agc ggc aaa tgt gat gga gta cgt cgt cgt tgt acg tgt      249
Gly Phe Ala Ser Gly Lys Cys Asp Gly Val Arg Arg Arg Cys Thr Cys
         55                  60                  65 tac aag aag tgt tga gcatatatat gnnntttatt aaaactatgt aaactagtca      304
Tyr Lys Lys Cys *
     70 cgtggtgact ttctcctgta nnnnnnnnnn nnnntgaagg tannttaaat n              355

<210> SEQ ID NO 164
<211> LENGTH: 72
<212> TYPE: PRT
<213> ORGANISM: Taraxacum kok-saghyz

<400> SEQUENCE: 164

Met Gly Lys Ser Leu Ser Val Phe Met Leu Leu Ala Leu Phe Ala
 1               5                  10                  15

Thr Asp Lys Thr Leu Val Ser Val Thr Glu Ala Lys Met Cys Gln Thr
             20                  25                  30

Thr Ser His Ala Phe Thr Cys Val Asn Asp Ser Gly Cys Cys Gly Ser
         35                  40                  45

Cys Glu Lys Gln Gly Phe Ala Ser Gly Lys Cys Asp Gly Val Arg Arg
     50                  55                  60

Arg Cys Thr Cys Tyr Lys Lys Cys
 65                  70

<210> SEQ ID NO 165
<211> LENGTH: 45
<212> TYPE: PRT
<213> ORGANISM: Taraxacum kok-saghyz

<400> SEQUENCE: 165

Lys Met Cys Gln Thr Thr Ser His Ala Phe Thr Cys Val Asn Asp Ser
 1               5                  10                  15

Gly Cys Cys Gly Ser Cys Glu Lys Gln Gly Phe Ala Ser Gly Lys Cys
             20                  25                  30

Asp Gly Val Arg Arg Arg Cys Thr Cys Tyr Lys Lys Cys
         35                  40                  45

<210> SEQ ID NO 166
<211> LENGTH: 330
<212> TYPE: DNA
<213> ORGANISM: Taraxacum kok-saghyz
<220> FEATURE:
<221> NAME/KEY: CDS
<222> LOCATION: (46)...(264)
<220> FEATURE:
<221> NAME/KEY: mat_peptide
<222> LOCATION: (127)...(261)
<220> FEATURE:
<221> NAME/KEY: misc_feature
<222> LOCATION: 314, 316, 317, 318, 319, 320, 321, 328, 329, 330
<223> OTHER INFORMATION: n = A,T,C or G

<400> SEQUENCE: 166
ggccattatg gccggggatt gttttctgt gcatcataat tcaaa atg gga aaa agc     57
                                                 Met Gly Lys Ser
                                                  1 ctg ttt gtg ttc acg ttg ctg ctt gct ctc ttt gct act gat aag act     105
Leu Phe Val Phe Thr Leu Leu Leu Ala Leu Phe Ala Thr Asp Lys Thr
 5                  10                  15                  20
```

```
ttg gtg agt gtg acc gaa gca aag atg tgt caa acg acg agc cat gtg      153
Leu Val Ser Val Thr Glu Ala Lys Met Cys Gln Thr Thr Ser His Val
             25                  30                  35 ttt agt tgt gtg aac gac tcg ggt tgc agt ggc tcc tgc gaa aag caa      201
Phe Ser Cys Val Asn Asp Ser Gly Cys Ser Gly Ser Cys Glu Lys Gln
         40                  45                  50 gga ttt gct ggc ggc aaa tgt gat gga gta cgt cgt cgt tgt acg tgt      249
Gly Phe Ala Gly Gly Lys Cys Asp Gly Val Arg Arg Arg Cys Thr Cys
     55                  60                  65 tac aag aag tgt tga gcatatatat gctctttatt aaaactatgt aaactagtca      304
Tyr Lys Lys Cys *
    70 cgtggtgacn tnnnnnntgt accnnn                                         330
```

<210> SEQ ID NO 167
<211> LENGTH: 72
<212> TYPE: PRT
<213> ORGANISM: Taraxacum kok-saghyz

<400> SEQUENCE: 167

```
Met Gly Lys Ser Leu Phe Val Phe Thr Leu Leu Leu Ala Leu Phe Ala
 1               5                  10                  15

Thr Asp Lys Thr Leu Val Ser Val Thr Glu Ala Lys Met Cys Gln Thr
             20                  25                  30

Thr Ser His Val Phe Ser Cys Val Asn Asp Ser Gly Cys Ser Gly Ser
         35                  40                  45

Cys Glu Lys Gln Gly Phe Ala Gly Gly Lys Cys Asp Gly Val Arg Arg
     50                  55                  60

Arg Cys Thr Cys Tyr Lys Lys Cys
65                  70
```

<210> SEQ ID NO 168
<211> LENGTH: 45
<212> TYPE: PRT
<213> ORGANISM: Taraxacum kok-saghyz

<400> SEQUENCE: 168

```
Lys Met Cys Gln Thr Thr Ser His Val Phe Ser Cys Val Asn Asp Ser
 1               5                  10                  15

Gly Cys Ser Gly Ser Cys Glu Lys Gln Gly Phe Ala Gly Gly Lys Cys
             20                  25                  30

Asp Gly Val Arg Arg Arg Cys Thr Cys Tyr Lys Lys Cys
         35                  40                  45
```

<210> SEQ ID NO 169
<211> LENGTH: 375
<212> TYPE: DNA
<213> ORGANISM: Taraxacum kok-saghyz
<220> FEATURE:
<221> NAME/KEY: CDS
<222> LOCATION: (46)...(264)
<220> FEATURE:
<221> NAME/KEY: mat_peptide
<222> LOCATION: (127)...(261)
<220> FEATURE:
<221> NAME/KEY: misc_feature
<222> LOCATION: 374, 375
<223> OTHER INFORMATION: n = A,T,C or G

<400> SEQUENCE: 169

```
ggccattatg gccggggatt gttttttctgt gcatcataat tcaaa atg gga aaa agc      57
                                                  Met Gly Lys Ser
```

```
                                                            1
ctg ttt gtg ttc atg ttg ctg ctt gct ctc ttt gct act gat aag act    105
Leu Phe Val Phe Met Leu Leu Leu Ala Leu Phe Ala Thr Asp Lys Thr
 5                  10                  15                  20 ttg gtg agt gtg gcc gaa gca aag atg tgt caa acg acg agc cat gca    153
Leu Val Ser Val Ala Glu Ala Lys Met Cys Gln Thr Thr Ser His Ala
                25                  30                  35 ttt agt tgt gtg aac gac tcg ggt tgc agt ggc tcc tgc gaa aag caa    201
Phe Ser Cys Val Asn Asp Ser Gly Cys Ser Gly Ser Cys Glu Lys Gln
            40                  45                  50 gga ttt gct agc ggc aaa tgt gat gga gta cgt cgt cgt tgt acg tgt    249
Gly Phe Ala Ser Gly Lys Cys Asp Gly Val Arg Arg Arg Cys Thr Cys
        55                  60                  65 tac aag aag tgt tga gcatatatat gctctttatt aaaactatgt aaactagtca    304
Tyr Lys Lys Cys *
        70 cgtggtgact ttctcctgta ccatctttgg tatctgatgg tatattaaat aaagtttgac   364 gtttgtagcn n                                                        375

<210> SEQ ID NO 170
<211> LENGTH: 72
<212> TYPE: PRT
<213> ORGANISM: Taraxacum kok-saghyz

<400> SEQUENCE: 170

Met Gly Lys Ser Leu Phe Val Phe Met Leu Leu Leu Ala Leu Phe Ala
 1               5                  10                  15

Thr Asp Lys Thr Leu Val Ser Val Ala Glu Ala Lys Met Cys Gln Thr
                20                  25                  30

Thr Ser His Ala Phe Ser Cys Val Asn Asp Ser Gly Cys Ser Gly Ser
            35                  40                  45

Cys Glu Lys Gln Gly Phe Ala Ser Gly Lys Cys Asp Gly Val Arg Arg
        50                  55                  60

Arg Cys Thr Cys Tyr Lys Lys Cys
65                  70

<210> SEQ ID NO 171
<211> LENGTH: 45
<212> TYPE: PRT
<213> ORGANISM: Taraxacum kok-saghyz

<400> SEQUENCE: 171

Lys Met Cys Gln Thr Thr Ser His Ala Phe Ser Cys Val Asn Asp Ser
 1               5                  10                  15

Gly Cys Ser Gly Ser Cys Glu Lys Gln Gly Phe Ala Ser Gly Lys Cys
                20                  25                  30

Asp Gly Val Arg Arg Arg Cys Thr Cys Tyr Lys Lys Cys
            35                  40                  45

<210> SEQ ID NO 172
<211> LENGTH: 372
<212> TYPE: DNA
<213> ORGANISM: Taraxacum kok-saghyz
<220> FEATURE:
<221> NAME/KEY: CDS
<222> LOCATION: (45)...(263)
<220> FEATURE:
<221> NAME/KEY: mat_peptide
<222> LOCATION: (126)...(260)

<400> SEQUENCE: 172
```

```
gccattatgg ccggggattg tttttctgtg catcataatt caaa atg gga aaa agc         56
                                                  Met Gly Lys Ser
                                                    1 ctg ttt gtg ttc atg ttg ctg ctt gct ctc ttt gct act gat aag act         104
Leu Phe Val Phe Met Leu Leu Leu Ala Leu Phe Ala Thr Asp Lys Thr
  5              10                  15                  20 ttg gtg agt gtg acc gaa gca aag atg tgt caa acg acg agc cat gca         152
Leu Val Ser Val Thr Glu Ala Lys Met Cys Gln Thr Thr Ser His Ala
                 25                  30                  35 ttt agt tgt gtg aac gac tcg ggt tgc agt ggc tcc tgc gaa aag caa         200
Phe Ser Cys Val Asn Asp Ser Gly Cys Ser Gly Ser Cys Glu Lys Gln
             40                  45                  50 gga ttt gct agc ggc aaa tgt gat gga gta cgt cgt cgt cgt acg tgt         248
Gly Phe Ala Ser Gly Lys Cys Asp Gly Val Arg Arg Arg Arg Thr Cys
         55                  60                  65 tac aag aag tgt tga gcatatatat gctctttatt aaaactatgt aaactagtca         303
Tyr Lys Lys Cys *
         70 cgtggtgact ttctcctgta ccatctttgg tatctgacgg tatattaaat aaagtttgac       363 gtttgtagc                                                                372

<210> SEQ ID NO 173
<211> LENGTH: 72
<212> TYPE: PRT
<213> ORGANISM: Taraxacum kok-saghyz

<400> SEQUENCE: 173

Met Gly Lys Ser Leu Phe Val Phe Met Leu Leu Leu Ala Leu Phe Ala
  1               5                  10                  15

Thr Asp Lys Thr Leu Val Ser Val Thr Glu Ala Lys Met Cys Gln Thr
             20                  25                  30

Thr Ser His Ala Phe Ser Cys Val Asn Asp Ser Gly Cys Ser Gly Ser
         35                  40                  45

Cys Glu Lys Gln Gly Phe Ala Ser Gly Lys Cys Asp Gly Val Arg Arg
     50                  55                  60

Arg Arg Thr Cys Tyr Lys Lys Cys
 65                  70

<210> SEQ ID NO 174
<211> LENGTH: 45
<212> TYPE: PRT
<213> ORGANISM: Taraxacum kok-saghyz

<400> SEQUENCE: 174

Lys Met Cys Gln Thr Thr Ser His Ala Phe Ser Cys Val Asn Asp Ser
  1               5                  10                  15

Gly Cys Ser Gly Ser Cys Glu Lys Gln Gly Phe Ala Ser Gly Lys Cys
             20                  25                  30

Asp Gly Val Arg Arg Arg Arg Thr Cys Tyr Lys Lys Cys
         35                  40                  45

<210> SEQ ID NO 175
<211> LENGTH: 372
<212> TYPE: DNA
<213> ORGANISM: Taraxacum kok-saghyz
<220> FEATURE:
<221> NAME/KEY: CDS
<222> LOCATION: (45)...(263)
<220> FEATURE:
<221> NAME/KEY: mat_peptide
```

<222> LOCATION: (153)...(260)

<400> SEQUENCE: 175

```
gccattatgg ccggggattg tttttctgtg catcataatt caaa atg gga aaa agc       56
                                              Met Gly Lys Ser
                                                1 ctg ttt gtg ttc atg ttg ctg ctt gct ctc ttt gct act gat aag act      104
Leu Phe Val Phe Met Leu Leu Leu Ala Leu Phe Ala Thr Asp Lys Thr
 5              10                  15                  20 ttg gtg agt gtg acc gaa gca aag atg cgt caa acg acg agc cat gca      152
Leu Val Ser Val Thr Glu Ala Lys Met Arg Gln Thr Thr Ser His Ala
             25                  30                  35 ttt agt tgt gtg aac gac tcg ggt tgc agt ggc tcc tgc gaa aag caa      200
Phe Ser Cys Val Asn Asp Ser Gly Cys Ser Gly Ser Cys Glu Lys Gln
 40                  45                  50 gga ttt gct agc ggc aaa tgt gat gga gta cgt cgt cgt tgt acg tgt      248
Gly Phe Ala Ser Gly Lys Cys Asp Gly Val Arg Arg Arg Cys Thr Cys
         55                  60                  65 tac aag aag tgt tga gcatatatat gctctttatt aaaactatgt aaactagtca      303
Tyr Lys Lys Cys *
         70 cgtggtgact ttctcctgta ccatctttgg tatctgatgg tatattaaat aaagtttgac    363 gtttgtaac                                                           372
```

<210> SEQ ID NO 176
<211> LENGTH: 72
<212> TYPE: PRT
<213> ORGANISM: Taraxacum kok-saghyz

<400> SEQUENCE: 176

```
Met Gly Lys Ser Leu Phe Val Phe Met Leu Leu Leu Ala Leu Phe Ala
 1               5                  10                  15

Thr Asp Lys Thr Leu Val Ser Val Thr Glu Ala Lys Met Arg Gln Thr
             20                  25                  30

Thr Ser His Ala Phe Ser Cys Val Asn Asp Ser Gly Cys Ser Gly Ser
         35                  40                  45

Cys Glu Lys Gln Gly Phe Ala Ser Gly Lys Cys Asp Gly Val Arg Arg
     50                  55                  60

Arg Cys Thr Cys Tyr Lys Lys Cys
 65                  70
```

<210> SEQ ID NO 177
<211> LENGTH: 36
<212> TYPE: PRT
<213> ORGANISM: Taraxacum kok-saghyz

<400> SEQUENCE: 177

```
Phe Ser Cys Val Asn Asp Ser Gly Cys Ser Gly Ser Cys Glu Lys Gln
 1               5                  10                  15

Gly Phe Ala Ser Gly Lys Cys Asp Gly Val Arg Arg Arg Cys Thr Cys
             20                  25                  30

Tyr Lys Lys Cys
         35
```

<210> SEQ ID NO 178
<211> LENGTH: 372
<212> TYPE: DNA
<213> ORGANISM: Taraxacum kok-saghyz
<220> FEATURE:
<221> NAME/KEY: CDS

```
<222> LOCATION: (43)...(261)
<220> FEATURE:
<221> NAME/KEY: mat_peptide
<222> LOCATION: (124)...(258)
<220> FEATURE:
<221> NAME/KEY: misc_feature
<222> LOCATION: 371, 372
<223> OTHER INFORMATION: n = A,T,C or G

<400> SEQUENCE: 178
```

```
cattatggcc ggggattgtt tttctgtgca tcataattca aa atg gga aaa agc           54
                                              Met Gly Lys Ser
                                                1 ctg ttt gtg ttc atg ttg ctg ctt gct ctc ttt gct act gat aag act         102
Leu Phe Val Phe Met Leu Leu Leu Ala Leu Phe Ala Thr Asp Lys Thr
  5                  10                  15                  20 ttg gtg agt gtg acc gaa gca aag gtg tgt caa acg acg agc cat gca         150
Leu Val Ser Val Thr Glu Ala Lys Val Cys Gln Thr Thr Ser His Ala
                 25                  30                  35 ttt agt tgt gtg aac gac tcg ggt tgc agt ggc tcc tgc gaa aag caa         198
Phe Ser Cys Val Asn Asp Ser Gly Cys Ser Gly Ser Cys Glu Lys Gln
             40                  45                  50 gga ttt gct agc ggc aaa tgt gat gga gta cgt cgt cgt tgt acg tgt         246
Gly Phe Ala Ser Gly Lys Cys Asp Gly Val Arg Arg Arg Cys Thr Cys
         55                  60                  65 tgc aag aag tgt tga gcatatatat gctcttattt aaaactatgt aaactagtca         301
Cys Lys Lys Cys *
         70 cgtggtgact ttctcctgta ccatctttgg tatctgatgg tatattaaat aaagtttgac       361 gtttgtagcn n                                                            372

<210> SEQ ID NO 179
<211> LENGTH: 72
<212> TYPE: PRT
<213> ORGANISM: Taraxacum kok-saghyz

<400> SEQUENCE: 179

Met Gly Lys Ser Leu Phe Val Phe Met Leu Leu Leu Ala Leu Phe Ala
  1               5                  10                  15

Thr Asp Lys Thr Leu Val Ser Val Thr Glu Ala Lys Val Cys Gln Thr
                 20                  25                  30

Thr Ser His Ala Phe Ser Cys Val Asn Asp Ser Gly Cys Ser Gly Ser
             35                  40                  45

Cys Glu Lys Gln Gly Phe Ala Ser Gly Lys Cys Asp Gly Val Arg Arg
     50                  55                  60

Arg Cys Thr Cys Cys Lys Lys Cys
 65                  70

<210> SEQ ID NO 180
<211> LENGTH: 45
<212> TYPE: PRT
<213> ORGANISM: Taraxacum kok-saghyz

<400> SEQUENCE: 180

Lys Val Cys Gln Thr Thr Ser His Ala Phe Ser Cys Val Asn Asp Ser
  1               5                  10                  15

Gly Cys Ser Gly Ser Cys Glu Lys Gln Gly Phe Ala Ser Gly Lys Cys
                 20                  25                  30

Asp Gly Val Arg Arg Arg Cys Thr Cys Cys Lys Lys Cys
             35                  40                  45
```

```
<210> SEQ ID NO 181
<211> LENGTH: 351
<212> TYPE: DNA
<213> ORGANISM: Taraxacum kok-saghyz
<220> FEATURE:
<221> NAME/KEY: CDS
<222> LOCATION: (47)...(265)
<220> FEATURE:
<221> NAME/KEY: mat_peptide
<222> LOCATION: (128)...(262)
<220> FEATURE:
<221> NAME/KEY: misc_feature
<222> LOCATION: 1, 2
<223> OTHER INFORMATION: n = A,T,C or G

<400> SEQUENCE: 181
nnggcattat ggccggggat tgtttttctg tgcatcataa ttcaaa atg gga aaa       55
                                                 Met Gly Lys
                                                   1 agc ctg ttt gtg ttc atg ttg ctg ctt gct ctc ttt gct act gat aag    103
Ser Leu Phe Val Phe Met Leu Leu Leu Ala Leu Phe Ala Thr Asp Lys
  5                  10                  15 act ttg gtg agt gtg acc gaa gca aag atg tgt caa acg acg agc cat    151
Thr Leu Val Ser Val Thr Glu Ala Lys Met Cys Gln Thr Thr Ser His
 20                  25                  30                  35 gca ttt agt tgt gtg aac gac tcg ggt tgc agt ggc tcc tgc gaa aag    199
Ala Phe Ser Cys Val Asn Asp Ser Gly Cys Ser Gly Ser Cys Glu Lys
             40                  45                  50 caa gga ttt gct agc ggc aaa tgt gat gga gta cgt cgt cgt tgt acg    247
Gln Gly Phe Ala Ser Gly Lys Cys Asp Gly Val Arg Arg Arg Cys Thr
         55                  60                  65 tgt tac gag aag tgt tga gcatatatat gctctttatt aaaactatgt            295
Cys Tyr Glu Lys Cys  *
         70 aaactagtca cgtggtgact ttctcctgta ccatctttgg tatctgatgg tatatt       351

<210> SEQ ID NO 182
<211> LENGTH: 72
<212> TYPE: PRT
<213> ORGANISM: Taraxacum kok-saghyz

<400> SEQUENCE: 182

Met Gly Lys Ser Leu Phe Val Phe Met Leu Leu Leu Ala Leu Phe Ala
  1               5                  10                  15

Thr Asp Lys Thr Leu Val Ser Val Thr Glu Ala Lys Met Cys Gln Thr
             20                  25                  30

Thr Ser His Ala Phe Ser Cys Val Asn Asp Ser Gly Cys Ser Gly Ser
         35                  40                  45

Cys Glu Lys Gln Gly Phe Ala Ser Gly Lys Cys Asp Gly Val Arg Arg
     50                  55                  60

Arg Cys Thr Cys Tyr Glu Lys Cys
 65                  70

<210> SEQ ID NO 183
<211> LENGTH: 45
<212> TYPE: PRT
<213> ORGANISM: Taraxacum kok-saghyz

<400> SEQUENCE: 183

Lys Met Cys Gln Thr Thr Ser His Ala Phe Ser Cys Val Asn Asp Ser
  1               5                  10                  15

Gly Cys Ser Gly Ser Cys Glu Lys Gln Gly Phe Ala Ser Gly Lys Cys
```

```
                        20                  25                  30
Asp Gly Val Arg Arg Cys Thr Cys Tyr Glu Lys Cys
        35                  40                  45

<210> SEQ ID NO 184
<211> LENGTH: 388
<212> TYPE: DNA
<213> ORGANISM: Taraxacum kok-saghyz
<220> FEATURE:
<221> NAME/KEY: CDS
<222> LOCATION: (20)...(277)
<220> FEATURE:
<221> NAME/KEY: mat_peptide
<222> LOCATION: (140)...(274)
<220> FEATURE:
<221> NAME/KEY: misc_feature
<222> LOCATION: 13, 14, 15, 383, 384, 385
<223> OTHER INFORMATION: n = A,T,C or G

<400> SEQUENCE: 184
acccgggaat tcnnncatt atg gcc ggg ggt att gtt ttt ctg tgc atc ata        52
                    Met Ala Gly Gly Ile Val Phe Leu Cys Ile Ile
                     1               5                  10 att caa aat ggg aaa aac ctg ttt gtg ttc atg ttg ctg ctt gct ctc        100
Ile Gln Asn Gly Lys Asn Leu Phe Val Phe Met Leu Leu Leu Ala Leu
            15                  20                  25 ttt gct act gat aag act ttg gtg agt gtg acc gaa gca aag atg tgt        148
Phe Ala Thr Asp Lys Thr Leu Val Ser Val Thr Glu Ala Lys Met Cys
        30                  35                  40 caa acg acg agc cat gca ttt agt tgt gtg aac gac tcg ggt tgc agt        196
Gln Thr Thr Ser His Ala Phe Ser Cys Val Asn Asp Ser Gly Cys Ser
    45                  50                  55 ggc tcc tgc gaa aag caa gga ttt gct agc ggc aaa tgt gat gga gta        244
Gly Ser Cys Glu Lys Gln Gly Phe Ala Ser Gly Lys Cys Asp Gly Val
60                  65                  70                  75 cgt cgt cgt tgt acg tgt tac aag aag tgt tga gcatatatat gctctttatt     297
Arg Arg Arg Cys Thr Cys Tyr Lys Lys Cys *
                80                  85 aaaactatgt aaactagtca cgtggtgact ttctcctgta ccatctttgg tatctgacgg     357
tatattaaat aaagtttgac gtttgnnnca t                                    388

<210> SEQ ID NO 185
<211> LENGTH: 85
<212> TYPE: PRT
<213> ORGANISM: Taraxacum kok-saghyz

<400> SEQUENCE: 185

Met Ala Gly Gly Ile Val Phe Leu Cys Ile Ile Gln Asn Gly Lys
 1               5                  10                  15

Asn Leu Phe Val Phe Met Leu Leu Leu Ala Leu Phe Ala Thr Asp Lys
            20                  25                  30

Thr Leu Val Ser Val Thr Glu Ala Lys Met Cys Gln Thr Thr Ser His
        35                  40                  45

Ala Phe Ser Cys Val Asn Asp Ser Gly Cys Ser Gly Ser Cys Glu Lys
    50                  55                  60

Gln Gly Phe Ala Ser Gly Lys Cys Asp Gly Val Arg Arg Arg Cys Thr
65                  70                  75                  80

Cys Tyr Lys Lys Cys
                85

<210> SEQ ID NO 186
```

<210> SEQ ID NO 187
<211> LENGTH: 388
<212> TYPE: DNA
<213> ORGANISM: Taraxacum kok-saghyz
<220> FEATURE:
<221> NAME/KEY: CDS
<222> LOCATION: (61)...(267)
<220> FEATURE:
<221> NAME/KEY: mat_peptide
<222> LOCATION: (142)...(264)
<220> FEATURE:
<221> NAME/KEY: misc_feature
<222> LOCATION: 14, 15, 16
<223> OTHER INFORMATION: n = A,T,C or G

<400> SEQUENCE: 187

```
gtacccggga attnnngcca ttatggccgg ggattgtttt tctgtgcatc ataattcaaa    60 atg gga aaa agc ctg ttt gtg ttc atg ttg ctg ctt gct ctc ttt gct    108
Met Gly Lys Ser Leu Phe Val Phe Met Leu Leu Leu Ala Leu Phe Ala
 1               5                  10                  15 acc gat aag act ttg gtg agt gtg acc gaa gca aag atg tgt caa acg    156
Thr Asp Lys Thr Leu Val Ser Val Thr Glu Ala Lys Met Cys Gln Thr
             20                  25                  30 acg agc cat gca ttt agt tgt gtg aac gac tcg ggt tgc agt ggc ccc    204
Thr Ser His Ala Phe Ser Cys Val Asn Asp Ser Gly Cys Ser Gly Pro
         35                  40                  45 tgc gaa aag caa gga ttt gct agc ggc aaa tgt gat gga gtg cgt cgt    252
Cys Glu Lys Gln Gly Phe Ala Ser Gly Lys Cys Asp Gly Val Arg Arg
     50                  55                  60 cgt tgt acg tgt tag aagaagtgtt gagcatatat atgctcttta ttaaaactat    307
Arg Cys Thr Cys *
 65 gtaaactagt cacgtggtga ctttctcctg taccatcttt ggtatctgat ggtatattaa    367 ataaagtttg acgtttgtag c    388
```

<210> SEQ ID NO 188
<211> LENGTH: 68
<212> TYPE: PRT
<213> ORGANISM: Taraxacum kok-saghyz

<400> SEQUENCE: 188

Met Gly Lys Ser Leu Phe Val Phe Met Leu Leu Leu Ala Leu Phe Ala
 1               5                  10                  15

Thr Asp Lys Thr Leu Val Ser Val Thr Glu Ala Lys Met Cys Gln Thr
             20                  25                  30

Thr Ser His Ala Phe Ser Cys Val Asn Asp Ser Gly Cys Ser Gly Pro
         35                  40                  45

Cys Glu Lys Gln Gly Phe Ala Ser Gly Lys Cys Asp Gly Val Arg Arg
     50                  55                  60

Arg Cys Thr Cys
65

<210> SEQ ID NO 189
<211> LENGTH: 41
<212> TYPE: PRT
<213> ORGANISM: Taraxacum kok-saghyz

<400> SEQUENCE: 189

Lys Met Cys Gln Thr Thr Ser His Ala Phe Ser Cys Val Asn Asp Ser
1               5                   10                  15

Gly Cys Ser Gly Pro Cys Glu Lys Gln Gly Phe Ala Ser Gly Lys Cys
            20                  25                  30

Asp Gly Val Arg Arg Arg Cys Thr Cys
        35                  40

<210> SEQ ID NO 190
<211> LENGTH: 378
<212> TYPE: DNA
<213> ORGANISM: Taraxacum kok-saghyz
<220> FEATURE:
<221> NAME/KEY: CDS
<222> LOCATION: (46)...(264)
<220> FEATURE:
<221> NAME/KEY: mat_peptide
<222> LOCATION: (127)...(261)
<220> FEATURE:
<221> NAME/KEY: misc_feature
<222> LOCATION: 1, 2, 3, 377, 378
<223> OTHER INFORMATION: n = A,T,C or G

<400> SEQUENCE: 190
nnncattatg gccggggatt gtttttctgt gcatcataat tcaaa atg gga aaa agc      57
                                                 Met Gly Lys Ser
                                                  1 ctg ttt gtg ttc atg ttg ctg ctt gct ctc ctt gct act gat aag act     105
Leu Phe Val Phe Met Leu Leu Leu Ala Leu Leu Ala Thr Asp Lys Thr
 5                  10                  15                  20 ttg gtg agt gtg acc gaa gca aag atg tgt caa acg acg agc cat gca     153
Leu Val Ser Val Thr Glu Ala Lys Met Cys Gln Thr Thr Ser His Ala
            25                  30                  35 ttt agt tgt gtg aac gac tcg ggt tgc agt ggc tcc tgc gaa aag caa     201
Phe Ser Cys Val Asn Asp Ser Gly Cys Ser Gly Ser Cys Glu Lys Gln
        40                  45                  50 gga ttt gct agc ggc aaa tgt gat gga gta cgt cgt cgt tgt acg tgt     249
Gly Phe Ala Ser Gly Lys Cys Asp Gly Val Arg Arg Arg Cys Thr Cys
    55                  60                  65 tac aag aag tgt tga gcatatatat gctctttatt aaaactatgt aaactagtca     304
Tyr Lys Lys Cys *
    70 cgtggtgact ttctcctgta ccatctttgg tatctgatgg tatattaaat aaagtttgac   364 gtttgtaaca aann                                                     378

<210> SEQ ID NO 191
<211> LENGTH: 72
<212> TYPE: PRT
<213> ORGANISM: Taraxacum kok-saghyz

<400> SEQUENCE: 191

Met Gly Lys Ser Leu Phe Val Phe Met Leu Leu Leu Ala Leu Leu Ala
1               5                   10                  15

Thr Asp Lys Thr Leu Val Ser Val Thr Glu Ala Lys Met Cys Gln Thr
            20                  25                  30

```
Thr Ser His Ala Phe Ser Cys Val Asn Asp Ser Gly Cys Ser Gly Ser
        35                  40                  45

Cys Glu Lys Gln Gly Phe Ala Ser Gly Lys Cys Asp Gly Val Arg Arg
 50                  55                  60

Arg Cys Thr Cys Tyr Lys Lys Cys
 65                  70

<210> SEQ ID NO 192
<211> LENGTH: 45
<212> TYPE: PRT
<213> ORGANISM: Taraxacum kok-saghyz

<400> SEQUENCE: 192

Lys Met Cys Gln Thr Thr Ser His Ala Phe Ser Cys Val Asn Asp Ser
 1               5                   10                  15

Gly Cys Ser Gly Ser Cys Glu Lys Gln Gly Phe Ala Ser Gly Lys Cys
             20                  25                  30

Asp Gly Val Arg Arg Arg Cys Thr Cys Tyr Lys Lys Cys
         35                  40                  45

<210> SEQ ID NO 193
<211> LENGTH: 409
<212> TYPE: DNA
<213> ORGANISM: Taraxacum kok-saghyz
<220> FEATURE:
<221> NAME/KEY: CDS
<222> LOCATION: (44)...(262)
<220> FEATURE:
<221> NAME/KEY: mat_peptide
<222> LOCATION: (125)...(259)
<220> FEATURE:
<221> NAME/KEY: misc_feature
<222> LOCATION: 368, 369, 370, 389, 390, 391, 392, 393, 403, 405, 406,
      407
<223> OTHER INFORMATION: n = A,T,C or G

<400> SEQUENCE: 193
ccattatggc cggggattgt ttttctgtgc atcataattc aaa atg gga aaa agc        55
                                              Met Gly Lys Ser
                                               1 ctg ttt gtg ttc acg ttg ctg ctt gct ctc ttt gct act gat aag act       103
Leu Phe Val Phe Thr Leu Leu Leu Ala Leu Phe Ala Thr Asp Lys Thr
 5                  10                  15                  20 ttg gtg agt gtg acc gaa gca aag atg tgt caa acg acg agc cat gca       151
Leu Val Ser Val Thr Glu Ala Lys Met Cys Gln Thr Thr Ser His Ala
             25                  30                  35 ttt agt tgt gtg aac gac tcg ggt tgc agt ggc tcc tgc gaa aag caa       199
Phe Ser Cys Val Asn Asp Ser Gly Cys Ser Gly Ser Cys Glu Lys Gln
         40                  45                  50 gga ttt gct agc ggc aaa tgt gat gga gta cgt cgt cgt tgt acg tgt       247
Gly Phe Ala Ser Gly Lys Cys Asp Gly Val Arg Arg Arg Cys Thr Cys
     55                  60                  65 tac aag aag tgt tga gcatatatat gctctttatt aaaactatgt aaactagtca       302
Tyr Lys Lys Cys *
     70 cgtggtgact tcctcctgta ccatctttgg tatctgacgg tatattaaat aaagtttgac     362 gtttgnnnca aaaaaaaaa aaaaaannnn naaaaaaaat ncnnnag                    409

<210> SEQ ID NO 194
<211> LENGTH: 72
<212> TYPE: PRT
<213> ORGANISM: Taraxacum kok-saghyz
```

<400> SEQUENCE: 194

```
Met Gly Lys Ser Leu Phe Val Phe Thr Leu Leu Ala Leu Phe Ala
1               5                   10                  15

Thr Asp Lys Thr Leu Val Ser Val Thr Glu Ala Lys Met Cys Gln Thr
            20                  25                  30

Thr Ser His Ala Phe Ser Cys Val Asn Asp Ser Gly Cys Ser Gly Ser
        35                  40                  45

Cys Glu Lys Gln Gly Phe Ala Ser Gly Lys Cys Asp Gly Val Arg Arg
    50                  55                  60

Arg Cys Thr Cys Tyr Lys Lys Cys
65                  70
```

<210> SEQ ID NO 195
<211> LENGTH: 45
<212> TYPE: PRT
<213> ORGANISM: Taraxacum kok-saghyz

<400> SEQUENCE: 195

```
Lys Met Cys Gln Thr Thr Ser His Ala Phe Ser Cys Val Asn Asp Ser
1               5                   10                  15

Gly Cys Ser Gly Ser Cys Glu Lys Gln Gly Phe Ala Ser Gly Lys Cys
            20                  25                  30

Asp Gly Val Arg Arg Arg Cys Thr Cys Tyr Lys Lys Cys
        35                  40                  45
```

<210> SEQ ID NO 196
<211> LENGTH: 410
<212> TYPE: DNA
<213> ORGANISM: Taraxacum kok-saghyz
<220> FEATURE:
<221> NAME/KEY: CDS
<222> LOCATION: (47)...(265)
<220> FEATURE:
<221> NAME/KEY: mat_peptide
<222> LOCATION: (128)...(262)
<220> FEATURE:
<221> NAME/KEY: misc_feature
<222> LOCATION: 1, 2, 20, 21, 22
<223> OTHER INFORMATION: n = A,T,C or G

<400> SEQUENCE: 196

```
nntcggccat tagggccggn nnttttttctg tgcatcataa ttcaaa atg gga aaa          55
                                              Met Gly Lys
                                              1 agc ctg ttt gtg ttc atg ttg ctg ctt gct ctt ttt gct act gat aag        103
Ser Leu Phe Val Phe Met Leu Leu Leu Ala Leu Phe Ala Thr Asp Lys
    5                   10                  15 act ttg gtg agt gtg acc gaa gca aag atg tgt caa acg acg agc cat        151
Thr Leu Val Ser Val Thr Glu Ala Lys Met Cys Gln Thr Thr Ser His
20                  25                  30                  35 gca ttt agt tgt gtg aga gac tcg ggt tgt agt ggc tcc tgc gaa aag        199
Ala Phe Ser Cys Val Arg Asp Ser Gly Cys Ser Gly Ser Cys Glu Lys
            40                  45                  50 caa gga ttt gct agc ggc aaa tgt gat ggt gta cgt cgt cgt tgt acg        247
Gln Gly Phe Ala Ser Gly Lys Cys Asp Gly Val Arg Arg Arg Cys Thr
        55                  60                  65 tgt tac aag aag tgt tga tcgctgtaat ttgcacttta ttaaaactat              295
Cys Tyr Lys Lys Cys *
        70 gtaaactagt cacgtggcga ctttcgcttg taccatcatt agtatctgat ggtatctacc     355
```

```
taatgtaata aataaaaata aagaggacat atggcagcac catattaatt cccaa       410
```

<210> SEQ ID NO 197
<211> LENGTH: 72
<212> TYPE: PRT
<213> ORGANISM: Taraxacum kok-saghyz

<400> SEQUENCE: 197

```
Met Gly Lys Ser Leu Phe Val Phe Met Leu Leu Leu Ala Leu Phe Ala
 1               5                   10                  15

Thr Asp Lys Thr Leu Val Ser Val Thr Glu Ala Lys Met Cys Gln Thr
             20                  25                  30

Thr Ser His Ala Phe Ser Cys Val Arg Asp Ser Gly Cys Ser Gly Ser
         35                  40                  45

Cys Glu Lys Gln Gly Phe Ala Ser Gly Lys Cys Asp Gly Val Arg Arg
     50                  55                  60

Arg Cys Thr Cys Tyr Lys Lys Cys
 65                  70
```

<210> SEQ ID NO 198
<211> LENGTH: 45
<212> TYPE: PRT
<213> ORGANISM: Taraxacum kok-saghyz

<400> SEQUENCE: 198

```
Lys Met Cys Gln Thr Thr Ser His Ala Phe Ser Cys Val Arg Asp Ser
 1               5                   10                  15

Gly Cys Ser Gly Ser Cys Glu Lys Gln Gly Phe Ala Ser Gly Lys Cys
             20                  25                  30

Asp Gly Val Arg Arg Arg Cys Thr Cys Tyr Lys Lys Cys
         35                  40                  45
```

<210> SEQ ID NO 199
<211> LENGTH: 379
<212> TYPE: DNA
<213> ORGANISM: Taraxacum kok-saghyz
<220> FEATURE:
<221> NAME/KEY: CDS
<222> LOCATION: (50)...(268)
<220> FEATURE:
<221> NAME/KEY: mat_peptide
<222> LOCATION: (131)...(265)
<220> FEATURE:
<221> NAME/KEY: misc_feature
<222> LOCATION: 378, 379
<223> OTHER INFORMATION: n = A,T,C or G

<400> SEQUENCE: 199

```
attcggccat tatggccggg gattgttttt ctgtgcatca taattcaaa atg gga aaa    58
                                                     Met Gly Lys
                                                      1 agc ctg gtt gtg ttc atg ttg ctg ctt gct ctc ttt gct act gat aag    106
Ser Leu Val Val Phe Met Leu Leu Leu Ala Leu Phe Ala Thr Asp Lys
     5                  10                  15 act ttg gtg agt gtg acc gaa gca aag atg tgt caa acg acg agc cat    154
Thr Leu Val Ser Val Thr Glu Ala Lys Met Cys Gln Thr Thr Ser His
 20                  25                  30                  35 gca ttt agt tgt gtg aac gac tcg ggt tgc agt ggc tcc tgc gaa aag    202
Ala Phe Ser Cys Val Asn Asp Ser Gly Cys Ser Gly Ser Cys Glu Lys
             40                  45                  50 caa gga ttt gct agc ggc aaa tgt gat gga gta cgt cgt cgt tgt acg    250
Gln Gly Phe Ala Ser Gly Lys Cys Asp Gly Val Arg Arg Arg Cys Thr
         55                  60                  65
```

-continued

```
tgt tac aag aag tgt tga gcatatatat gctctttatt aaaactatgt         298
Cys Tyr Lys Lys Cys *
        70 aaactagtca cgtggtgact ttctcctgta ccatctttgg tatctgatgg tgtattaaat  358 aaagtttgac gtttgtagcn n                                          379
```

<210> SEQ ID NO 200
<211> LENGTH: 72
<212> TYPE: PRT
<213> ORGANISM: Taraxacum kok-saghyz

<400> SEQUENCE: 200

```
Met Gly Lys Ser Leu Val Val Phe Met Leu Leu Leu Ala Leu Phe Ala
 1               5                  10                  15

Thr Asp Lys Thr Leu Val Ser Val Thr Glu Ala Lys Met Cys Gln Thr
            20                  25                  30

Thr Ser His Ala Phe Ser Cys Val Asn Asp Ser Gly Cys Ser Gly Ser
        35                  40                  45

Cys Glu Lys Gln Gly Phe Ala Ser Gly Lys Cys Asp Gly Val Arg Arg
    50                  55                  60

Arg Cys Thr Cys Tyr Lys Lys Cys
65                  70
```

<210> SEQ ID NO 201
<211> LENGTH: 45
<212> TYPE: PRT
<213> ORGANISM: Taraxacum kok-saghyz

<400> SEQUENCE: 201

```
Lys Met Cys Gln Thr Thr Ser His Ala Phe Ser Cys Val Asn Asp Ser
 1               5                  10                  15

Gly Cys Ser Gly Ser Cys Glu Lys Gln Gly Phe Ala Ser Gly Lys Cys
            20                  25                  30

Asp Gly Val Arg Arg Arg Cys Thr Cys Tyr Lys Lys Cys
        35                  40                  45
```

<210> SEQ ID NO 202
<211> LENGTH: 373
<212> TYPE: DNA
<213> ORGANISM: Taraxacum kok-saghyz
<220> FEATURE:
<221> NAME/KEY: CDS
<222> LOCATION: (35)...(253)
<220> FEATURE:
<221> NAME/KEY: mat_peptide
<222> LOCATION: (116)...(250)
<220> FEATURE:
<221> NAME/KEY: misc_feature
<222> LOCATION: 298, 299, 300, 362, 363, 364, 365, 366, 367, 369, 370,
      371, 372, 373
<223> OTHER INFORMATION: n = A,T,C or G

<400> SEQUENCE: 202

```
ggccattatg gccggggtg catcataatt caaa atg gga aaa agc ctg ttt gtg    55
                                    Met Gly Lys Ser Leu Phe Val
                                     1               5 ttc atg ttg ctg ctt gct ctc ttt gct acc gat aag act ttg gtg agt   103
Phe Met Leu Leu Leu Ala Leu Phe Ala Thr Asp Lys Thr Leu Val Ser
            10                  15                  20 gtg acc gaa gta aag atg tgt caa acg acg agc cat gca ttt agt tgt   151
Val Thr Glu Val Lys Met Cys Gln Thr Thr Ser His Ala Phe Ser Cys
        25                  30                  35
```

```
gtg aac gac tcg ggt tgc agt ggc tcc tgc gaa aag caa gga ttt gct      199
Val Asn Asp Ser Gly Cys Ser Gly Ser Cys Glu Lys Gln Gly Phe Ala
 40              45                  50                  55 agc ggc aaa tgt gat gga gta cgt cgt cgt tgt acg tgt tac aag aag      247
Ser Gly Lys Cys Asp Gly Val Arg Arg Arg Cys Thr Cys Tyr Lys Lys
             60                  65                  70 tgt tga gcatatatat gctctttatt aaaactatgt aaactagtca cgtgnnnact       303
Cys * ttctcctgta ccatctttgg tatctgacgg tatattaaat aaagtttgac gtttgtagnn    363 nnnntnnnnn                                                           373

<210> SEQ ID NO 203
<211> LENGTH: 72
<212> TYPE: PRT
<213> ORGANISM: Taraxacum kok-saghyz

<400> SEQUENCE: 203

Met Gly Lys Ser Leu Phe Val Phe Met Leu Leu Ala Leu Phe Ala
 1               5                  10                  15

Thr Asp Lys Thr Leu Val Ser Val Thr Glu Val Lys Met Cys Gln Thr
             20                  25                  30

Thr Ser His Ala Phe Ser Cys Val Asn Asp Ser Gly Cys Ser Gly Ser
         35                  40                  45

Cys Glu Lys Gln Gly Phe Ala Ser Gly Lys Cys Asp Gly Val Arg Arg
     50                  55                  60

Arg Cys Thr Cys Tyr Lys Lys Cys
 65                  70

<210> SEQ ID NO 204
<211> LENGTH: 45
<212> TYPE: PRT
<213> ORGANISM: Taraxacum kok-saghyz

<400> SEQUENCE: 204

Lys Met Cys Gln Thr Thr Ser His Ala Phe Ser Cys Val Asn Asp Ser
 1               5                  10                  15

Gly Cys Ser Gly Ser Cys Glu Lys Gln Gly Phe Ala Ser Gly Lys Cys
             20                  25                  30

Asp Gly Val Arg Arg Arg Cys Thr Cys Tyr Lys Lys Cys
         35                  40                  45

<210> SEQ ID NO 205
<211> LENGTH: 413
<212> TYPE: DNA
<213> ORGANISM: Taraxacum kok-saghyz
<220> FEATURE:
<221> NAME/KEY: CDS
<222> LOCATION: (43)...(261)
<220> FEATURE:
<221> NAME/KEY: mat_peptide
<222> LOCATION: (124)...(258)
<220> FEATURE:
<221> NAME/KEY: misc_feature
<222> LOCATION: 385, 386, 387, 388, 389, 391, 392, 393, 394, 395, 396,
      397, 398, 399, 400, 401, 402, 403, 404, 405, 406, 407, 408, 409,
      410, 411, 412
<223> OTHER INFORMATION: n = A,T,C or G

<400> SEQUENCE: 205
ggccattatg gccaggggtt tttctgtgca tcataattca aa atg gga aaa agc       54
                                              Met Gly Lys Ser
                                               1
```

```
ctg ttt gtg ttc atg ttg ctg ctt gct ctc ttt gct act gat aag act    102
Leu Phe Val Phe Met Leu Leu Leu Ala Leu Phe Ala Thr Asp Lys Thr
 5                  10                  15                  20 ttg gtg agt gtg acc gaa gca aag atg tgt caa acg acg agc cat gca    150
Leu Val Ser Val Thr Glu Ala Lys Met Cys Gln Thr Thr Ser His Ala
             25                  30                  35 ttt agt tgt gtg aac gac tcg ggt tgc agt ggc tcc tgc gaa aag caa    198
Phe Ser Cys Val Asn Asp Ser Gly Cys Ser Gly Ser Cys Glu Lys Gln
         40                  45                  50 gga ttt gct agc ggc aaa tgt gat gga gta cgt cgt tgt tgt acg tgt    246
Gly Phe Ala Ser Gly Lys Cys Asp Gly Val Arg Arg Cys Cys Thr Cys
     55                  60                  65 tac aag aag tgt tga gcatatatat gctctttatt aaaactatgt aaactagtca    301
Tyr Lys Lys Cys *
 70 cgtggtgact ttctcctgta ccatctttgg tatctgacgg tatattaaat aaagtttgac   361 gtttgtagca tatcatgcaa ctannnnncn nnnnnnnnnn nnnnnnnnnn nc            413

<210> SEQ ID NO 206
<211> LENGTH: 72
<212> TYPE: PRT
<213> ORGANISM: Taraxacum kok-saghyz

<400> SEQUENCE: 206

Met Gly Lys Ser Leu Phe Val Phe Met Leu Leu Leu Ala Leu Phe Ala
 1               5                  10                  15

Thr Asp Lys Thr Leu Val Ser Val Thr Glu Ala Lys Met Cys Gln Thr
             20                  25                  30

Thr Ser His Ala Phe Ser Cys Val Asn Asp Ser Gly Cys Ser Gly Ser
         35                  40                  45

Cys Glu Lys Gln Gly Phe Ala Ser Gly Lys Cys Asp Gly Val Arg Arg
     50                  55                  60

Cys Cys Thr Cys Tyr Lys Lys Cys
 65                  70

<210> SEQ ID NO 207
<211> LENGTH: 45
<212> TYPE: PRT
<213> ORGANISM: Taraxacum kok-saghyz

<400> SEQUENCE: 207

Lys Met Cys Gln Thr Thr Ser His Ala Phe Ser Cys Val Asn Asp Ser
 1               5                  10                  15

Gly Cys Ser Gly Ser Cys Glu Lys Gln Gly Phe Ala Ser Gly Lys Cys
             20                  25                  30

Asp Gly Val Arg Arg Cys Cys Thr Cys Tyr Lys Lys Cys
         35                  40                  45

<210> SEQ ID NO 208
<211> LENGTH: 346
<212> TYPE: DNA
<213> ORGANISM: Taraxacum kok-saghyz
<220> FEATURE:
<221> NAME/KEY: CDS
<222> LOCATION: (46)...(264)
<220> FEATURE:
<221> NAME/KEY: mat_peptide
<222> LOCATION: (127)...(261)
<220> FEATURE:
<221> NAME/KEY: misc_feature
<222> LOCATION: 282, 283, 284, 285, 303, 334, 335, 336, 344
```

<223> OTHER INFORMATION: n = A,T,C or G

<400> SEQUENCE: 208

```
ggccattatg gccggggatt gttttctgt gcatcataat tcaaa atg gga aaa agc        57
                                              Met Gly Lys Ser
                                               1 ctg ttt gtg ttc atg ttg ctg ctt gct ctc ttt gct act gat aag act       105
Leu Phe Val Phe Met Leu Leu Leu Ala Leu Phe Ala Thr Asp Lys Thr
 5              10                  15                  20 ttg gtg agt gtg acc gaa gca aag atg tgt caa acg acg agc cat gca       153
Leu Val Ser Val Thr Glu Ala Lys Met Cys Gln Thr Thr Ser His Ala
            25                  30                  35 ttt agt tgt gtg aac gac tcg gat tgc agt ggc tcc tgc gaa aag caa       201
Phe Ser Cys Val Asn Asp Ser Asp Cys Ser Gly Ser Cys Glu Lys Gln
        40                  45                  50 gga ttt gct agc ggc aaa tgt gat gga gta cgt cgt cgt tgt acg tgt       249
Gly Phe Ala Ser Gly Lys Cys Asp Gly Val Arg Arg Arg Cys Thr Cys
    55                  60                  65 tac aag aag tgt tga gcatatatat gctctttnnn naagctatgt aaactagtna       304
Tyr Lys Lys Cys *
        70 cgtggtgact ttctcctgta ccatctttgn nntctgacgn ta                        346
```

<210> SEQ ID NO 209
<211> LENGTH: 72
<212> TYPE: PRT
<213> ORGANISM: Taraxacum kok-saghyz

<400> SEQUENCE: 209

```
Met Gly Lys Ser Leu Phe Val Phe Met Leu Leu Leu Ala Leu Phe Ala
 1               5                  10                  15

Thr Asp Lys Thr Leu Val Ser Val Thr Glu Ala Lys Met Cys Gln Thr
            20                  25                  30

Thr Ser His Ala Phe Ser Cys Val Asn Asp Ser Asp Cys Ser Gly Ser
        35                  40                  45

Cys Glu Lys Gln Gly Phe Ala Ser Gly Lys Cys Asp Gly Val Arg Arg
    50                  55                  60

Arg Cys Thr Cys Tyr Lys Lys Cys
65                  70
```

<210> SEQ ID NO 210
<211> LENGTH: 45
<212> TYPE: PRT
<213> ORGANISM: Taraxacum kok-saghyz

<400> SEQUENCE: 210

```
Lys Met Cys Gln Thr Thr Ser His Ala Phe Ser Cys Val Asn Asp Ser
 1               5                  10                  15

Asp Cys Ser Gly Ser Cys Glu Lys Gln Gly Phe Ala Ser Gly Lys Cys
            20                  25                  30

Asp Gly Val Arg Arg Arg Cys Thr Cys Tyr Lys Lys Cys
        35                  40                  45
```

<210> SEQ ID NO 211
<211> LENGTH: 432
<212> TYPE: DNA
<213> ORGANISM: Picramnia pentandra
<220> FEATURE:
<221> NAME/KEY: CDS
<222> LOCATION: (38)...(271)
<220> FEATURE:

```
<221> NAME/KEY: mat_peptide
<222> LOCATION: (119)...(268)

<400> SEQUENCE: 211
gcacgagata atcgctactt tgttttctg gaaaaaa atg gac aag aag ttg ttt       55
                                        Met Asp Lys Lys Leu Phe
                                         1               5 ggg ttt tta ctg ttg atg ttc atc tta ttt gct tca cag gaa agc atg     103
Gly Phe Leu Leu Leu Met Phe Ile Leu Phe Ala Ser Gln Glu Ser Met
         10                  15                  20 gtt caa gtt gaa gca aaa gtt tgc acc aaa ccg agt aag ttc ttc aag     151
Val Gln Val Glu Ala Lys Val Cys Thr Lys Pro Ser Lys Phe Phe Lys
     25                  30                  35 ggt tta tgc ggc act gac ggg gca tgt acc aca gct tgc agg aag gaa     199
Gly Leu Cys Gly Thr Asp Gly Ala Cys Thr Thr Ala Cys Arg Lys Glu
 40                  45                  50 ggc tta cac agt ggg tat tgt cag ctt aag ggg ttt ctt aat tcc gtt     247
Gly Leu His Ser Gly Tyr Cys Gln Leu Lys Gly Phe Leu Asn Ser Val
         55                  60                  65              70 tgc gtt tgc aga aag cat tgt taa attcaaacag acaatgtact agtctcctat    301
Cys Val Cys Arg Lys His Cys *
                 75 acatgtcgct gcctaaaata cactataggg cctttagccc tcttttgtac caaataatat   361 ttataataat catcatcatc ataaatattt gatgatgcca aacttatgat accaaaaaaa   421 aaaaaaaaaa a                                                        432

<210> SEQ ID NO 212
<211> LENGTH: 77
<212> TYPE: PRT
<213> ORGANISM: Picramnia pentandra

<400> SEQUENCE: 212

Met Asp Lys Lys Leu Phe Gly Phe Leu Leu Met Phe Ile Leu Phe
 1               5                  10                  15

Ala Ser Gln Glu Ser Met Val Gln Val Glu Ala Lys Val Cys Thr Lys
                 20                  25                  30

Pro Ser Lys Phe Phe Lys Gly Leu Cys Gly Thr Asp Gly Ala Cys Thr
             35                  40                  45

Thr Ala Cys Arg Lys Glu Gly Leu His Ser Gly Tyr Cys Gln Leu Lys
         50                  55                  60

Gly Phe Leu Asn Ser Val Cys Val Cys Arg Lys His Cys
 65                  70                  75

<210> SEQ ID NO 213
<211> LENGTH: 50
<212> TYPE: PRT
<213> ORGANISM: Picramnia pentandra

<400> SEQUENCE: 213

Lys Val Cys Thr Lys Pro Ser Lys Phe Phe Lys Gly Leu Cys Gly Thr
 1               5                  10                  15

Asp Gly Ala Cys Thr Thr Ala Cys Arg Lys Glu Gly Leu His Ser Gly
                 20                  25                  30

Tyr Cys Gln Leu Lys Gly Phe Leu Asn Ser Val Cys Val Cys Arg Lys
             35                  40                  45

His Cys
 50
```

<210> SEQ ID NO 214
<211> LENGTH: 474
<212> TYPE: DNA
<213> ORGANISM: Picramnia pentandra
<220> FEATURE:
<221> NAME/KEY: CDS
<222> LOCATION: (47)...(280)
<220> FEATURE:
<221> NAME/KEY: mat_peptide
<222> LOCATION: (128)...(277)

<400> SEQUENCE: 214

```
gcacgagaca ctcagagaca acctcctttt taacttgctg agaaaa atg gat aag          55
                                                 Met Asp Lys
                                                   1 aaa ttc ttc ggc ctc ttg ctg ttg gtg ttc atc tta ttt gct ttc gag        103
Lys Phe Phe Gly Leu Leu Leu Leu Val Phe Ile Leu Phe Ala Phe Glu
  5                  10                  15 gga aac atg ctt caa gtt gaa gca aaa gtt tgc acc aaa ccg agc aag        151
Gly Asn Met Leu Gln Val Glu Ala Lys Val Cys Thr Lys Pro Ser Lys
 20                  25                  30                  35 ttc ttt aag ggt tta tgc ggt gcc gat cgt gac tgt act gta gct tgt        199
Phe Phe Lys Gly Leu Cys Gly Ala Asp Arg Asp Cys Thr Val Ala Cys
                 40                  45                  50 aag aag gaa ggc ttg gcc act gga ttt tgt cag aaa aaa gga ttt ttt        247
Lys Lys Glu Gly Leu Ala Thr Gly Phe Cys Gln Lys Lys Gly Phe Phe
             55                  60                  65 aac ttt gtt tgc gta tgc aga aag cct tgt tga attcaataaa agaggtgtac      300
Asn Phe Val Cys Val Cys Arg Lys Pro Cys *
         70                  75 ccccacaaag agaacttaag cataatatga tattctcgtt gtttgtgtaa aataaaaccg      360
ggcacttaat agggccttta gccatccttt gtaccaaata tttatagtaa taagaaccat      420
cgtcgtcatc tgtgatgatg gcaaattgat aataccaaaa aaaaaaaaaa aaaa            474
```

<210> SEQ ID NO 215
<211> LENGTH: 77
<212> TYPE: PRT
<213> ORGANISM: Picramnia pentandra

<400> SEQUENCE: 215

```
Met Asp Lys Lys Phe Phe Gly Leu Leu Leu Leu Val Phe Ile Leu Phe
  1               5                  10                  15

Ala Phe Glu Gly Asn Met Leu Gln Val Glu Ala Lys Val Cys Thr Lys
             20                  25                  30

Pro Ser Lys Phe Phe Lys Gly Leu Cys Gly Ala Asp Arg Asp Cys Thr
         35                  40                  45

Val Ala Cys Lys Lys Glu Gly Leu Ala Thr Gly Phe Cys Gln Lys Lys
     50                  55                  60

Gly Phe Phe Asn Phe Val Cys Val Cys Arg Lys Pro Cys
 65                  70                  75
```

<210> SEQ ID NO 216
<211> LENGTH: 50
<212> TYPE: PRT
<213> ORGANISM: Picramnia pentandra

<400> SEQUENCE: 216

```
Lys Val Cys Thr Lys Pro Ser Lys Phe Phe Lys Gly Leu Cys Gly Ala
  1               5                  10                  15

Asp Arg Asp Cys Thr Val Ala Cys Lys Lys Glu Gly Leu Ala Thr Gly
             20                  25                  30
```

```
Phe Cys Gln Lys Lys Gly Phe Phe Asn Phe Val Cys Val Cys Arg Lys
            35                  40                  45

Pro Cys
    50

<210> SEQ ID NO 217
<211> LENGTH: 343
<212> TYPE: DNA
<213> ORGANISM: Picramnia pentandra
<220> FEATURE:
<221> NAME/KEY: CDS
<222> LOCATION: (38)...(268)
<220> FEATURE:
<221> NAME/KEY: mat_peptide
<222> LOCATION: (116)...(265)
<220> FEATURE:
<221> NAME/KEY: misc_feature
<222> LOCATION: 304, 313
<223> OTHER INFORMATION: n = A,T,C or G

<400> SEQUENCE: 217
cacaactata atcgctactt tgtttttctg gaaaaaa atg gac aag ttg ttt ggg       55
                                        Met Asp Lys Leu Phe Gly
                                          1               5 ttt tta ctg ttg atg ttc atc tta ttt gct tca cag gaa agc atg gtt      103
Phe Leu Leu Leu Met Phe Ile Leu Phe Ala Ser Gln Glu Ser Met Val
         10                  15                  20 caa gtt gaa gca aaa gtt tgc acc aaa ccg agt aag ttc ttc aag ggt      151
Gln Val Glu Ala Lys Val Cys Thr Lys Pro Ser Lys Phe Phe Lys Gly
             25                  30                  35 tta tgc ggc act gac ggg gca tgt acc aca gct tgc agg aag gaa ggc      199
Leu Cys Gly Thr Asp Gly Ala Cys Thr Thr Ala Cys Arg Lys Glu Gly
         40                  45                  50 tta cac agt ggg tat tgt cag ctt aag ggg ttt ctt aat tcc gtt tgc      247
Leu His Ser Gly Tyr Cys Gln Leu Lys Gly Phe Leu Asn Ser Val Cys
 55                  60                  65                  70 gtt tgc aga aag cat tgt tag attcagacag acaatgtact agtctcctat         298
Val Cys Arg Lys His Cys *
                 75 acatgncgct gcctnaaatc actacaaggg ctttaggccc ttttg                     343

<210> SEQ ID NO 218
<211> LENGTH: 76
<212> TYPE: PRT
<213> ORGANISM: Picramnia pentandra

<400> SEQUENCE: 218

Met Asp Lys Leu Phe Gly Phe Leu Leu Leu Met Phe Ile Leu Phe Ala
  1               5                  10                  15

Ser Gln Glu Ser Met Val Gln Val Glu Ala Lys Val Cys Thr Lys Pro
             20                  25                  30

Ser Lys Phe Phe Lys Gly Leu Cys Gly Thr Asp Gly Ala Cys Thr Thr
         35                  40                  45

Ala Cys Arg Lys Glu Gly Leu His Ser Gly Tyr Cys Gln Leu Lys Gly
     50                  55                  60

Phe Leu Asn Ser Val Cys Val Cys Arg Lys His Cys
 65                  70                  75

<210> SEQ ID NO 219
<211> LENGTH: 50
<212> TYPE: PRT
<213> ORGANISM: Picramnia pentandra
```

<400> SEQUENCE: 219

Lys Val Cys Thr Lys Pro Ser Lys Phe Phe Lys Gly Leu Cys Gly Thr
1               5                   10                  15

Asp Gly Ala Cys Thr Thr Ala Cys Arg Lys Glu Gly Leu His Ser Gly
            20                  25                  30

Tyr Cys Gln Leu Lys Gly Phe Leu Asn Ser Val Cys Val Cys Arg Lys
        35                  40                  45

His Cys
    50

<210> SEQ ID NO 220
<211> LENGTH: 512
<212> TYPE: DNA
<213> ORGANISM: Picramnia pentandra
<220> FEATURE:
<221> NAME/KEY: CDS
<222> LOCATION: (31)...(264)
<220> FEATURE:
<221> NAME/KEY: mat_peptide
<222> LOCATION: (112)...(261)
<220> FEATURE:
<221> NAME/KEY: misc_feature
<222> LOCATION: 330, 408, 409, 412, 425, 452, 457, 465, 488, 489, 490,
       512
<223> OTHER INFORMATION: n = A,T,C or G

<400> SEQUENCE: 220
ataatcgcta ctttgttttt ctggaaaaaa atg gac aag aag ttg ttt ggg ttt         54
                                 Met Asp Lys Lys Leu Phe Gly Phe
                                   1               5 tta ctg ttg atg ttc atc tta ttt gct tca cag gaa agc atg gtt caa        102
Leu Leu Leu Met Phe Ile Leu Phe Ala Ser Gln Glu Ser Met Val Gln
     10                  15                  20 gtt gaa gca aaa gtt tgc acc aaa ccg agt aag ttc ttc aag ggt tta        150
Val Glu Ala Lys Val Cys Thr Lys Pro Ser Lys Phe Phe Lys Gly Leu
 25                  30                  35                  40 tgc ggc act gac ggg gca tgt acc aca gct tgc agg aag gaa ggc tta        198
Cys Gly Thr Asp Gly Ala Cys Thr Thr Ala Cys Arg Lys Glu Gly Leu
                 45                  50                  55 cac agt ggg tat tgt cag ctt aag ggg ttt ctt aat tcc gtt tgc gtt        246
His Ser Gly Tyr Cys Gln Leu Lys Gly Phe Leu Asn Ser Val Cys Val
             60                  65                  70 tgc aga aag cat tgt taa attcaaacag acaatgtact atctccctat              294
Cys Arg Lys His Cys *
         75 acatgtcgct gcctaaaata cactataggc ctttanccc ttttggtacc aaataatatt       354 aatataacat caaccacata aatatttgga tgagccaaac ttatgatacc aagnnaanaa      414 aaaaaacccc naggggggc ccgtaccatt cccctanat ganctatta nattaacggc         474 ctcgtttaaa ctcnnacgg gaaaacctgg gttacaan                               512

<210> SEQ ID NO 221
<211> LENGTH: 77
<212> TYPE: PRT
<213> ORGANISM: Picramnia pentandra

<400> SEQUENCE: 221

Met Asp Lys Lys Leu Phe Gly Phe Leu Leu Leu Met Phe Ile Leu Phe
1               5                   10                  15

Ala Ser Gln Glu Ser Met Val Gln Val Glu Ala Lys Val Cys Thr Lys
            20                  25                  30

```
Pro Ser Lys Phe Phe Lys Gly Leu Cys Gly Thr Asp Gly Ala Cys Thr
         35                  40                  45

Thr Ala Cys Arg Lys Glu Gly Leu His Ser Gly Tyr Cys Gln Leu Lys
     50                  55                  60

Gly Phe Leu Asn Ser Val Cys Val Cys Arg Lys His Cys
 65                  70                  75

<210> SEQ ID NO 222
<211> LENGTH: 50
<212> TYPE: PRT
<213> ORGANISM: Picramnia pentandra

<400> SEQUENCE: 222

Lys Val Cys Thr Lys Pro Ser Lys Phe Phe Lys Gly Leu Cys Gly Thr
  1               5                  10                  15

Asp Gly Ala Cys Thr Thr Ala Cys Arg Lys Glu Gly Leu His Ser Gly
             20                  25                  30

Tyr Cys Gln Leu Lys Gly Phe Leu Asn Ser Val Cys Val Cys Arg Lys
         35                  40                  45

His Cys
    50

<210> SEQ ID NO 223
<211> LENGTH: 511
<212> TYPE: DNA
<213> ORGANISM: Picramnia pentandra
<220> FEATURE:
<221> NAME/KEY: CDS
<222> LOCATION: (31)...(264)
<220> FEATURE:
<221> NAME/KEY: mat_peptide
<222> LOCATION: (112)...(261)
<220> FEATURE:
<221> NAME/KEY: misc_feature
<222> LOCATION: 351, 430, 432, 443, 452, 460, 465, 467, 472, 486, 491,
      498
<223> OTHER INFORMATION: n = A,T,C or G

<400> SEQUENCE: 223
gacaacctac tttttaactt gctgaaaaaa atg gat aag aaa ttc ttc ggg ctc      54
                                 Met Asp Lys Lys Phe Phe Gly Leu
                                  1               5 ttg ctg ttg gtg ttc atc tta ttc gct tcc gag gga aac atg ctt caa      102
Leu Leu Leu Val Phe Ile Leu Phe Ala Ser Glu Gly Asn Met Leu Gln
 10                  15                  20 gtt gaa gca aaa gtt tgc acc aaa ccg agc aag ttc ttt aag ggt tta      150
Val Glu Ala Lys Val Cys Thr Lys Pro Ser Lys Phe Phe Lys Gly Leu
 25                  30                  35                  40 tgc ggt ttc gat cgt gac tgc act gta gct tgt aag aag gaa ggc ttg      198
Cys Gly Phe Asp Arg Asp Cys Thr Val Ala Cys Lys Lys Glu Gly Leu
             45                  50                  55 gcc agt gga ttt tgt cag aat aaa ggg ttt ttt aat gtt gtt tgc gta      246
Ala Ser Gly Phe Cys Gln Asn Lys Gly Phe Phe Asn Val Val Cys Val
         60                  65                  70 tgc aga aag cct tgt tga attcaataaa aagagtgtac cttacacaga             294
Cys Arg Lys Pro Cys *
     75 gaacttaagc ataatatgat ccccgtgggt taaataaaaa ccgggtactt aatatantgt    354 ctttggcccc ctttgcccca aatatttaat aagaatatct cctcaccgtg atgatggaaa   414 ttgataaaaa caattnanaa aaaccccang ggggccngt accatncccc nanatgancc    474
```
tattaattca cnggccncgt ttanaactcg tgacggg                            511

<210> SEQ ID NO 224
<211> LENGTH: 77
<212> TYPE: PRT
<213> ORGANISM: Picramnia pentandra

<400> SEQUENCE: 224

Met Asp Lys Lys Phe Phe Gly Leu Leu Leu Val Phe Ile Leu Phe
1               5                   10                  15

Ala Ser Glu Gly Asn Met Leu Gln Val Glu Ala Lys Val Cys Thr Lys
            20                  25                  30

Pro Ser Lys Phe Phe Lys Gly Leu Cys Gly Phe Asp Arg Asp Cys Thr
        35                  40                  45

Val Ala Cys Lys Lys Glu Gly Leu Ala Ser Gly Phe Cys Gln Asn Lys
50                  55                  60

Gly Phe Phe Asn Val Val Cys Val Cys Arg Lys Pro Cys
65                  70                  75

<210> SEQ ID NO 225
<211> LENGTH: 50
<212> TYPE: PRT
<213> ORGANISM: Picramnia pentandra

<400> SEQUENCE: 225

Lys Val Cys Thr Lys Pro Ser Lys Phe Phe Lys Gly Leu Cys Gly Phe
1               5                   10                  15

Asp Arg Asp Cys Thr Val Ala Cys Lys Lys Glu Gly Leu Ala Ser Gly
            20                  25                  30

Phe Cys Gln Asn Lys Gly Phe Phe Asn Val Val Cys Val Cys Arg Lys
        35                  40                  45

Pro Cys
    50

<210> SEQ ID NO 226
<211> LENGTH: 498
<212> TYPE: DNA
<213> ORGANISM: Nicotiana benthamiana
<220> FEATURE:
<221> NAME/KEY: CDS
<222> LOCATION: (1)...(261)
<220> FEATURE:
<221> NAME/KEY: mat_peptide
<222> LOCATION: (82)...(255)

<400> SEQUENCE: 226 atg gct aaa tac aca gcc ttc att acc ctc atc ttc tgt ctt ctc ctt      48
Met Ala Lys Tyr Thr Ala Phe Ile Thr Leu Ile Phe Cys Leu Leu Leu
1               5                   10                  15 gtt gct gct act gaa atg caa atg gca gaa gca aaa tac tgc tgg aag      96
Val Ala Ala Thr Glu Met Gln Met Ala Glu Ala Lys Tyr Cys Trp Lys
            20                  25                  30 aaa agt cac aag tgg cat ggg cct tgc cac tat tct tac aaa tgt agc     144
Lys Ser His Lys Trp His Gly Pro Cys His Tyr Ser Tyr Lys Cys Ser
        35                  40                  45 cac cat tgc aag cag tat ttt gga gct gaa tat gga att tgt aag aaa     192
His His Cys Lys Gln Tyr Phe Gly Ala Glu Tyr Gly Ile Cys Lys Lys
50                  55                  60 tac caa tgg gga cac aaa cat cac cac tgg gca aaa tat gct tgc tat     240
Tyr Gln Trp Gly His Lys His His His Trp Ala Lys Tyr Ala Cys Tyr
65                  70                  75                  80

```
tgc tat tct cct tgc cat taa tcatgaggaa ttgactttag agtctcaaca      291
Cys Tyr Ser Pro Cys His  *
                85 attggcttgg actgatatat acaaataaga agctgacttc ttgttaatgc agagaactaa  351 atactgcatc aataattagt tagtgtgatt ttattgtgtg tttgtgtgtc acaatgtaat  411 aagttttgct aagtctagct tgacttttgg tcgagctaat agcatatgcc tgaacaatta  471 tgctgctttc atttaattta tgttcca                                     498

<210> SEQ ID NO 227
<211> LENGTH: 86
<212> TYPE: PRT
<213> ORGANISM: Nicotiana benthamiana

<400> SEQUENCE: 227

Met Ala Lys Tyr Thr Ala Phe Ile Thr Leu Ile Phe Cys Leu Leu Leu
1               5                   10                  15

Val Ala Ala Thr Glu Met Gln Met Ala Glu Ala Lys Tyr Cys Trp Lys
            20                  25                  30

Lys Ser His Lys Trp His Gly Pro Cys His Tyr Ser Tyr Lys Cys Ser
        35                  40                  45

His His Cys Lys Gln Tyr Phe Gly Ala Glu Tyr Gly Ile Cys Lys Lys
    50                  55                  60

Tyr Gln Trp Gly His Lys His His Trp Ala Lys Tyr Ala Cys Tyr
65                  70                  75                  80

Cys Tyr Ser Pro Cys His
                85

<210> SEQ ID NO 228
<211> LENGTH: 58
<212> TYPE: PRT
<213> ORGANISM: Nicotiana benthamiana

<400> SEQUENCE: 228

Lys Tyr Cys Trp Lys Lys Ser His Lys Trp His Gly Pro Cys His Tyr
1               5                   10                  15

Ser Tyr Lys Cys Ser His His Cys Lys Gln Tyr Phe Gly Ala Glu Tyr
            20                  25                  30

Gly Ile Cys Lys Lys Tyr Gln Trp Gly His Lys His His Trp Ala
        35                  40                  45

Lys Tyr Ala Cys Tyr Cys Tyr Ser Pro Cys
    50                  55

<210> SEQ ID NO 229
<211> LENGTH: 507
<212> TYPE: DNA
<213> ORGANISM: Nicotiana benthamiana
<220> FEATURE:
<221> NAME/KEY: CDS
<222> LOCATION: (5)...(265)
<220> FEATURE:
<221> NAME/KEY: mat_peptide
<222> LOCATION: (86)...(259)
<220> FEATURE:
<221> NAME/KEY: misc_feature
<222> LOCATION: 464, 469, 507
<223> OTHER INFORMATION: n = A,T,C or G

<400> SEQUENCE: 229 agcc atg cct aaa tac aca gcc ttc att gcc ctc atc tta tgt ctt ctc   49
     Met Pro Lys Tyr Thr Ala Phe Ile Ala Leu Ile Leu Cys Leu Leu
     1               5                   10                  15
```

```
ctt gtt gct gct act gaa atg caa atg gca gaa gga aaa tac tgc tgg      97
Leu Val Ala Ala Thr Glu Met Gln Met Ala Glu Gly Lys Tyr Cys Trp
            20                  25                  30 aag aaa aat cac aag tgg cat ggg cct tgc cac tat tct tac aaa tgt     145
Lys Lys Asn His Lys Trp His Gly Pro Cys His Tyr Ser Tyr Lys Cys
        35                  40                  45 aac cac cac tgc aag cac tat ttt gga gct gaa tat gga gtt tgt aag     193
Asn His His Cys Lys His Tyr Phe Gly Ala Glu Tyr Gly Val Cys Lys
    50                  55                  60 aaa tac caa tgg gga cac aaa cat cat cac tgg gca aaa tat gct tgc     241
Lys Tyr Gln Trp Gly His Lys His His His Trp Ala Lys Tyr Ala Cys
65                  70                  75                  80 tat tgc tat tct cct tgt cat taa tcacgaggaa ttgacttcag agcctcaacg    295
Tyr Cys Tyr Ser Pro Cys His *
            85 attggcttgg agtgatatat atataaataa gaaactgact ttttctgttt gcagagttct   355 aattactgca tcaacaatca gttagtgtga ttttgttatg tgtttgtgta tgtcacaatg   415 taataagttt tgttaaatcc ttagcttgcc tggttttggg ccaactaant gtanttgccc   475 gaaaaaatta tattgccttt caatttaatt tn                                 507

<210> SEQ ID NO 230
<211> LENGTH: 86
<212> TYPE: PRT
<213> ORGANISM: Nicotiana benthamiana

<400> SEQUENCE: 230

Met Pro Lys Tyr Thr Ala Phe Ile Ala Leu Ile Leu Cys Leu Leu Leu
1               5                   10                  15

Val Ala Ala Thr Glu Met Gln Met Ala Glu Gly Lys Tyr Cys Trp Lys
            20                  25                  30

Lys Asn His Lys Trp His Gly Pro Cys His Tyr Ser Tyr Lys Cys Asn
        35                  40                  45

His His Cys Lys His Tyr Phe Gly Ala Glu Tyr Gly Val Cys Lys Lys
    50                  55                  60

Tyr Gln Trp Gly His Lys His His His Trp Ala Lys Tyr Ala Cys Tyr
65                  70                  75                  80

Cys Tyr Ser Pro Cys His
            85

<210> SEQ ID NO 231
<211> LENGTH: 58
<212> TYPE: PRT
<213> ORGANISM: Nicotiana benthamiana

<400> SEQUENCE: 231

Lys Tyr Cys Trp Lys Lys Asn His Lys Trp His Gly Pro Cys His Tyr
1               5                   10                  15

Ser Tyr Lys Cys Asn His His Cys Lys His Tyr Phe Gly Ala Glu Tyr
            20                  25                  30

Gly Val Cys Lys Lys Tyr Gln Trp Gly His Lys His His His Trp Ala
        35                  40                  45

Lys Tyr Ala Cys Tyr Cys Tyr Ser Pro Cys
    50                  55

<210> SEQ ID NO 232
<211> LENGTH: 480
<212> TYPE: DNA
```

```
<213> ORGANISM: Nicotiana benthamiana
<220> FEATURE:
<221> NAME/KEY: CDS
<222> LOCATION: (4)...(264)
<220> FEATURE:
<221> NAME/KEY: mat_peptide
<222> LOCATION: (85)...(258)
<220> FEATURE:
<221> NAME/KEY: misc_feature
<222> LOCATION: 447, 472
<223> OTHER INFORMATION: n = A,T,C or G

<400> SEQUENCE: 232
```

| | | | | | | | | | | | | | | | | |
|---|---|---|---|---|---|---|---|---|---|---|---|---|---|---|---|---|
| gcc | atg | gct | aaa | tac | aca | gcc | ttc | att | acc | ctc | atc | ttc | tgt | ctt | ctc | 48 |
| | Met | Ala | Lys | Tyr | Thr | Ala | Phe | Ile | Thr | Leu | Ile | Phe | Cys | Leu | Leu | |
| | 1 | | | 5 | | | | | 10 | | | | | 15 | | |

| | | | | | | | | | | | | | | | | |
|---|---|---|---|---|---|---|---|---|---|---|---|---|---|---|---|---|
| ctt | gtt | gct | gct | act | gaa | atg | caa | atg | gca | gaa | gca | aaa | tac | tgc | tgg | 96 |
| Leu | Val | Ala | Ala | Thr | Glu | Met | Gln | Met | Ala | Glu | Ala | Lys | Tyr | Cys | Trp | |
| | | | 20 | | | | | 25 | | | | | 30 | | | |

| | | | | | | | | | | | | | | | | |
|---|---|---|---|---|---|---|---|---|---|---|---|---|---|---|---|---|
| aag | aaa | agt | cac | aag | tgg | cat | ggg | cct | tgc | cac | tat | tct | tac | aaa | tgt | 144 |
| Lys | Lys | Ser | His | Lys | Trp | His | Gly | Pro | Cys | His | Tyr | Ser | Tyr | Lys | Cys | |
| | | 35 | | | | | 40 | | | | | 45 | | | | |

| | | | | | | | | | | | | | | | | |
|---|---|---|---|---|---|---|---|---|---|---|---|---|---|---|---|---|
| agc | cac | cat | tgc | aag | cac | tat | ttt | gga | gct | gaa | tat | gga | att | tgt | aag | 192 |
| Ser | His | His | Cys | Lys | His | Tyr | Phe | Gly | Ala | Glu | Tyr | Gly | Ile | Cys | Lys | |
| | 50 | | | | | 55 | | | | | 60 | | | | | |

| | | | | | | | | | | | | | | | | |
|---|---|---|---|---|---|---|---|---|---|---|---|---|---|---|---|---|
| aaa | tac | caa | tgg | gga | cac | aaa | cat | cat | cac | tgg | gca | aaa | tat | gct | tgc | 240 |
| Lys | Tyr | Gln | Trp | Gly | His | Lys | His | His | His | Trp | Ala | Lys | Tyr | Ala | Cys | |
| 65 | | | | | 70 | | | | | 75 | | | | | | |

| | | | | | | | | |
|---|---|---|---|---|---|---|---|---|
| tat | tgc | tat | tct | cct | tgc | aat | taa | tcatgaggaa ttgactttag agtctcaaca | 294 |
| Tyr | Cys | Tyr | Ser | Pro | Cys | Asn | * | |
| 80 | | | | 85 | | | | |

```
attggcttgg actgatatat acaaataaga agctgacttc ttgttaatgc agagaactaa      354
atactgcatc aataattagt tagtgtgatt ttattgtgtg tttgtgtgtc acaatgtaat      414
aagttttgtt aagtctagct tgacttttgg tcnagctaat agcatatgcc tgaacaantt      474
atgctg                                                                480

<210> SEQ ID NO 233
<211> LENGTH: 86
<212> TYPE: PRT
<213> ORGANISM: Nicotiana benthamiana

<400> SEQUENCE: 233

Met Ala Lys Tyr Thr Ala Phe Ile Thr Leu Ile Phe Cys Leu Leu Leu
1               5                   10                  15

Val Ala Ala Thr Glu Met Gln Met Ala Glu Ala Lys Tyr Cys Trp Lys
            20                  25                  30

Lys Ser His Lys Trp His Gly Pro Cys His Tyr Ser Tyr Lys Cys Ser
        35                  40                  45

His His Cys Lys His Tyr Phe Gly Ala Glu Tyr Gly Ile Cys Lys Lys
    50                  55                  60

Tyr Gln Trp Gly His Lys His His Trp Ala Lys Tyr Ala Cys Tyr
65                  70                  75                  80

Cys Tyr Ser Pro Cys Asn
                85

<210> SEQ ID NO 234
<211> LENGTH: 58
<212> TYPE: PRT
<213> ORGANISM: Nicotiana benthamiana

<400> SEQUENCE: 234
```

```
Lys Tyr Cys Trp Lys Lys Ser His Lys Trp His Gly Pro Cys His Tyr
1               5                   10                  15

Ser Tyr Lys Cys Ser His His Cys Lys His Tyr Phe Gly Ala Glu Tyr
            20                  25                  30

Gly Ile Cys Lys Lys Tyr Gln Trp Gly His Lys His His His Trp Ala
        35                  40                  45

Lys Tyr Ala Cys Tyr Cys Tyr Ser Pro Cys
    50                  55
```

<210> SEQ ID NO 235
<211> LENGTH: 683
<212> TYPE: DNA
<213> ORGANISM: Zea mays
<220> FEATURE:
<221> NAME/KEY: CDS
<222> LOCATION: (221)...(475)
<220> FEATURE:
<221> NAME/KEY: mat_peptide
<222> LOCATION: (326)...(472)

<400> SEQUENCE: 235

```
ggcgtcgccg cggccggaga cgccgctgct cgagtgggag atcgacctcg ccaagctcga    60
catccagaac cagatcgctc atggcacctt tggcgtcgtc taccgcggca cctacgacgg   120
ccacgacgtc gcagtgaagg ttctggactg ggggcatgat gggcagaccc catagctgac   180
gacaccaccg tggtcgacaa aataaaaagg agagagagag atg gcc ctg tcg tct    235
                                             Met Ala Leu Ser Ser
                                             1               5 cgc cgt atg gcc gcc gca cca ttc ttc gtc gtc gtc ctt ctc gtc ctc    283
Arg Arg Met Ala Ala Ala Pro Phe Phe Val Val Val Leu Leu Val Leu
            10                  15                  20 gtg gcg gca gag agg acg atg ggc agg gtg gtg gtg gaa gag acg ctc    331
Val Ala Ala Glu Arg Thr Met Gly Arg Val Val Val Glu Glu Thr Leu
            25                  30                  35 tgc ctg tcg cag agc cat gcc ttc aaa ggc gtg tgc ctc agc aac acc    379
Cys Leu Ser Gln Ser His Ala Phe Lys Gly Val Cys Leu Ser Asn Thr
        40                  45                  50 aac tgc gac aac gta tgc aag acg gag aag ttc aca ggc ggc gag tgc    427
Asn Cys Asp Asn Val Cys Lys Thr Glu Lys Phe Thr Gly Gly Glu Cys
 55                  60                  65 aag atg gac ggc gtc atg cgc aag tgc tac tgc aag aag gtc tgc tag    475
Lys Met Asp Gly Val Met Arg Lys Cys Tyr Cys Lys Lys Val Cys *
 70                  75                  80 ggcggcagca agccccagcc gtacggctgg ttgatccggt tgcacagtgc acagctcgtt   535
tgggcacgcg gtcatgttcc ggcttctcgg ctttatttta tttcttcttt gttataataa   595
atagactctg ttagtcacgt gcgttttagt ctgggttgta cgttattaat tctctagtgt   655
attgtatttg cgaaaaaaaa aaaaaaaa                                      683
```

<210> SEQ ID NO 236
<211> LENGTH: 84
<212> TYPE: PRT
<213> ORGANISM: Zea mays

<400> SEQUENCE: 236

```
Met Ala Leu Ser Ser Arg Arg Met Ala Ala Ala Pro Phe Phe Val Val
1               5                   10                  15

Val Leu Leu Val Leu Val Ala Ala Glu Arg Thr Met Gly Arg Val Val
            20                  25                  30
```

```
Val Glu Glu Thr Leu Cys Leu Ser Gln Ser His Ala Phe Lys Gly Val
            35                  40                  45

Cys Leu Ser Asn Thr Asn Cys Asp Asn Val Cys Lys Thr Glu Lys Phe
    50                  55                  60

Thr Gly Gly Glu Cys Lys Met Asp Gly Val Met Arg Lys Cys Tyr Cys
65                  70                  75                  80

Lys Lys Val Cys

<210> SEQ ID NO 237
<211> LENGTH: 49
<212> TYPE: PRT
<213> ORGANISM: Zea mays

<400> SEQUENCE: 237

Thr Leu Cys Leu Ser Gln Ser His Ala Phe Lys Gly Val Cys Leu Ser
1               5                   10                  15

Asn Thr Asn Cys Asp Asn Val Cys Lys Thr Glu Lys Phe Thr Gly Gly
                20                  25                  30

Glu Cys Lys Met Asp Gly Val Met Arg Lys Cys Tyr Cys Lys Lys Val
            35                  40                  45

Cys

<210> SEQ ID NO 238
<211> LENGTH: 441
<212> TYPE: DNA
<213> ORGANISM: Zea mays
<220> FEATURE:
<221> NAME/KEY: CDS
<222> LOCATION: (8)...(247)
<220> FEATURE:
<221> NAME/KEY: mat_peptide
<222> LOCATION: (89)...(241)

<400> SEQUENCE: 238 aataacc atg gcg gca tct aac aag att gca gcg gca cat gtc gtc ttc       49
        Met Ala Ala Ser Asn Lys Ile Ala Ala Ala His Val Val Phe
            1               5                   10 gtc ctt gcc ttg ctc ctt gtg gcc tat cgt gcg gag gca act gtc tgc       97
Val Leu Ala Leu Leu Leu Val Ala Tyr Arg Ala Glu Ala Thr Val Cys
15                  20                  25                  30 atg agg cat aac aat ttc tat cac ggc cca tgc atg agc aac aag gac      145
Met Arg His Asn Asn Phe Tyr His Gly Pro Cys Met Ser Asn Lys Asp
                35                  40                  45 tgt gcc aac tcg tgc gtt caa cat aac ctc ggt gtc ggc ggg tat tgc      193
Cys Ala Asn Ser Cys Val Gln His Asn Leu Gly Val Gly Gly Tyr Cys
            50                  55                  60 agg ggc aag atc cca ttc aac aaa gaa tgc atg tgt aca ttt gaa tgc      241
Arg Gly Lys Ile Pro Phe Asn Lys Glu Cys Met Cys Thr Phe Glu Cys
        65                  70                  75 cca tga gtcaaaagcc actatatctg acgggcgcaa cttgttatat atctagggat      297
Pro * gggatgtcgt ttggcatgtc ctccattttg aaagtgtcca agtgagactt tatacatata      357
tgcagttgag agatggaatt aataataaga gcaaacaatt atgttgttgt gcatgtttta      417
aaaaaaaaaa aaaaaaaaaa aaaa                                             441

<210> SEQ ID NO 239
<211> LENGTH: 79
<212> TYPE: PRT
<213> ORGANISM: Zea mays
```

<400> SEQUENCE: 239

Met Ala Ala Ser Asn Lys Ile Ala Ala His Val Val Phe Val Leu
1               5                   10                  15

Ala Leu Leu Leu Val Ala Tyr Arg Ala Glu Ala Thr Val Cys Met Arg
            20                  25                  30

His Asn Asn Phe Tyr His Gly Pro Cys Met Ser Asn Lys Asp Cys Ala
            35                  40                  45

Asn Ser Cys Val Gln His Asn Leu Gly Val Gly Gly Tyr Cys Arg Gly
        50                  55                  60

Lys Ile Pro Phe Asn Lys Glu Cys Met Cys Thr Phe Glu Cys Pro
65                  70                  75

<210> SEQ ID NO 240
<211> LENGTH: 51
<212> TYPE: PRT
<213> ORGANISM: Zea mays

<400> SEQUENCE: 240

Thr Val Cys Met Arg His Asn Asn Phe Tyr His Gly Pro Cys Met Ser
1               5                   10                  15

Asn Lys Asp Cys Ala Asn Ser Cys Val Gln His Asn Leu Gly Val Gly
            20                  25                  30

Gly Tyr Cys Arg Gly Lys Ile Pro Phe Asn Lys Glu Cys Met Cys Thr
        35                  40                  45

Phe Glu Cys
    50

<210> SEQ ID NO 241
<211> LENGTH: 446
<212> TYPE: DNA
<213> ORGANISM: Zea mays
<220> FEATURE:
<221> NAME/KEY: CDS
<222> LOCATION: (1)...(264)
<220> FEATURE:
<221> NAME/KEY: mat_peptide
<222> LOCATION: (76)...(228)

<400> SEQUENCE: 241 gca tcc aac aag att gta ggg gtg cct gtt gtc ttc atc ctc gcc ttg     48
Ala Ser Asn Lys Ile Val Gly Val Pro Val Val Phe Ile Leu Ala Leu
1               5                   10                  15 ctc ctt gtt tcc ggt tat gtg gag gcg gaa atc tgc gca agg cct aat     96
Leu Leu Val Ser Gly Tyr Val Glu Ala Glu Ile Cys Ala Arg Pro Asn
            20                  25                  30 cct cat tat cct ggc gca tgc agg agc aat aag gac tgt gca ggc tcg    144
Pro His Tyr Pro Gly Ala Cys Arg Ser Asn Lys Asp Cys Ala Gly Ser
        35                  40                  45 tgc att cag caa aac ctc ggc acc agc ggg tac tgc aag ggc agt gtc    192
Cys Ile Gln Gln Asn Leu Gly Thr Ser Gly Tyr Cys Lys Gly Ser Val
    50                  55                  60 ccc ctt ttc aaa tca tgc tat tgt acc ttt gaa tgt ccc atg gag gac    240
Pro Leu Phe Lys Ser Cys Tyr Cys Thr Phe Glu Cys Pro Met Glu Asp
65                  70                  75                  80 gag gca gag gag gga ggg cac tag tcgtgagccg ccatctgcat gactaaattc    294
Glu Ala Glu Glu Gly Gly His *
                85 aaagtatctg agtgtttatg caattgacct gtggaataag gcgggcaaaa taaacaatat    354 atttgtacac atccatgctt taagaaatcg tgtgaaagca attaagagat atgaacaaaa    414

```
ctgttattat ttgaaaaaaa aaaaaaaaaa aa                                    446
```

<210> SEQ ID NO 242
<211> LENGTH: 87
<212> TYPE: PRT
<213> ORGANISM: Zea mays

<400> SEQUENCE: 242

```
Ala Ser Asn Lys Ile Val Gly Val Pro Val Val Phe Ile Leu Ala Leu
 1               5                  10                  15

Leu Leu Val Ser Gly Tyr Val Glu Ala Glu Ile Cys Ala Arg Pro Asn
             20                  25                  30

Pro His Tyr Pro Gly Ala Cys Arg Ser Asn Lys Asp Cys Ala Gly Ser
         35                  40                  45

Cys Ile Gln Gln Asn Leu Gly Thr Ser Gly Tyr Cys Lys Gly Ser Val
     50                  55                  60

Pro Leu Phe Lys Ser Cys Tyr Cys Thr Phe Glu Cys Pro Met Glu Asp
 65                  70                  75                  80

Glu Ala Glu Glu Gly Gly His
                 85
```

<210> SEQ ID NO 243
<211> LENGTH: 51
<212> TYPE: PRT
<213> ORGANISM: Zea mays

<400> SEQUENCE: 243

```
Glu Ile Cys Ala Arg Pro Asn Pro His Tyr Pro Gly Ala Cys Arg Ser
 1               5                  10                  15

Asn Lys Asp Cys Ala Gly Ser Cys Ile Gln Gln Asn Leu Gly Thr Ser
             20                  25                  30

Gly Tyr Cys Lys Gly Ser Val Pro Leu Phe Lys Ser Cys Tyr Cys Thr
         35                  40                  45

Phe Glu Cys
     50
```

<210> SEQ ID NO 244
<211> LENGTH: 481
<212> TYPE: DNA
<213> ORGANISM: Zea mays
<220> FEATURE:
<221> NAME/KEY: CDS
<222> LOCATION: (3)...(272)
<220> FEATURE:
<221> NAME/KEY: mat_peptide
<222> LOCATION: (87)...(239)

<400> SEQUENCE: 244

```
cg gac gcg tgg ggt aag gac gca gtg atc gct gct atc ttc atc cag       47
   Asp Ala Trp Gly Lys Asp Ala Val Ile Ala Ala Ile Phe Ile Gln
    1               5                  10                  15 gtc ttg ctc ctc atg gca tcg tcc tat tgt gcg gag gca aag ata tgc     95
Val Leu Leu Leu Met Ala Ser Ser Tyr Cys Ala Glu Ala Lys Ile Cys
             20                  25                  30 acg aag cct aat cca ttt tac ctg acc tta tgc caa agc gac aag gcc    143
Thr Lys Pro Asn Pro Phe Tyr Leu Thr Leu Cys Gln Ser Asp Lys Ala
         35                  40                  45 tgc gga gac tcg tgc att cac ttt ggc atc ggc acc agc ggg ttc tgc    191
Cys Gly Asp Ser Cys Ile His Phe Gly Ile Gly Thr Ser Gly Phe Cys
     50                  55                  60 aaa ggc aga cga cca ccc acc aga gtc tgc acg tgt aac ttc gaa tgt    239
```

```
Lys Gly Arg Arg Pro Pro Thr Arg Val Cys Thr Cys Asn Phe Glu Cys
        65                  70                  75 cca ggg caa gag cga agc aac acg ttt aca tga tggggatgag ccgctatatc    292
Pro Gly Gln Glu Arg Ser Asn Thr Phe Thr  *
        80                  85 tagcttaatt attagcatgc ccaaactgaa tatccaataa tttgagtgtt tctgtagttg    352
attgttcgct gtttgtttca aaacgggcta tcagcaagga ccagagctgc atgtgtaaca    412
tttgttttca acagttaaca tatgtgtcca ctcttgtctt tggagaaaaa aaaaaaaaaa    472
aaaaaaaaa                                                            481

<210> SEQ ID NO 245
<211> LENGTH: 89
<212> TYPE: PRT
<213> ORGANISM: Zea mays

<400> SEQUENCE: 245

Asp Ala Trp Gly Lys Asp Ala Val Ile Ala Ala Ile Phe Ile Gln Val
 1               5                  10                  15

Leu Leu Leu Met Ala Ser Ser Tyr Cys Ala Glu Ala Lys Ile Cys Thr
            20                  25                  30

Lys Pro Asn Pro Phe Tyr Leu Thr Leu Cys Gln Ser Asp Lys Ala Cys
        35                  40                  45

Gly Asp Ser Cys Ile His Phe Gly Ile Gly Thr Ser Gly Phe Cys Lys
    50                  55                  60

Gly Arg Arg Pro Pro Thr Arg Val Cys Thr Cys Asn Phe Glu Cys Pro
65                  70                  75                  80

Gly Gln Glu Arg Ser Asn Thr Phe Thr
                85

<210> SEQ ID NO 246
<211> LENGTH: 51
<212> TYPE: PRT
<213> ORGANISM: Zea mays

<400> SEQUENCE: 246

Lys Ile Cys Thr Lys Pro Asn Pro Phe Tyr Leu Thr Leu Cys Gln Ser
 1               5                  10                  15

Asp Lys Ala Cys Gly Asp Ser Cys Ile His Phe Gly Ile Gly Thr Ser
            20                  25                  30

Gly Phe Cys Lys Gly Arg Arg Pro Pro Thr Arg Val Cys Thr Cys Asn
        35                  40                  45

Phe Glu Cys
    50

<210> SEQ ID NO 247
<211> LENGTH: 458
<212> TYPE: DNA
<213> ORGANISM: Zea mays
<220> FEATURE:
<221> NAME/KEY: CDS
<222> LOCATION: (26)...(355)
<220> FEATURE:
<221> NAME/KEY: mat_peptide
<222> LOCATION: (128)...(256)

<400> SEQUENCE: 247
cccacgcgtc cgcccacgcg tccgg tcg tcc agc aag cag gtt gtg gtg gcc      52
                            Ser Ser Ser Lys Gln Val Val Val Ala
                             1               5
```

```
acc gtc gct cta gcg ctg ctc ctc cac gct tca cat ctt gca gcc gga      100
Thr Val Ala Leu Ala Leu Leu Leu His Ala Ser His Leu Ala Ala Gly
 10              15                  20                  25 gcc gaa gga gaa acg gtg aca ccg ttg agc aca tgc gaa acc ccg atc      148
Ala Glu Gly Glu Thr Val Thr Pro Leu Ser Thr Cys Glu Thr Pro Ile
             30                  35                  40 tgc gtc ccc tgc tgg ggc aag aac cag gtc tgc atc gcc gct tgc gtt      196
Cys Val Pro Cys Trp Gly Lys Asn Gln Val Cys Ile Ala Ala Cys Val
         45                  50                  55 gcg ttg cgc tac acc ggc ggt ttc tgc aat ggt gac acc tgc gta tgc      244
Ala Leu Arg Tyr Thr Gly Gly Phe Cys Asn Gly Asp Thr Cys Val Cys
     60                  65                  70 acc aag cag tgc ctt gcg gaa gcg gaa gcg gtg gcg gag gct ggt ggg      292
Thr Lys Gln Cys Leu Ala Glu Ala Glu Ala Val Ala Glu Ala Gly Gly
 75                  80                  85 ccg tcc ccg ccg ccc gtg cag ccg ccg ccg ctc ggg aag cgt ggg atg      340
Pro Ser Pro Pro Pro Val Gln Pro Pro Pro Leu Gly Lys Arg Gly Met
 90                  95                  100                 105 gga atg ctc aag tga tggacgatta cgtagcttgt tggccgacag atggctgagg      395
Gly Met Leu Lys * catatgtcaa ataaactctc attgttaaaa cataatatat tctactaaaa aaaaaaaaaa      455
aaa                                                                  458

<210> SEQ ID NO 248
<211> LENGTH: 109
<212> TYPE: PRT
<213> ORGANISM: Zea mays

<400> SEQUENCE: 248

Ser Ser Ser Lys Gln Val Val Ala Thr Val Ala Leu Ala Leu Leu
 1               5                  10                  15

Leu His Ala Ser His Leu Ala Ala Gly Ala Glu Gly Glu Thr Val Thr
                 20                  25                  30

Pro Leu Ser Thr Cys Glu Thr Pro Ile Cys Val Pro Cys Trp Gly Lys
             35                  40                  45

Asn Gln Val Cys Ile Ala Ala Cys Val Ala Leu Arg Tyr Thr Gly Gly
         50                  55                  60

Phe Cys Asn Gly Asp Thr Cys Val Cys Thr Lys Gln Cys Leu Ala Glu
 65                  70                  75                  80

Ala Glu Ala Val Ala Glu Ala Gly Gly Pro Ser Pro Pro Val Gln
                 85                  90                  95

Pro Pro Pro Leu Gly Lys Arg Gly Met Gly Met Leu Lys
             100                 105

<210> SEQ ID NO 249
<211> LENGTH: 43
<212> TYPE: PRT
<213> ORGANISM: Zea mays

<400> SEQUENCE: 249

Ser Thr Cys Glu Thr Pro Ile Cys Val Pro Cys Trp Gly Lys Asn Gln
 1               5                  10                  15

Val Cys Ile Ala Ala Cys Val Ala Leu Arg Tyr Thr Gly Gly Phe Cys
                 20                  25                  30

Asn Gly Asp Thr Cys Val Cys Thr Lys Gln Cys
             35                  40

<210> SEQ ID NO 250
```

```
<211> LENGTH: 405
<212> TYPE: DNA
<213> ORGANISM: Zea mays
<220> FEATURE:
<221> NAME/KEY: CDS
<222> LOCATION: (92)...(349)
<220> FEATURE:
<221> NAME/KEY: mat_peptide
<222> LOCATION: (275)...(343)
<220> FEATURE:
<221> NAME/KEY: misc_feature
<222> LOCATION: 361, 367, 374, 398
<223> OTHER INFORMATION: n = A,T,C or G

<400> SEQUENCE: 250
cacaccttgc gacctgcgtt gtcacccacc catcaaggtt ggggccgcca gcaggttcag      60
ccgttcctgt tcttgataaa acgagagaag g atg gcg gca gtg tct cag gga        112
                                  Met Ala Ala Val Ser Gln Gly
                                   1               5 gct gtc cta ttc ttg ttt ctc ctc gtc gca gca gag gtg gga acc           160
Ala Val Leu Phe Leu Phe Leu Leu Val Ala Ala Glu Val Gly Thr
         10                  15                  20 atc gat gcc aaa atg gga gta gcc atg ccc atg cat gcc ttg ata atg       208
Ile Asp Ala Lys Met Gly Val Ala Met Pro Met His Ala Leu Ile Met
     25                  30                  35 gag aac gtg aaa cag cag cag gag aag gag aag gag aag gag gag aaa       256
Glu Asn Val Lys Gln Gln Gln Glu Lys Glu Lys Glu Lys Glu Glu Lys
 40                  45                  50                  55 agc acg gag aag gaa gag agt cga tgc tta tcg cag agt ctc cag ttc       304
Ser Thr Glu Lys Glu Glu Ser Arg Cys Leu Ser Gln Ser Leu Gln Phe
                 60                  65                  70 gag ggc ttc tgc ttc aac agc gac aga tgc gcc gag tgt gca tga           349
Glu Gly Phe Cys Phe Asn Ser Asp Arg Cys Ala Glu Cys Ala *
             75                  80                  85 aggagagctt tnccggtngc gagtncaagc gggacgttgg ccatgcgcna gtgctt         405

<210> SEQ ID NO 251
<211> LENGTH: 85
<212> TYPE: PRT
<213> ORGANISM: Zea mays

<400> SEQUENCE: 251

Met Ala Ala Val Ser Gln Gly Ala Val Leu Phe Leu Phe Leu Leu Leu
 1               5                  10                  15

Val Ala Ala Glu Val Gly Thr Ile Asp Ala Lys Met Gly Val Ala Met
                 20                  25                  30

Pro Met His Ala Leu Ile Met Glu Asn Val Lys Gln Gln Gln Glu Lys
             35                  40                  45

Glu Lys Glu Lys Glu Lys Glu Lys Ser Thr Glu Lys Glu Glu Ser Arg Cys
         50                  55                  60

Leu Ser Gln Ser Leu Gln Phe Glu Gly Phe Cys Phe Asn Ser Asp Arg
 65                  70                  75                  80

Cys Ala Glu Cys Ala
             85

<210> SEQ ID NO 252
<211> LENGTH: 23
<212> TYPE: PRT
<213> ORGANISM: Zea mays

<400> SEQUENCE: 252

Ser Arg Cys Leu Ser Gln Ser Leu Gln Phe Glu Gly Phe Cys Phe Asn
```

```
                  1               5                  10                 15
Ser Asp Arg Cys Ala Glu Cys
                20

<210> SEQ ID NO 253
<211> LENGTH: 403
<212> TYPE: DNA
<213> ORGANISM: Zea mays
<220> FEATURE:
<221> NAME/KEY: CDS
<222> LOCATION: (27)...(284)
<220> FEATURE:
<221> NAME/KEY: mat_peptide
<222> LOCATION: (93)...(239)

<400> SEQUENCE: 253
aaaaacaaat ctccctaatt tcagtc atg aag gcc cag gtc gca gca gca act       53
                              Met Lys Ala Gln Val Ala Ala Ala Thr
                               1               5 gtc ttg gtc ttg ctc ctc cta atc ttt gct gcg gag gct cgt acg tgc      101
Val Leu Val Leu Leu Leu Leu Ile Phe Ala Ala Glu Ala Arg Thr Cys
 10                  15                  20                  25 atg tcg cga agc cag gaa cag aaa ggg agg tgc ttt cac gat acg gat      149
Met Ser Arg Ser Gln Glu Gln Lys Gly Arg Cys Phe His Asp Thr Asp
                 30                  35                  40 tgt gcc gcc gtc tgc gtc aaa cag agc ttc acc gga ggc tta tgc aac      197
Cys Ala Ala Val Cys Val Lys Gln Ser Phe Thr Gly Gly Leu Cys Asn
             45                  50                  55 ggg cgg ccg ccg ttc aag cag tgc ttc tgc act aag cca tgc aag aga      245
Gly Arg Pro Pro Phe Lys Gln Cys Phe Cys Thr Lys Pro Cys Lys Arg
         60                  65                  70 gag aga gct gat gct aca ctc cgg tcg tca ggc ctc tga tcatgtgtgc       294
Glu Arg Ala Asp Ala Thr Leu Arg Ser Ser Gly Leu *
     75                  80                  85 ttgatccaca tgacagcgcg actctcgcat gtatgcctag gttgatgtgt atgtaataaa    354
taaacaaaat agtaaatgac atgttttctt aaaaaaaaaa aaaaaaaa                 403

<210> SEQ ID NO 254
<211> LENGTH: 85
<212> TYPE: PRT
<213> ORGANISM: Zea mays

<400> SEQUENCE: 254

Met Lys Ala Gln Val Ala Ala Ala Thr Val Leu Val Leu Leu Leu Leu
 1               5                  10                  15

Ile Phe Ala Ala Glu Ala Arg Thr Cys Met Ser Arg Ser Gln Glu Gln
                 20                  25                  30

Lys Gly Arg Cys Phe His Asp Thr Asp Cys Ala Ala Val Cys Val Lys
             35                  40                  45

Gln Ser Phe Thr Gly Gly Leu Cys Asn Gly Arg Pro Pro Phe Lys Gln
         50                  55                  60

Cys Phe Cys Thr Lys Pro Cys Lys Arg Glu Arg Ala Asp Ala Thr Leu
 65                  70                  75                  80

Arg Ser Ser Gly Leu
                 85

<210> SEQ ID NO 255
<211> LENGTH: 49
<212> TYPE: PRT
<213> ORGANISM: Zea mays
```

<400> SEQUENCE: 255

Arg Thr Cys Met Ser Arg Ser Gln Glu Gln Lys Gly Arg Cys Phe His
1               5                   10                  15

Asp Thr Asp Cys Ala Ala Val Cys Val Lys Gln Ser Phe Thr Gly Gly
            20                  25                  30

Leu Cys Asn Gly Arg Pro Pro Phe Lys Gln Cys Phe Cys Thr Lys Pro
        35                  40                  45

Cys

<210> SEQ ID NO 256
<211> LENGTH: 600
<212> TYPE: DNA
<213> ORGANISM: Zea mays
<220> FEATURE:
<221> NAME/KEY: CDS
<222> LOCATION: (62)...(409)
<220> FEATURE:
<221> NAME/KEY: mat_peptide
<222> LOCATION: (218)...(352)

<400> SEQUENCE: 256
aaaagggatt tgcatatcca cgcatttct cagatgcttt agaaacgtta gttgctgatg      60 g atg cac tct gga cta tat ata ggt aga caa gac acc agt gct ctt tgc   109
  Met His Ser Gly Leu Tyr Ile Gly Arg Gln Asp Thr Ser Ala Leu Cys
  1               5                   10                  15 ttc ctc ctc gca caa caa agc agc tca ctt gag ttc aat tca gcc atg    157
Phe Leu Leu Ala Gln Gln Ser Ser Ser Leu Glu Phe Asn Ser Ala Met
            20                  25                  30 agg agc cag gtc gca gca gta gcc atg ttt ttg ctc ctc ctg gcc ttg    205
Arg Ser Gln Val Ala Ala Val Ala Met Phe Leu Leu Leu Ala Leu
        35                  40                  45 ggt gct gag gcc gac ctc tgc gtc acg cgt agc agg acc ttc aaa ggg    253
Gly Ala Glu Ala Asp Leu Cys Val Thr Arg Ser Arg Thr Phe Lys Gly
    50                  55                  60 tgg tgc cac cag agc gag aac tgc atc acc gtc tgc aag agc gag ggc    301
Trp Cys His Gln Ser Glu Asn Cys Ile Thr Val Cys Lys Ser Glu Gly
65                  70                  75                  80 aat acc ggc ggg ttc tgc aag ctc ggg gct tgc atg tgc acc aaa gag    349
Asn Thr Gly Gly Phe Cys Lys Leu Gly Ala Cys Met Cys Thr Lys Glu
                85                  90                  95 tgt gtc cga agt act gac gct gct ggt gct aat aaa gcc cca cag cac    397
Cys Val Arg Ser Thr Asp Ala Ala Gly Ala Asn Lys Ala Pro Gln His
            100                 105                 110 cat ttg agt tga tgagtagtaa tgaagaacgc ttttttttat gcccgcgcaa        449
His Leu Ser *
        115 gctctagaat tcgaggccga gatgaccaaa aataaatgat tttgttactc tactaaaaaa    509 aaaaaaaaaa aaaaaaaaaa aaaaaaaaaa aaaaaaaaaa aaaaaaaaaa aaaaaaaaaa    569 aaaaaaaaaa aaaaaaaaaa aaaaaaaaaa a                                   600

<210> SEQ ID NO 257
<211> LENGTH: 115
<212> TYPE: PRT
<213> ORGANISM: Zea mays

<400> SEQUENCE: 257

Met His Ser Gly Leu Tyr Ile Gly Arg Gln Asp Thr Ser Ala Leu Cys
1               5                   10                  15

Phe Leu Leu Ala Gln Gln Ser Ser Ser Leu Glu Phe Asn Ser Ala Met

```
                    20                  25                  30
Arg Ser Gln Val Ala Ala Val Ala Met Phe Leu Leu Leu Ala Leu
            35                  40                  45
Gly Ala Glu Ala Asp Leu Cys Val Thr Arg Ser Arg Thr Phe Lys Gly
        50                  55                  60
Trp Cys His Gln Ser Glu Asn Cys Ile Thr Val Cys Lys Ser Glu Gly
65                  70                  75                  80
Asn Thr Gly Gly Phe Cys Lys Leu Gly Ala Cys Met Cys Thr Lys Glu
                85                  90                  95
Cys Val Arg Ser Thr Asp Ala Ala Gly Ala Asn Lys Ala Pro Gln His
            100                 105                 110
His Leu Ser
        115

<210> SEQ ID NO 258
<211> LENGTH: 45
<212> TYPE: PRT
<213> ORGANISM: Zea mays

<400> SEQUENCE: 258

Asp Leu Cys Val Thr Arg Ser Arg Thr Phe Lys Gly Trp Cys His Gln
1               5                   10                  15
Ser Glu Asn Cys Ile Thr Val Cys Lys Ser Glu Gly Asn Thr Gly Gly
            20                  25                  30
Phe Cys Lys Leu Gly Ala Cys Met Cys Thr Lys Glu Cys
        35                  40                  45

<210> SEQ ID NO 259
<211> LENGTH: 507
<212> TYPE: DNA
<213> ORGANISM: Zea mays
<220> FEATURE:
<221> NAME/KEY: CDS
<222> LOCATION: (27)...(341)
<220> FEATURE:
<221> NAME/KEY: mat_peptide
<222> LOCATION: (144)...(272)

<400> SEQUENCE: 259
cgcgtaccac tcctcttcat ttcacc atg tcg ttc agc aag cga gtt gct gtg      53
                            Met Ser Phe Ser Lys Arg Val Ala Val
                            1               5 gcc gcc gcc ctc gcc ttg gcc ctg cag ctt atc ctg gct tca cat ctt     101
Ala Ala Ala Leu Ala Leu Ala Leu Gln Leu Ile Leu Ala Ser His Leu
 10                  15                  20                  25 gca gca gct gga gcc aaa aaa gac gaa aca ata gca ccg tta cag acg     149
Ala Ala Ala Gly Ala Lys Lys Asp Glu Thr Ile Ala Pro Leu Gln Thr
                30                  35                  40 tgc gag acc atg atc aag gtc ccc tgc tgg ggc aaa aac gcg atc tgc     197
Cys Glu Thr Met Ile Lys Val Pro Cys Trp Gly Lys Asn Ala Ile Cys
            45                  50                  55 atc ccc atc tgc atc gcg atg cgc tac acc ggc ggt ttc tgc gac gtc     245
Ile Pro Ile Cys Ile Ala Met Arg Tyr Thr Gly Gly Phe Cys Asp Val
        60                  65                  70 gcc acc tgc atg tgc acc aag caa tgc ctc gcc gcc gcc gag gct gag     293
Ala Thr Cys Met Cys Thr Lys Gln Cys Leu Ala Ala Ala Glu Ala Glu
    75                  80                  85 gca gat ggg gca tcg cag cag gcc gtg gcg aca ccg cgg ctg aac tga     341
Ala Asp Gly Ala Ser Gln Gln Ala Val Ala Thr Pro Arg Leu Asn *
 90                  95                 100
```

```
tggattgttt ggtgggcggg cggctggggc atgcatgccg agaataaact cgatgttata    401
acaatgcgac cgagagtaga cccaggttgc ttgtcatatg tagcagatta ttgatgaagt    461
tatttgatga ttgatcgtct cgatctttaa caaaaaaaaa aaaaaa                   507
```

```
<210> SEQ ID NO 260
<211> LENGTH: 104
<212> TYPE: PRT
<213> ORGANISM: Zea mays

<400> SEQUENCE: 260
```

Met Ser Phe Ser Lys Arg Val Ala Val Ala Ala Leu Ala Leu Ala
1               5                   10                  15

Leu Gln Leu Ile Leu Ala Ser His Leu Ala Ala Gly Ala Lys Lys
            20                  25                  30

Asp Glu Thr Ile Ala Pro Leu Gln Thr Cys Glu Thr Met Ile Lys Val
        35                  40                  45

Pro Cys Trp Gly Lys Asn Ala Ile Cys Ile Pro Ile Cys Ile Ala Met
    50                  55                  60

Arg Tyr Thr Gly Gly Phe Cys Asp Val Ala Thr Cys Met Cys Thr Lys
65                  70                  75                  80

Gln Cys Leu Ala Ala Ala Glu Ala Glu Ala Asp Gly Ala Ser Gln Gln
                85                  90                  95

Ala Val Ala Thr Pro Arg Leu Asn
            100

```
<210> SEQ ID NO 261
<211> LENGTH: 43
<212> TYPE: PRT
<213> ORGANISM: Zea mays

<400> SEQUENCE: 261
```

Gln Thr Cys Glu Thr Met Ile Lys Val Pro Cys Trp Gly Lys Asn Ala
1               5                   10                  15

Ile Cys Ile Pro Ile Cys Ile Ala Met Arg Tyr Thr Gly Gly Phe Cys
            20                  25                  30

Asp Val Ala Thr Cys Met Cys Thr Lys Gln Cys
        35                  40

```
<210> SEQ ID NO 262
<211> LENGTH: 398
<212> TYPE: DNA
<213> ORGANISM: Triticum aestivum
<220> FEATURE:
<221> NAME/KEY: CDS
<222> LOCATION: (36)...(266)
<220> FEATURE:
<221> NAME/KEY: mat_peptide
<222> LOCATION: (96)...(263)

<400> SEQUENCE: 262
```

```
tgtacttgct tttgtgattt tcattcctg aagaa atg ggc gac atc aag gtg         53
                                     Met Gly Asp Ile Lys Val
                                     1               5 cca aga ctg tta tgc gtt cta cta ctc atg cca ctt ctt tta gtt cct     101
Pro Arg Leu Leu Cys Val Leu Leu Leu Met Pro Leu Leu Leu Val Pro
            10                  15                  20 tgc tca gaa gcc aag acc tgc gag gta gct agc agt acc tat ctg aca     149
Cys Ser Glu Ala Lys Thr Cys Glu Val Ala Ser Ser Thr Tyr Leu Thr
        25                  30                  35 ata gca tgc agg gtg gat cca tgt gct aaa gcc tgc cac aag gag ggt     197
Ile Ala Cys Arg Val Asp Pro Cys Ala Lys Ala Cys His Lys Glu Gly
```

```
Ile Ala Cys Arg Val Asp Pro Cys Ala Lys Ala Cys His Lys Glu Gly
         40                  45                  50 ttt acc aag ggg tta tgt tac ata tac cca cca ttt aca att ctt tgt    245
Phe Thr Lys Gly Leu Cys Tyr Ile Tyr Pro Pro Phe Thr Ile Leu Cys
 55                  60                  65                  70 atc tgc gaa aaa gag tgt tga acaaagaaaa cgttgcaatt cgcgtaggat       296
Ile Cys Glu Lys Glu Cys  *
                 75 gtgtgatgta acaaataata aggttgggta gtatgatgaa ttaaaaaaaa aaaaaaaaa   356 aaaaaaaaaa aaaaaaaaaa aaaaaaaaaa aaaaaaaaaa aa                     398

<210> SEQ ID NO 263
<211> LENGTH: 76
<212> TYPE: PRT
<213> ORGANISM: Triticum aestivum

<400> SEQUENCE: 263

Met Gly Asp Ile Lys Val Pro Arg Leu Leu Cys Val Leu Leu Leu Met
 1               5                  10                  15

Pro Leu Leu Leu Val Pro Cys Ser Glu Ala Lys Thr Cys Glu Val Ala
             20                  25                  30

Ser Ser Thr Tyr Leu Thr Ile Ala Cys Arg Val Asp Pro Cys Ala Lys
         35                  40                  45

Ala Cys His Lys Glu Gly Phe Thr Lys Gly Leu Cys Tyr Ile Tyr Pro
     50                  55                  60

Pro Phe Thr Ile Leu Cys Ile Cys Glu Lys Glu Cys
65                  70                  75

<210> SEQ ID NO 264
<211> LENGTH: 56
<212> TYPE: PRT
<213> ORGANISM: Triticum aestivum

<400> SEQUENCE: 264

Val Pro Cys Ser Glu Ala Lys Thr Cys Glu Val Ala Ser Ser Thr Tyr
 1               5                  10                  15

Leu Thr Ile Ala Cys Arg Val Asp Pro Cys Ala Lys Ala Cys His Lys
             20                  25                  30

Glu Gly Phe Thr Lys Gly Leu Cys Tyr Ile Tyr Pro Pro Phe Thr Ile
         35                  40                  45

Leu Cys Ile Cys Glu Lys Glu Cys
     50                  55

<210> SEQ ID NO 265
<211> LENGTH: 364
<212> TYPE: DNA
<213> ORGANISM: Triticum aestivum
<220> FEATURE:
<221> NAME/KEY: CDS
<222> LOCATION: (11)...(295)
<220> FEATURE:
<221> NAME/KEY: mat_peptide
<222> LOCATION: (122)...(265)

<400> SEQUENCE: 265
gcacgaggat atg gca tca tac atg aag aag gtt gct gaa gga cca ctg    49
            Met Ala Ser Tyr Met Lys Lys Val Ala Glu Gly Pro Leu
             1               5                  10 gga acc ggc aag gct ttc ata tgc ctg gcg atg ttg atg ctg ctc gtg    97
Gly Thr Gly Lys Ala Phe Ile Cys Leu Ala Met Leu Met Leu Leu Val
 15                  20                  25
```

```
ctg tca tct gga aaa atg ggg gcg cat ggc tgc gaa aag cgg aag agc      145
Leu Ser Ser Gly Lys Met Gly Ala His Gly Cys Glu Lys Arg Lys Ser
 30              35                  40                  45 ggg agg tgg acc aac gac act tgc atc ata gca ggc acc tgc aac ggg      193
Gly Arg Trp Thr Asn Asp Thr Cys Ile Ile Ala Gly Thr Cys Asn Gly
             50                  55                  60 ccc tgc cgg gac gag ggc ttc gac aac ggc cat tgc cat aac acc tgg      241
Pro Cys Arg Asp Glu Gly Phe Asp Asn Gly His Cys His Asn Thr Trp
             65                  70                  75 gaa tgc atc tgc tac aag aac tgc ggc tta tcc ctc cag cca ccg cat      289
Glu Cys Ile Cys Tyr Lys Asn Cys Gly Leu Ser Leu Gln Pro Pro His
         80                  85                  90 gca tga acgatcggca tgtactccga ctaaataaa ttaataagtt ctattcgtgg        345
Ala * cataaaaaaa aaaaaaaaa                                                  364
```

<210> SEQ ID NO 266
<211> LENGTH: 94
<212> TYPE: PRT
<213> ORGANISM: Triticum aestivum

<400> SEQUENCE: 266

```
Met Ala Ser Tyr Met Lys Lys Val Ala Glu Gly Pro Leu Gly Thr Gly
 1               5                  10                  15

Lys Ala Phe Ile Cys Leu Ala Met Leu Met Leu Leu Val Leu Ser Ser
             20                  25                  30

Gly Lys Met Gly Ala His Gly Cys Glu Lys Arg Lys Ser Gly Arg Trp
         35                  40                  45

Thr Asn Asp Thr Cys Ile Ile Ala Gly Thr Cys Asn Gly Pro Cys Arg
     50                  55                  60

Asp Glu Gly Phe Asp Asn Gly His Cys His Asn Thr Trp Glu Cys Ile
 65                  70                  75                  80

Cys Tyr Lys Asn Cys Gly Leu Ser Leu Gln Pro Pro His Ala
                 85                  90
```

<210> SEQ ID NO 267
<211> LENGTH: 48
<212> TYPE: PRT
<213> ORGANISM: Triticum aestivum

<400> SEQUENCE: 267

```
His Gly Cys Glu Lys Arg Lys Ser Gly Arg Trp Thr Asn Asp Thr Cys
 1               5                  10                  15

Ile Ile Ala Gly Thr Cys Asn Gly Pro Cys Arg Asp Glu Gly Phe Asp
             20                  25                  30

Asn Gly His Cys His Asn Thr Trp Glu Cys Ile Cys Tyr Lys Asn Cys
         35                  40                  45
```

<210> SEQ ID NO 268
<211> LENGTH: 527
<212> TYPE: DNA
<213> ORGANISM: Triticum aestivum
<220> FEATURE:
<221> NAME/KEY: CDS
<222> LOCATION: (41)...(364)
<220> FEATURE:
<221> NAME/KEY: mat_peptide
<222> LOCATION: (131)...(280)

<400> SEQUENCE: 268

```
gcacgaggca aagcgaagcc taatcgtgtt cgtgttggcc atg ggg ttc aac agg         55
                                            Met Gly Phe Asn Arg
                                             1               5 gca cag ttg ttt gcc gcc ttc gcc ctg ggc ttg ctc atc atg tcc cac        103
Ala Gln Leu Phe Ala Ala Phe Ala Leu Gly Leu Leu Ile Met Ser His
         10                  15                  20 ggt gcg gag gcg gtt cat ccc cgt ccc cgg ata tgc cac tcc cca agc        151
Gly Ala Glu Ala Val His Pro Arg Pro Arg Ile Cys His Ser Pro Ser
             25                  30                  35 cat ctt tat cgt ggc tca tgc aac aac agg aaa tgc gtg gag gtg tgc        199
His Leu Tyr Arg Gly Ser Cys Asn Asn Arg Lys Cys Val Glu Val Cys
         40                  45                  50 cac cac gag cac ttc acc ggc ggc tac tgc tca cgt aaa ggg att gtt        247
His His Glu His Phe Thr Gly Gly Tyr Cys Ser Arg Lys Gly Ile Val
     55                  60                  65 aaa aga ctt cat tgt gaa tgt acc ata aaa tgc ggc cat cat agt cct        295
Lys Arg Leu His Cys Glu Cys Thr Ile Lys Cys Gly His His Ser Pro
 70                  75                  80                  85 cca ccg cca tcg gaa gtg ccg gag ccg ccg tcg tct gaa cgg cca cca        343
Pro Pro Pro Ser Glu Val Pro Glu Pro Pro Ser Ser Glu Arg Pro Pro
                 90                  95                 100 cca cca cca aga gtc atg tag gcgagaaaag tttatggagc catgaaacac          394
Pro Pro Pro Arg Val Met  *
                 105 tcactgaaag gataatattt gcgtctccgt ggaaatattc aatttgtaag gaactgtatg      454 catcattgat cgcatgaaaa taatttgaag tgccgaagca ataaaaaaaa aaaaattaaa      514 aaaaaaaaaa aag                                                        527

<210> SEQ ID NO 269
<211> LENGTH: 107
<212> TYPE: PRT
<213> ORGANISM: Triticum aestivum

<400> SEQUENCE: 269

Met Gly Phe Asn Arg Ala Gln Leu Phe Ala Ala Phe Ala Leu Gly Leu
 1               5                  10                  15

Leu Ile Met Ser His Gly Ala Glu Ala Val His Pro Arg Pro Arg Ile
             20                  25                  30

Cys His Ser Pro Ser His Leu Tyr Arg Gly Ser Cys Asn Asn Arg Lys
         35                  40                  45

Cys Val Glu Val Cys His His Glu His Phe Thr Gly Gly Tyr Cys Ser
     50                  55                  60

Arg Lys Gly Ile Val Lys Arg Leu His Cys Glu Cys Thr Ile Lys Cys
 65                  70                  75                  80

Gly His His Ser Pro Pro Pro Ser Glu Val Pro Glu Pro Pro Ser
                 85                  90                  95

Ser Glu Arg Pro Pro Pro Pro Arg Val Met
            100                 105

<210> SEQ ID NO 270
<211> LENGTH: 50
<212> TYPE: PRT
<213> ORGANISM: Triticum aestivum

<400> SEQUENCE: 270

Arg Ile Cys His Ser Pro Ser His Leu Tyr Arg Gly Ser Cys Asn Asn
 1               5                  10                  15

Arg Lys Cys Val Glu Val Cys His His Glu His Phe Thr Gly Gly Tyr
```

```
                    20                  25                  30
Cys Ser Arg Lys Gly Ile Val Lys Arg Leu His Cys Glu Cys Thr Ile
         35                  40                  45

Lys Cys
    50

<210> SEQ ID NO 271
<211> LENGTH: 626
<212> TYPE: DNA
<213> ORGANISM: Triticum aestivum
<220> FEATURE:
<221> NAME/KEY: CDS
<222> LOCATION: (238)...(468)
<220> FEATURE:
<221> NAME/KEY: mat_peptide
<222> LOCATION: (271)...(456)

<400> SEQUENCE: 271
gcacgagaga caacacacag ttccacgtag cagcagtagg atagctcggt ccagtacgtc        60
gtctcgggtg agccagagca gaccgatggc gctctctcgt cgcagggccc cttccgccct       120
cctcctgctg gtcctccttg tggccacaga tacgtcgcgc tgccgagctc tactgtaggt       180
ttgttccctc gatgatgatg ctctgctgac cgtggtttgg ttgatgtgca tgcagag atg      240
                                                                Met
                                                                  1 ggg gcg acg acg acc aag gtg gcg gag gcg cgg gac tgc gtg tcg cag         288
Gly Ala Thr Thr Thr Lys Val Ala Glu Ala Arg Asp Cys Val Ser Gln
          5                  10                  15 agc cac aac ttc aag ggc gcc tgc ctc agc agc agc aac tgc gcc gcc         336
Ser His Asn Phe Lys Gly Ala Cys Leu Ser Ser Ser Asn Cys Ala Ala
         20                  25                  30 gtc tgc cgc acc gag aac ttc ccc cgg cga gtg cca cac gcc gca ctt         384
Val Cys Arg Thr Glu Asn Phe Pro Arg Arg Val Pro His Ala Ala Leu
         35                  40                  45 cga gcg caa gtg ctt ctg cga gag gct ctg cta gtc cgc ccg ctc gcc         432
Arg Ala Gln Val Leu Leu Arg Glu Ala Leu Leu Val Arg Pro Leu Ala
 50                  55                  60                  65 ccg tcc tgc cga gac gtc cca tgc atg cta ctg tag gtcatccgtg              478
Pro Ser Cys Arg Asp Val Pro Cys Met Leu Leu *
                 70                  75 ccgttagctc gttctgttcc gttcgccagt gcgtccacgt tcgaccctac ttgttcgtgt       538
gtcccgctag gtaaaactaa taaagtggaa aatcaatcgg ggtctcgagt ttagttggct       598
gtacgtggtg ttggttggca cctgattt                                          626

<210> SEQ ID NO 272
<211> LENGTH: 76
<212> TYPE: PRT
<213> ORGANISM: Triticum aestivum

<400> SEQUENCE: 272

Met Gly Ala Thr Thr Thr Lys Val Ala Glu Ala Arg Asp Cys Val Ser
  1               5                  10                  15

Gln Ser His Asn Phe Lys Gly Ala Cys Leu Ser Ser Ser Asn Cys Ala
             20                  25                  30

Ala Val Cys Arg Thr Glu Asn Phe Pro Arg Arg Val Pro His Ala Ala
         35                  40                  45

Leu Arg Ala Gln Val Leu Leu Arg Glu Ala Leu Leu Val Arg Pro Leu
     50                  55                  60

Ala Pro Ser Cys Arg Asp Val Pro Cys Met Leu Leu
 65                  70                  75
```

-continued

```
<210> SEQ ID NO 273
<211> LENGTH: 62
<212> TYPE: PRT
<213> ORGANISM: Triticum aestivum

<400> SEQUENCE: 273

Arg Asp Cys Val Ser Gln Ser His Asn Phe Lys Gly Ala Cys Leu Ser
 1               5                  10                  15

Ser Ser Asn Cys Ala Ala Val Cys Arg Thr Glu Asn Phe Pro Arg Arg
                20                  25                  30

Val Pro His Ala Ala Leu Arg Ala Gln Val Leu Leu Arg Glu Ala Leu
            35                  40                  45

Leu Val Arg Pro Leu Ala Pro Ser Cys Arg Asp Val Pro Cys
        50                  55                  60

<210> SEQ ID NO 274
<211> LENGTH: 392
<212> TYPE: DNA
<213> ORGANISM: Triticum aestivum
<220> FEATURE:
<221> NAME/KEY: CDS
<222> LOCATION: (54)...(278)
<220> FEATURE:
<221> NAME/KEY: mat_peptide
<222> LOCATION: (141)...(275)

<400> SEQUENCE: 274
ttgaaggtct taatctgtca tagaaccctc tcaatctttc acaggaaaac tag atg        56
                                                           Met
                                                             1 gat cgg tcc atg aag gtc ttt gcg gtc gtc ttc ctg ctc ctt gtg gcc      104
Asp Arg Ser Met Lys Val Phe Ala Val Val Phe Leu Leu Leu Val Ala
        5                  10                  15 aca ggc ttc cag gga gcg gtg cag gtt gct ttg gcg agg gac tgt act      152
Thr Gly Phe Gln Gly Ala Val Gln Val Ala Leu Ala Arg Asp Cys Thr
     20                  25                  30 tca cag agc cac aag ttt gtg ggg ctg tgc ctg agc gac cgc aac tgt      200
Ser Gln Ser His Lys Phe Val Gly Leu Cys Leu Ser Asp Arg Asn Cys
 35                  40                  45 gca agt gtt tgc ctg acc gag tat ttc acc gga ggc aag tgc gac cac      248
Ala Ser Val Cys Leu Thr Glu Tyr Phe Thr Gly Gly Lys Cys Asp His
 50                  55                  60                  65 cga cgt tgt gtc tgt acc aag ggc tgc tag atggcccgta atcttcttgc        298
Arg Arg Cys Val Cys Thr Lys Gly Cys *
                 70 acacatgctt ccgtgtaata ataataactg ctgaataata agactagatc tgcatctatg    358 catgtatgat gcataaaaaa aaaaaaaaaa aaaa                                392

<210> SEQ ID NO 275
<211> LENGTH: 74
<212> TYPE: PRT
<213> ORGANISM: Triticum aestivum

<400> SEQUENCE: 275

Met Asp Arg Ser Met Lys Val Phe Ala Val Val Phe Leu Leu Leu Val
 1               5                  10                  15

Ala Thr Gly Phe Gln Gly Ala Val Gln Val Ala Leu Ala Arg Asp Cys
                20                  25                  30

Thr Ser Gln Ser His Lys Phe Val Gly Leu Cys Leu Ser Asp Arg Asn
```

```
                    35                  40                  45
Cys Ala Ser Val Cys Leu Thr Glu Tyr Phe Thr Gly Gly Lys Cys Asp
 50                  55                  60

His Arg Arg Cys Val Cys Thr Lys Gly Cys
 65                  70

<210> SEQ ID NO 276
<211> LENGTH: 45
<212> TYPE: PRT
<213> ORGANISM: Triticum aestivum

<400> SEQUENCE: 276

Arg Asp Cys Thr Ser Gln Ser His Lys Phe Val Gly Leu Cys Leu Ser
  1               5                  10                  15

Asp Arg Asn Cys Ala Ser Val Cys Leu Thr Glu Tyr Phe Thr Gly Gly
                 20                  25                  30

Lys Cys Asp His Arg Arg Cys Val Cys Thr Lys Gly Cys
             35                  40                  45

<210> SEQ ID NO 277
<211> LENGTH: 640
<212> TYPE: DNA
<213> ORGANISM: Triticum aestivum
<220> FEATURE:
<221> NAME/KEY: CDS
<222> LOCATION: (58)...(294)
<220> FEATURE:
<221> NAME/KEY: mat_peptide
<222> LOCATION: (151)...(291)

<400> SEQUENCE: 277
gcacgaggag gaagtagagt tcacatcccc ctttaaccct tctaccacct atcaata atg      60
                                                                 Met
                                                                   1 gcg tca tca cac aag ttc ttc cct gcc gtc ctc ctc ctc ctg ctg cta        108
Ala Ser Ser His Lys Phe Phe Pro Ala Val Leu Leu Leu Leu Leu Leu
            5                  10                  15 gtt gtc acc atg gag gtg gcg ccg gcg cag gca gag gag ggg agg gtg        156
Val Val Thr Met Glu Val Ala Pro Ala Gln Ala Glu Glu Gly Arg Val
         20                  25                  30 tgc gag acg gat agc act cgg ttc aag ggg ata tgc atg gtt ggc aca        204
Cys Glu Thr Asp Ser Thr Arg Phe Lys Gly Ile Cys Met Val Gly Thr
     35                  40                  45 aac tgc gcc aac att tgc ctc acc gag ggc ttc acc agc ggc aag tgc        252
Asn Cys Ala Asn Ile Cys Leu Thr Glu Gly Phe Thr Ser Gly Lys Cys
 50                  55                  60                  65 tcc ggc ttg aag agg aag tgc att tgc acc aaa cca tgc tag              294
Ser Gly Leu Lys Arg Lys Cys Ile Cys Thr Lys Pro Cys   *
                 70                  75 ctagatgata aaacgtggat ggcaatgacc gtacataccc atggacctgt tctcaggatg     354
gtcagagtca catcgatctg ccgtgcacgc ctctaacata cttcaggttc acggcgtcac     414
gatgttcttt cttcagcagt tactatgaag gatatcactt tatttctttc aacaagttag     474
aagatgtatg gtctaagcat gcaagtgttc attgtattct attagtatat gtgtattttt     534
gttacctttt tctctatgtt attacagttt ttattgctga tcaatttgat ttcttgtggt     594
aataacaaat ataagagagc tccctttata ttaccaaaaa aaaaaa                    640

<210> SEQ ID NO 278
<211> LENGTH: 78
<212> TYPE: PRT
```

<213> ORGANISM: Triticum aestivum

<400> SEQUENCE: 278

```
Met Ala Ser Ser His Lys Phe Phe Pro Ala Val Leu Leu Leu Leu
1               5                   10                  15

Leu Val Val Thr Met Glu Val Ala Pro Ala Gln Ala Glu Glu Gly Arg
            20                  25                  30

Val Cys Glu Thr Asp Ser Thr Arg Phe Lys Gly Ile Cys Met Val Gly
        35                  40                  45

Thr Asn Cys Ala Asn Ile Cys Leu Thr Glu Gly Phe Thr Ser Gly Lys
    50                  55                  60

Cys Ser Gly Leu Lys Arg Lys Cys Ile Cys Thr Lys Pro Cys
65                  70                  75
```

<210> SEQ ID NO 279
<211> LENGTH: 47
<212> TYPE: PRT
<213> ORGANISM: Triticum aestivum

<400> SEQUENCE: 279

```
Arg Val Cys Glu Thr Asp Ser Thr Arg Phe Lys Gly Ile Cys Met Val
1               5                   10                  15

Gly Thr Asn Cys Ala Asn Ile Cys Leu Thr Glu Gly Phe Thr Ser Gly
            20                  25                  30

Lys Cys Ser Gly Leu Lys Arg Lys Cys Ile Cys Thr Lys Pro Cys
        35                  40                  45
```

<210> SEQ ID NO 280
<211> LENGTH: 600
<212> TYPE: DNA
<213> ORGANISM: Triticum aestivum
<220> FEATURE:
<221> NAME/KEY: CDS
<222> LOCATION: (23)...(253)
<220> FEATURE:
<221> NAME/KEY: mat_peptide
<222> LOCATION: (107)...(250)
<220> FEATURE:
<221> NAME/KEY: misc_feature
<222> LOCATION: 566, 567, 568, 574, 575
<223> OTHER INFORMATION: n = A,T,C or G

<400> SEQUENCE: 280

```
gcacgaggat aacttgcaat cc atg aat tca tcc cgc aag ttc ttc atg gtt        52
                         Met Asn Ser Ser Arg Lys Phe Phe Met Val
                         1               5                   10 gtt gcc gtc ctt gcc ttg ctc gtc gtg gct aca gtg gtg gcg ccg gcg        100
Val Ala Val Leu Ala Leu Leu Val Val Ala Thr Val Val Ala Pro Ala
            15                  20                  25 cag gcg gta gac tgc agg aca gcg agc acc cgg ttc aac ggc ata tgc        148
Gln Ala Val Asp Cys Arg Thr Ala Ser Thr Arg Phe Asn Gly Ile Cys
        30                  35                  40 atc ctg gac agc agt tgc gcc aac atg tgc atc acc gag ggg ttc ctg        196
Ile Leu Asp Ser Ser Cys Ala Asn Met Cys Ile Thr Glu Gly Phe Leu
    45                  50                  55 gct ggc ggg gag tgt gaa ggt ctc cac cga cgc tgc atg tgc aaa aca        244
Ala Gly Gly Glu Cys Glu Gly Leu His Arg Arg Cys Met Cys Lys Thr
60                  65                  70 cca tgc tag gcgaagcata tgcatagtct ggactgcttc atcaggaagt                 293
Pro Cys *
75 ttttccgatt tagataaaaa caaggaaaaa gatttttttt tctaaaagaa aagaaaatgg        353
```

```
agttgtaaca catactgtgt tcttttagtt tttttttca catgttcctt tgggagattg      413
tggttgtgca tttgatgcat ttttgttgat cgtacaatcc agtttgatgt gttttgttg      473 taaacttgaa gttggccatt ttgtcattgt gtaagattat tttccaagat tcattcattt     533
gtgatcatgc aatgcagtat tgtactacca aannnaaaaa nnaaaaaaaa aaaaaaaaac     593
cctccgg                                                               600

<210> SEQ ID NO 281
<211> LENGTH: 76
<212> TYPE: PRT
<213> ORGANISM: Triticum aestivum

<400> SEQUENCE: 281

Met Asn Ser Ser Arg Lys Phe Phe Met Val Val Ala Val Leu Ala Leu
1               5                   10                  15

Leu Val Ala Thr Val Val Ala Pro Ala Gln Ala Val Asp Cys Arg
            20                  25                  30

Thr Ala Ser Thr Arg Phe Asn Gly Ile Cys Ile Leu Asp Ser Ser Cys
        35                  40                  45

Ala Asn Met Cys Ile Thr Glu Gly Phe Leu Ala Gly Gly Glu Cys Glu
    50                  55                  60

Gly Leu His Arg Arg Cys Met Cys Lys Thr Pro Cys
65                  70                  75

<210> SEQ ID NO 282
<211> LENGTH: 48
<212> TYPE: PRT
<213> ORGANISM: Triticum aestivum

<400> SEQUENCE: 282

Val Asp Cys Arg Thr Ala Ser Thr Arg Phe Asn Gly Ile Cys Ile Leu
1               5                   10                  15

Asp Ser Ser Cys Ala Asn Met Cys Ile Thr Glu Gly Phe Leu Ala Gly
            20                  25                  30

Gly Glu Cys Glu Gly Leu His Arg Arg Cys Met Cys Lys Thr Pro Cys
        35                  40                  45

<210> SEQ ID NO 283
<211> LENGTH: 630
<212> TYPE: DNA
<213> ORGANISM: Triticum aestivum
<220> FEATURE:
<221> NAME/KEY: CDS
<222> LOCATION: (102)...(350)
<220> FEATURE:
<221> NAME/KEY: mat_peptide
<222> LOCATION: (201)...(347)

<400> SEQUENCE: 283
gcacgagtct agtctctagt ctagctaggc actactctag ctcccaagtg gccaagtata      60
ctcgccagag tacgtagagt gtagttgagc gtcgtccaag g atg gcg tgg acc tcc    116
                                             Met Ala Trp Thr Ser
                                              1               5 cgc cgc atg gtc gcg tcc gcg ctc gtc ttc ctg ctg atg ctg ctc gcc      164
Arg Arg Met Val Ala Ser Ala Leu Val Phe Leu Leu Met Leu Leu Ala
            10                  15                  20 gcc tca gag atg ggg acg acg agg gtg gcg gag gcg agg cac tgc acg      212
Ala Ser Glu Met Gly Thr Thr Arg Val Ala Glu Ala Arg His Cys Thr
        25                  30                  35
```

```
tcg cag agc cac cgg ttc gtc ggc gcc tgc atg agc aag agc aac tgc      260
Ser Gln Ser His Arg Phe Val Gly Ala Cys Met Ser Lys Ser Asn Cys
        40                  45                  50 gag aac gtc tgc agg acg gag ggc ttc ccg tgg ggc gag tgc agg tgg      308
Glu Asn Val Cys Arg Thr Glu Gly Phe Pro Trp Gly Glu Cys Arg Trp
 55                  60                  65 cac ggc ata gag cgc aag tgc cac tgc aag cgg atc tgc tag              350
His Gly Ile Glu Arg Lys Cys His Cys Lys Arg Ile Cys *
 70                  75                  80 taattaacta gccggctggc cagcgcatgc atgcacgacg accgacctac ctgctgctgg    410
tccgtttgcg tttgtttctt gtcctttggg ccttgctgtg gcgcgcagtc ttgcgtacgt    470
gcgtgtgcgt gtgtcttttc agttactctc aattagtcat agcagacgtg cgtgggtgcg    530
agcgtgtgtc tcgttgcatt gatgaaccgg cttcacgtgc tgtggttttc agttctgat     590 gtgttttagc taatctcgaa tataataat aaggccccgt                           630

<210> SEQ ID NO 284
<211> LENGTH: 82
<212> TYPE: PRT
<213> ORGANISM: Triticum aestivum

<400> SEQUENCE: 284

Met Ala Trp Thr Ser Arg Arg Met Val Ala Ser Ala Leu Val Phe Leu
 1               5                  10                  15

Leu Met Leu Leu Ala Ala Ser Glu Met Gly Thr Thr Arg Val Ala Glu
             20                  25                  30

Ala Arg His Cys Thr Ser Gln Ser His Arg Phe Val Gly Ala Cys Met
         35                  40                  45

Ser Lys Ser Asn Cys Glu Asn Val Cys Arg Thr Glu Gly Phe Pro Trp
     50                  55                  60

Gly Glu Cys Arg Trp His Gly Ile Glu Arg Lys Cys His Cys Lys Arg
 65                  70                  75                  80

Ile Cys

<210> SEQ ID NO 285
<211> LENGTH: 49
<212> TYPE: PRT
<213> ORGANISM: Triticum aestivum

<400> SEQUENCE: 285

Arg His Cys Thr Ser Gln Ser His Arg Phe Val Gly Ala Cys Met Ser
 1               5                  10                  15

Lys Ser Asn Cys Glu Asn Val Cys Arg Thr Glu Gly Phe Pro Trp Gly
             20                  25                  30

Glu Cys Arg Trp His Gly Ile Glu Arg Lys Cys His Cys Lys Arg Ile
         35                  40                  45

Cys

<210> SEQ ID NO 286
<211> LENGTH: 545
<212> TYPE: DNA
<213> ORGANISM: Triticum aestivum
<220> FEATURE:
<221> NAME/KEY: CDS
<222> LOCATION: (45)...(293)
<220> FEATURE:
<221> NAME/KEY: mat_peptide
<222> LOCATION: (135)...(290)

<400> SEQUENCE: 286
```

```
ttccttcctt ccctcccccc ttcattcctt cattccttgg agac atg gcg atg gcg      56
                                                  Met Ala Met Ala
                                                   1 gcg ccc aag ctc atg gtg cca ggc ctg tgc ctg ctt ctg ctg atc atg      104
Ala Pro Lys Leu Met Val Pro Gly Leu Cys Leu Leu Leu Leu Ile Met
 5              10                  15                  20 ccg ctc ctc ttg ctc cct gga tct caa ggg gcg act tgc aag gag ctg      152
Pro Leu Leu Leu Leu Pro Gly Ser Gln Gly Ala Thr Cys Lys Glu Leu
            25                  30                  35 agc aag acc tat gac tct ccc aac tgc gag acc ggc cga tgc gtg gag      200
Ser Lys Thr Tyr Asp Ser Pro Asn Cys Glu Thr Gly Arg Cys Val Glu
        40                  45                  50 cac tgc caa gtg gag ggc tac ggt agc ggg gtg tgc cag ggg agc tac      248
His Cys Gln Val Glu Gly Tyr Gly Ser Gly Val Cys Gln Gly Ser Tyr
    55                  60                  65 ttc gac ccc tac aag ata ctc tgc ttc tgc aac aaa aac tgc tga          293
Phe Asp Pro Tyr Lys Ile Leu Cys Phe Cys Asn Lys Asn Cys    *
70                  75                  80 gccgccagcg acggcgcatt gcttcgggcc ggggtgtaat aagatgttag ctaaggcgag    353
ccgtcgtcga tgcgcgactc gcacaagttt gtagctgtaa taggtttcat ctgtaccaat    413
tttattttca actgctcgtc tccccagtta agagattggt cgtcagcttg cggaaatgga    473
tcgcttgttc cgctctttc atttcgttcc tgttgaaaag gaatttctat ctaaaaaaaa     533
aaaaaaaaaa aa                                                        545
```

<210> SEQ ID NO 287
<211> LENGTH: 82
<212> TYPE: PRT
<213> ORGANISM: Triticum aestivum

<400> SEQUENCE: 287

```
Met Ala Met Ala Ala Pro Lys Leu Met Val Pro Gly Leu Cys Leu Leu
 1               5                  10                  15

Leu Leu Ile Met Pro Leu Leu Leu Pro Gly Ser Gln Gly Ala Thr
            20                  25                  30

Cys Lys Glu Leu Ser Lys Thr Tyr Asp Ser Pro Asn Cys Glu Thr Gly
        35                  40                  45

Arg Cys Val Glu His Cys Gln Val Glu Gly Tyr Gly Ser Gly Val Cys
    50                  55                  60

Gln Gly Ser Tyr Phe Asp Pro Tyr Lys Ile Leu Cys Phe Cys Asn Lys
65                  70                  75                  80

Asn Cys
```

<210> SEQ ID NO 288
<211> LENGTH: 52
<212> TYPE: PRT
<213> ORGANISM: Triticum aestivum

<400> SEQUENCE: 288

```
Ala Thr Cys Lys Glu Leu Ser Lys Thr Tyr Asp Ser Pro Asn Cys Glu
 1               5                  10                  15

Thr Gly Arg Cys Val Glu His Cys Gln Val Glu Gly Tyr Gly Ser Gly
            20                  25                  30

Val Cys Gln Gly Ser Tyr Phe Asp Pro Tyr Lys Ile Leu Cys Phe Cys
        35                  40                  45

Asn Lys Asn Cys
    50
```

<210> SEQ ID NO 289
<211> LENGTH: 601
<212> TYPE: DNA
<213> ORGANISM: Triticum aestivum
<220> FEATURE:
<221> NAME/KEY: CDS
<222> LOCATION: (70)...(297)
<220> FEATURE:
<221> NAME/KEY: mat_peptide
<222> LOCATION: (154)...(294)

<400> SEQUENCE: 289

```
gcacgaggta caatcccaga taagtgtaca ttttacaggg tgcgttttag cagatacaaa      60 taaggaaga atg gag tca tca cac aag ctt ttc ccg gcc gta gcc atc ctc     111
         Met Glu Ser Ser His Lys Leu Phe Pro Ala Val Ala Ile Leu
           1               5                  10 ctc ctg ctc gtc gtc gcc acc gag gtg gtg cca gcg cag gca cga gag     159
Leu Leu Leu Val Val Ala Thr Glu Val Val Pro Ala Gln Ala Arg Glu
 15              20                  25                  30 tgt gag aca gag agc gag cgg ttc aac ggg ctg tgc ttc gtg tcc gca     207
Cys Glu Thr Glu Ser Glu Arg Phe Asn Gly Leu Cys Phe Val Ser Ala
                 35                  40                  45 aac tgc gcc ggt gtg tgc aat gcg gag ggg ttc acc ggt ggc aag tgc     255
Asn Cys Ala Gly Val Cys Asn Ala Glu Gly Phe Thr Gly Gly Lys Cys
             50                  55                  60 tcc ggc ttg aag agg agc tgc atg tgc acg aag gag tgc tag            297
Ser Gly Leu Lys Arg Ser Cys Met Cys Thr Lys Glu Cys  *
         65                  70                  75 acgatatcat gatatattta ggtggttgga tggcgacaat tatgaactta ttcttcgcat    357
ggtttgaatt acttttgttc gtatgtctga taaagttcca ggttcaccgc gacgttatcc    417
ttgggttcga atgaaggaaa atgttttctt tctttaaagc aaagaaaatg tgtggcccat    477
gagagtgttc atggaatcac atgtatctcc ttttttccct gtatttgtct cttctttccg    537
ggtgtgccta gctcctatct aaatgagacg taactaagta tcaaaaaaaa aaaaaaaaa     597 aaaa                                                                 601
```

<210> SEQ ID NO 290
<211> LENGTH: 75
<212> TYPE: PRT
<213> ORGANISM: Triticum aestivum

<400> SEQUENCE: 290

```
Met Glu Ser Ser His Lys Leu Phe Pro Ala Val Ala Ile Leu Leu Leu
  1               5                  10                  15

Leu Val Val Ala Thr Glu Val Val Pro Ala Gln Ala Arg Glu Cys Glu
             20                  25                  30

Thr Glu Ser Glu Arg Phe Asn Gly Leu Cys Phe Val Ser Ala Asn Cys
         35                  40                  45

Ala Gly Val Cys Asn Ala Glu Gly Phe Thr Gly Gly Lys Cys Ser Gly
     50                  55                  60

Leu Lys Arg Ser Cys Met Cys Thr Lys Glu Cys
 65                  70                  75
```

<210> SEQ ID NO 291
<211> LENGTH: 47
<212> TYPE: PRT
<213> ORGANISM: Triticum aestivum

<400> SEQUENCE: 291

```
Arg Glu Cys Glu Thr Glu Ser Glu Arg Phe Asn Gly Leu Cys Phe Val
 1               5                  10                  15

Ser Ala Asn Cys Ala Gly Val Cys Asn Ala Glu Gly Phe Thr Gly Gly
            20                  25                  30

Lys Cys Ser Gly Leu Lys Arg Ser Cys Met Cys Thr Lys Glu Cys
            35                  40                  45
```

<210> SEQ ID NO 292
<211> LENGTH: 578
<212> TYPE: DNA
<213> ORGANISM: Beta vulgaris
<220> FEATURE:
<221> NAME/KEY: CDS
<222> LOCATION: (62)...(301)
<220> FEATURE:
<221> NAME/KEY: mat_peptide
<222> LOCATION: (152)...(292)

<400> SEQUENCE: 292

```
gcacgaggat tacttctaaa aaacttacct atacctcttg tgaattttgt attgcaaaac    60 t atg aag ctg tca atg aag ccc ttt gcc gca att ttt ctt gtg ctc tta   109
  Met Lys Leu Ser Met Lys Pro Phe Ala Ala Ile Phe Leu Val Leu Leu
   1               5                  10                  15 ctt gtc ttg gcc aca gag att ggg cca aga gtc gca gaa gca aga act    157
Leu Val Leu Ala Thr Glu Ile Gly Pro Arg Val Ala Glu Ala Arg Thr
            20                  25                  30 tgt gga act cca agc cag agg ttc agg gga tta tgt gtt aga aag aga    205
Cys Gly Thr Pro Ser Gln Arg Phe Arg Gly Leu Cys Val Arg Lys Arg
        35                  40                  45 aat tgt gaa tca gtt tgc aac agt gaa gga ttt cct gat gga agt tgt    253
Asn Cys Glu Ser Val Cys Asn Ser Glu Gly Phe Pro Asp Gly Ser Cys
 50                  55                  60 caa ggc gca cgc aga aga tgt att tgc aac agg cct tgc gcc aaa taa    301
Gln Gly Ala Arg Arg Arg Cys Ile Cys Asn Arg Pro Cys Ala Lys  *
 65                  70                  75 ttatgtacct tagcttcttc aagctacttg tttaagttgg ttaagtcata agtgtctact   361
actctacgta ctatgtggtt ctgaaataat acaatcttac tatatgtgct attagctact   421
tgtggtggct ttgaggttta aaaaatgtat tacagtgagt gtgttgttcg attgaaaaca   481
ttatggttct ggtactgaaa attattgtta ttattgcttg atgtatctag tgttcataca   541
tcgtggttat gtatatatat gacttgtaat gtctgtt                            578
```

<210> SEQ ID NO 293
<211> LENGTH: 79
<212> TYPE: PRT
<213> ORGANISM: Beta vulgaris

<400> SEQUENCE: 293

```
Met Lys Leu Ser Met Lys Pro Phe Ala Ala Ile Phe Leu Val Leu Leu
 1               5                  10                  15

Leu Val Leu Ala Thr Glu Ile Gly Pro Arg Val Ala Glu Ala Arg Thr
            20                  25                  30

Cys Gly Thr Pro Ser Gln Arg Phe Arg Gly Leu Cys Val Arg Lys Arg
        35                  40                  45

Asn Cys Glu Ser Val Cys Asn Ser Glu Gly Phe Pro Asp Gly Ser Cys
 50                  55                  60

Gln Gly Ala Arg Arg Arg Cys Ile Cys Asn Arg Pro Cys Ala Lys
 65                  70                  75
```

<210> SEQ ID NO 294
<211> LENGTH: 47
<212> TYPE: PRT
<213> ORGANISM: Beta vulgaris

<400> SEQUENCE: 294

Arg Thr Cys Gly Thr Pro Ser Gln Arg Phe Arg Gly Leu Cys Val Arg
1               5                   10                  15

Lys Arg Asn Cys Glu Ser Val Cys Asn Ser Glu Gly Phe Pro Asp Gly
            20                  25                  30

Ser Cys Gln Gly Ala Arg Arg Arg Cys Ile Cys Asn Arg Pro Cys
        35                  40                  45

<210> SEQ ID NO 295
<211> LENGTH: 307
<212> TYPE: DNA
<213> ORGANISM: Hedera helix
<220> FEATURE:
<221> NAME/KEY: CDS
<222> LOCATION: (3)...(158)
<220> FEATURE:
<221> NAME/KEY: mat_peptide
<222> LOCATION: (3)...(140)
<220> FEATURE:
<221> NAME/KEY: misc_feature
<222> LOCATION: 263, 270, 285, 294, 301, 306
<223> OTHER INFORMATION: n = A,T,C or G

<400> SEQUENCE: 295 ag ata tgc gag tac gag aac aga gat ttc gat gga tta tgc acg gat        47
   Ile Cys Glu Tyr Glu Asn Arg Asp Phe Asp Gly Leu Cys Thr Asp
   1               5                   10                  15 gat cgc aag tgt aag gaa ctt tgc gag aaa gat gga tct ttt gat ggt        95
Asp Arg Lys Cys Lys Glu Leu Cys Glu Lys Asp Gly Ser Phe Asp Gly
            20                  25                  30 cac tgc gtc ggc tta tta caa aaa tgt tat tgc cgc tgg aat tgt ccg       143
His Cys Val Gly Leu Leu Gln Lys Cys Tyr Cys Arg Trp Asn Cys Pro
        35                  40                  45 cca aaa gca ccc taa tcatatcatg attcacatga gttgaatcac ctatggtatt       198
Pro Lys Ala Pro  *
        50 atatatgtct cgatcataaa taaataaata aataaagcac ttctattggc tctgccaaaa     258 aaaanaaaaa anaagaaaaa aaaaaanaat aaaaanaata aanaaaang                 307

<210> SEQ ID NO 296
<211> LENGTH: 51
<212> TYPE: PRT
<213> ORGANISM: Hedera helix

<400> SEQUENCE: 296

Ile Cys Glu Tyr Glu Asn Arg Asp Phe Asp Gly Leu Cys Thr Asp Asp
1               5                   10                  15

Arg Lys Cys Lys Glu Leu Cys Glu Lys Asp Gly Ser Phe Asp Gly His
            20                  25                  30

Cys Val Gly Leu Leu Gln Lys Cys Tyr Cys Arg Trp Asn Cys Pro Pro
        35                  40                  45

Lys Ala Pro
        50

<210> SEQ ID NO 297
<211> LENGTH: 46
<212> TYPE: PRT

<213> ORGANISM: Hedera helix

<400> SEQUENCE: 297

```
Ile Cys Glu Tyr Glu Asn Arg Asp Phe Asp Gly Leu Cys Thr Asp Asp
1               5                   10                  15

Arg Lys Cys Lys Glu Leu Cys Glu Lys Asp Gly Ser Phe Asp Gly His
            20                  25                  30

Cys Val Gly Leu Leu Gln Lys Cys Tyr Cys Arg Trp Asn Cys
        35                  40                  45
```

<210> SEQ ID NO 298
<211> LENGTH: 385
<212> TYPE: DNA
<213> ORGANISM: Tulipa gesneriana
<220> FEATURE:
<221> NAME/KEY: CDS
<222> LOCATION: (1)...(192)
<220> FEATURE:
<221> NAME/KEY: mat_peptide
<222> LOCATION: (34)...(168)
<220> FEATURE:
<221> NAME/KEY: misc_feature
<222> LOCATION: 357, 364, 367, 369, 374, 379, 380
<223> OTHER INFORMATION: n = A,T,C or G

<400> SEQUENCE: 298

```
ggc cac gga ttc acc ctg ggc tat att tgg agg ggc gtg tgc ttt gtg      48
Gly His Gly Phe Thr Leu Gly Tyr Ile Trp Arg Gly Val Cys Phe Val
1               5                   10                  15 aca gag cac tgt gag cgg acc tgc ttg gat gaa ggg tat gtc tac ggt      96
Thr Glu His Cys Glu Arg Thr Cys Leu Asp Glu Gly Tyr Val Tyr Gly
            20                  25                  30 tgg tgc gat gcc acg gat tca ccc tgg gct ata ttt aca aca tat tgc     144
Trp Cys Asp Ala Thr Asp Ser Pro Trp Ala Ile Phe Thr Thr Tyr Cys
        35                  40                  45 gtg tgt ttc tcg ctc acc aca tgc cgg tca agt atg gaa aac ggc gat     192
Val Cys Phe Ser Leu Thr Thr Cys Arg Ser Ser Met Glu Asn Gly Asp
    50                  55                  60 tag aagtaacgac aagccatggt gtcaataaca ttaatggctc atctcttact          245
acgcatctat ctccataata atgtggtgag cttacatatg atcctggttt tgttgctgct   305
gattattgga tcttaaagct caaataaatt gttaatgcaa tgtaaaaaaa anaaaaaana   365
anancaaant caanncaaaa                                                385
```

<210> SEQ ID NO 299
<211> LENGTH: 64
<212> TYPE: PRT
<213> ORGANISM: Tulipa gesneriana

<400> SEQUENCE: 299

```
Gly His Gly Phe Thr Leu Gly Tyr Ile Trp Arg Gly Val Cys Phe Val
1               5                   10                  15

Thr Glu His Cys Glu Arg Thr Cys Leu Asp Glu Gly Tyr Val Tyr Gly
            20                  25                  30

Trp Cys Asp Ala Thr Asp Ser Pro Trp Ala Ile Phe Thr Thr Tyr Cys
        35                  40                  45

Val Cys Phe Ser Leu Thr Thr Cys Arg Ser Ser Met Glu Asn Gly Asp
    50                  55                  60
```

<210> SEQ ID NO 300
<211> LENGTH: 45
<212> TYPE: PRT

<213> ORGANISM: Tulipa gesneriana

<400> SEQUENCE: 300

Gly Val Cys Phe Val Thr Glu His Cys Glu Arg Thr Cys Leu Asp Glu
1               5                   10                  15

Gly Tyr Val Tyr Gly Trp Cys Asp Ala Thr Asp Ser Pro Trp Ala Ile
            20                  25                  30

Phe Thr Thr Tyr Cys Val Cys Phe Ser Leu Thr Thr Cys
        35                  40                  45

<210> SEQ ID NO 301
<211> LENGTH: 482
<212> TYPE: DNA
<213> ORGANISM: Amaranthus retroflexus
<220> FEATURE:
<221> NAME/KEY: CDS
<222> LOCATION: (31)...(258)
<220> FEATURE:
<221> NAME/KEY: mat_peptide
<222> LOCATION: (109)...(252)

<400> SEQUENCE: 301
gcacgaggat caagatcctc aaattaatca atg aag aca ttt gga gct ttc gtt    54
                                  Met Lys Thr Phe Gly Ala Phe Val
                                  1               5 ctt att ttt ctt ctt gca tcc ttc gcc ata aca ggg cca aga atg acg   102
Leu Ile Phe Leu Leu Ala Ser Phe Ala Ile Thr Gly Pro Arg Met Thr
    10                  15                  20 gaa gca agg atg tgc aaa gct ccg agc aaa ctg ttt agg gga atg tgt   150
Glu Ala Arg Met Cys Lys Ala Pro Ser Lys Leu Phe Arg Gly Met Cys
 25                  30                  35                  40 ggt att agg gat tcc aac tgt gat agt gtt tgc agg gcg gaa gga atg   198
Gly Ile Arg Asp Ser Asn Cys Asp Ser Val Cys Arg Ala Glu Gly Met
                45                  50                  55 gct gct gga gat tgc cat ggc ctt cgt aga cga tgc att tgc agc agg   246
Ala Ala Gly Asp Cys His Gly Leu Arg Arg Arg Cys Ile Cys Ser Arg
            60                  65                  70 cct tgt cct taa attaccttat gtaatctcct aaaaataatg ataacaaatg        298
Pro Cys Pro  *
        75 tttctatctt caccattagc tttaattatt atcacctggc tagtagctac atgcatataa  358 tgtaatctta tatagcgtct tgctatcact ctatctctat gtttaaataa tttcgtcttt  418 tatgtattaa ttgtttcttt tcacatctat aaattaacga taagatatct gtattcgtac  478 actt                                                               482

<210> SEQ ID NO 302
<211> LENGTH: 75
<212> TYPE: PRT
<213> ORGANISM: Amaranthus retroflexus

<400> SEQUENCE: 302

Met Lys Thr Phe Gly Ala Phe Val Leu Ile Phe Leu Leu Ala Ser Phe
1               5                   10                  15

Ala Ile Thr Gly Pro Arg Met Thr Glu Ala Arg Met Cys Lys Ala Pro
            20                  25                  30

Ser Lys Leu Phe Arg Gly Met Cys Gly Ile Arg Asp Ser Asn Cys Asp
        35                  40                  45

Ser Val Cys Arg Ala Glu Gly Met Ala Ala Gly Asp Cys His Gly Leu
    50                  55                  60

Arg Arg Arg Cys Ile Cys Ser Arg Pro Cys Pro
65                  70                  75

<210> SEQ ID NO 303
<211> LENGTH: 48
<212> TYPE: PRT
<213> ORGANISM: Amaranthus retroflexus

<400> SEQUENCE: 303

Arg Met Cys Lys Ala Pro Ser Lys Leu Phe Arg Gly Met Cys Gly Ile
1               5                   10                  15

Arg Asp Ser Asn Cys Asp Ser Val Cys Arg Ala Glu Gly Met Ala Ala
            20                  25                  30

Gly Asp Cys His Gly Leu Arg Arg Arg Cys Ile Cys Ser Arg Pro Cys
        35                  40                  45

<210> SEQ ID NO 304
<211> LENGTH: 462
<212> TYPE: DNA
<213> ORGANISM: Allium porrum
<220> FEATURE:
<221> NAME/KEY: CDS
<222> LOCATION: (30)...(224)
<220> FEATURE:
<221> NAME/KEY: mat_peptide
<222> LOCATION: (81)...(221)
<220> FEATURE:
<221> NAME/KEY: misc_feature
<222> LOCATION: 275, 364, 409, 413, 415, 424, 431, 454, 458
<223> OTHER INFORMATION: n = A,T,C or G

<400> SEQUENCE: 304
atatccatta ctttcgacgt ttaacatga ttg att gat cga ttt tat tta aca      53
                                Leu Ile Asp Arg Phe Tyr Leu Thr
                                 1               5 gcg aac ata gtg cca gtg gct gaa gcg aag gta tgc gaa tat ccg agc     101
Ala Asn Ile Val Pro Val Ala Glu Ala Lys Val Cys Glu Tyr Pro Ser
     10                  15                  20 gag tcg ttc cga tat gtg tgc ctg cga gac aag agc tgc gca aag aca     149
Glu Ser Phe Arg Tyr Val Cys Leu Arg Asp Lys Ser Cys Ala Lys Thr
 25                  30                  35                  40 tgc act aag gat ggc tat ggt ggc gga tac tgc cat ggc gtt cgc aaa     197
Cys Thr Lys Asp Gly Tyr Gly Gly Gly Tyr Cys His Gly Val Arg Lys
                 45                  50                  55 cga tgc ttg tgc acc aag cct tgt taa ttgttcatgg atatcatgtt           244
Arg Cys Leu Cys Thr Lys Pro Cys  *
             60 tcctttatat gtttatcttc gtcttgtgtt ntgtttcatg tgcttgtgtc ctgtgtaatg   304 gtccgtttgt gaatgatgtg cggtaaggta attaactgtg aatgcacggt taatgattan   364 atgatgaata acatgcacc tgggctgcat gcttcctgca cttcngtcnc nagtaagtan    424 acatccnggg agtacaagct aaaatttagn cgcntttc                           462

<210> SEQ ID NO 305
<211> LENGTH: 64
<212> TYPE: PRT
<213> ORGANISM: Allium porrum

<400> SEQUENCE: 305

Leu Ile Asp Arg Phe Tyr Leu Thr Ala Asn Ile Val Pro Val Ala Glu
1               5                   10                  15

Ala Lys Val Cys Glu Tyr Pro Ser Glu Ser Phe Arg Tyr Val Cys Leu
            20                  25                  30

Arg Asp Lys Ser Cys Ala Lys Thr Cys Thr Lys Asp Gly Tyr Gly Gly
         35                  40                  45

Gly Tyr Cys His Gly Val Arg Lys Arg Cys Leu Cys Thr Lys Pro Cys
         50                  55                  60

<210> SEQ ID NO 306
<211> LENGTH: 47
<212> TYPE: PRT
<213> ORGANISM: Allium porrum

<400> SEQUENCE: 306

Lys Val Cys Glu Tyr Pro Ser Glu Ser Phe Arg Tyr Val Cys Leu Arg
  1               5                  10                  15

Asp Lys Ser Cys Ala Lys Thr Cys Thr Lys Asp Gly Tyr Gly Gly Gly
             20                  25                  30

Tyr Cys His Gly Val Arg Lys Arg Cys Leu Cys Thr Lys Pro Cys
         35                  40                  45

<210> SEQ ID NO 307
<211> LENGTH: 478
<212> TYPE: DNA
<213> ORGANISM: Nicotiana benthamiana
<220> FEATURE:
<221> NAME/KEY: CDS
<222> LOCATION: (31)...(264)
<220> FEATURE:
<221> NAME/KEY: mat_peptide
<222> LOCATION: (121)...(261)
<220> FEATURE:
<221> NAME/KEY: misc_feature
<222> LOCATION: 396
<223> OTHER INFORMATION: n = A,T,C or G

<400> SEQUENCE: 307
aacaaattaa agaattttaa gaaaaacaag atg gct ggc ttt ccc aaa gtg ctt         54
                                Met Ala Gly Phe Pro Lys Val Leu
                                  1               5 gca act gtt ttc ctt acg ctg atg ctg gtt ttt gct act gag atg gga        102
Ala Thr Val Phe Leu Thr Leu Met Leu Val Phe Ala Thr Glu Met Gly
         10                  15                  20 cca atg gtg act gag gcg agg acc tgc gag tca cag agc cac cga ttc        150
Pro Met Val Thr Glu Ala Arg Thr Cys Glu Ser Gln Ser His Arg Phe
 25                  30                  35                  40 aag ggt ttg tgt ttc agt agg agc aac tgt gcg tct gtt tgc cat act        198
Lys Gly Leu Cys Phe Ser Arg Ser Asn Cys Ala Ser Val Cys His Thr
                 45                  50                  55 gag ggc ttt aac ggt ggc cac tgc cgt gga ttc cgt cgc cgt tgc ttc        246
Glu Gly Phe Asn Gly Gly His Cys Arg Gly Phe Arg Arg Arg Cys Phe
             60                  65                  70 tgc acc aga cac tgt taa ttattattat tatgtgtact gctgtgtaat              294
Cys Thr Arg His Cys *
         75 atgaacgtct cttctcgttt cttctggtgt tgtcatgaa ataagaatga ccatctgaac         354 tcagaaacag atcagaatgg ttaattccct tccgttcct angagttaaa tggttgctgg         414 caacttttaa ttgcgaactc tttctgtaac tattgggtat tacgatatat taaaaaaaaa         474 acca                                                                     478

<210> SEQ ID NO 308
<211> LENGTH: 77
<212> TYPE: PRT
<213> ORGANISM: Nicotiana benthamiana

<400> SEQUENCE: 308

Met Ala Gly Phe Pro Lys Val Leu Ala Thr Val Phe Leu Thr Leu Met
1               5                   10                  15

Leu Val Phe Ala Thr Glu Met Gly Pro Met Val Thr Glu Ala Arg Thr
            20                  25                  30

Cys Glu Ser Gln Ser His Arg Phe Lys Gly Leu Cys Phe Ser Arg Ser
        35                  40                  45

Asn Cys Ala Ser Val Cys His Thr Glu Gly Phe Asn Gly Gly His Cys
    50                  55                  60

Arg Gly Phe Arg Arg Arg Cys Phe Cys Thr Arg His Cys
65                  70                  75

<210> SEQ ID NO 309
<211> LENGTH: 47
<212> TYPE: PRT
<213> ORGANISM: Nicotiana benthamiana

<400> SEQUENCE: 309

Arg Thr Cys Glu Ser Gln Ser His Arg Phe Lys Gly Leu Cys Phe Ser
1               5                   10                  15

Arg Ser Asn Cys Ala Ser Val Cys His Thr Glu Gly Phe Asn Gly Gly
            20                  25                  30

His Cys Arg Gly Phe Arg Arg Arg Cys Phe Cys Thr Arg His Cys
        35                  40                  45

<210> SEQ ID NO 310
<211> LENGTH: 537
<212> TYPE: DNA
<213> ORGANISM: Tulipa gesneriana
<220> FEATURE:
<221> NAME/KEY: CDS
<222> LOCATION: (29)...(253)
<220> FEATURE:
<221> NAME/KEY: mat_peptide
<222> LOCATION: (107)...(250)
<220> FEATURE:
<221> NAME/KEY: misc_feature
<222> LOCATION: 426, 440, 479, 486, 511, 513, 528
<223> OTHER INFORMATION: n = A,T,C or G

<400> SEQUENCE: 310
ggtcttccag tactccttac ccttcact atg gcg aag ctt ccc aca gtc ctc       52
                                Met Ala Lys Leu Pro Thr Val Leu
                                 1               5 ctg ctc ctc ttc ctc gtc gtg gcc ttt gaa atg gga acg acg acg gtg    100
Leu Leu Leu Phe Leu Val Val Ala Phe Glu Met Gly Thr Thr Thr Val
    10                  15                  20 gag gcg agg acg tgc ctg tca cag agc cac aag ttc gaa ggt acc tgc    148
Glu Ala Arg Thr Cys Leu Ser Gln Ser His Lys Phe Glu Gly Thr Cys
 25                  30                  35                  40 ctg agg gag tcc aac tgc gcg acc gtc tgc cag acg gag ggg ttc cat    196
Leu Arg Glu Ser Asn Cys Ala Thr Val Cys Gln Thr Glu Gly Phe His
                45                  50                  55 gga gga ggg act tgc cag ggc ttc cgc cgc cgc tgc ttc tgc gta aga    244
Gly Gly Gly Thr Cys Gln Gly Phe Arg Arg Arg Cys Phe Cys Val Arg
         60                  65                  70 aac tgt tga tgatgcttca tgcttcgaat ctattcggag cagtatggca             293
Asn Cys * agagcccatg gtgctctatt tcatgggttt atcaagtgtt ttgagatgaa taagatggac   353
cttagtgtgc ttgcttcacc taagttcaag tgtttcctgc ctaaatttgt ataatttgtt   413

```
tgagtttccg tcnactgtcc tctgtantttt ggagccggtt gtacggtaac atttaatatc    473
aaaaanttcc aantttaaaa aaaaaaaaaa aaaacccnan gggggggggcc ggtancaaat    533 tccc                                                                  537
```

```
<210> SEQ ID NO 311
<211> LENGTH: 74
<212> TYPE: PRT
<213> ORGANISM: Tulipa gesneriana

<400> SEQUENCE: 311

Met Ala Lys Leu Pro Thr Val Leu Leu Leu Phe Leu Val Val Ala
 1               5                  10                  15

Phe Glu Met Gly Thr Thr Thr Val Glu Ala Arg Thr Cys Leu Ser Gln
            20                  25                  30

Ser His Lys Phe Glu Gly Thr Cys Leu Arg Glu Ser Asn Cys Ala Thr
        35                  40                  45

Val Cys Gln Thr Glu Gly Phe His Gly Gly Gly Thr Cys Gln Gly Phe
    50                  55                  60

Arg Arg Arg Cys Phe Cys Val Arg Asn Cys
65                  70
```

```
<210> SEQ ID NO 312
<211> LENGTH: 48
<212> TYPE: PRT
<213> ORGANISM: Tulipa gesneriana

<400> SEQUENCE: 312

Arg Thr Cys Leu Ser Gln Ser His Lys Phe Glu Gly Thr Cys Leu Arg
 1               5                  10                  15

Glu Ser Asn Cys Ala Thr Val Cys Gln Thr Glu Gly Phe His Gly Gly
            20                  25                  30

Gly Thr Cys Gln Gly Phe Arg Arg Arg Cys Phe Cys Val Arg Asn Cys
        35                  40                  45
```

```
<210> SEQ ID NO 313
<211> LENGTH: 469
<212> TYPE: DNA
<213> ORGANISM: Beta vulgaris
<220> FEATURE:
<221> NAME/KEY: CDS
<222> LOCATION: (21)...(257)
<220> FEATURE:
<221> NAME/KEY: mat_peptide
<222> LOCATION: (111)...(251)
<220> FEATURE:
<221> NAME/KEY: misc_feature
<222> LOCATION: 467, 468, 469
<223> OTHER INFORMATION: n = A,T,C or G

<400> SEQUENCE: 313
gcacgaggag aaaacataaa atg gaa cgc tct tca cgt ctg ttt tca gct gtt    53
                      Met Glu Arg Ser Ser Arg Leu Phe Ser Ala Val
                       1               5                  10 ctt ctt gtg ctt ctg ctt gtg att tct aca gag gtt gga acc aag gtg    101
Leu Leu Val Leu Leu Leu Val Ile Ser Thr Glu Val Gly Thr Lys Val
            15                  20                  25 gta gaa gca aga ata tgt gag tca cca agt tac agg ttc agg gga att    149
Val Glu Ala Arg Ile Cys Glu Ser Pro Ser Tyr Arg Phe Arg Gly Ile
        30                  35                  40 tgt gtg agc agg aac aac tgt gct aat atc tgc aaa act gaa ggt ttt    197
Cys Val Ser Arg Asn Asn Cys Ala Asn Ile Cys Lys Thr Glu Gly Phe
```

```
ccc ggt ggc cgt tgc cgc ggt ttc cgc cgt cgt tgc ttc tgt tac aaa    245
Pro Gly Gly Arg Cys Arg Gly Phe Arg Arg Arg Cys Phe Cys Tyr Lys
 60              65                  70                  75 cac tgc gcc taa ttgtagtact ccatgcattt ctgatcaagt gctagtagta        297
His Cys Ala * cactatgcaa ttcatatatg tgttatgtta cataaatgaa gtgccttctt taattaccta  357
ctatggtttt tgtaatcttt aagaataagt tcagttgtaa tcgttgtcat ttgcatatca  417
tattagttat ggttaatttt aatgtatgat ctttaatttg agttgtcaan nn          469

<210> SEQ ID NO 314
<211> LENGTH: 78
<212> TYPE: PRT
<213> ORGANISM: Beta vulgaris

<400> SEQUENCE: 314

Met Glu Arg Ser Ser Arg Leu Phe Ser Ala Val Leu Leu Val Leu Leu
 1               5                  10                  15

Leu Val Ile Ser Thr Glu Val Gly Thr Lys Val Val Glu Ala Arg Ile
             20                  25                  30

Cys Glu Ser Pro Ser Tyr Arg Phe Arg Gly Ile Cys Val Ser Arg Asn
         35                  40                  45

Asn Cys Ala Asn Ile Cys Lys Thr Glu Gly Phe Pro Gly Gly Arg Cys
     50                  55                  60

Arg Gly Phe Arg Arg Arg Cys Phe Cys Tyr Lys His Cys Ala
 65                  70                  75

<210> SEQ ID NO 315
<211> LENGTH: 47
<212> TYPE: PRT
<213> ORGANISM: Beta vulgaris

<400> SEQUENCE: 315

Arg Ile Cys Glu Ser Pro Ser Tyr Arg Phe Arg Gly Ile Cys Val Ser
 1               5                  10                  15

Arg Asn Asn Cys Ala Asn Ile Cys Lys Thr Glu Gly Phe Pro Gly Gly
             20                  25                  30

Arg Cys Arg Gly Phe Arg Arg Arg Cys Phe Cys Tyr Lys His Cys
         35                  40                  45

<210> SEQ ID NO 316
<211> LENGTH: 468
<212> TYPE: DNA
<213> ORGANISM: Cyamopsis tetragonoloba
<220> FEATURE:
<221> NAME/KEY: CDS
<222> LOCATION: (97)...(327)
<220> FEATURE:
<221> NAME/KEY: mat_peptide
<222> LOCATION: (184)...(324)

<400> SEQUENCE: 316
gcacgaggaa aacatatata gtaacaataa ttgtattgaa ttcaatttga tcgaggagta  60
ggagattaca cttaattatt taatcaatca ataatc atg gag aac aaa act aca   114
                                         Met Glu Asn Lys Thr Thr
                                          1               5 ctt gcc ttc ttc ttc ttc ctc ctc ttc gtc ttt gct tcc gat gtg ggg  162
Leu Ala Phe Phe Phe Phe Leu Leu Phe Val Phe Ala Ser Asp Val Gly
             10                  15                  20
```

```
gtg gtt aag aaa gca gag ggg aga ttg tgc gag aca agg agc cac tcg      210
Val Val Lys Lys Ala Glu Gly Arg Leu Cys Glu Thr Arg Ser His Ser
         25                  30                  35 ttc agg gga gca tgc ctg agt gac aca aac tgt gca cat gtt tgt gcc      258
Phe Arg Gly Ala Cys Leu Ser Asp Thr Asn Cys Ala His Val Cys Ala
 40                  45                  50 gcc gaa gga ttc act ggt ggt gat tgc cgt ggt ttt cgc cgc cgt tgc      306
Ala Glu Gly Phe Thr Gly Gly Asp Cys Arg Gly Phe Arg Arg Arg Cys
 55                  60                  65                  70 ttc tgc acc aag ttc tgt tga tctatcaaac aaacaccccc tactaataaa         357
Phe Cys Thr Lys Phe Cys  *
             75 tatatatata tatattaatc acaaataaaa tactaccaaa ctgatacttt ctatgtatca    417 tgcgtgcgtg gtgtaacttt caaatatata attaagtatt atattgcctc t             468

<210> SEQ ID NO 317
<211> LENGTH: 76
<212> TYPE: PRT
<213> ORGANISM: Cyamopsis tetragonoloba

<400> SEQUENCE: 317

Met Glu Asn Lys Thr Thr Leu Ala Phe Phe Phe Leu Leu Phe Val
 1               5                  10                  15

Phe Ala Ser Asp Val Gly Val Val Lys Lys Ala Glu Gly Arg Leu Cys
             20                  25                  30

Glu Thr Arg Ser His Ser Phe Arg Gly Ala Cys Leu Ser Asp Thr Asn
         35                  40                  45

Cys Ala His Val Cys Ala Ala Glu Gly Phe Thr Gly Gly Asp Cys Arg
     50                  55                  60

Gly Phe Arg Arg Arg Cys Phe Cys Thr Lys Phe Cys
 65                  70                  75

<210> SEQ ID NO 318
<211> LENGTH: 47
<212> TYPE: PRT
<213> ORGANISM: Cyamopsis tetragonoloba

<400> SEQUENCE: 318

Arg Leu Cys Glu Thr Arg Ser His Ser Phe Arg Gly Ala Cys Leu Ser
 1               5                  10                  15

Asp Thr Asn Cys Ala His Val Cys Ala Ala Glu Gly Phe Thr Gly Gly
             20                  25                  30

Asp Cys Arg Gly Phe Arg Arg Arg Cys Phe Cys Thr Lys Phe Cys
         35                  40                  45

<210> SEQ ID NO 319
<211> LENGTH: 425
<212> TYPE: DNA
<213> ORGANISM: Cyamopsis tetragonoloba
<220> FEATURE:
<221> NAME/KEY: CDS
<222> LOCATION: (51)...(281)
<220> FEATURE:
<221> NAME/KEY: mat_peptide
<222> LOCATION: (138)...(278)

<400> SEQUENCE: 319
gcacgagggg agtaggagat tacacttaat tatttaatca atcaataatc atg gag       56
                                                      Met Glu
                                                       1 aac aaa act aca ctt gcc tcc ttc ttc ttc ctc ctc ttc gtc ttt gct     104
```

```
                Asn Lys Thr Thr Leu Ala Ser Phe Phe Leu Leu Phe Val Phe Ala
                      5                  10                  15 tcc gat gtg ggg gtg gtt aag aaa gca gag ggg aga ttg tgc gag aca              152
Ser Asp Val Gly Val Val Lys Lys Ala Glu Gly Arg Leu Cys Glu Thr
     20                  25                  30 agg agc cac tcg ttc agg gga gca tgc ctg agt gac aca aac tgt gca              200
Arg Ser His Ser Phe Arg Gly Ala Cys Leu Ser Asp Thr Asn Cys Ala
 35                  40                  45                  50 cat gtt tgt gcc gcc gaa gga ttc act ggt ggt gat tgc cgt ggt ttt              248
His Val Cys Ala Ala Glu Gly Phe Thr Gly Gly Asp Cys Arg Gly Phe
             55                  60                  65 cgc cgc cgt tgc ttc tgc acc aag ttc tgt tga tctatcaaac aaacaccccc            301
Arg Arg Arg Cys Phe Cys Thr Lys Phe Cys  *
         70                  75 tactaataaa tatatatata tatattaatc acaaataaaa tactaccaaa ctgatacttt            361
ctatgtatca tgcgtgcgtg gtgtaacttt caaatatata attaagtatt atattgcctc            421
tatc                                                                        425

<210> SEQ ID NO 320
<211> LENGTH: 76
<212> TYPE: PRT
<213> ORGANISM: Cyamopsis tetragonoloba

<400> SEQUENCE: 320

Met Glu Asn Lys Thr Thr Leu Ala Ser Phe Phe Leu Leu Phe Val
 1               5                  10                  15

Phe Ala Ser Asp Val Gly Val Val Lys Lys Ala Glu Gly Arg Leu Cys
             20                  25                  30

Glu Thr Arg Ser His Ser Phe Arg Gly Ala Cys Leu Ser Asp Thr Asn
         35                  40                  45

Cys Ala His Val Cys Ala Ala Glu Gly Phe Thr Gly Gly Asp Cys Arg
     50                  55                  60

Gly Phe Arg Arg Arg Cys Phe Cys Thr Lys Phe Cys
 65                  70                  75

<210> SEQ ID NO 321
<211> LENGTH: 47
<212> TYPE: PRT
<213> ORGANISM: Cyamopsis tetragonoloba

<400> SEQUENCE: 321

Arg Leu Cys Glu Thr Arg Ser His Ser Phe Arg Gly Ala Cys Leu Ser
 1               5                  10                  15

Asp Thr Asn Cys Ala His Val Cys Ala Ala Glu Gly Phe Thr Gly Gly
             20                  25                  30

Asp Cys Arg Gly Phe Arg Arg Arg Cys Phe Cys Thr Lys Phe Cys
         35                  40                  45

<210> SEQ ID NO 322
<211> LENGTH: 459
<212> TYPE: DNA
<213> ORGANISM: Cyamopsis tetragonoloba
<220> FEATURE:
<221> NAME/KEY: CDS
<222> LOCATION: (102)...(308)
<220> FEATURE:
<221> NAME/KEY: mat_peptide
<222> LOCATION: (165)...(305)

<400> SEQUENCE: 322
```

```
ttcggcacga ggcaaaacat atatagtaac aataattgta ttgaattcaa tttgatcgag    60
gagtaggaga ttacacttaa ttatttaatc aatcaataat c atg gag aac aaa act   116
                                             Met Glu Asn Lys Thr
                                              1               5 aca ctt gcc ttc ttc ttc ctc ctc ttc gtc ttt gct tcc gag ggg         164
Thr Leu Ala Phe Phe Phe Leu Leu Phe Val Phe Ala Ser Glu Gly
             10                  15                  20 aga ttg tgc gag aca agg agc cac tcg ttc agg gga gca tgc ctg agt     212
Arg Leu Cys Glu Thr Arg Ser His Ser Phe Arg Gly Ala Cys Leu Ser
             25                  30                  35 gac aca aac tgt gca cat gtt tgt gcc gcc gaa gga ttc act ggt ggt     260
Asp Thr Asn Cys Ala His Val Cys Ala Ala Glu Gly Phe Thr Gly Gly
             40                  45                  50 gat tgc cgt ggt ttt cgc cgc cgt tgc ttc tgc acc aag ttc tgt tga    308
Asp Cys Arg Gly Phe Arg Arg Arg Cys Phe Cys Thr Lys Phe Cys *
             55                  60                  65 tctatcaaac aaacaccccc tactaataaa tatatatata tatattaatc acaaataaaa  368
tactaccaaa ctgatacttt ctatgtatca tgcgtgcgtg gtgtaacttt caaatatata  428
attaagtatt atattgcctc tatctttgtt t                                 459

<210> SEQ ID NO 323
<211> LENGTH: 68
<212> TYPE: PRT
<213> ORGANISM: Cyamopsis tetragonoloba

<400> SEQUENCE: 323

Met Glu Asn Lys Thr Thr Leu Ala Phe Phe Phe Leu Leu Phe Val
 1               5                  10                  15

Phe Ala Ser Glu Gly Arg Leu Cys Glu Thr Arg Ser His Ser Phe Arg
             20                  25                  30

Gly Ala Cys Leu Ser Asp Thr Asn Cys Ala His Val Cys Ala Ala Glu
         35                  40                  45

Gly Phe Thr Gly Gly Asp Cys Arg Gly Phe Arg Arg Arg Cys Phe Cys
     50                  55                  60

Thr Lys Phe Cys
65

<210> SEQ ID NO 324
<211> LENGTH: 47
<212> TYPE: PRT
<213> ORGANISM: Cyamopsis tetragonoloba

<400> SEQUENCE: 324

Arg Leu Cys Glu Thr Arg Ser His Ser Phe Arg Gly Ala Cys Leu Ser
 1               5                  10                  15

Asp Thr Asn Cys Ala His Val Cys Ala Ala Glu Gly Phe Thr Gly Gly
             20                  25                  30

Asp Cys Arg Gly Phe Arg Arg Arg Cys Phe Cys Thr Lys Phe Cys
         35                  40                  45

<210> SEQ ID NO 325
<211> LENGTH: 425
<212> TYPE: DNA
<213> ORGANISM: Zea mays
<220> FEATURE:
<221> NAME/KEY: CDS
<222> LOCATION: (63)...(299)
<220> FEATURE:
<221> NAME/KEY: mat_peptide
<222> LOCATION: (156)...(296)
```

<400> SEQUENCE: 325

```
tcagcttgta ttcccactct gtcgcacagc gtcgcccgtc gccgctgaga tcctaggaag      60 aa atg gag ctc tct cgc aag ctc ttc acg gcc gtc ctc ctc gtc atg         107
   Met Glu Leu Ser Arg Lys Leu Phe Thr Ala Val Leu Leu Val Met
   1               5                  10                  15 ctg ctg ctg ctg tcc gca gag gtc ggg ccg gtg gcg gtg gcg gag gcg       155
Leu Leu Leu Leu Ser Ala Glu Val Gly Pro Val Ala Val Ala Glu Ala
                20                  25                  30 cgg acg tgc cag tcg cag agc cac agg ttc cgg ggc ccc tgc ctc cgc       203
Arg Thr Cys Gln Ser Gln Ser His Arg Phe Arg Gly Pro Cys Leu Arg
            35                  40                  45 cgg tcc aac tgc gcc aac gtc tgc agg acc gag ggg ttc ccc ggc ggc       251
Arg Ser Asn Cys Ala Asn Val Cys Arg Thr Glu Gly Phe Pro Gly Gly
        50                  55                  60 agg tgc cgc ggc ttc cgc cgc cgc tgc ttc tgc acc acg cac tgc cac       299
Arg Cys Arg Gly Phe Arg Arg Arg Cys Phe Cys Thr Thr His Cys His
    65                  70                  75 tga ttcgctcgcc cagcggccgg ctggcgtcgc cgtcgatcgc gtcgcgacca            352
gtccatggct ccatgcatga ataacaaggg tgtgcgcggt ttgtgttgtg atgccaaaaa     412
aaaaaaaaaa aaa                                                        425
```

<210> SEQ ID NO 326
<211> LENGTH: 79
<212> TYPE: PRT
<213> ORGANISM: Zea mays

<400> SEQUENCE: 326

```
Met Glu Leu Ser Arg Lys Leu Phe Thr Ala Val Leu Leu Val Met Leu
1               5                  10                  15

Leu Leu Leu Ser Ala Glu Val Gly Pro Val Ala Val Ala Glu Ala Arg
            20                  25                  30

Thr Cys Gln Ser Gln Ser His Arg Phe Arg Gly Pro Cys Leu Arg Arg
        35                  40                  45

Ser Asn Cys Ala Asn Val Cys Arg Thr Glu Gly Phe Pro Gly Gly Arg
    50                  55                  60

Cys Arg Gly Phe Arg Arg Arg Cys Phe Cys Thr Thr His Cys His
65                  70                  75
```

<210> SEQ ID NO 327
<211> LENGTH: 47
<212> TYPE: PRT
<213> ORGANISM: Zea mays

<400> SEQUENCE: 327

```
Arg Thr Cys Gln Ser Gln Ser His Arg Phe Arg Gly Pro Cys Leu Arg
1               5                  10                  15

Arg Ser Asn Cys Ala Asn Val Cys Arg Thr Glu Gly Phe Pro Gly Gly
            20                  25                  30

Arg Cys Arg Gly Phe Arg Arg Arg Cys Phe Cys Thr Thr His Cys
        35                  40                  45
```

<210> SEQ ID NO 328
<211> LENGTH: 442
<212> TYPE: DNA
<213> ORGANISM: Triticum aestivum
<220> FEATURE:
<221> NAME/KEY: CDS
<222> LOCATION: (51)...(287)

```
<220> FEATURE:
<221> NAME/KEY: mat_peptide
<222> LOCATION: (141)...(281)
<220> FEATURE:
<221> NAME/KEY: misc_feature
<222> LOCATION: 411
<223> OTHER INFORMATION: n = A,T,C or G

<400> SEQUENCE: 328
gcacgaggac accccaccag acacactcgt acactagctg taatagatcg atg ggc        56
                                                      Met Gly
                                                       1 aag ctc gtc tcc gcc gcg ctc ctc ctg gtg ctg ctg ctc gcg gcg acg      104
Lys Leu Val Ser Ala Ala Leu Leu Leu Val Leu Leu Leu Ala Ala Thr
         5                  10                  15 ggg gag atg gga ggc ccg gtg gcg gtg gcg gaa gct cgg agg tgc gag      152
Gly Glu Met Gly Gly Pro Val Ala Val Ala Glu Ala Arg Arg Cys Glu
     20                  25                  30 tcg ctg agc cac agg ttc gcg ggc ctc tgc ctg cgc ggc cac aac tgc      200
Ser Leu Ser His Arg Phe Ala Gly Leu Cys Leu Arg Gly His Asn Cys
 35                  40                  45                  50 gcc aac gtc tgc cgg acc gag ggc ttt ccc gac ggg aag tgc cgc ggc      248
Ala Asn Val Cys Arg Thr Glu Gly Phe Pro Asp Gly Lys Cys Arg Gly
                 55                  60                  65 gcc cgc cgc cgc tgc ttc tgc acc acc cac tgc cgc tag tagcctagct       297
Ala Arg Arg Arg Cys Phe Cys Thr Thr His Cys Arg *
                 70                  75 gcatgcatgc tggcaccttt gtgcgtgtgc cgtgtccatg tccatgaata aacctaagct    357
tgtctctcct ggcaggccga gctgggtata agaaacaact tgtgcttgtg tcanaaaaaa    417
aaaaaaaaaa aaaaaaaaaa aaaaa                                          442

<210> SEQ ID NO 329
<211> LENGTH: 78
<212> TYPE: PRT
<213> ORGANISM: Triticum aestivum

<400> SEQUENCE: 329

Met Gly Lys Leu Val Ser Ala Ala Leu Leu Val Leu Leu Leu Ala
 1               5                  10                  15

Ala Thr Gly Glu Met Gly Gly Pro Val Ala Val Ala Glu Ala Arg Arg
                 20                  25                  30

Cys Glu Ser Leu Ser His Arg Phe Ala Gly Leu Cys Leu Arg Gly His
             35                  40                  45

Asn Cys Ala Asn Val Cys Arg Thr Glu Gly Phe Pro Asp Gly Lys Cys
 50                  55                  60

Arg Gly Ala Arg Arg Arg Cys Phe Cys Thr Thr His Cys Arg
 65                  70                  75

<210> SEQ ID NO 330
<211> LENGTH: 47
<212> TYPE: PRT
<213> ORGANISM: Triticum aestivum

<400> SEQUENCE: 330

Arg Arg Cys Glu Ser Leu Ser His Arg Phe Ala Gly Leu Cys Leu Arg
 1               5                  10                  15

Gly His Asn Cys Ala Asn Val Cys Arg Thr Glu Gly Phe Pro Asp Gly
                 20                  25                  30

Lys Cys Arg Gly Ala Arg Arg Arg Cys Phe Cys Thr Thr His Cys
             35                  40                  45
```

<210> SEQ ID NO 331
<211> LENGTH: 587
<212> TYPE: DNA
<213> ORGANISM: Triticum aestivum
<220> FEATURE:
<221> NAME/KEY: CDS
<222> LOCATION: (74)...(313)
<220> FEATURE:
<221> NAME/KEY: mat_peptide
<222> LOCATION: (167)...(307)

<400> SEQUENCE: 331

```
gcacgagggt tcagcttgt attcccactc tgtcgcacag cgtcgcccgt cgccgctgag      60
atcctaggaa gaa atg gag ctc tct cgc aag ctc ttc acg gcc gtc ctc       109
           Met Glu Leu Ser Arg Lys Leu Phe Thr Ala Val Leu
             1               5                  10 ctc gtc atg ctg ctg ctg tcc gca gag gtc ggg ccg gtg gcg gtg          157
Leu Val Met Leu Leu Leu Ser Ala Glu Val Gly Pro Val Ala Val
         15                  20                  25 gcg gag gcg cgg acg tgc cag tcg cag agc cac agg ttc cgg ggc ccc      205
Ala Glu Ala Arg Thr Cys Gln Ser Gln Ser His Arg Phe Arg Gly Pro
 30                  35                  40 tgc ctc cgc cgg tcc aac tgc gcc aac gtc tgc agg acc gag ggg ttc      253
Cys Leu Arg Arg Ser Asn Cys Ala Asn Val Cys Arg Thr Glu Gly Phe
 45                  50                  55                  60 ccc ggc ggc agg tgc cgc ggc ttc cgc cgc cgc tgc ttc tgc acc acg      301
Pro Gly Gly Arg Cys Arg Gly Phe Arg Arg Arg Cys Phe Cys Thr Thr
                 65                  70                  75 cac tgc cac tga ttcgctcgcc cagcggccgg ctggcgtcgc cgtcgatcgc          353
His Cys His * gtcgcgacca gtccatggct ccatgcatga ataacaaggg tgtgcgcggt ttgtgttgtg    413
atgccaaatt gtatcctcgt cgtgtgttga gcagcggcgt gctgttgtac gtacgtctgc    473
ctctgttcca tgtttcggga ttttccatag caaatgcatg cgtcgatcga gatctactcc    533
gaaagaaatt cgatagactt cgcataattt ccattcaaaa aaaaaaaaaa aaaa          587
```

<210> SEQ ID NO 332
<211> LENGTH: 79
<212> TYPE: PRT
<213> ORGANISM: Triticum aestivum

<400> SEQUENCE: 332

```
Met Glu Leu Ser Arg Lys Leu Phe Thr Ala Val Leu Leu Val Met Leu
  1               5                  10                  15

Leu Leu Ser Ala Glu Val Gly Pro Val Ala Val Ala Glu Ala Arg
             20                  25                  30

Thr Cys Gln Ser Gln Ser His Arg Phe Arg Gly Pro Cys Leu Arg Arg
         35                  40                  45

Ser Asn Cys Ala Asn Val Cys Arg Thr Glu Gly Phe Pro Gly Gly Arg
     50                  55                  60

Cys Arg Gly Phe Arg Arg Arg Cys Phe Cys Thr Thr His Cys His
 65                  70                  75
```

<210> SEQ ID NO 333
<211> LENGTH: 47
<212> TYPE: PRT
<213> ORGANISM: Triticum aestivum

<400> SEQUENCE: 333

```
Arg Thr Cys Gln Ser Gln Ser His Arg Phe Arg Gly Pro Cys Leu Arg
  1               5                  10                  15

Arg Ser Asn Cys Ala Asn Val Cys Arg Thr Glu Gly Phe Pro Gly Gly
                 20                  25                  30

Arg Cys Arg Gly Phe Arg Arg Cys Phe Cys Thr Thr His Cys
             35                  40                  45
```

<210> SEQ ID NO 334
<211> LENGTH: 459
<212> TYPE: DNA
<213> ORGANISM: Tulipa gesneriana
<220> FEATURE:
<221> NAME/KEY: CDS
<222> LOCATION: (3)...(224)
<220> FEATURE:
<221> NAME/KEY: mat_peptide
<222> LOCATION: (81)...(221)
<220> FEATURE:
<221> NAME/KEY: misc_feature
<222> LOCATION: 319, 357, 393, 395, 414, 418, 441
<223> OTHER INFORMATION: n = A,T,C or G

<400> SEQUENCE: 334

```
gg gag cgc cca att cgt gcc atc ttc ttc ctg gtg ctt ctc ctt gtc        47
   Glu Arg Pro Ile Arg Ala Ile Phe Phe Leu Val Leu Leu Leu Val
     1               5                  10                  15 gcc tct gag atg gtg acg acg gca gtg gag gcg aga act tgc gag tcg       95
Ala Ser Glu Met Val Thr Thr Ala Val Glu Ala Arg Thr Cys Glu Ser
                 20                  25                  30 aag agc aac agg ttc aag ggc ccg tgt atc cgg gca agc aac tgc gcc      143
Lys Ser Asn Arg Phe Lys Gly Pro Cys Ile Arg Ala Ser Asn Cys Ala
             35                  40                  45 aac gtt tgc agg aca gag ggc ttc cat ggc ggc aag tgc cgc ggt ctc      191
Asn Val Cys Arg Thr Glu Gly Phe His Gly Gly Lys Cys Arg Gly Leu
         50                  55                  60 cgt cgc cga tgc ttc tgc acc acc cat tgc tag cttcctgcct agctgggat     244
Arg Arg Arg Cys Phe Cys Thr Thr His Cys *
     65                  70 gatgatgatc atcttgttcg tccttccaac tttgtgtgtt tctacgaata aaatgtaact    304
cgtgtggatg tttcncttt ttttttcggg aacttgtgtg gatgtctcaa agntacctgt     364
gcctacattc cgtgggatta attgggaana ntttggggaat gttaaaccan aaanatttta   424
aagaaaagta accaaanatt gggaaaagga aatgg                               459
```

<210> SEQ ID NO 335
<211> LENGTH: 73
<212> TYPE: PRT
<213> ORGANISM: Tulipa gesneriana

<400> SEQUENCE: 335

```
Glu Arg Pro Ile Arg Ala Ile Phe Phe Leu Val Leu Leu Leu Val Ala
  1               5                  10                  15

Ser Glu Met Val Thr Thr Ala Val Glu Ala Arg Thr Cys Glu Ser Lys
                 20                  25                  30

Ser Asn Arg Phe Lys Gly Pro Cys Ile Arg Ala Ser Asn Cys Ala Asn
             35                  40                  45

Val Cys Arg Thr Glu Gly Phe His Gly Gly Lys Cys Arg Gly Leu Arg
         50                  55                  60

Arg Arg Cys Phe Cys Thr Thr His Cys
 65                  70
```

<210> SEQ ID NO 336
<211> LENGTH: 47
<212> TYPE: PRT
<213> ORGANISM: Tulipa gesneriana

<400> SEQUENCE: 336

Arg Thr Cys Glu Ser Lys Ser Asn Arg Phe Lys Gly Pro Cys Ile Arg
1               5                   10                  15

Ala Ser Asn Cys Ala Asn Val Cys Arg Thr Glu Gly Phe His Gly Gly
            20                  25                  30

Lys Cys Arg Gly Leu Arg Arg Arg Cys Phe Cys Thr Thr His Cys
        35                  40                  45

<210> SEQ ID NO 337
<211> LENGTH: 399
<212> TYPE: DNA
<213> ORGANISM: Triticum aestivum
<220> FEATURE:
<221> NAME/KEY: CDS
<222> LOCATION: (34)...(288)
<220> FEATURE:
<221> NAME/KEY: mat_peptide
<222> LOCATION: (139)...(279)

<400> SEQUENCE: 337
caaccctgat acactcatac caagcagtaa tcg atg tcg atg gag gct tca cgc         54
                                    Met Ser Met Glu Ala Ser Arg
                                    1               5 aag ctc ctc tcg gcg gcg ctc ctc ctg gtg ctg ctg ctg gcg gcc acg        102
Lys Leu Leu Ser Ala Ala Leu Leu Leu Val Leu Leu Leu Ala Ala Thr
            10                  15                  20 ggg gag atg gga ggc ccg gtg gcg gtg gct gag gcg cgg acg tgc gag        150
Gly Glu Met Gly Gly Pro Val Ala Val Ala Glu Ala Arg Thr Cys Glu
        25                  30                  35 gcg aag agc cac agg ttc agg ggc ccc tgc gtg cgc cac cgc aac tgc        198
Ala Lys Ser His Arg Phe Arg Gly Pro Cys Val Arg His Arg Asn Cys
40                  45                  50                  55 gcc aac gtc tgc aag acc gag ggc ttc ccc ggc ggc aag tgc cgc ggc        246
Ala Asn Val Cys Lys Thr Glu Gly Phe Pro Gly Gly Lys Cys Arg Gly
                60                  65                  70 ttc cgc cac cgc tgc ttc tgc acc acc cac tgc cgc cag tga               288
Phe Arg His Arg Cys Phe Cys Thr Thr His Cys Arg Gln *
                75                  80 ccaacctatt gcctctactt cgtccgtacg tccgcctagc tgcagcctgc ctgcgtgcat       348
gctggcttgc tcgcacctct gtgcgtgtat tgtagtactg tgtccatgaa t               399

<210> SEQ ID NO 338
<211> LENGTH: 84
<212> TYPE: PRT
<213> ORGANISM: Triticum aestivum

<400> SEQUENCE: 338

Met Ser Met Glu Ala Ser Arg Lys Leu Leu Ser Ala Ala Leu Leu Leu
1               5                   10                  15

Val Leu Leu Leu Ala Ala Thr Gly Glu Met Gly Gly Pro Val Ala Val
            20                  25                  30

Ala Glu Ala Arg Thr Cys Glu Ala Lys Ser His Arg Phe Arg Gly Pro
        35                  40                  45

Cys Val Arg His Arg Asn Cys Ala Asn Val Cys Lys Thr Glu Gly Phe
    50                  55                  60

Pro Gly Gly Lys Cys Arg Gly Phe Arg His Arg Cys Phe Cys Thr Thr

His Cys Arg Gln

<210> SEQ ID NO 339
<211> LENGTH: 47
<212> TYPE: PRT
<213> ORGANISM: Triticum aestivum

<400> SEQUENCE: 339

Arg Thr Cys Glu Ala Lys Ser His Arg Phe Arg Gly Pro Cys Val Arg
1               5                   10                  15

His Arg Asn Cys Ala Asn Val Cys Lys Thr Glu Gly Phe Pro Gly Gly
            20                  25                  30

Lys Cys Arg Gly Phe Arg His Arg Cys Phe Cys Thr Thr His Cys
        35                  40                  45

<210> SEQ ID NO 340
<211> LENGTH: 553
<212> TYPE: DNA
<213> ORGANISM: Triticum aestivum
<220> FEATURE:
<221> NAME/KEY: CDS
<222> LOCATION: (52)...(297)
<220> FEATURE:
<221> NAME/KEY: mat_peptide
<222> LOCATION: (151)...(291)
<220> FEATURE:
<221> NAME/KEY: misc_feature
<222> LOCATION: 550
<223> OTHER INFORMATION: n = A,T,C or G

<400> SEQUENCE: 340
gctctatccc tcccacagca ccctgacttg caagctgtag tgtaccgatc c atg gag      57
                                                         Met Glu
                                                         1 gct tca cgc agg ctc ctc tcc gcg gcg ctc ctc ctc gtc ctg ctg ctc     105
Ala Ser Arg Arg Leu Leu Ser Ala Ala Leu Leu Leu Val Leu Leu Leu
        5                   10                  15 gcc gcc aca ggg gag ctg gga ggc ccg gtg atg gtg gcg gag gcg cgg     153
Ala Ala Thr Gly Glu Leu Gly Gly Pro Val Met Val Ala Glu Ala Arg
    20                  25                  30 acg tgc gag tcg cgg agc cac agg ttc agg ggg ccc tgc gtg cgc agg     201
Thr Cys Glu Ser Arg Ser His Arg Phe Arg Gly Pro Cys Val Arg Arg
35                  40                  45                  50 tcc aac tgc gcc aac gtc tgc aag acc gag ggc ttc ccc gac ggc aag     249
Ser Asn Cys Ala Asn Val Cys Lys Thr Glu Gly Phe Pro Asp Gly Lys
                55                  60                  65 tgc cgc ggg ttc cgc cgc cgc tgc ttc tgc acc acc cac tgc cac cat     297
Cys Arg Gly Phe Arg Arg Arg Cys Phe Cys Thr Thr His Cys His His
            70                  75                  80 taa caagcctctc cttcgggtga tgccttcttt ggggtggcct ttctgcgaag           350
cgtccgtgcg tgcgtgtcca tgaataaacc tcagcttgtc tcggcaagct aggtgcgaag    410
tcccttcttt gttttttgta tgattattgc cagtgtttgt ttcttgttgg gttcgtcctc    470
aagagttgct gcgaagattt atgggattat cccagtcaaa cccttccgtc aagtaagatt    530
taatttgggg aaatcaatgn att                                            553

<210> SEQ ID NO 341
<211> LENGTH: 82
<212> TYPE: PRT
<213> ORGANISM: Triticum aestivum

<400> SEQUENCE: 341

Met Glu Ala Ser Arg Arg Leu Leu Ser Ala Ala Leu Leu Val Leu
1               5                   10                  15

Leu Leu Ala Ala Thr Gly Glu Leu Gly Gly Pro Val Met Val Ala Glu
            20                  25                  30

Ala Arg Thr Cys Glu Ser Arg Ser His Arg Phe Arg Gly Pro Cys Val
        35                  40                  45

Arg Arg Ser Asn Cys Ala Asn Val Cys Lys Thr Glu Gly Phe Pro Asp
    50                  55                  60

Gly Lys Cys Arg Gly Phe Arg Arg Cys Phe Cys Thr Thr His Cys
65                  70                  75                  80

His His

<210> SEQ ID NO 342
<211> LENGTH: 47
<212> TYPE: PRT
<213> ORGANISM: Triticum aestivum

<400> SEQUENCE: 342

Arg Thr Cys Glu Ser Arg Ser His Arg Phe Arg Gly Pro Cys Val Arg
1               5                   10                  15

Arg Ser Asn Cys Ala Asn Val Cys Lys Thr Glu Gly Phe Pro Asp Gly
            20                  25                  30

Lys Cys Arg Gly Phe Arg Arg Cys Phe Cys Thr Thr His Cys
        35                  40                  45

<210> SEQ ID NO 343
<211> LENGTH: 445
<212> TYPE: DNA
<213> ORGANISM: Tulipa gesneriana
<220> FEATURE:
<221> NAME/KEY: CDS
<222> LOCATION: (3)...(218)
<220> FEATURE:
<221> NAME/KEY: mat_peptide
<222> LOCATION: (75)...(215)
<220> FEATURE:
<221> NAME/KEY: misc_feature
<222> LOCATION: 383, 425
<223> OTHER INFORMATION: n = A,T,C or G

<400> SEQUENCE: 343

```
gc cca att cgt gcc atc ttc ttc ctg gtg ctt ctc ctt gtc gcc tct        47
   Pro Ile Arg Ala Ile Phe Phe Leu Val Leu Leu Leu Val Ala Ser
    1               5                   10                  15 gag atg gcc acg acg gca gtg gag gcg aga act tgc gag tcg aag agc       95
Glu Met Ala Thr Thr Ala Val Glu Ala Arg Thr Cys Glu Ser Lys Ser
            20                  25                  30 aat agg ttc aag ggc ccg tgt att cgg gca agc aac tgc gcc aac gtc       143
Asn Arg Phe Lys Gly Pro Cys Ile Arg Ala Ser Asn Cys Ala Asn Val
        35                  40                  45 tgc aga aca gag ggc ttc cat ggt ggc aag tgc cgc ggt ctc cgt cgc       191
Cys Arg Thr Glu Gly Phe His Gly Gly Lys Cys Arg Gly Leu Arg Arg
    50                  55                  60 cga tgc ttc tgc acc acc cat tgc tag cttcctgcct agctggggat             238
Arg Cys Phe Cys Thr Thr His Cys  *
65                  70 gatgatgatc atcttgttgg tccttccaac tttgtgtgtt tctacgaata agatgtagct     298
cgtgtggatg tctctccttt ttttttttccg ggaacttgtg tggatgtctc aaggctacct    358
gtgcttacat tcgtggatta ttggnataag tatggaagtg tgagactaga atgattttaa     418
```

```
agaaaangta cctaataatt gggaaaa                                          445

<210> SEQ ID NO 344
<211> LENGTH: 71
<212> TYPE: PRT
<213> ORGANISM: Tulipa gesneriana

<400> SEQUENCE: 344

Pro Ile Arg Ala Ile Phe Phe Leu Val Leu Leu Val Ala Ser Glu
1               5                   10                  15

Met Ala Thr Thr Ala Val Glu Ala Arg Thr Cys Glu Ser Lys Ser Asn
            20                  25                  30

Arg Phe Lys Gly Pro Cys Ile Arg Ala Ser Asn Cys Ala Asn Val Cys
        35                  40                  45

Arg Thr Glu Gly Phe His Gly Gly Lys Cys Arg Gly Leu Arg Arg Arg
    50                  55                  60

Cys Phe Cys Thr Thr His Cys
65                  70

<210> SEQ ID NO 345
<211> LENGTH: 47
<212> TYPE: PRT
<213> ORGANISM: Tulipa gesneriana

<400> SEQUENCE: 345

Arg Thr Cys Glu Ser Lys Ser Asn Arg Phe Lys Gly Pro Cys Ile Arg
1               5                   10                  15

Ala Ser Asn Cys Ala Asn Val Cys Arg Thr Glu Gly Phe His Gly Gly
            20                  25                  30

Lys Cys Arg Gly Leu Arg Arg Arg Cys Phe Cys Thr Thr His Cys
        35                  40                  45

<210> SEQ ID NO 346
<211> LENGTH: 609
<212> TYPE: DNA
<213> ORGANISM: Glycine max
<220> FEATURE:
<221> NAME/KEY: CDS
<222> LOCATION: (131)...(352)
<220> FEATURE:
<221> NAME/KEY: mat_peptide
<222> LOCATION: (209)...(349)

<400> SEQUENCE: 346
gcacgagtgt acttgcggtt tactctcttt ttagctagct ataaatagat aagagtaccc     60
aacccatttg tttatattca gggttgtata ttgatatatc taggtgtggg tggtacgtaa    120
ttaattagcc atg gac aag gca cga ttt ggg ttt ttc ttc atg ttg ctc       169
            Met Asp Lys Ala Arg Phe Gly Phe Phe Phe Met Leu Leu
                1               5                   10 att ctc ctt tct tct cag atg gtg gta caa aca gag gga agg cac tgt      217
Ile Leu Leu Ser Ser Gln Met Val Val Gln Thr Glu Gly Arg His Cys
    15                  20                  25 gag tca aag agc cat cgg ttt aaa ggg atg tgc ctc agt aag cac aac      265
Glu Ser Lys Ser His Arg Phe Lys Gly Met Cys Leu Ser Lys His Asn
30                  35                  40                  45 tgc gct tcg gtt tgc cat ctt gaa ggc ttc acg ggt ggc aag tgt cgt      313
Cys Ala Ser Val Cys His Leu Glu Gly Phe Thr Gly Gly Lys Cys Arg
                50                  55                  60 gga ttt cgt aga cgc tgt ttc tgc acc agg cac tgt tag ttggtccatg       362
Gly Phe Arg Arg Arg Cys Phe Cys Thr Arg His Cys *
```

-continued

```
            65                  70
aaatttatc cttgttggtt gctctttcac ctttctgttt ctgggattaa gaaataaata    422
ctccttagtg agtcgtgttt ttaatttcta ggttcatttg ggttggcttt atatcttatg    482
ctttgatcta cctcgcttct gtttcaattt ggttggccaa tgttgcaatt ttaatttcta    542
gtgttgtatg tttctctttt gtggtgtact tgccataaaa aataacaggt gatctctctc    602
accctac                                                              609
```

<210> SEQ ID NO 347
<211> LENGTH: 73
<212> TYPE: PRT
<213> ORGANISM: Glycine max

<400> SEQUENCE: 347

```
Met Asp Lys Ala Arg Phe Gly Phe Phe Met Leu Leu Ile Leu Leu
 1               5                  10                  15

Ser Ser Gln Met Val Val Gln Thr Glu Gly Arg His Cys Glu Ser Lys
            20                  25                  30

Ser His Arg Phe Lys Gly Met Cys Leu Ser Lys His Asn Cys Ala Ser
        35                  40                  45

Val Cys His Leu Glu Gly Phe Thr Gly Gly Lys Cys Arg Gly Phe Arg
    50                  55                  60

Arg Arg Cys Phe Cys Thr Arg His Cys
65                  70
```

<210> SEQ ID NO 348
<211> LENGTH: 47
<212> TYPE: PRT
<213> ORGANISM: Glycine max

<400> SEQUENCE: 348

```
Arg His Cys Glu Ser Lys Ser His Arg Phe Lys Gly Met Cys Leu Ser
 1               5                  10                  15

Lys His Asn Cys Ala Ser Val Cys His Leu Glu Gly Phe Thr Gly Gly
            20                  25                  30

Lys Cys Arg Gly Phe Arg Arg Arg Cys Phe Cys Thr Arg His Cys
        35                  40                  45
```

<210> SEQ ID NO 349
<211> LENGTH: 477
<212> TYPE: DNA
<213> ORGANISM: Brassica napus
<220> FEATURE:
<221> NAME/KEY: CDS
<222> LOCATION: (58)...(291)
<220> FEATURE:
<221> NAME/KEY: mat_peptide
<222> LOCATION: (148)...(288)
<220> FEATURE:
<221> NAME/KEY: misc_feature
<222> LOCATION: 473, 474, 475, 476, 477
<223> OTHER INFORMATION: n = A,T,C or G

<400> SEQUENCE: 349

```
ccacgcgtcc gcccacgcgt ccgcttgggt tcaactctct atatctctct tcaaaaa atg    60
                                                                Met
                                                                  1 aag ctc act ttt cgt ttt atc tca gca gtt gcg ctt ttg ttc atg ctc     108
Lys Leu Thr Phe Arg Phe Ile Ser Ala Val Ala Leu Leu Phe Met Leu
            5                  10                  15 ctc gtc gcc aca ggg atg ggt ccg gtg acg gcg aag gca cgc atg tgt     156
```

-continued

```
                Leu Val Ala Thr Gly Met Gly Pro Val Thr Ala Lys Ala Arg Met Cys
                             20                  25                  30 gaa acg agt agc cag ttg ttc aat gga ccg tgt ctg agc aca acc aat      204
Glu Thr Ser Ser Gln Leu Phe Asn Gly Pro Cys Leu Ser Thr Thr Asn
         35                  40                  45 tgc gcc aat att tgc cag aat gaa ggt ttt cca gat ggt gac tgc aaa      252
Cys Ala Asn Ile Cys Gln Asn Glu Gly Phe Pro Asp Gly Asp Cys Lys
 50                  55                  60                  65 gga ttc cgc ctt cgc tgc atc tgc aac aga cca tgt tga tgaaagacaa      301
Gly Phe Arg Leu Arg Cys Ile Cys Asn Arg Pro Cys *
                 70                  75 gttacaaagg aaacagacca tgttgatcca tgatcgtttt atgttgtttt ttttttcttt    361 ctatttatc cttagtcctt caaatgactt aatgggatat aaatctcgaa agcccttag     421 tttgtgtatt tcaattttct tctgaggtta aattataata acacagttta gnnnnn       477

<210> SEQ ID NO 350
<211> LENGTH: 77
<212> TYPE: PRT
<213> ORGANISM: Brassica napus

<400> SEQUENCE: 350

Met Lys Leu Thr Phe Arg Phe Ile Ser Ala Val Ala Leu Leu Phe Met
 1               5                  10                  15

Leu Leu Val Ala Thr Gly Met Gly Pro Val Thr Ala Lys Ala Arg Met
             20                  25                  30

Cys Glu Thr Ser Ser Gln Leu Phe Asn Gly Pro Cys Leu Ser Thr Thr
         35                  40                  45

Asn Cys Ala Asn Ile Cys Gln Asn Glu Gly Phe Pro Asp Gly Asp Cys
 50                  55                  60

Lys Gly Phe Arg Leu Arg Cys Ile Cys Asn Arg Pro Cys
65                  70                  75

<210> SEQ ID NO 351
<211> LENGTH: 47
<212> TYPE: PRT
<213> ORGANISM: Brassica napus

<400> SEQUENCE: 351

Arg Met Cys Glu Thr Ser Ser Gln Leu Phe Asn Gly Pro Cys Leu Ser
 1               5                  10                  15

Thr Thr Asn Cys Ala Asn Ile Cys Gln Asn Glu Gly Phe Pro Asp Gly
             20                  25                  30

Asp Cys Lys Gly Phe Arg Leu Arg Cys Ile Cys Asn Arg Pro Cys
         35                  40                  45

<210> SEQ ID NO 352
<211> LENGTH: 429
<212> TYPE: DNA
<213> ORGANISM: Triticum aestivum
<220> FEATURE:
<221> NAME/KEY: CDS
<222> LOCATION: (24)...(245)
<220> FEATURE:
<221> NAME/KEY: mat_peptide
<222> LOCATION: (111)...(245)

<400> SEQUENCE: 352
cttagtcctc cataagaaat ctc atg gat ctc tcc atg aaa gtc ttt gtg gtc   53
                         Met Asp Leu Ser Met Lys Val Phe Val Val
                          1               5                  10
```

```
gtc ctc cta ctt ctt gtg gct att gag gac cag gga cca gtg caa gta      101
Val Leu Leu Leu Leu Val Ala Ile Glu Asp Gln Gly Pro Val Gln Val
            15                  20                  25 gct ttg gcg agg gac tgc aag tca cag agc tac aag ttc aag ggg atg      149
Ala Leu Ala Arg Asp Cys Lys Ser Gln Ser Tyr Lys Phe Lys Gly Met
        30                  35                  40 tgc gtg cgc aat gac aat tgt gca agt gtt tgc ctg acc gag ggt ttc      197
Cys Val Arg Asn Asp Asn Cys Ala Ser Val Cys Leu Thr Glu Gly Phe
                45                  50                  55 ccc aga ggc aag tgc aag ggc ttt gca tgt tcc tgc tac aag gat tgc      245
Pro Arg Gly Lys Cys Lys Gly Phe Ala Cys Ser Cys Tyr Lys Asp Cys
        60                  65                  70 tag atggccctga tttgtctatt gcgtacatgc ttttgtgtaa taaaatttg            298 aataaataat agtagatcta aaaaaaaaag ggggggggccc ggtaaccaaa tttcgcccta   358
ataagtggag tccgtaatta cgccgcggct cactgggccg tccgttttac aaacgtccgt   418
ggactgggga a                                                          429

<210> SEQ ID NO 353
<211> LENGTH: 74
<212> TYPE: PRT
<213> ORGANISM: Triticum aestivum

<400> SEQUENCE: 353

Met Asp Leu Ser Met Lys Val Phe Val Val Leu Leu Leu Val
1               5                   10                  15

Ala Ile Glu Asp Gln Gly Pro Val Gln Val Ala Leu Ala Arg Asp Cys
            20                  25                  30

Lys Ser Gln Ser Tyr Lys Phe Lys Gly Met Cys Val Arg Asn Asp Asn
        35                  40                  45

Cys Ala Ser Val Cys Leu Thr Glu Gly Phe Pro Arg Gly Lys Cys Lys
    50                  55                  60

Gly Phe Ala Cys Ser Cys Tyr Lys Asp Cys
65                  70

<210> SEQ ID NO 354
<211> LENGTH: 45
<212> TYPE: PRT
<213> ORGANISM: Triticum aestivum

<400> SEQUENCE: 354

Arg Asp Cys Lys Ser Gln Ser Tyr Lys Phe Lys Gly Met Cys Val Arg
1               5                   10                  15

Asn Asp Asn Cys Ala Ser Val Cys Leu Thr Glu Gly Phe Pro Arg Gly
            20                  25                  30

Lys Cys Lys Gly Phe Ala Cys Ser Cys Tyr Lys Asp Cys
        35                  40                  45

<210> SEQ ID NO 355
<211> LENGTH: 347
<212> TYPE: DNA
<213> ORGANISM: Triticum aestivum
<220> FEATURE:
<221> NAME/KEY: CDS
<222> LOCATION: (61)...(291)
<220> FEATURE:
<221> NAME/KEY: mat_peptide
<222> LOCATION: (148)...(288)

<400> SEQUENCE: 355
gcacgagctt gaaggtctta atctgtcata caatcctctt agtctttcat aggaaatctc    60
```

```
atg gat ctc tcc atg aag gtt gtt gtg gtc gtt ctc ctg ctt ctt gtg      108
Met Asp Leu Ser Met Lys Val Val Val Val Leu Leu Leu Leu Leu Val
 1               5                  10                  15 acc aca gag gac cag gga cca gtg cag cta gct ttg gcg agg gac tgt      156
Thr Thr Glu Asp Gln Gly Pro Val Gln Leu Ala Leu Ala Arg Asp Cys
                20                  25                  30 cag tca aag agc ttc aag ttc aag ggg atg tgt gtg cgc gat gac aac      204
Gln Ser Lys Ser Phe Lys Phe Lys Gly Met Cys Val Arg Asp Asp Asn
         35                  40                  45 tgt gca agt gtt tgc ctg ctc gag ggt ttc acc gga ggc aag tgc aag      252
Cys Ala Ser Val Cys Leu Leu Glu Gly Phe Thr Gly Gly Lys Cys Lys
     50                  55                  60 ggc ttt tgg cat cgt tgt tac tgc acc aag gac tgc tag atggccctga      301
Gly Phe Trp His Arg Cys Tyr Cys Thr Lys Asp Cys *
 65                  70                  75 tttgtctatt gcatatatgc ttccgtctaa aaaaaaaaaa aaaaaa                   347
```

<210> SEQ ID NO 356
<211> LENGTH: 76
<212> TYPE: PRT
<213> ORGANISM: Triticum aestivum

<400> SEQUENCE: 356

```
Met Asp Leu Ser Met Lys Val Val Val Val Leu Leu Leu Leu Val
 1               5                  10                  15

Thr Thr Glu Asp Gln Gly Pro Val Gln Leu Ala Leu Ala Arg Asp Cys
                20                  25                  30

Gln Ser Lys Ser Phe Lys Phe Lys Gly Met Cys Val Arg Asp Asp Asn
         35                  40                  45

Cys Ala Ser Val Cys Leu Leu Glu Gly Phe Thr Gly Gly Lys Cys Lys
     50                  55                  60

Gly Phe Trp His Arg Cys Tyr Cys Thr Lys Asp Cys
 65                  70                  75
```

<210> SEQ ID NO 357
<211> LENGTH: 47
<212> TYPE: PRT
<213> ORGANISM: Triticum aestivum

<400> SEQUENCE: 357

```
Arg Asp Cys Gln Ser Lys Ser Phe Lys Phe Lys Gly Met Cys Val Arg
 1               5                  10                  15

Asp Asp Asn Cys Ala Ser Val Cys Leu Leu Glu Gly Phe Thr Gly Gly
                20                  25                  30

Lys Cys Lys Gly Phe Trp His Arg Cys Tyr Cys Thr Lys Asp Cys
         35                  40                  45
```

<210> SEQ ID NO 358
<211> LENGTH: 551
<212> TYPE: DNA
<213> ORGANISM: Zea mays
<220> FEATURE:
<221> NAME/KEY: CDS
<222> LOCATION: (70)...(303)
<220> FEATURE:
<221> NAME/KEY: mat_peptide
<222> LOCATION: (163)...(303)

<400> SEQUENCE: 358
accctatatc tctatagcca acacacacac aaatactctc cattccattc catctcaaag   60

```
gatagaata atg ggc ggt ctc tcc acc aag ctt ttc gtg gtc ctc ctc ctg      111
        Met Gly Gly Leu Ser Thr Lys Leu Phe Val Val Leu Leu Leu
         1               5                  10 ctc gtt tgt tac acc ggg acg caa ggc ggg ccg gtg act atg gtg tcg        159
Leu Val Cys Tyr Thr Gly Thr Gln Gly Gly Pro Val Thr Met Val Ser
 15              20                  25                  30 gcg agg aag tgc gag tcg cag agc ttc cgc ttc aag gga cct tgc tcg        207
Ala Arg Lys Cys Glu Ser Gln Ser Phe Arg Phe Lys Gly Pro Cys Ser
                 35                  40                  45 agg gac gcc aac tgc gca aac gtc tgc ctg acc gaa ggt ttc acc ggc        255
Arg Asp Ala Asn Cys Ala Asn Val Cys Leu Thr Glu Gly Phe Thr Gly
             50                  55                  60 ggc gtg tgc aag ggc cta cgc cac cgc tgc ttc tgc acc agg gac tgc        303
Gly Val Cys Lys Gly Leu Arg His Arg Cys Phe Cys Thr Arg Asp Cys
         65                  70                  75 tag tactgcctcg tctcgcctcg cctcggctcg tgtcctgcgt gtgcatagcc             356
gcagcggatc agtaaaacat gcatgcatgc gttaccgaat atttggcagt accagcaagt      416
taatggatta ataatatgt aatggaacaa agcctgtttt gaacgtggaa ctgctgagtg       476
ctagcagcgc tcgtgtttat tggcttaaaa aaaaaaaaaa aaaaaaaaaa aaaaaaaaaa      536
aaaaaaaaaa aaaaa                                                       551

<210> SEQ ID NO 359
<211> LENGTH: 78
<212> TYPE: PRT
<213> ORGANISM: Zea mays

<400> SEQUENCE: 359

Met Gly Gly Leu Ser Thr Lys Leu Phe Val Val Leu Leu Leu Val
 1               5                  10                  15

Cys Tyr Thr Gly Thr Gln Gly Gly Pro Val Thr Met Val Ser Ala Arg
             20                  25                  30

Lys Cys Glu Ser Gln Ser Phe Arg Phe Lys Gly Pro Cys Ser Arg Asp
         35                  40                  45

Ala Asn Cys Ala Asn Val Cys Leu Thr Glu Gly Phe Thr Gly Val
 50                  55                  60

Cys Lys Gly Leu Arg His Arg Cys Phe Cys Thr Arg Asp Cys
65                   70                  75

<210> SEQ ID NO 360
<211> LENGTH: 47
<212> TYPE: PRT
<213> ORGANISM: Zea mays

<400> SEQUENCE: 360

Arg Lys Cys Glu Ser Gln Ser Phe Arg Phe Lys Gly Pro Cys Ser Arg
 1               5                  10                  15

Asp Ala Asn Cys Ala Asn Val Cys Leu Thr Glu Gly Phe Thr Gly Gly
             20                  25                  30

Val Cys Lys Gly Leu Arg His Arg Cys Phe Cys Thr Arg Asp Cys
         35                  40                  45

<210> SEQ ID NO 361
<211> LENGTH: 311
<212> TYPE: DNA
<213> ORGANISM: Vernonia mespilifolia
<220> FEATURE:
<221> NAME/KEY: CDS
<222> LOCATION: (2)...(145)
<220> FEATURE:
```

-continued

```
<221> NAME/KEY: mat_peptide
<222> LOCATION: (2)...(142)
<220> FEATURE:
<221> NAME/KEY: misc_feature
<222> LOCATION: 281, 289, 296
<223> OTHER INFORMATION: n = A,T,C or G

<400> SEQUENCE: 361 c gaa tgt gcc agt ctc aag agc cat ttg tac cat gga gct tgt ttc cat     49
  Glu Cys Ala Ser Leu Lys Ser His Leu Tyr His Gly Ala Cys Phe His
   1               5                  10                  15 gac cat aac tgc gct ctc gtc tgc cgc aac gag ggt ttc tcc ggc gga       97
Asp His Asn Cys Ala Leu Val Cys Arg Asn Glu Gly Phe Ser Gly Gly
             20                  25                  30 agg tgc aga ggc ttc cgc cgc cgc tgt ttc tgc acc agg att tgc tag      145
Arg Cys Arg Gly Phe Arg Arg Arg Cys Phe Cys Thr Arg Ile Cys *
             35                  40                  45 tccccggccc gcccataact gcaatattct tgctacctag cttctatctt aatttagctt    205
tatctgttat gtaattccgt ttccatctat tgatctccaa gcaccgatcg attgatctta    265
attaaaaaaa aaaanaaaa  aaanaaaaaa naaaaaaaaa aaaaaa                   311

<210> SEQ ID NO 362
<211> LENGTH: 47
<212> TYPE: PRT
<213> ORGANISM: Vernonia mespilifolia

<400> SEQUENCE: 362

Glu Cys Ala Ser Leu Lys Ser His Leu Tyr His Gly Ala Cys Phe His
 1               5                  10                  15

Asp His Asn Cys Ala Leu Val Cys Arg Asn Glu Gly Phe Ser Gly Gly
             20                  25                  30

Arg Cys Arg Gly Phe Arg Arg Arg Cys Phe Cys Thr Arg Ile Cys
             35                  40                  45

<210> SEQ ID NO 363
<211> LENGTH: 47
<212> TYPE: PRT
<213> ORGANISM: Vernonia mespilifolia

<400> SEQUENCE: 363

Glu Cys Ala Ser Leu Lys Ser His Leu Tyr His Gly Ala Cys Phe His
 1               5                  10                  15

Asp His Asn Cys Ala Leu Val Cys Arg Asn Glu Gly Phe Ser Gly Gly
             20                  25                  30

Arg Cys Arg Gly Phe Arg Arg Arg Cys Phe Cys Thr Arg Ile Cys
             35                  40                  45

<210> SEQ ID NO 364
<211> LENGTH: 493
<212> TYPE: DNA
<213> ORGANISM: Picramnia pentandra
<220> FEATURE:
<221> NAME/KEY: CDS
<222> LOCATION: (25)...(249)
<220> FEATURE:
<221> NAME/KEY: mat_peptide
<222> LOCATION: (106)...(246)
<220> FEATURE:
<221> NAME/KEY: misc_feature
<222> LOCATION: 254, 271, 321, 370, 377, 408, 419, 424, 437, 439, 463,
      480
<223> OTHER INFORMATION: n = A,T,C or G

<400> SEQUENCE: 364
```

```
cagtcttttg agttgagata agtc atg gag agg aaa gcc ttt gga ctc ata        51
                         Met Glu Arg Lys Ala Phe Gly Leu Ile
                          1               5 ttt cta atc ctc act gtt ttg gct tct caa aac atg ttg ctg cct act        99
Phe Leu Ile Leu Thr Val Leu Ala Ser Gln Asn Met Leu Leu Pro Thr
 10              15                  20                  25 gag gca aga ata tgc tca tcg ctg agc cac ggg tac aaa ggg ccg tgc       147
Glu Ala Arg Ile Cys Ser Ser Leu Ser His Gly Tyr Lys Gly Pro Cys
                 30                  35                  40 gca agc gac cac aac tgt gct ttg gtg tgc agg aat gag ggc ttc tct       195
Ala Ser Asp His Asn Cys Ala Leu Val Cys Arg Asn Glu Gly Phe Ser
                 45                  50                  55 ggt gga gac tgc cat ggg ctc cgt cgc cgc tgc ttt tgc act aag gct       243
Gly Gly Asp Cys His Gly Leu Arg Arg Arg Cys Phe Cys Thr Lys Ala
 60                  65                  70 tgt tga ttggncagtg acatgacaca anccacatag caaaaccatg catatctatg        299
Cys  * ctatatgaat agtgtgtgtg gncctcttat taattaatgg cctttttgtag catttcagac    359 gttttttagcc ntgaatanag aaagaacatt gacttcttct tgtggtggnt gctgctcaan    419
aaaanaaaaa aaaactcnan ggggccggt accaattcgc ctanatgatc tataaatcac      479
nggcctcgtt taaa                                                       493

<210> SEQ ID NO 365
<211> LENGTH: 74
<212> TYPE: PRT
<213> ORGANISM: Picramnia pentandra

<400> SEQUENCE: 365

Met Glu Arg Lys Ala Phe Gly Leu Ile Phe Leu Ile Leu Thr Val Leu
 1               5                  10                  15

Ala Ser Gln Asn Met Leu Leu Pro Thr Glu Ala Arg Ile Cys Ser Ser
                20                  25                  30

Leu Ser His Gly Tyr Lys Gly Pro Cys Ala Ser Asp His Asn Cys Ala
             35                  40                  45

Leu Val Cys Arg Asn Glu Gly Phe Ser Gly Gly Asp Cys His Gly Leu
         50                  55                  60

Arg Arg Arg Cys Phe Cys Thr Lys Ala Cys
 65                  70

<210> SEQ ID NO 366
<211> LENGTH: 47
<212> TYPE: PRT
<213> ORGANISM: Picramnia pentandra

<400> SEQUENCE: 366

Arg Ile Cys Ser Ser Leu Ser His Gly Tyr Lys Gly Pro Cys Ala Ser
 1               5                  10                  15

Asp His Asn Cys Ala Leu Val Cys Arg Asn Glu Gly Phe Ser Gly Gly
                20                  25                  30

Asp Cys His Gly Leu Arg Arg Arg Cys Phe Cys Thr Lys Ala Cys
             35                  40                  45

<210> SEQ ID NO 367
<211> LENGTH: 345
<212> TYPE: DNA
<213> ORGANISM: Vernonia mespilifolia
<220> FEATURE:
<221> NAME/KEY: CDS
```

<222> LOCATION: (39)...(263)
<220> FEATURE:
<221> NAME/KEY: mat_peptide
<222> LOCATION: (132)...(260)

<400> SEQUENCE: 367

```
gaaaaacagc cagctgatcg atcagtatta attaatta atg gcg tct tct tca tcc         56
                                          Met Ala Ser Ser Ser Ser
                                          1               5 tcc tcc tct tat tgg tta att cct tct cct tat gaa gaa gaa aaa ggg          104
Ser Ser Ser Tyr Trp Leu Ile Pro Ser Pro Tyr Glu Glu Glu Lys Gly
            10                  15                  20 ata ggg atg atg atg gtg gca aag gcg aga aca tgc gag tcg cag agc         152
Ile Gly Met Met Met Val Ala Lys Ala Arg Thr Cys Glu Ser Gln Ser
        25                  30                  35 cat gga ttc aaa ggg agg tgc atg agc aac aac aac tgt ggt acg tct         200
His Gly Phe Lys Gly Arg Cys Met Ser Asn Asn Asn Cys Gly Thr Ser
    40                  45                  50 cgt ttg cag aaa cga agg gaa ttt gtc gta cgt gga aga tgt ttt tgc         248
Arg Leu Gln Lys Arg Arg Glu Phe Val Val Arg Gly Arg Cys Phe Cys
55                  60                  65                  70 acc aaa tct tgt taa ttacttactc actagcttct ttctactcca tccatcttcg         303
Thr Lys Ser Cys  * atctatatat cgatcaggaa tgaaatgaag gaagctaaaa ta                           345
```

<210> SEQ ID NO 368
<211> LENGTH: 74
<212> TYPE: PRT
<213> ORGANISM: Vernonia mespilifolia

<400> SEQUENCE: 368

```
Met Ala Ser Ser Ser Ser Ser Ser Tyr Trp Leu Ile Pro Ser Pro
1               5                   10                  15

Tyr Glu Glu Glu Lys Gly Ile Gly Met Met Met Val Ala Lys Ala Arg
            20                  25                  30

Thr Cys Glu Ser Gln Ser His Gly Phe Lys Gly Arg Cys Met Ser Asn
        35                  40                  45

Asn Asn Cys Gly Thr Ser Arg Leu Gln Lys Arg Arg Glu Phe Val Val
    50                  55                  60

Arg Gly Arg Cys Phe Cys Thr Lys Ser Cys
65                  70
```

<210> SEQ ID NO 369
<211> LENGTH: 43
<212> TYPE: PRT
<213> ORGANISM: Vernonia mespilifolia

<400> SEQUENCE: 369

```
Arg Thr Cys Glu Ser Gln Ser His Gly Phe Lys Gly Arg Cys Met Ser
1               5                   10                  15

Asn Asn Asn Cys Gly Thr Ser Arg Leu Gln Lys Arg Arg Glu Phe Val
            20                  25                  30

Val Arg Gly Arg Cys Phe Cys Thr Lys Ser Cys
        35                  40
```

<210> SEQ ID NO 370
<211> LENGTH: 369
<212> TYPE: DNA
<213> ORGANISM: Vernonia mespilifolia
<220> FEATURE:
<221> NAME/KEY: CDS -continued

```
<222> LOCATION: (1)...(234)
<220> FEATURE:
<221> NAME/KEY: mat_peptide
<222> LOCATION: (91)...(231)

<400> SEQUENCE: 370 gtc ttc ttc atc ctc ctc ctc tta ttg gtt cct act ccg tat gaa gaa      48
Val Phe Phe Ile Leu Leu Leu Leu Val Pro Thr Pro Tyr Glu Glu
 1               5                  10                  15 gaa aaa ggg ata ggg atg ggg atg atg atg gtg gca aag gcg aga acg      96
Glu Lys Gly Ile Gly Met Gly Met Met Met Val Ala Lys Ala Arg Thr
             20                  25                  30 tgc gag tcg cag agc cat gga ttc aag ggg agg tgc atg agc aac aac     144
Cys Glu Ser Gln Ser His Gly Phe Lys Gly Arg Cys Met Ser Asn Asn
         35                  40                  45 aat tgt ggt ctc gtt tgc aga aac gaa ggg ttt gcc ggt gga att tgt     192
Asn Cys Gly Leu Val Cys Arg Asn Glu Gly Phe Ala Gly Gly Ile Cys
     50                  55                  60 cgt ggt gca cgt gga aga tgt ttt tgc acc aaa tct tgt taa             234
Arg Gly Ala Arg Gly Arg Cys Phe Cys Thr Lys Ser Cys  *
 65                  70                  75 ttactcactt caattctact ccatcttcta tcgatcggga atgaatgaaa tgatgaagga   294
agctagctaa aataaattta tccaatgcat atatattaat taatgcattt aatttctaaa  354
aaaaaaaaaa aaaaa                                                   369

<210> SEQ ID NO 371
<211> LENGTH: 77
<212> TYPE: PRT
<213> ORGANISM: Vernonia mespilifolia

<400> SEQUENCE: 371

Val Phe Phe Ile Leu Leu Leu Leu Val Pro Thr Pro Tyr Glu Glu
 1               5                  10                  15

Glu Lys Gly Ile Gly Met Gly Met Met Met Val Ala Lys Ala Arg Thr
             20                  25                  30

Cys Glu Ser Gln Ser His Gly Phe Lys Gly Arg Cys Met Ser Asn Asn
         35                  40                  45

Asn Cys Gly Leu Val Cys Arg Asn Glu Gly Phe Ala Gly Gly Ile Cys
     50                  55                  60

Arg Gly Ala Arg Gly Arg Cys Phe Cys Thr Lys Ser Cys
 65                  70                  75

<210> SEQ ID NO 372
<211> LENGTH: 47
<212> TYPE: PRT
<213> ORGANISM: Vernonia mespilifolia

<400> SEQUENCE: 372

Arg Thr Cys Glu Ser Gln Ser His Gly Phe Lys Gly Arg Cys Met Ser
 1               5                  10                  15

Asn Asn Asn Cys Gly Leu Val Cys Arg Asn Glu Gly Phe Ala Gly Gly
             20                  25                  30

Ile Cys Arg Gly Ala Arg Gly Arg Cys Phe Cys Thr Lys Ser Cys
         35                  40                  45

<210> SEQ ID NO 373
<211> LENGTH: 520
<212> TYPE: DNA
<213> ORGANISM: Oryza sativa
<220> FEATURE:
```

```
<221> NAME/KEY: CDS
<222> LOCATION: (3)...(467)
<220> FEATURE:
<221> NAME/KEY: mat_peptide
<222> LOCATION: (213)...(359)

<400> SEQUENCE: 373 gc caa cat gta tgt aga cca ccg gga aaa ggt cac tgc tcg gta tca         47
   Gln His Val Cys Arg Pro Pro Gly Lys Gly His Cys Ser Val Ser
   1               5                  10                  15 gct tat ctg tcc atc gaa gag aga ggt cat gat ttt cgg aag cct aaa        95
Ala Tyr Leu Ser Ile Glu Glu Arg Gly His Asp Phe Arg Lys Pro Lys
                20                  25                  30 gca ggc tgg cac act cct acc caa agc tcc aaa agg gtg ggg ttg gcg       143
Ala Gly Trp His Thr Pro Thr Gln Ser Ser Lys Arg Val Gly Leu Ala
            35                  40                  45 cac tgc cat att gtt cga cga act tgg cga tct tct cca ggg tgg atc       191
His Cys His Ile Val Arg Arg Thr Trp Arg Ser Ser Pro Gly Trp Ile
        50                  55                  60 cct gag aat tgc tgc agt agt cca gct tgt cta agc caa att gcc ctt       239
Pro Glu Asn Cys Cys Ser Ser Pro Ala Cys Leu Ser Gln Ile Ala Leu
    65                  70                  75 gta tat cgc ggg aag tgc agg ggc aac aga aac tgc gcc atg atc tgc       287
Val Tyr Arg Gly Lys Cys Arg Gly Asn Arg Asn Cys Ala Met Ile Cys
80                  85                  90                  95 gtc cac gag gag tac acc ggc ggc tac tgc tcc aag ggc gtc ttc tcc       335
Val His Glu Glu Tyr Thr Gly Gly Tyr Cys Ser Lys Gly Val Phe Ser
                100                 105                 110 aag tgc atg tgc acc aag cgg tgt ggc ggc ggc ggc ggt ggc ggc gga       383
Lys Cys Met Cys Thr Lys Arg Cys Gly Gly Gly Gly Gly Gly Gly Gly
            115                 120                 125 gga gga gga ggc ggc ggc ggc gat gag ccg ccg ttg cgt gag gcc cgt       431
Gly Gly Gly Gly Gly Gly Gly Asp Glu Pro Pro Leu Arg Glu Ala Arg
        130                 135                 140 gtc cac cgc tcg tcg ccg ccg ttg gag ccc aag tga ttgtttggtt            477
Val His Arg Ser Ser Pro Pro Leu Glu Pro Lys  *
    145                 150 tgagatagag aaaaggaaaa aagaaaaggc tatgccctcg tgc                       520

<210> SEQ ID NO 374
<211> LENGTH: 154
<212> TYPE: PRT
<213> ORGANISM: Oryza sativa

<400> SEQUENCE: 374

Gln His Val Cys Arg Pro Pro Gly Lys Gly His Cys Ser Val Ser Ala
1               5                   10                  15

Tyr Leu Ser Ile Glu Glu Arg Gly His Asp Phe Arg Lys Pro Lys Ala
                20                  25                  30

Gly Trp His Thr Pro Thr Gln Ser Ser Lys Arg Val Gly Leu Ala His
            35                  40                  45

Cys His Ile Val Arg Arg Thr Trp Arg Ser Ser Pro Gly Trp Ile Pro
        50                  55                  60

Glu Asn Cys Cys Ser Ser Pro Ala Cys Leu Ser Gln Ile Ala Leu Val
65                  70                  75                  80

Tyr Arg Gly Lys Cys Arg Gly Asn Arg Asn Cys Ala Met Ile Cys Val
                85                  90                  95

His Glu Glu Tyr Thr Gly Gly Tyr Cys Ser Lys Gly Val Phe Ser Lys
            100                 105                 110
```

```
Cys Met Cys Thr Lys Arg Cys Gly Gly Gly Gly Gly Gly Gly
        115                 120                 125

Gly Gly Gly Gly Gly Asp Glu Pro Pro Leu Arg Glu Ala Arg Val
    130                 135                 140

His Arg Ser Ser Pro Pro Leu Glu Pro Lys
145                 150

<210> SEQ ID NO 375
<211> LENGTH: 49
<212> TYPE: PRT
<213> ORGANISM: Oryza sativa

<400> SEQUENCE: 375

Pro Ala Cys Leu Ser Gln Ile Ala Leu Val Tyr Arg Gly Lys Cys Arg
1               5                   10                  15

Gly Asn Arg Asn Cys Ala Met Ile Cys Val His Glu Glu Tyr Thr Gly
                20                  25                  30

Gly Tyr Cys Ser Lys Gly Val Phe Ser Lys Cys Met Cys Thr Lys Arg
            35                  40                  45

Cys

<210> SEQ ID NO 376
<211> LENGTH: 458
<212> TYPE: DNA
<213> ORGANISM: Parthenium argentatum
<220> FEATURE:
<221> NAME/KEY: CDS
<222> LOCATION: (7)...(240)
<220> FEATURE:
<221> NAME/KEY: mat_peptide
<222> LOCATION: (100)...(240)
<220> FEATURE:
<221> NAME/KEY: misc_feature
<222> LOCATION: 452
<223> OTHER INFORMATION: n = A,T,C or G

<400> SEQUENCE: 376 gtgaac atg aag tct tcc atg aag ctg ttt gca aca ttg ttg ctt gtt      48
       Met Lys Ser Ser Met Lys Leu Phe Ala Thr Leu Leu Leu Val
        1               5                   10 gtc atg tgt cta atg gcc aat gaa atg ggt ggt ccg atc gtg gtg gaa    96
Val Met Cys Leu Met Ala Asn Glu Met Gly Gly Pro Ile Val Val Glu
 15                  20                  25                  30 gcg aga aca tgt ctg tcg caa agc cgc aag ttc aag ggg gcg tgc ttg   144
Ala Arg Thr Cys Leu Ser Gln Ser Arg Lys Phe Lys Gly Ala Cys Leu
                 35                  40                  45 agc gac acc aac tgt ggt aac gtg tgc aaa tct gaa ggg ttt cct aga   192
Ser Asp Thr Asn Cys Gly Asn Val Cys Lys Ser Glu Gly Phe Pro Arg
             50                  55                  60 gga gat tgt cgt ggt ttt cga cgc cgg tgc ttt tgc gtc aaa cac tgt   240
Gly Asp Cys Arg Gly Phe Arg Arg Arg Cys Phe Cys Val Lys His Cys
         65                  70                  75 tag atcgatccgt cgatcgatct acaggctaca ttaactactt catggccaag         293
actagcgtca cgtgaatcct ttgagagtcc ggtttgagtt acatatgttt attttacggt  353
gtgttacata agcactttct tttcgtttac tatcctccaa gtttggatat ttctacgtgt  413
aataaaaagt gggaaagtta taagtcata acttataanc ataaa                   458

<210> SEQ ID NO 377
<211> LENGTH: 78
<212> TYPE: PRT
<213> ORGANISM: Parthenium argentatum
```

<400> SEQUENCE: 377

Met Lys Ser Ser Met Lys Leu Phe Ala Thr Leu Leu Leu Val Val Met
1               5                   10                  15

Cys Leu Met Ala Asn Glu Met Gly Gly Pro Ile Val Val Glu Ala Arg
            20                  25                  30

Thr Cys Leu Ser Gln Ser Arg Lys Phe Lys Gly Ala Cys Leu Ser Asp
        35                  40                  45

Thr Asn Cys Gly Asn Val Cys Lys Ser Glu Gly Phe Pro Arg Gly Asp
    50                  55                  60

Cys Arg Gly Phe Arg Arg Cys Phe Cys Val Lys His Cys
65                  70                  75

<210> SEQ ID NO 378
<211> LENGTH: 47
<212> TYPE: PRT
<213> ORGANISM: Parthenium argentatum

<400> SEQUENCE: 378

Arg Thr Cys Leu Ser Gln Ser Arg Lys Phe Lys Gly Ala Cys Leu Ser
1               5                   10                  15

Asp Thr Asn Cys Gly Asn Val Cys Lys Ser Glu Gly Phe Pro Arg Gly
            20                  25                  30

Asp Cys Arg Gly Phe Arg Arg Cys Phe Cys Val Lys His Cys
        35                  40                  45

<210> SEQ ID NO 379
<211> LENGTH: 464
<212> TYPE: DNA
<213> ORGANISM: Cyamopsis tetragonoloba
<220> FEATURE:
<221> NAME/KEY: CDS
<222> LOCATION: (32)...(256)
<220> FEATURE:
<221> NAME/KEY: mat_peptide
<222> LOCATION: (116)...(253)
<220> FEATURE:
<221> NAME/KEY: misc_feature
<222> LOCATION: 1, 2
<223> OTHER INFORMATION: n = A,T,C or G

<400> SEQUENCE: 379
nnaagaatta attaagtgaa tttaagcaat t atg gag aag aaa tca gtc gct         52
                                  Met Glu Lys Lys Ser Val Ala
                                  1               5 ggt ttt tgc tgc ctc ctc ctt gtc ctc ttt gtt gct cag gaa ata gtg       100
Gly Phe Cys Cys Leu Leu Leu Val Leu Phe Val Ala Gln Glu Ile Val
        10                  15                  20 gtg aaa aca gag gca aga aca tgt gag agt ccg gca gac aca tac agg       148
Val Lys Thr Glu Ala Arg Thr Cys Glu Ser Pro Ala Asp Thr Tyr Arg
    25                  30                  35 gga ccc tgt ttc act gag ggt agc tgc gat gat cat tgc aag aac aaa       196
Gly Pro Cys Phe Thr Glu Gly Ser Cys Asp Asp His Cys Lys Asn Lys
40                  45                  50                  55 gaa cac tta atc agt gga aca tgc aaa cag tta gcc tgc tgg tgc acc       244
Glu His Leu Ile Ser Gly Thr Cys Lys Gln Leu Ala Cys Trp Cys Thr
            60                  65                  70 aga aac tgt taa ttaattacta atattattgg atgcagtaca gtgccttaat           296
Arg Asn Cys * taattattac tatcaataaa taaattactg tatacaaata acagcactta aactgcttct     356
taattatgta tcggtgccac tatacatact catatatatg tactgcgtac ataacacctc     416

```
tgttatgtac tttatgttaa acaaataaac gatcttgtta ttgcttgc                    464
```

```
<210> SEQ ID NO 380
<211> LENGTH: 74
<212> TYPE: PRT
<213> ORGANISM: Cyamopsis tetragonoloba

<400> SEQUENCE: 380

Met Glu Lys Lys Ser Val Ala Gly Phe Cys Cys Leu Leu Leu Val Leu
1               5                   10                  15

Phe Val Ala Gln Glu Ile Val Val Lys Thr Glu Ala Arg Thr Cys Glu
            20                  25                  30

Ser Pro Ala Asp Thr Tyr Arg Gly Pro Cys Phe Thr Glu Gly Ser Cys
        35                  40                  45

Asp Asp His Cys Lys Asn Lys Glu His Leu Ile Ser Gly Thr Cys Lys
    50                  55                  60

Gln Leu Ala Cys Trp Cys Thr Arg Asn Cys
65                  70

<210> SEQ ID NO 381
<211> LENGTH: 46
<212> TYPE: PRT
<213> ORGANISM: Cyamopsis tetragonoloba

<400> SEQUENCE: 381

Arg Thr Cys Glu Ser Pro Ala Asp Thr Tyr Arg Gly Pro Cys Phe Thr
1               5                   10                  15

Glu Gly Ser Cys Asp Asp His Cys Lys Asn Lys Glu His Leu Ile Ser
            20                  25                  30

Gly Thr Cys Lys Gln Leu Ala Cys Trp Cys Thr Arg Asn Cys
        35                  40                  45

<210> SEQ ID NO 382
<211> LENGTH: 538
<212> TYPE: DNA
<213> ORGANISM: Triticum aestivum
<220> FEATURE:
<221> NAME/KEY: CDS
<222> LOCATION: (89)...(334)
<220> FEATURE:
<221> NAME/KEY: mat_peptide
<222> LOCATION: (188)...(331)

<400> SEQUENCE: 382
gcacgaggat cagaagccat agcttgtttc acctaaagag agaaaaaaag gctttgctcc      60
atcaacctac ctaccccac agaagcaa atg gag ttc aag ccc aag gcg acc         112
                              Met Glu Phe Lys Pro Lys Ala Thr
                              1               5 gtg tgc gcg atg atg ctg gtg ctg ctc ctg ctt tcc tcc tac agc ggc        160
Val Cys Ala Met Met Leu Val Leu Leu Leu Ser Ser Tyr Ser Gly
    10                  15                  20 ggc ggt ggc atc ggc gtg gcg gag gcg cgc att tgc acg ggg aag agc        208
Gly Gly Gly Ile Gly Val Ala Glu Ala Arg Ile Cys Thr Gly Lys Ser
25                  30                  35                  40 cag cac cac tcg ttc ccg tgc gtc tcg gac aag agc tgc acc aag acg        256
Gln His His Ser Phe Pro Cys Val Ser Asp Lys Ser Cys Thr Lys Thr
                45                  50                  55 tgc ctc agc gag cac ggc gca aaa tgg acg gcc ggc tac tgc aaa atc        304
Cys Leu Ser Glu His Gly Ala Lys Trp Thr Ala Gly Tyr Cys Lys Ile
            60                  65                  70
```

```
agg cgc tgc acc tgc cag agg gag tgc tag ggcagacgct ccgcgcgcga    354
Arg Arg Cys Thr Cys Gln Arg Glu Cys *
        75                  80 gctcccccac cccgccccg tccatggcgc cgtctgtcaa acgaagccac ctatgtatct    414
taagtcttaa ctaccatgta cccactcgcc gcctctgtca ggagatgtaa taaaacgtgg    474
cgcggcgacc cgccggcgcg tcaccgctgt acgtagcatg atgcatgcca cgcgttgctt    534
ttgt                                                                538

<210> SEQ ID NO 383
<211> LENGTH: 81
<212> TYPE: PRT
<213> ORGANISM: Triticum aestivum

<400> SEQUENCE: 383

Met Glu Phe Lys Pro Lys Ala Thr Val Cys Ala Met Met Leu Val Leu
1               5                   10                  15

Leu Leu Ser Ser Tyr Ser Gly Gly Gly Ile Gly Val Ala Glu
            20                  25                  30

Ala Arg Ile Cys Thr Gly Lys Ser Gln His His Ser Phe Pro Cys Val
        35                  40                  45

Ser Asp Lys Ser Cys Thr Lys Thr Cys Leu Ser Glu His Gly Ala Lys
    50                  55                  60

Trp Thr Ala Gly Tyr Cys Lys Ile Arg Arg Cys Thr Cys Gln Arg Glu
65                  70                  75                  80

Cys

<210> SEQ ID NO 384
<211> LENGTH: 48
<212> TYPE: PRT
<213> ORGANISM: Triticum aestivum

<400> SEQUENCE: 384

Arg Ile Cys Thr Gly Lys Ser Gln His His Ser Phe Pro Cys Val Ser
1               5                   10                  15

Asp Lys Ser Cys Thr Lys Thr Cys Leu Ser Glu His Gly Ala Lys Trp
            20                  25                  30

Thr Ala Gly Tyr Cys Lys Ile Arg Arg Cys Thr Cys Gln Arg Glu Cys
        35                  40                  45

<210> SEQ ID NO 385
<211> LENGTH: 466
<212> TYPE: DNA
<213> ORGANISM: Glycine max
<220> FEATURE:
<221> NAME/KEY: CDS
<222> LOCATION: (33)...(287)
<220> FEATURE:
<221> NAME/KEY: mat_peptide
<222> LOCATION: (126)...(266)
<220> FEATURE:
<221> NAME/KEY: misc_feature
<222> LOCATION: 430
<223> OTHER INFORMATION: n = A,T,C or G

<400> SEQUENCE: 385
gcattctttc ctgaaacttt actctcacac ac atg gct cgc tca gtg cct ttg    53
                                   Met Ala Arg Ser Val Pro Leu
                                   1               5 gtt tca acc att ttt gtc ttg ctt ctt ctt ctg ata gcc acc gag atg    101
Val Ser Thr Ile Phe Val Leu Leu Leu Leu Leu Ile Ala Thr Glu Met
        10                  15                  20
```

-continued

```
ggg cca aca atg gtg gca gaa gca aga act tgt gag tct cag agc cat      149
Gly Pro Thr Met Val Ala Glu Ala Arg Thr Cys Glu Ser Gln Ser His
     25                  30                  35 cgt ttc aag ggg cca tgt tta agt gac acc aac tgt ggc tct gtt tgc      197
Arg Phe Lys Gly Pro Cys Leu Ser Asp Thr Asn Cys Gly Ser Val Cys
 40                  45                  50                  55 cga acc gaa ggt ttc tct gga gga cac tgc cgt ggc ttc agt cgc aga      245
Arg Thr Glu Gly Phe Ser Gly Gly His Cys Arg Gly Phe Ser Arg Arg
                 60                  65                  70 tgc ttc tgc acc aaa gaa tgt aat aaa aat aat aat aat taa              287
Cys Phe Cys Thr Lys Glu Cys Asn Lys Asn Asn Asn Asn *
             75                  80 gagtgctttg atagaagatg atagatccat caccttccta ctccgtgttt gagaataaag    347
ggttacccat tctactaagg gtttgtctct taatttaatt agttagatct tttatgatat    407
gagtgagtgt gaaggaatta ttnatctgtg tcctaaatta ataattggat aatttgttt     466
```

```
<210> SEQ ID NO 386
<211> LENGTH: 84
<212> TYPE: PRT
<213> ORGANISM: Glycine max

<400> SEQUENCE: 386
```

Met Ala Arg Ser Val Pro Leu Val Ser Thr Ile Phe Val Leu Leu Leu
 1               5                  10                  15

Leu Leu Ile Ala Thr Glu Met Gly Pro Thr Met Val Ala Glu Ala Arg
             20                  25                  30

Thr Cys Glu Ser Gln Ser His Arg Phe Lys Gly Pro Cys Leu Ser Asp
         35                  40                  45

Thr Asn Cys Gly Ser Val Cys Arg Thr Glu Gly Phe Ser Gly Gly His
     50                  55                  60

Cys Arg Gly Phe Ser Arg Arg Cys Phe Cys Thr Lys Glu Cys Asn Lys
 65                  70                  75                  80

Asn Asn Asn Asn

```
<210> SEQ ID NO 387
<211> LENGTH: 47
<212> TYPE: PRT
<213> ORGANISM: Glycine max

<400> SEQUENCE: 387
```

Arg Thr Cys Glu Ser Gln Ser His Arg Phe Lys Gly Pro Cys Leu Ser
 1               5                  10                  15

Asp Thr Asn Cys Gly Ser Val Cys Arg Thr Glu Gly Phe Ser Gly Gly
             20                  25                  30

His Cys Arg Gly Phe Ser Arg Arg Cys Phe Cys Thr Lys Glu Cys
         35                  40                  45

```
<210> SEQ ID NO 388
<211> LENGTH: 463
<212> TYPE: DNA
<213> ORGANISM: Licania michauxii
<220> FEATURE:
<221> NAME/KEY: CDS
<222> LOCATION: (57)...(281)
<220> FEATURE:
<221> NAME/KEY: mat_peptide
<222> LOCATION: (138)...(278)
<220> FEATURE:
<221> NAME/KEY: misc_feature
<222> LOCATION: 460
```

<223> OTHER INFORMATION: n = A,T,C or G

<400> SEQUENCE: 388

```
tcacaacttg ctgttattga ttttgcactg aaacaaatca attgcagcac agagat atg      59
                                                                 Met
                                                                  1 gag aag aag atc tcc ggg att ttc ttc ctg ctg ctc att gtt ctg gct      107
Glu Lys Lys Ile Ser Gly Ile Phe Phe Leu Leu Leu Ile Val Leu Ala
        5                  10                 15 agc cca gag gtg gtg atg ccc act gag gcc agg gtc tgt gag tcg caa      155
Ser Pro Glu Val Val Met Pro Thr Glu Ala Arg Val Cys Glu Ser Gln
     20                  25                 30 agc cac ggc ttc aag ggt atg tgc gtg cgt gac cac aac tgt gct atg      203
Ser His Gly Phe Lys Gly Met Cys Val Arg Asp His Asn Cys Ala Met
 35                  40                 45 gtg tgc agg gtt gaa ggc ttc tcc ggt ggc atc tgc cgt gga ttc cgg      251
Val Cys Arg Val Glu Gly Phe Ser Gly Gly Ile Cys Arg Gly Phe Arg
 50                  55                 60                  65 cgc cgt tgc ttc tgc act agg cgt tgt tag ttaaaaatta atgctgggcg        301
Arg Arg Cys Phe Cys Thr Arg Arg Cys *
                 70 atcataacca agatgacaac gcaaccatta aagaataaag ctttccaagg ggttttctta    361 aatgcactaa ttaatgaata agtggcgctc ctttcccct taaggaaag accccctttc     421 cttttggttg ctaaaaaaaa aaaaaaaaaa aaccccgang gg                       463
```

<210> SEQ ID NO 389
<211> LENGTH: 74
<212> TYPE: PRT
<213> ORGANISM: Licania michauxii

<400> SEQUENCE: 389

```
Met Glu Lys Lys Ile Ser Gly Ile Phe Phe Leu Leu Leu Ile Val Leu
 1               5                  10                 15

Ala Ser Pro Glu Val Val Met Pro Thr Glu Ala Arg Val Cys Glu Ser
             20                  25                 30

Gln Ser His Gly Phe Lys Gly Met Cys Val Arg Asp His Asn Cys Ala
         35                  40                 45

Met Val Cys Arg Val Glu Gly Phe Ser Gly Gly Ile Cys Arg Gly Phe
     50                  55                 60

Arg Arg Arg Cys Phe Cys Thr Arg Arg Cys
 65                  70
```

<210> SEQ ID NO 390
<211> LENGTH: 47
<212> TYPE: PRT
<213> ORGANISM: Licania michauxii

<400> SEQUENCE: 390

```
Arg Val Cys Glu Ser Gln Ser His Gly Phe Lys Gly Met Cys Val Arg
 1               5                  10                 15

Asp His Asn Cys Ala Met Val Cys Arg Val Glu Gly Phe Ser Gly Gly
             20                  25                 30

Ile Cys Arg Gly Phe Arg Arg Arg Cys Phe Cys Thr Arg Arg Cys
         35                  40                 45
```

<210> SEQ ID NO 391
<211> LENGTH: 475
<212> TYPE: DNA
<213> ORGANISM: Chyrsobalanus icaco

```
<220> FEATURE:
<221> NAME/KEY: CDS
<222> LOCATION: (40)...(261)
<220> FEATURE:
<221> NAME/KEY: mat_peptide
<222> LOCATION: (118)...(258)
<220> FEATURE:
<221> NAME/KEY: misc_feature
<222> LOCATION: 462
<223> OTHER INFORMATION: n = A,T,C or G

<400> SEQUENCE: 391 aattttgca ctgaaacaaa tcatttgcag cacagagat atg gag aag aag atc         54
                                          Met Glu Lys Lys Ile
                                            1               5 tcc ggt att ttc ttc ctg ctg ctc att gtc ctg gct agc cag gtg gtg     102
Ser Gly Ile Phe Phe Leu Leu Leu Ile Val Leu Ala Ser Gln Val Val
             10                  15                  20 aag cct act gag gcc agg gtc tgt gag tcg caa agc cac ggc ttc aag     150
Lys Pro Thr Glu Ala Arg Val Cys Glu Ser Gln Ser His Gly Phe Lys
             25                  30                  35 ggc atg tgc atg cgt gac cac aac tgt gct atg gtt tgt agg gtt gaa     198
Gly Met Cys Met Arg Asp His Asn Cys Ala Met Val Cys Arg Val Glu
         40                  45                  50 ggc ttc tcc ggt ggc atc tgc cgt ggc ttc cgg cgc cgt tgc ttt tgc     246
Gly Phe Ser Gly Gly Ile Cys Arg Gly Phe Arg Arg Arg Cys Phe Cys
     55                  60                  65 act agg cgt tgt tag ttaaaaattg atgctggcga tcataaccag atgacaacgc     301
Thr Arg Arg Cys *
 70 aaccattaag aataagcttt ctagggtttt gttaaatgca ctaatcatga ataagtggcg   361 ttcttcccct caggggagac gcctttcctt tgttgctctt tgatgtttct gtcgctgtat   421 tccagctttg gaacgcatgt tctcatcctg gttatgttgg naaaaaaaaa aaat          475

<210> SEQ ID NO 392
<211> LENGTH: 73
<212> TYPE: PRT
<213> ORGANISM: Chyrsobalanus icaco

<400> SEQUENCE: 392

Met Glu Lys Lys Ile Ser Gly Ile Phe Phe Leu Leu Leu Ile Val Leu
 1               5                  10                  15

Ala Ser Gln Val Val Lys Pro Thr Glu Ala Arg Val Cys Glu Ser Gln
             20                  25                  30

Ser His Gly Phe Lys Gly Met Cys Met Arg Asp His Asn Cys Ala Met
         35                  40                  45

Val Cys Arg Val Glu Gly Phe Ser Gly Gly Ile Cys Arg Gly Phe Arg
     50                  55                  60

Arg Arg Cys Phe Cys Thr Arg Arg Cys
 65                  70

<210> SEQ ID NO 393
<211> LENGTH: 47
<212> TYPE: PRT
<213> ORGANISM: Chyrsobalanus icaco

<400> SEQUENCE: 393

Arg Val Cys Glu Ser Gln Ser His Gly Phe Lys Gly Met Cys Met Arg
 1               5                  10                  15

Asp His Asn Cys Ala Met Val Cys Arg Val Glu Gly Phe Ser Gly Gly
             20                  25                  30
```

```
Ile Cys Arg Gly Phe Arg Arg Arg Cys Phe Cys Thr Arg Arg Cys
         35                  40                  45
```

<210> SEQ ID NO 394
<211> LENGTH: 486
<212> TYPE: DNA
<213> ORGANISM: Ricinus communis
<220> FEATURE:
<221> NAME/KEY: CDS
<222> LOCATION: (168)...(398)
<220> FEATURE:
<221> NAME/KEY: mat_peptide
<222> LOCATION: (255)...(395)
<220> FEATURE:
<221> NAME/KEY: misc_feature
<222> LOCATION: 69, 70
<223> OTHER INFORMATION: n = A,T,C or G

<400> SEQUENCE: 394

```
cgcagctgtt gctgtgagat tagaaaatga tgattacgta gtagccatgt atcatgactg      60
ttgcaaaann tataataagt ttatgtgggt cctctgttaa aaaaaaaaaa aaaaaaaaa     120 ctcgaaagag caacctagca aaagatttgt ggcagtgaga aaagtg atg gag aaa       176
                                                   Met Glu Lys
                                                     1 aga tct gct ggg ctt ttc ata ttg atg ctt att gtg ttg gtt ttg gct      224
Arg Ser Ala Gly Leu Phe Ile Leu Met Leu Ile Val Leu Val Leu Ala
      5                  10                  15 tct caa cac atg gtg ctg cct aca gag gca aga gtt tgc caa tcg cag      272
Ser Gln His Met Val Leu Pro Thr Glu Ala Arg Val Cys Gln Ser Gln
 20                  25                  30                  35 agc cat aaa ttc cat ggt gcg tgc tgg gga gat cac aat tgt gca acg      320
Ser His Lys Phe His Gly Ala Cys Trp Gly Asp His Asn Cys Ala Thr
              40                  45                  50 gtt tgc agg act gaa ggt ttt tcc ggt ggc agg tgt cgc gga ttt cgt      368
Val Cys Arg Thr Glu Gly Phe Ser Gly Gly Arg Cys Arg Gly Phe Arg
         55                  60                  65 cgc aaa tgc ttt tgt acc agg ggc tgt taa aacgctgctt cccattagac        418
Arg Lys Cys Phe Cys Thr Arg Gly Cys *
 70                  75 aacgttgcag gcttttcag gacatggaat atgatatatg cagttttaa ataaagcgtt     478 tttacatt                                                            486
```

<210> SEQ ID NO 395
<211> LENGTH: 76
<212> TYPE: PRT
<213> ORGANISM: Ricinus communis

<400> SEQUENCE: 395

```
Met Glu Lys Arg Ser Ala Gly Leu Phe Ile Leu Met Leu Ile Val Leu
  1               5                  10                  15

Val Leu Ala Ser Gln His Met Val Leu Pro Thr Glu Ala Arg Val Cys
             20                  25                  30

Gln Ser Gln Ser His Lys Phe His Gly Ala Cys Trp Gly Asp His Asn
         35                  40                  45

Cys Ala Thr Val Cys Arg Thr Glu Gly Phe Ser Gly Gly Arg Cys Arg
     50                  55                  60

Gly Phe Arg Arg Lys Cys Phe Cys Thr Arg Gly Cys
 65                  70                  75
```

<210> SEQ ID NO 396

```
<211> LENGTH: 47
<212> TYPE: PRT
<213> ORGANISM: Ricinus communis

<400> SEQUENCE: 396

Arg Val Cys Gln Ser Gln Ser His Lys Phe His Gly Ala Cys Trp Gly
1               5                   10                  15

Asp His Asn Cys Ala Thr Val Cys Arg Thr Glu Gly Phe Ser Gly Gly
            20                  25                  30

Arg Cys Arg Gly Phe Arg Arg Lys Cys Phe Cys Thr Arg Gly Cys
        35                  40                  45

<210> SEQ ID NO 397
<211> LENGTH: 396
<212> TYPE: DNA
<213> ORGANISM: Vernonia mespilifolia
<220> FEATURE:
<221> NAME/KEY: CDS
<222> LOCATION: (19)...(252)
<220> FEATURE:
<221> NAME/KEY: mat_peptide
<222> LOCATION: (109)...(249)
<220> FEATURE:
<221> NAME/KEY: misc_feature
<222> LOCATION: 383
<223> OTHER INFORMATION: n = A,T,C or G

<400> SEQUENCE: 397
attaatatta atattaat atg gcg ccg gcg gct acc aac acc ttt gct atc      51
                    Met Ala Pro Ala Ala Thr Asn Thr Phe Ala Ile
                    1               5                   10 ctt ttc acc ttt ctc ctc ctc ttc tct tct tct gag ttg gga gtg aca     99
Leu Phe Thr Phe Leu Leu Leu Phe Ser Ser Ser Glu Leu Gly Val Thr
            15                  20                  25 gta caa ggt cga atg tgc cag tcg cag agt cat aag tac cat gga gct    147
Val Gln Gly Arg Met Cys Gln Ser Gln Ser His Lys Tyr His Gly Ala
        30                  35                  40 tgt ttc cgt cac cat aac tgt gct ctt gtc tgc cgg aac gag ggt ttc    195
Cys Phe Arg His His Asn Cys Ala Leu Val Cys Arg Asn Glu Gly Phe
    45                  50                  55 tcc ggc ggc agg tgc agg ggc ttc cgt cgc cgt tgt ttc tgc acc agg    243
Ser Gly Gly Arg Cys Arg Gly Phe Arg Arg Arg Cys Phe Cys Thr Arg
60                  65                  70                  75 ctt tgc taa ttacacttac atccggccat catcatcatc atatcatcac            292
Leu Cys * tccatcatca acttcaacag acctgcatta atgcacgtac cttaattagc ttaatttcct  352
tttgtaatat atctgttata tctatgtatc ntaatttgtg ttaa                   396

<210> SEQ ID NO 398
<211> LENGTH: 77
<212> TYPE: PRT
<213> ORGANISM: Vernonia mespilifolia

<400> SEQUENCE: 398

Met Ala Pro Ala Ala Thr Asn Thr Phe Ala Ile Leu Phe Thr Phe Leu
1               5                   10                  15

Leu Leu Phe Ser Ser Ser Glu Leu Gly Val Thr Val Gln Gly Arg Met
            20                  25                  30

Cys Gln Ser Gln Ser His Lys Tyr His Gly Ala Cys Phe Arg His His
        35                  40                  45

Asn Cys Ala Leu Val Cys Arg Asn Glu Gly Phe Ser Gly Gly Arg Cys
    50                  55                  60
```

```
Arg Gly Phe Arg Arg Arg Cys Phe Cys Thr Arg Leu Cys
 65                  70                  75

<210> SEQ ID NO 399
<211> LENGTH: 47
<212> TYPE: PRT
<213> ORGANISM: Vernonia mespilifolia

<400> SEQUENCE: 399

Arg Met Cys Gln Ser Gln Ser His Lys Tyr His Gly Ala Cys Phe Arg
  1               5                  10                  15

His His Asn Cys Ala Leu Val Cys Arg Asn Glu Gly Phe Ser Gly Gly
                 20                  25                  30

Arg Cys Arg Gly Phe Arg Arg Arg Cys Phe Cys Thr Arg Leu Cys
             35                  40                  45

<210> SEQ ID NO 400
<211> LENGTH: 442
<212> TYPE: DNA
<213> ORGANISM: Vernonia mespilifolia
<220> FEATURE:
<221> NAME/KEY: CDS
<222> LOCATION: (19)...(243)
<220> FEATURE:
<221> NAME/KEY: mat_peptide
<222> LOCATION: (103)...(243)

<400> SEQUENCE: 400
attaatatta atattaat atg gct acc aac acc ttt gct atc ctt ttc acc      51
                    Met Ala Thr Asn Thr Phe Ala Ile Leu Phe Thr
                      1               5                  10 ttt ctc ctc ctc ttc tct tct tct tct gag ttg gga gtg aca gta caa     99
Phe Leu Leu Leu Phe Ser Ser Ser Ser Glu Leu Gly Val Thr Val Gln
             15                  20                  25 ggt cga atg tgc cag tcg cag agt cat aag tac cat gga gct tgt ttc    147
Gly Arg Met Cys Gln Ser Gln Ser His Lys Tyr His Gly Ala Cys Phe
         30                  35                  40 cgt cac cat aac tgt gct ctc gtc tgc cgc aac gag ggt ttc tcc ggc    195
Arg His His Asn Cys Ala Leu Val Cys Arg Asn Glu Gly Phe Ser Gly
     45                  50                  55 ggc agg tgc agg ggc ttc cgt cgc cgt tgt ttc tgc acc agg ctt tgc    243
Gly Arg Cys Arg Gly Phe Arg Arg Arg Cys Phe Cys Thr Arg Leu Cys
 60                  65                  70                  75 taa ttacacttac atccgatccg gccatcatca tcatatcata tcatcactcc         296
atccatcatc aacttcaaca gacctgcatt aatgcacctt aattagctta agttcctttt  356
gtaatatatc tgttatatct atgtatctta atttgtgtta gttacttcat gattccatgc  416
accccatcaa aaaaaaaaaa aaaaaa                                       442

<210> SEQ ID NO 401
<211> LENGTH: 75
<212> TYPE: PRT
<213> ORGANISM: Vernonia mespilifolia

<400> SEQUENCE: 401

Met Ala Thr Asn Thr Phe Ala Ile Leu Phe Thr Phe Leu Leu Leu Phe
  1               5                  10                  15

Ser Ser Ser Ser Glu Leu Gly Val Thr Val Gln Gly Arg Met Cys Gln
                 20                  25                  30

Ser Gln Ser His Lys Tyr His Gly Ala Cys Phe Arg His His Asn Cys
             35                  40                  45
```

```
Ala Leu Val Cys Arg Asn Glu Gly Phe Ser Gly Gly Arg Cys Arg Gly
    50                  55                  60

Phe Arg Arg Arg Cys Phe Cys Thr Arg Leu Cys
65                  70                  75

<210> SEQ ID NO 402
<211> LENGTH: 47
<212> TYPE: PRT
<213> ORGANISM: Vernonia mespilifolia

<400> SEQUENCE: 402

Arg Met Cys Gln Ser Gln Ser His Lys Tyr His Gly Ala Cys Phe Arg
1               5                   10                  15

His His Asn Cys Ala Leu Val Cys Arg Asn Glu Gly Phe Ser Gly Gly
            20                  25                  30

Arg Cys Arg Gly Phe Arg Arg Arg Cys Phe Cys Thr Arg Leu Cys
        35                  40                  45

<210> SEQ ID NO 403
<211> LENGTH: 573
<212> TYPE: DNA
<213> ORGANISM: Ricinus communis
<220> FEATURE:
<221> NAME/KEY: CDS
<222> LOCATION: (14)...(241)
<220> FEATURE:
<221> NAME/KEY: mat_peptide
<222> LOCATION: (98)...(241)
<220> FEATURE:
<221> NAME/KEY: misc_feature
<222> LOCATION: 518, 519, 520, 522, 523
<223> OTHER INFORMATION: n = A,T,C or G

<400> SEQUENCE: 403
gcacgaggga aac atg gag aaa cga tct ctt ggc ctt ttc cta ttg atg        49
            Met Glu Lys Arg Ser Leu Gly Leu Phe Leu Leu Met
            1               5                   10 ctt att gtg ttg tta ggt tct caa gat gtg gtg ttg cca act gag gca       97
Leu Ile Val Leu Leu Gly Ser Gln Asp Val Val Leu Pro Thr Glu Ala
        15                  20                  25 cgg gtc tgt gag tca aag agc cat cac ttc cat ggt cca tgt ttg aga      145
Arg Val Cys Glu Ser Lys Ser His His Phe His Gly Pro Cys Leu Arg
    30                  35                  40 gat cac aat tgt gca tta gtg tgt cgg act gaa ggt aat ttc tcc ggc      193
Asp His Asn Cys Ala Leu Val Cys Arg Thr Glu Gly Asn Phe Ser Gly
45                  50                  55                  60 gga agg tgc aga ggg ttc cga cgc cgc tgc ttt tgc acc agg cgt tgc      241
Gly Arg Cys Arg Gly Phe Arg Arg Arg Cys Phe Cys Thr Arg Arg Cys
                65                  70                  75 tga tgaaaggtct catgggagta agaatgctc catctatctt ccagggtatg            294
aagggagcag cagtttacga ataaagagtg tttcttttct ctccaaggga gaagaaacat    354
tattgctttc aatttattgc gttttatgga atgtctgttc tttctgtatt tgctttatc    414 agtaattaat ttagctccta atactctgat tatgttcgaa atgagcttta aatttcagat    474
atggtaaatt gacctaattt gtcgaatatg ttctgttaat tccnnnaannt taattgagc    534 ccttaaagtt gataatgttc aatcgagtcc cttaactcg                            573

<210> SEQ ID NO 404
<211> LENGTH: 76
<212> TYPE: PRT
<213> ORGANISM: Ricinus communis
```

-continued

<400> SEQUENCE: 404

Met Glu Lys Arg Ser Leu Gly Leu Phe Leu Leu Met Leu Ile Val Leu
1               5                   10                  15

Leu Gly Ser Gln Asp Val Val Leu Pro Thr Glu Ala Arg Val Cys Glu
            20                  25                  30

Ser Lys Ser His His Phe His Gly Pro Cys Leu Arg Asp His Asn Cys
        35                  40                  45

Ala Leu Val Cys Arg Thr Glu Gly Asn Phe Ser Gly Gly Arg Cys Arg
    50                  55                  60

Gly Phe Arg Arg Arg Cys Phe Cys Thr Arg Arg Cys
65                  70                  75

<210> SEQ ID NO 405
<211> LENGTH: 48
<212> TYPE: PRT
<213> ORGANISM: Ricinus communis

<400> SEQUENCE: 405

Arg Val Cys Glu Ser Lys Ser His His Phe His Gly Pro Cys Leu Arg
1               5                   10                  15

Asp His Asn Cys Ala Leu Val Cys Arg Thr Glu Gly Asn Phe Ser Gly
            20                  25                  30

Gly Arg Cys Arg Gly Phe Arg Arg Arg Cys Phe Cys Thr Arg Arg Cys
        35                  40                  45

<210> SEQ ID NO 406
<211> LENGTH: 448
<212> TYPE: DNA
<213> ORGANISM: Eucalyptus grandis
<220> FEATURE:
<221> NAME/KEY: CDS
<222> LOCATION: (68)...(301)
<220> FEATURE:
<221> NAME/KEY: mat_peptide
<222> LOCATION: (158)...(298)

<400> SEQUENCE: 406
actttcgtgc cgtgcccatt cctccatcca tccatctctc tctctctctc tctctctctc        60 tctcaca atg gat ttc tcg aag cga ttg att cca gct gct ctt att gtg         109
        Met Asp Phe Ser Lys Arg Leu Ile Pro Ala Ala Leu Ile Val
        1               5                   10 atg ctg ctg ctt gtg gca act gag atg gag ccg atg gtg gtg gag gcg         157
Met Leu Leu Leu Val Ala Thr Glu Met Glu Pro Met Val Val Glu Ala
15                  20                  25                  30 aga act tgc gag tcc caa agc cag cgt ttc aag ggg gca tgc gtg agt         205
Arg Thr Cys Glu Ser Gln Ser Gln Arg Phe Lys Gly Ala Cys Val Ser
                35                  40                  45 aag acc aac tgc gcc tct gtt tgc cag acg gag ggc ttc cac ggc ggg         253
Lys Thr Asn Cys Ala Ser Val Cys Gln Thr Glu Gly Phe His Gly Gly
            50                  55                  60 cac tgc cgg ggc ttt cgt cgc cgt tgc ttc tgc acc aag cat tgc tag         301
His Cys Arg Gly Phe Arg Arg Arg Cys Phe Cys Thr Lys His Cys *
        65                  70                  75 agagtggcct tcgcacgaag cttttgaatt acatcttatc gtatctcacc aatactttaa        361
aataatccgg tcttgcatcg gaatgtcgtt gtgtggtttt agatgtaatc ttcctttggc        421
tgtgtactgt atttaccaag ggtgctt                                             448

<210> SEQ ID NO 407

```
<211> LENGTH: 77
<212> TYPE: PRT
<213> ORGANISM: Eucalyptus grandis

<400> SEQUENCE: 407

Met Asp Phe Ser Lys Arg Leu Ile Pro Ala Ala Leu Ile Val Met Leu
1               5                   10                  15

Leu Leu Val Ala Thr Glu Met Glu Pro Met Val Val Glu Ala Arg Thr
            20                  25                  30

Cys Glu Ser Gln Ser Gln Arg Phe Lys Gly Ala Cys Val Ser Lys Thr
        35                  40                  45

Asn Cys Ala Ser Val Cys Gln Thr Glu Gly Phe His Gly Gly His Cys
    50                  55                  60

Arg Gly Phe Arg Arg Arg Cys Phe Cys Thr Lys His Cys
65                  70                  75

<210> SEQ ID NO 408
<211> LENGTH: 47
<212> TYPE: PRT
<213> ORGANISM: Eucalyptus grandis

<400> SEQUENCE: 408

Arg Thr Cys Glu Ser Gln Ser Gln Arg Phe Lys Gly Ala Cys Val Ser
1               5                   10                  15

Lys Thr Asn Cys Ala Ser Val Cys Gln Thr Glu Gly Phe His Gly Gly
            20                  25                  30

His Cys Arg Gly Phe Arg Arg Arg Cys Phe Cys Thr Lys His Cys
        35                  40                  45

<210> SEQ ID NO 409
<211> LENGTH: 504
<212> TYPE: DNA
<213> ORGANISM: Tropaeolum majus
<220> FEATURE:
<221> NAME/KEY: CDS
<222> LOCATION: (38)...(271)
<220> FEATURE:
<221> NAME/KEY: mat_peptide
<222> LOCATION: (128)...(268)

<400> SEQUENCE: 409
gcacgaggtc catatctctc tttcaagata tcaaata atg gag cgt tct aca cgt      55
                                        Met Glu Arg Ser Thr Arg
                                        1               5 ttg ttt tcg tcg ttc tta gtc atc ttt ttg ctt ctt gtg gtc acg gag      103
Leu Phe Ser Ser Phe Leu Val Ile Phe Leu Leu Leu Val Val Thr Glu
            10                  15                  20 atc gga ccg atg gtc gcg gag gca aga aca tgc gag tcg caa agc cat      151
Ile Gly Pro Met Val Ala Glu Ala Arg Thr Cys Glu Ser Gln Ser His
        25                  30                  35 cgt ttc aag gga cca tgt gtg agt aag acc aat tgt gca tcg gtt tgc      199
Arg Phe Lys Gly Pro Cys Val Ser Lys Thr Asn Cys Ala Ser Val Cys
    40                  45                  50 aaa acc gaa ggt ttt tat gga gga cat tgc cga ggt ttt cgt cat cga      247
Lys Thr Glu Gly Phe Tyr Gly Gly His Cys Arg Gly Phe Arg His Arg
55                  60                  65                  70 tgt ttc tgt acc aaa cat tgt taa agtcattcaa gaatttcccc taaacgatga    301
Cys Phe Cys Thr Lys His Cys *
                    75 tatgaatttc attgttcata tcattgcttt tatttaaagc ttgaaatttg agtcgatgaa    361 aaaaataatt tattagattt ttataatgtt tagttcttat ttgtgatcta tgttatgttt    421
```

```
tgagtaagtt gttattgtgg tttgactttg ggagtttgtt tttcgtattt gtcgtctttt    481
aaataaaaaa tatttataaa gat                                            504
```

```
<210> SEQ ID NO 410
<211> LENGTH: 77
<212> TYPE: PRT
<213> ORGANISM: Tropaeolum majus

<400> SEQUENCE: 410

Met Glu Arg Ser Thr Arg Leu Phe Ser Ser Phe Leu Val Ile Phe Leu
1               5                   10                  15

Leu Leu Val Val Thr Glu Ile Gly Pro Met Val Ala Glu Ala Arg Thr
            20                  25                  30

Cys Glu Ser Gln Ser His Arg Phe Lys Gly Pro Cys Val Ser Lys Thr
        35                  40                  45

Asn Cys Ala Ser Val Cys Lys Thr Glu Gly Phe Tyr Gly Gly His Cys
    50                  55                  60

Arg Gly Phe Arg His Arg Cys Phe Cys Thr Lys His Cys
65                  70                  75

<210> SEQ ID NO 411
<211> LENGTH: 47
<212> TYPE: PRT
<213> ORGANISM: Tropaeolum majus

<400> SEQUENCE: 411

Arg Thr Cys Glu Ser Gln Ser His Arg Phe Lys Gly Pro Cys Val Ser
1               5                   10                  15

Lys Thr Asn Cys Ala Ser Val Cys Lys Thr Glu Gly Phe Tyr Gly Gly
            20                  25                  30

His Cys Arg Gly Phe Arg His Arg Cys Phe Cys Thr Lys His Cys
        35                  40                  45

<210> SEQ ID NO 412
<211> LENGTH: 523
<212> TYPE: DNA
<213> ORGANISM: Cyamopsis tetragonoloba
<220> FEATURE:
<221> NAME/KEY: CDS
<222> LOCATION: (53)...(271)
<220> FEATURE:
<221> NAME/KEY: mat_peptide
<222> LOCATION: (128)...(268)
<220> FEATURE:
<221> NAME/KEY: misc_feature
<222> LOCATION: 497, 498, 499, 509, 510, 511, 512, 513, 514, 515, 516,
      517, 518, 519, 520, 521, 522, 523
<223> OTHER INFORMATION: n = A,T,C or G

<400> SEQUENCE: 412
gcacgaggca caagcttagc ttcttcttct tcttctttac tctctctgct tt atg ggt      58
                                                          Met Gly
                                                          1 cgc tct ttg ttc cct ttc gtt ttt gtt ttc ctt ctg gtt gtt gtc tcc     106
Arg Ser Leu Phe Pro Phe Val Phe Val Phe Leu Leu Val Val Val Ser
        5                   10                  15 act gaa atg gtg gca gaa gga agg tca tgt gag tca cag agc cat cgg     154
Thr Glu Met Val Ala Glu Gly Arg Ser Cys Glu Ser Gln Ser His Arg
            20                  25                  30 ttt aag ggg ccg tgc gtg agt gat acc aac tgt gct tct gtt tgt tac     202
Phe Lys Gly Pro Cys Val Ser Asp Thr Asn Cys Ala Ser Val Cys Tyr
        35                  40                  45                  50
```

```
acg gaa cgc ttc agc ggt gga cac tgc cgt ggc ttc cgt cgc aga tgc    250
Thr Glu Arg Phe Ser Gly Gly His Cys Arg Gly Phe Arg Arg Arg Cys
             55                  60                  65 ttt tgc acc aaa cat tgc taa ttcctaatta acatgtactt tctgcaaatg        301
Phe Cys Thr Lys His Cys *
             70 gaagatcatg gatctatcac ctttcttcgc tttcacaata atgttaccta cctatatata   361 tgcctttctt taatttccct agcttgtctt taatttatc taattagatc atgattttg     421 ttttatggtt gatgagtgaa tgttatggac tcttatctac ttatcatctg tcttcttaat   481 tattattcaa gtaatnnnaa cttttttannn nnnnnnnnnn nn                     523
```

<210> SEQ ID NO 413
<211> LENGTH: 72
<212> TYPE: PRT
<213> ORGANISM: Cyamopsis tetragonoloba

<400> SEQUENCE: 413

```
Met Gly Arg Ser Leu Phe Pro Phe Val Phe Val Phe Leu Leu Val Val
 1               5                  10                  15

Val Ser Thr Glu Met Val Ala Glu Gly Arg Ser Cys Glu Ser Gln Ser
            20                  25                  30

His Arg Phe Lys Gly Pro Cys Val Ser Asp Thr Asn Cys Ala Ser Val
        35                  40                  45

Cys Tyr Thr Glu Arg Phe Ser Gly Gly His Cys Arg Gly Phe Arg Arg
    50                  55                  60

Arg Cys Phe Cys Thr Lys His Cys
65                  70
```

<210> SEQ ID NO 414
<211> LENGTH: 47
<212> TYPE: PRT
<213> ORGANISM: Cyamopsis tetragonoloba

<400> SEQUENCE: 414

```
Arg Ser Cys Glu Ser Gln Ser His Arg Phe Lys Gly Pro Cys Val Ser
 1               5                  10                  15

Asp Thr Asn Cys Ala Ser Val Cys Tyr Thr Glu Arg Phe Ser Gly Gly
            20                  25                  30

His Cys Arg Gly Phe Arg Arg Arg Cys Phe Cys Thr Lys His Cys
        35                  40                  45
```

<210> SEQ ID NO 415
<211> LENGTH: 455
<212> TYPE: DNA
<213> ORGANISM: Vitis vinifera
<220> FEATURE:
<221> NAME/KEY: CDS
<222> LOCATION: (67)...(291)
<220> FEATURE:
<221> NAME/KEY: mat_peptide
<222> LOCATION: (148)...(288)
<220> FEATURE:
<221> NAME/KEY: misc_feature
<222> LOCATION: 64, 331, 335, 338, 389, 429, 442
<223> OTHER INFORMATION: n = A,T,C or G

<400> SEQUENCE: 415

```
tatagctcag ttttttctttc ttctctttct tcaacccata agcgcaagcc acagggctct   60 ctancc atg gag agg aaa tct ctt ggc ttc ttc ttc ttc ctc ctc ctc      108
       Met Glu Arg Lys Ser Leu Gly Phe Phe Phe Phe Leu Leu Leu
```

```
              1               5                   10
atc ctc ttg gct tct cag atg gtg gtg cca agt gag gca aga gtc tgt    156
Ile Leu Leu Ala Ser Gln Met Val Val Pro Ser Glu Ala Arg Val Cys
 15              20                  25                  30 gag tca caa agc cat aag ttc gag ggt gca tgc acg gga gac cac aac    204
Glu Ser Gln Ser His Lys Phe Glu Gly Ala Cys Thr Gly Asp His Asn
                 35                  40                  45 tgt gct ctg gtc tgc agg aat gaa ggc ttc tcc ggc ggc aag tgc aaa    252
Cys Ala Leu Val Cys Arg Asn Glu Gly Phe Ser Gly Gly Lys Cys Lys
             50                  55                  60 ggc ttc cgc cgc cga tgc ttc tgc act aag ctc tgt taa aatcccactt    301
Gly Phe Arg Arg Arg Cys Phe Cys Thr Lys Leu Cys *
             65                  70 ttcttctgct gtttgtagct aagagttcan gtantanaca aagaactgag cccataggct    361
tgctgggttg cctcggttct tggttgangt gggttttatt tcagggttta ctgtttggct    421
tttgtgangt acatctcaat naataaaaag tctg    455

<210> SEQ ID NO 416
<211> LENGTH: 74
<212> TYPE: PRT
<213> ORGANISM: Vitis vinifera

<400> SEQUENCE: 416

Met Glu Arg Lys Ser Leu Gly Phe Phe Phe Leu Leu Leu Ile Leu
 1               5                  10                  15

Leu Ala Ser Gln Met Val Val Pro Ser Glu Ala Arg Val Cys Glu Ser
             20                  25                  30

Gln Ser His Lys Phe Glu Gly Ala Cys Thr Gly Asp His Asn Cys Ala
         35                  40                  45

Leu Val Cys Arg Asn Glu Gly Phe Ser Gly Gly Lys Cys Lys Gly Phe
     50                  55                  60

Arg Arg Arg Cys Phe Cys Thr Lys Leu Cys
 65                  70

<210> SEQ ID NO 417
<211> LENGTH: 47
<212> TYPE: PRT
<213> ORGANISM: Vitis vinifera

<400> SEQUENCE: 417

Arg Val Cys Glu Ser Gln Ser His Lys Phe Glu Gly Ala Cys Thr Gly
 1               5                  10                  15

Asp His Asn Cys Ala Leu Val Cys Arg Asn Glu Gly Phe Ser Gly Gly
             20                  25                  30

Lys Cys Lys Gly Phe Arg Arg Arg Cys Phe Cys Thr Lys Leu Cys
         35                  40                  45

<210> SEQ ID NO 418
<211> LENGTH: 438
<212> TYPE: DNA
<213> ORGANISM: Vitis vinifera
<220> FEATURE:
<221> NAME/KEY: CDS
<222> LOCATION: (73)...(297)
<220> FEATURE:
<221> NAME/KEY: mat_peptide
<222> LOCATION: (154)...(294)
<220> FEATURE:
<221> NAME/KEY: misc_feature
<222> LOCATION: 438
<223> OTHER INFORMATION: n = A,T,C or G
```

<400> SEQUENCE: 418

```
cttctctata gctcagtttt tctttcttct ctttcttcaa cccataagcg caagccacag      60
ggctctctat cc atg gag agg aaa tct ctt ggc ttc ttc ttc ttc ctc ctc     111
              Met Glu Arg Lys Ser Leu Gly Phe Phe Phe Phe Leu Leu
                1               5                  10 ctc atc ctc ttg gct tct cag atg gtg gtg cca agt gag gca aga gtc      159
Leu Ile Leu Leu Ala Ser Gln Met Val Val Pro Ser Glu Ala Arg Val
 15                  20                  25 tgt gag tca caa agc cat aag ttc gag ggt gca tgc atg gga gac cac      207
Cys Glu Ser Gln Ser His Lys Phe Glu Gly Ala Cys Met Gly Asp His
 30                  35                  40                  45 aac tgt gct ctg gtc tgc agg aat gaa ggc ttc tcc ggc ggc aag tgc      255
Asn Cys Ala Leu Val Cys Arg Asn Glu Gly Phe Ser Gly Gly Lys Cys
                 50                  55                  60 aaa ggc ctc cgc cgc cga tgc ttc tgc act aag ctc tgt taa              297
Lys Gly Leu Arg Arg Arg Cys Phe Cys Thr Lys Leu Cys *
             65                  70 aatcccacct ttcttctgct gtttgtagct aagagttcaa gtaataaaca aagaactgag    357
cccataggct tgctggttgc ctcggttctt ggttgagtgg gttttatttc agggtttact    417
gtttggcttt tgtgagtaca n                                              438
```

<210> SEQ ID NO 419
<211> LENGTH: 74
<212> TYPE: PRT
<213> ORGANISM: Vitis vinifera

<400> SEQUENCE: 419

```
Met Glu Arg Lys Ser Leu Gly Phe Phe Phe Phe Leu Leu Ile Leu
 1               5                  10                  15

Leu Ala Ser Gln Met Val Val Pro Ser Glu Ala Arg Val Cys Glu Ser
             20                  25                  30

Gln Ser His Lys Phe Glu Gly Ala Cys Met Gly Asp His Asn Cys Ala
         35                  40                  45

Leu Val Cys Arg Asn Glu Gly Phe Ser Gly Gly Lys Cys Lys Gly Leu
     50                  55                  60

Arg Arg Arg Cys Phe Cys Thr Lys Leu Cys
 65                  70
```

<210> SEQ ID NO 420
<211> LENGTH: 47
<212> TYPE: PRT
<213> ORGANISM: Vitis vinifera

<400> SEQUENCE: 420

```
Arg Val Cys Glu Ser Gln Ser His Lys Phe Glu Gly Ala Cys Met Gly
 1               5                  10                  15

Asp His Asn Cys Ala Leu Val Cys Arg Asn Glu Gly Phe Ser Gly Gly
             20                  25                  30

Lys Cys Lys Gly Leu Arg Arg Arg Cys Phe Cys Thr Lys Leu Cys
         35                  40                  45
```

<210> SEQ ID NO 421
<211> LENGTH: 293
<212> TYPE: DNA
<213> ORGANISM: Vitis vinifera
<220> FEATURE:
<221> NAME/KEY: CDS
<222> LOCATION: (62)...(289)

```
<220> FEATURE:
<221> NAME/KEY: mat_peptide
<222> LOCATION: (146)...(286)

<400> SEQUENCE: 421
ctcagttttt ctttcttctc tttcttcaac ccataagcgc aagccacagg gctctctatc        60 c atg gag agg aaa tct ctt ggc ttc ttc ttc ttc ctc ctc ctc atc ctc      109
  Met Glu Arg Lys Ser Leu Gly Phe Phe Phe Phe Leu Leu Leu Ile Leu
  1               5                   10                  15 ttg gct tct caa gag atg gtg gtg cca agt gag gca aga gtc tgt gag        157
Leu Ala Ser Gln Glu Met Val Val Pro Ser Glu Ala Arg Val Cys Glu
            20                  25                  30 tca caa agc cat aag ttc gag ggt gca tgc atg gga gac cac aac tgt        205
Ser Gln Ser His Lys Phe Glu Gly Ala Cys Met Gly Asp His Asn Cys
        35                  40                  45 gct ctg gtc tgc agg aat gaa ggc ttc tcc ggc ggc aag tgc aaa ggc        253
Ala Leu Val Cys Arg Asn Glu Gly Phe Ser Gly Gly Lys Cys Lys Gly
    50                  55                  60 ctc cgc cgc cga tgc ttc tgc act aag ctc tgt taa aatc                   293
Leu Arg Arg Arg Cys Phe Cys Thr Lys Leu Cys   *
65                  70                  75

<210> SEQ ID NO 422
<211> LENGTH: 75
<212> TYPE: PRT
<213> ORGANISM: Vitis vinifera

<400> SEQUENCE: 422

Met Glu Arg Lys Ser Leu Gly Phe Phe Phe Phe Leu Leu Leu Ile Leu
1               5                   10                  15

Leu Ala Ser Gln Glu Met Val Val Pro Ser Glu Ala Arg Val Cys Glu
            20                  25                  30

Ser Gln Ser His Lys Phe Glu Gly Ala Cys Met Gly Asp His Asn Cys
        35                  40                  45

Ala Leu Val Cys Arg Asn Glu Gly Phe Ser Gly Gly Lys Cys Lys Gly
    50                  55                  60

Leu Arg Arg Arg Cys Phe Cys Thr Lys Leu Cys
65                  70                  75

<210> SEQ ID NO 423
<211> LENGTH: 47
<212> TYPE: PRT
<213> ORGANISM: Vitis vinifera

<400> SEQUENCE: 423

Arg Val Cys Glu Ser Gln Ser His Lys Phe Glu Gly Ala Cys Met Gly
1               5                   10                  15

Asp His Asn Cys Ala Leu Val Cys Arg Asn Glu Gly Phe Ser Gly Gly
            20                  25                  30

Lys Cys Lys Gly Leu Arg Arg Arg Cys Phe Cys Thr Lys Leu Cys
        35                  40                  45

<210> SEQ ID NO 424
<211> LENGTH: 550
<212> TYPE: DNA
<213> ORGANISM: Eucalyptus grandis
<220> FEATURE:
<221> NAME/KEY: CDS
<222> LOCATION: (8)...(226)
<220> FEATURE:
<221> NAME/KEY: mat_peptide
<222> LOCATION: (83)...(223)
```

-continued

<400> SEQUENCE: 424

```
gcacgag gag aag agc aag atg aga tgc atg ggg ctt ttc atg atg gtg         49
        Glu Lys Ser Lys Met Arg Cys Met Gly Leu Phe Met Met Val
        1               5                   10 ctc ctc gtc ctc gct gcc cag gag gcg gag ggg agg gtg tgc gag tcc         97
Leu Leu Val Leu Ala Ala Gln Glu Ala Glu Gly Arg Val Cys Glu Ser
15                  20                  25                  30 cag agc cac ggc ttc aag ggg gct tgc gcc agc aac cac aac tgc gcc        145
Gln Ser His Gly Phe Lys Gly Ala Cys Ala Ser Asn His Asn Cys Ala
                35                  40                  45 ctg gtc tgc cgc aac gag ggc ttc tcc ggc ggc cgt tgc cgt gga ttc        193
Leu Val Cys Arg Asn Glu Gly Phe Ser Gly Gly Arg Cys Arg Gly Phe
            50                  55                  60 cgg cac cgc tgc ttc tgc acc aag ctt tgt tga cggccaatgc acgtgcatgc     246
Arg His Arg Cys Phe Cys Thr Lys Leu Cys  *
65                  70 aaccgaataa cgaagtgttg gatgactagc tgaggctggt gtgtgccgtg tcgtagtgag      306
tgagcgagtg agccaaataa atatgttcga agattctgag ttccttagtt tctaagcttt      366
ctaggacttt gatgtgcttt gaccattcac tgttctctct cttctatcgc tttgcgtaat      426
ttcttgattc gggggaaaaa aaaaaaaaaa aaaaaaaaaa aaaaaaaaaa aaaaaaaaaa      486
aaaaaaaaaa aaaaaaaaaa aaaaaaaaaa aaaaaaaaaa aaaaaaaaaa aaaaaaaaaa      546
aaaa                                                                   550
```

<210> SEQ ID NO 425
<211> LENGTH: 72
<212> TYPE: PRT
<213> ORGANISM: Eucalyptus grandis

<400> SEQUENCE: 425

```
Glu Lys Ser Lys Met Arg Cys Met Gly Leu Phe Met Met Val Leu Leu
1               5                   10                  15

Val Leu Ala Ala Gln Glu Ala Glu Gly Arg Val Cys Glu Ser Gln Ser
                20                  25                  30

His Gly Phe Lys Gly Ala Cys Ala Ser Asn His Asn Cys Ala Leu Val
            35                  40                  45

Cys Arg Asn Glu Gly Phe Ser Gly Gly Arg Cys Arg Gly Phe Arg His
50                  55                  60

Arg Cys Phe Cys Thr Lys Leu Cys
65                  70
```

<210> SEQ ID NO 426
<211> LENGTH: 47
<212> TYPE: PRT
<213> ORGANISM: Eucalyptus grandis

<400> SEQUENCE: 426

```
Arg Val Cys Glu Ser Gln Ser His Gly Phe Lys Gly Ala Cys Ala Ser
1               5                   10                  15

Asn His Asn Cys Ala Leu Val Cys Arg Asn Glu Gly Phe Ser Gly Gly
                20                  25                  30

Arg Cys Arg Gly Phe Arg His Arg Cys Phe Cys Thr Lys Leu Cys
            35                  40                  45
```

<210> SEQ ID NO 427
<211> LENGTH: 338
<212> TYPE: DNA

<213> ORGANISM: Cyamopsis tetragonoloba
<220> FEATURE:
<221> NAME/KEY: CDS
<222> LOCATION: (14)...(241)
<220> FEATURE:
<221> NAME/KEY: mat_peptide
<222> LOCATION: (101)...(241)

<400> SEQUENCE: 427

```
cattgcttgt gag atg atg atg atg aag aaa tca att gct ttg atc ttc         49
              Met Met Met Met Lys Lys Ser Ile Ala Leu Ile Phe
                1               5                  10 ttc ttc ctc ctc ctt gtc ttc gct tct caa atg gtg gtg gag acg gaa         97
Phe Phe Leu Leu Leu Val Phe Ala Ser Gln Met Val Val Glu Thr Glu
         15                  20                  25 gcg agg gtg tgc cag tca cag agc cac cac ttt aag ggg cca tgc ttg        145
Ala Arg Val Cys Gln Ser Gln Ser His His Phe Lys Gly Pro Cys Leu
     30                  35                  40 gga gac cat aac tgt gca ctc gtc tgc agg aat gaa gct ttc tcc ggt        193
Gly Asp His Asn Cys Ala Leu Val Cys Arg Asn Glu Ala Phe Ser Gly
 45                  50                  55                  60 ggc cgc tgc cga ggt ttc cgc cgt cgc tgt ttt tgc act aag ctt tgt        241
Gly Arg Cys Arg Gly Phe Arg Arg Arg Cys Phe Cys Thr Lys Leu Cys
                 65                  70                  75 tga caagctcatc aagagcctta attaccataa gagacccttc ttatgtaata             294
atcaaaggca attaatgaat aatttgttgt gcatttggag gatt                       338
```

<210> SEQ ID NO 428
<211> LENGTH: 76
<212> TYPE: PRT
<213> ORGANISM: Cyamopsis tetragonoloba

<400> SEQUENCE: 428

```
Met Met Met Met Lys Lys Ser Ile Ala Leu Ile Phe Phe Phe Leu Leu
  1               5                  10                  15

Leu Val Phe Ala Ser Gln Met Val Val Glu Thr Glu Ala Arg Val Cys
             20                  25                  30

Gln Ser Gln Ser His His Phe Lys Gly Pro Cys Leu Gly Asp His Asn
         35                  40                  45

Cys Ala Leu Val Cys Arg Asn Glu Ala Phe Ser Gly Gly Arg Cys Arg
     50                  55                  60

Gly Phe Arg Arg Arg Cys Phe Cys Thr Lys Leu Cys
 65                  70                  75
```

<210> SEQ ID NO 429
<211> LENGTH: 47
<212> TYPE: PRT
<213> ORGANISM: Cyamopsis tetragonoloba

<400> SEQUENCE: 429

```
Arg Val Cys Gln Ser Gln Ser His His Phe Lys Gly Pro Cys Leu Gly
  1               5                  10                  15

Asp His Asn Cys Ala Leu Val Cys Arg Asn Glu Ala Phe Ser Gly Gly
             20                  25                  30

Arg Cys Arg Gly Phe Arg Arg Arg Cys Phe Cys Thr Lys Leu Cys
         35                  40                  45
```

<210> SEQ ID NO 430
<211> LENGTH: 494
<212> TYPE: DNA
<213> ORGANISM: Nicotiana benthamiana

```
<220> FEATURE:
<221> NAME/KEY: CDS
<222> LOCATION: (44)...(280)
<220> FEATURE:
<221> NAME/KEY: mat_peptide
<222> LOCATION: (137)...(277)
<220> FEATURE:
<221> NAME/KEY: misc_feature
<222> LOCATION: 417, 419, 449
<223> OTHER INFORMATION: n = A,T,C or G

<400> SEQUENCE: 430
ctaagctgcc tctctctgtc aaaaaatact tttgtctgtg aaa atg gca aaa tcc       55
                                              Met Ala Lys Ser
                                                1 atg cgc ttc ttt gcc act gtg tta ctt ctg gca atg ctt gtc atg gct      103
Met Arg Phe Phe Ala Thr Val Leu Leu Leu Ala Met Leu Val Met Ala
 5                  10                  15                  20 act gag atg gga cca atg aca gtt gcc gag gca aga cgt tgc gag tcg      151
Thr Glu Met Gly Pro Met Thr Val Ala Glu Ala Arg Arg Cys Glu Ser
                 25                  30                  35 aaa agc caa cgt ttt aag gga cca tgt gtt aga gtg aaa aat tgt gcc      199
Lys Ser Gln Arg Phe Lys Gly Pro Cys Val Arg Val Lys Asn Cys Ala
     40                  45                  50 gcc gtt tgt gag acc gaa gga ttt tcc ggt ggt gac tgc cgt gga ctc      247
Ala Val Cys Glu Thr Glu Gly Phe Ser Gly Gly Asp Cys Arg Gly Leu
 55                  60                  65 cgt cgc cgt tgt ttt tgt act agg cca tgc taa gaatgttact atatgttata    300
Arg Arg Arg Cys Phe Cys Thr Arg Pro Cys *
                 70                  75 tatgtaaaac ctgaatttga gaaactattg aataagcatt atgattgttc aacgattaac    360
gtgctagttt gttactaatt aaactatcgt gatctttgac cgttatgcaa atataangna    420
catttaaggg ggttgtgatt tccaagggng aattcccgtg ttccgcaacg ttatggataa    480
attctccttc aacc                                                      494

<210> SEQ ID NO 431
<211> LENGTH: 78
<212> TYPE: PRT
<213> ORGANISM: Nicotiana benthamiana

<400> SEQUENCE: 431

Met Ala Lys Ser Met Arg Phe Phe Ala Thr Val Leu Leu Leu Ala Met
 1               5                  10                  15

Leu Val Met Ala Thr Glu Met Gly Pro Met Thr Val Ala Glu Ala Arg
                 20                  25                  30

Arg Cys Glu Ser Lys Ser Gln Arg Phe Lys Gly Pro Cys Val Arg Val
             35                  40                  45

Lys Asn Cys Ala Ala Val Cys Glu Thr Glu Gly Phe Ser Gly Gly Asp
         50                  55                  60

Cys Arg Gly Leu Arg Arg Arg Cys Phe Cys Thr Arg Pro Cys
 65                  70                  75

<210> SEQ ID NO 432
<211> LENGTH: 47
<212> TYPE: PRT
<213> ORGANISM: Nicotiana benthamiana

<400> SEQUENCE: 432

Arg Arg Cys Glu Ser Lys Ser Gln Arg Phe Lys Gly Pro Cys Val Arg
 1               5                  10                  15
```

```
Val Lys Asn Cys Ala Ala Val Cys Glu Thr Glu Gly Phe Ser Gly Gly
         20                  25                  30

Asp Cys Arg Gly Leu Arg Arg Arg Cys Phe Cys Thr Arg Pro Cys
         35                  40                  45
```

<210> SEQ ID NO 433
<211> LENGTH: 469
<212> TYPE: DNA
<213> ORGANISM: Parthenium argentatum
<220> FEATURE:
<221> NAME/KEY: CDS
<222> LOCATION: (25)...(261)
<220> FEATURE:
<221> NAME/KEY: mat_peptide
<222> LOCATION: (118)...(261)
<220> FEATURE:
<221> NAME/KEY: misc_feature
<222> LOCATION: 428, 433, 442, 469
<223> OTHER INFORMATION: n = A,T,C or G

<400> SEQUENCE: 433

```
ctctctctct ctctctcggt caag atg aag tct tcc atg aag ctg ttt gca         51
                          Met Lys Ser Ser Met Lys Leu Phe Ala
                           1               5 gca tta ttg ctt gtt gtc atg tgt ctg atg gcc aat gaa atg ggt ggt        99
Ala Leu Leu Leu Val Val Met Cys Leu Met Ala Asn Glu Met Gly Gly
 10                  15                  20                  25 ccg atg gtg gtg gaa gcg agg aca tgt gag tcg caa agc cac aag ttc       147
Pro Met Val Val Glu Ala Arg Thr Cys Glu Ser Gln Ser His Lys Phe
                 30                  35                  40 aag ggg aca tgt tta agt gac acc aat tgt ggt aat gtg tgc cac tct       195
Lys Gly Thr Cys Leu Ser Asp Thr Asn Cys Gly Asn Val Cys His Ser
             45                  50                  55 gag ggg ttt ccg ggt gga aag tgt cgt ggg ctt cga cgc cgg tgt ttc       243
Glu Gly Phe Pro Gly Gly Lys Cys Arg Gly Leu Arg Arg Arg Cys Phe
         60                  65                  70 tgc acc aag aat tgc tag atcgaaccaa tatgtttcat ggccggttgt              291
Cys Thr Lys Asn Cys  *
     75 ttgagagtta tgtttgagtt gttttttaaag ttcacttgtg tttgtgcgtt acatgttgcc    351 tgaataagtt tccaactcct tggtggttgg gtgggttggg ttttttccaaa acaataatcc    411 cgtacccttg ggggtcnttt cntataaaaa ngaaaatggt gaattggttc aacccacn       469
```

<210> SEQ ID NO 434
<211> LENGTH: 78
<212> TYPE: PRT
<213> ORGANISM: Parthenium argentatum

<400> SEQUENCE: 434

```
Met Lys Ser Ser Met Lys Leu Phe Ala Ala Leu Leu Leu Val Val Met
 1               5                  10                  15

Cys Leu Met Ala Asn Glu Met Gly Gly Pro Met Val Val Glu Ala Arg
                 20                  25                  30

Thr Cys Glu Ser Gln Ser His Lys Phe Lys Gly Thr Cys Leu Ser Asp
             35                  40                  45

Thr Asn Cys Gly Asn Val Cys His Ser Glu Gly Phe Pro Gly Gly Lys
         50                  55                  60

Cys Arg Gly Leu Arg Arg Arg Cys Phe Cys Thr Lys Asn Cys
 65                  70                  75
```

<210> SEQ ID NO 435

```
<211> LENGTH: 47
<212> TYPE: PRT
<213> ORGANISM: Parthenium argentatum

<400> SEQUENCE: 435

Arg Thr Cys Glu Ser Gln Ser His Lys Phe Lys Gly Thr Cys Leu Ser
 1               5                  10                  15

Asp Thr Asn Cys Gly Asn Val Cys His Ser Glu Gly Phe Pro Gly Gly
             20                  25                  30

Lys Cys Arg Gly Leu Arg Arg Arg Cys Phe Cys Thr Lys Asn Cys
         35                  40                  45

<210> SEQ ID NO 436
<211> LENGTH: 420
<212> TYPE: DNA
<213> ORGANISM: Cyamopsis tetragonoloba
<220> FEATURE:
<221> NAME/KEY: CDS
<222> LOCATION: (31)...(264)
<220> FEATURE:
<221> NAME/KEY: mat_peptide
<222> LOCATION: (118)...(261)

<400> SEQUENCE: 436
gcacgaggca aataattaat taagtgaatt atg gag agg aaa tca gtt gct gga       54
                                 Met Glu Arg Lys Ser Val Ala Gly
                                  1               5 ttg tgg tgc ctc atg ctc gtt gtt gtg tta gtt gca gaa gaa gta gtg      102
Leu Trp Cys Leu Met Leu Val Val Val Leu Val Ala Glu Glu Val Val
     10                  15                  20 gtg aaa aca gag gga aag aca tgt gag aat ctt gca gat aca ttc agg      150
Val Lys Thr Glu Gly Lys Thr Cys Glu Asn Leu Ala Asp Thr Phe Arg
 25                  30                  35                  40 ggt cca tgc ttc cct gga acc gcc agc tgc aac gat cac tgc aag aac      198
Gly Pro Cys Phe Pro Gly Thr Ala Ser Cys Asn Asp His Cys Lys Asn
                 45                  50                  55 aaa gag cac ttg ctc agc gga agg tgc aga gac gat ttt cgc tgc tgg      246
Lys Glu His Leu Leu Ser Gly Arg Cys Arg Asp Asp Phe Arg Cys Trp
             60                  65                  70 tgc acc aaa aac tgt taa ttcccccaaa caacatacat gcagtgccgc             294
Cys Thr Lys Asn Cys *
         75 cactctcttc attttaataa atatgaataa gcaccgcatg ccactatact catatactac    354 atgtacttaa cgcctctgtt atgtacttta tgttaaacaa ataataataa taaactcttg    414 ttatat                                                                420

<210> SEQ ID NO 437
<211> LENGTH: 77
<212> TYPE: PRT
<213> ORGANISM: Cyamopsis tetragonoloba

<400> SEQUENCE: 437

Met Glu Arg Lys Ser Val Ala Gly Leu Trp Cys Leu Met Leu Val Val
 1               5                  10                  15

Val Leu Val Ala Glu Glu Val Val Val Lys Thr Glu Gly Lys Thr Cys
             20                  25                  30

Glu Asn Leu Ala Asp Thr Phe Arg Gly Pro Cys Phe Pro Gly Thr Ala
         35                  40                  45

Ser Cys Asn Asp His Cys Lys Asn Lys Glu His Leu Leu Ser Gly Arg
     50                  55                  60
```

```
Cys Arg Asp Asp Phe Arg Cys Trp Cys Thr Lys Asn Cys
 65                  70                  75
```

<210> SEQ ID NO 438
<211> LENGTH: 48
<212> TYPE: PRT
<213> ORGANISM: Cyamopsis tetragonoloba

<400> SEQUENCE: 438

```
Lys Thr Cys Glu Asn Leu Ala Asp Thr Phe Arg Gly Pro Cys Phe Pro
 1               5                  10                  15

Gly Thr Ala Ser Cys Asn Asp His Cys Lys Asn Lys Glu His Leu Leu
             20                  25                  30

Ser Gly Arg Cys Arg Asp Asp Phe Arg Cys Trp Cys Thr Lys Asn Cys
         35                  40                  45
```

<210> SEQ ID NO 439
<211> LENGTH: 563
<212> TYPE: DNA
<213> ORGANISM: Cyamopsis tetragonoloba
<220> FEATURE:
<221> NAME/KEY: CDS
<222> LOCATION: (106)...(333)
<220> FEATURE:
<221> NAME/KEY: mat_peptide
<222> LOCATION: (190)...(330)

<400> SEQUENCE: 439

```
gcacgaggaa attatatatt taaacaagta gtagttaatc atcaataata ctatagaatc      60
gaattgaatt gaatactgta attaattaag ctaaggtagc tagct atg gag aag aaa    117
                                              Met Glu Lys Lys
                                               1 tca ctg gct gga ttc tgc tgc ctc ttc ctc att ctc ttt ctt gct caa      165
Ser Leu Ala Gly Phe Cys Cys Leu Phe Leu Ile Leu Phe Leu Ala Gln
 5              10                  15                  20 gaa ata gtg gtg aaa aca gag gca agg aca tgt gag agt ctg gca gac      213
Glu Ile Val Val Lys Thr Glu Ala Arg Thr Cys Glu Ser Leu Ala Asp
            25                  30                  35 aca tac agg gga ccc tgt ttc aca gat ggt agc tgc gat gat cac tgc      261
Thr Tyr Arg Gly Pro Cys Phe Thr Asp Gly Ser Cys Asp Asp His Cys
        40                  45                  50 aag aac aaa gag cac tta atc agt gga aga tgc aga aat gat ttt cgc      309
Lys Asn Lys Glu His Leu Ile Ser Gly Arg Cys Arg Asn Asp Phe Arg
    55                  60                  65 tgt tgg tgc acc aga aac tgt taa attctggact tcccccatc aagatgcatg      363
Cys Trp Cys Thr Arg Asn Cys *
70                  75 cacaacgaac cttaattatt atatatacat caataataaa caaatataa ataaaactag      423 ctgcctctgt atcttgacca tgtattatta ctagtaccac ctctgtctga atttcataca      483
tactatttta aatgttctga gtacataacg gatgagttat gtactttatg tcaaacaata      543
ataaactgtt gttatgtacc                                                 563
```

<210> SEQ ID NO 440
<211> LENGTH: 75
<212> TYPE: PRT
<213> ORGANISM: Cyamopsis tetragonoloba

<400> SEQUENCE: 440

```
Met Glu Lys Lys Ser Leu Ala Gly Phe Cys Cys Leu Phe Leu Ile Leu
 1               5                  10                  15
```

```
Phe Leu Ala Gln Glu Ile Val Val Lys Thr Glu Ala Arg Thr Cys Glu
            20                  25                  30
Ser Leu Ala Asp Thr Tyr Arg Gly Pro Cys Phe Thr Asp Gly Ser Cys
            35                  40                  45
Asp Asp His Cys Lys Asn Lys Glu His Leu Ile Ser Gly Arg Cys Arg
 50                  55                  60
Asn Asp Phe Arg Cys Trp Cys Thr Arg Asn Cys
 65                  70                  75

<210> SEQ ID NO 441
<211> LENGTH: 47
<212> TYPE: PRT
<213> ORGANISM: Cyamopsis tetragonoloba

<400> SEQUENCE: 441

Arg Thr Cys Glu Ser Leu Ala Asp Thr Tyr Arg Gly Pro Cys Phe Thr
 1               5                  10                  15
Asp Gly Ser Cys Asp Asp His Cys Lys Asn Lys Glu His Leu Ile Ser
            20                  25                  30
Gly Arg Cys Arg Asn Asp Phe Arg Cys Trp Cys Thr Arg Asn Cys
            35                  40                  45

<210> SEQ ID NO 442
<211> LENGTH: 524
<212> TYPE: DNA
<213> ORGANISM: Licania michauxii
<220> FEATURE:
<221> NAME/KEY: CDS
<222> LOCATION: (42)...(278)
<220> FEATURE:
<221> NAME/KEY: mat_peptide
<222> LOCATION: (135)...(275)
<220> FEATURE:
<221> NAME/KEY: misc_feature
<222> LOCATION: 358, 380, 419, 455, 478, 497, 517, 523
<223> OTHER INFORMATION: n = A,T,C or G

<400> SEQUENCE: 442
tctctttctc tctctcgttc tctttctgtc tgaaagtaga a atg gag cgc tta atg        56
                                             Met Glu Arg Leu Met
                                              1               5 cgt ctt tct tca gct gct ttc atc ttt gtg ctg ctg ctt gtg gcc act         104
Arg Leu Ser Ser Ala Ala Phe Ile Phe Val Leu Leu Leu Val Ala Thr
            10                  15                  20 gga atg ggg cca aca atg gtg gca gag gcc agg aca tgc gag tca cag         152
Gly Met Gly Pro Thr Met Val Ala Glu Ala Arg Thr Cys Glu Ser Gln
            25                  30                  35 agc cac cgc ttc aag ggg ata tgc gtg aga aag agc aac tgt gct gcg         200
Ser His Arg Phe Lys Gly Ile Cys Val Arg Lys Ser Asn Cys Ala Ala
        40                  45                  50 gtt tgc caa act gag ggc ttc cat gga gga cac tgc cga ggg ttc cgg         248
Val Cys Gln Thr Glu Gly Phe His Gly Gly His Cys Arg Gly Phe Arg
        55                  60                  65 cgt cgc tgc ttc tgc act aaa cat tgt tag ggaaaatctc tgctgagata           298
Arg Arg Cys Phe Cys Thr Lys His Cys *
 70                  75 ctggcgttga tcacctcctc ttaacagaac cgagatgatc tttcttgcgt gtgcgagtan       358
accagaataa catgtctctt gnggctttat gtgtgcctgc atatgtgggg ttctttcttc       418
nccttgtcct gtgcgatggt ttaattaatg ggaaaancttt gcttttttgg gtttaactgn      478
aaaaaaaaaa aaaaaaaanc tcgagggggg gcccgggtna ccaang                     524
```

<210> SEQ ID NO 443
<211> LENGTH: 78
<212> TYPE: PRT
<213> ORGANISM: Licania michauxii

<400> SEQUENCE: 443

```
Met Glu Arg Leu Met Arg Leu Ser Ser Ala Ala Phe Ile Phe Val Leu
1               5                   10                  15

Leu Leu Val Ala Thr Gly Met Gly Pro Thr Met Val Ala Glu Ala Arg
            20                  25                  30

Thr Cys Glu Ser Gln Ser His Arg Phe Lys Gly Ile Cys Val Arg Lys
        35                  40                  45

Ser Asn Cys Ala Ala Val Cys Gln Thr Glu Gly Phe His Gly Gly His
    50                  55                  60

Cys Arg Gly Phe Arg Arg Arg Cys Phe Cys Thr Lys His Cys
65                  70                  75
```

<210> SEQ ID NO 444
<211> LENGTH: 47
<212> TYPE: PRT
<213> ORGANISM: Licania michauxii

<400> SEQUENCE: 444

```
Arg Thr Cys Glu Ser Gln Ser His Arg Phe Lys Gly Ile Cys Val Arg
1               5                   10                  15

Lys Ser Asn Cys Ala Ala Val Cys Gln Thr Glu Gly Phe His Gly Gly
            20                  25                  30

His Cys Arg Gly Phe Arg Arg Arg Cys Phe Cys Thr Lys His Cys
        35                  40                  45
```

<210> SEQ ID NO 445
<211> LENGTH: 447
<212> TYPE: DNA
<213> ORGANISM: Vitis vinifera
<220> FEATURE:
<221> NAME/KEY: CDS
<222> LOCATION: (27)...(260)
<220> FEATURE:
<221> NAME/KEY: mat_peptide
<222> LOCATION: (117)...(257)
<220> FEATURE:
<221> NAME/KEY: misc_feature
<222> LOCATION: 412, 434, 447
<223> OTHER INFORMATION: n = A,T,C or G

<400> SEQUENCE: 445

```
cctgtcttct catacaaaag caaaag atg aag ggc tct caa cgt ttg ttt tca         53
                            Met Lys Gly Ser Gln Arg Leu Phe Ser
                              1               5 gct ttt ctc ctt gtg att ctc ctc ttc atg gcc act gag atg ggc ccg        101
Ala Phe Leu Leu Val Ile Leu Leu Phe Met Ala Thr Glu Met Gly Pro
 10              15                  20                  25 atg gtg gct gag gct agg acc tgt gag agt cag agc cac cgg ttc aag        149
Met Val Ala Glu Ala Arg Thr Cys Glu Ser Gln Ser His Arg Phe Lys
             30                  35                  40 gga acg tgt gtc agg cag agc aac tgt gct gct gtt tgc cag acc gag        197
Gly Thr Cys Val Arg Gln Ser Asn Cys Ala Ala Val Cys Gln Thr Glu
             45                  50                  55 ggt ttc cat gga gga aat tgc cgt ggc ttt cgt cgt cga tgc ttc tgc        245
Gly Phe His Gly Gly Asn Cys Arg Gly Phe Arg Arg Arg Cys Phe Cys
         60                  65                  70 act aag cat tgt taa ttagctagtg tgagagcttt caaacatata tgtgtcgaag        300
Thr Lys His Cys
```

```
Thr Lys His Cys *
    75 tacttaagta gtgatgggtg aaaccatctc ttcttttcaa ctttgtgtgt gtgcctggaa      360 aatgacactt ctgtatgagc tgggccgtac tatgggctcg tgttggccct tngtgtgttt      420 ggtttggatc tggngtccaa aatgatn                                          447

<210> SEQ ID NO 446
<211> LENGTH: 77
<212> TYPE: PRT
<213> ORGANISM: Vitis vinifera

<400> SEQUENCE: 446

Met Lys Gly Ser Gln Arg Leu Phe Ser Ala Phe Leu Leu Val Ile Leu
1               5                   10                  15

Leu Phe Met Ala Thr Glu Met Gly Pro Met Val Ala Glu Ala Arg Thr
            20                  25                  30

Cys Glu Ser Gln Ser His Arg Phe Lys Gly Thr Cys Val Arg Gln Ser
        35                  40                  45

Asn Cys Ala Ala Val Cys Gln Thr Glu Gly Phe His Gly Gly Asn Cys
    50                  55                  60

Arg Gly Phe Arg Arg Arg Cys Phe Cys Thr Lys His Cys
65                  70                  75

<210> SEQ ID NO 447
<211> LENGTH: 47
<212> TYPE: PRT
<213> ORGANISM: Vitis vinifera

<400> SEQUENCE: 447

Arg Thr Cys Glu Ser Gln Ser His Arg Phe Lys Gly Thr Cys Val Arg
1               5                   10                  15

Gln Ser Asn Cys Ala Ala Val Cys Gln Thr Glu Gly Phe His Gly Gly
            20                  25                  30

Asn Cys Arg Gly Phe Arg Arg Arg Cys Phe Cys Thr Lys His Cys
        35                  40                  45

<210> SEQ ID NO 448
<211> LENGTH: 473
<212> TYPE: DNA
<213> ORGANISM: Vitis vinifera
<220> FEATURE:
<221> NAME/KEY: CDS
<222> LOCATION: (31)...(264)
<220> FEATURE:
<221> NAME/KEY: mat_peptide
<222> LOCATION: (121)...(261)
<220> FEATURE:
<221> NAME/KEY: misc_feature
<222> LOCATION: 336, 378, 392, 399, 404, 412, 418, 442, 461
<223> OTHER INFORMATION: n = A,T,C or G

<400> SEQUENCE: 448
atctcctgtc ttctcataca aaagcaaaag atg aag ggc tct caa cgt ttg ttt      54
                                Met Lys Gly Ser Gln Arg Leu Phe
                                  1               5 tca gct ttt ctc ctt gtg att ctc ctc ttc atg gct act gag atg ggc      102
Ser Ala Phe Leu Leu Val Ile Leu Leu Phe Met Ala Thr Glu Met Gly
        10                  15                  20 ccg atg gtg gct gag gct agg acc tgt gag agt cag agc cac cgg ttc      150
Pro Met Val Ala Glu Ala Arg Thr Cys Glu Ser Gln Ser His Arg Phe
    25                  30                  35                  40
```

```
aag gga acg tgt gtc agg cag agc aac tgt gct gct gtt tgc caa acc    198
Lys Gly Thr Cys Val Arg Gln Ser Asn Cys Ala Ala Val Cys Gln Thr
             45                  50                  55 gag ggt ttc cat gga gga aat tgc cgt ggc ttt cgt cgt cga tgc ttc    246
Glu Gly Phe His Gly Gly Asn Cys Arg Gly Phe Arg Arg Arg Cys Phe
         60                  65                  70 tgc act aag cat tgt taa ttagcgagtg tgagagcttt caaacatata            294
Cys Thr Lys His Cys *
             75 tgtgtaaaag tactggagta ataatggatg ggtgaaaaca ancccccttt tcaactttgg   354 gggtggtgcc tggaaaaatg acanctctgg atgaaccngg ccctnctaan ggctccgngt   414 ggcnccgttt gggtttgatc tgcgggcnaa tatgaatatt ataaatnaaa atcccaagg    473

<210> SEQ ID NO 449
<211> LENGTH: 77
<212> TYPE: PRT
<213> ORGANISM: Vitis vinifera

<400> SEQUENCE: 449

Met Lys Gly Ser Gln Arg Leu Phe Ser Ala Phe Leu Leu Val Ile Leu
 1               5                  10                  15

Leu Phe Met Ala Thr Glu Met Gly Pro Met Val Ala Glu Ala Arg Thr
             20                  25                  30

Cys Glu Ser Gln Ser His Arg Phe Lys Gly Thr Cys Val Arg Gln Ser
         35                  40                  45

Asn Cys Ala Ala Val Cys Gln Thr Glu Gly Phe His Gly Gly Asn Cys
     50                  55                  60

Arg Gly Phe Arg Arg Arg Cys Phe Cys Thr Lys His Cys
65                  70                  75

<210> SEQ ID NO 450
<211> LENGTH: 47
<212> TYPE: PRT
<213> ORGANISM: Vitis vinifera

<400> SEQUENCE: 450

Arg Thr Cys Glu Ser Gln Ser His Arg Phe Lys Gly Thr Cys Val Arg
 1               5                  10                  15

Gln Ser Asn Cys Ala Ala Val Cys Gln Thr Glu Gly Phe His Gly Gly
             20                  25                  30

Asn Cys Arg Gly Phe Arg Arg Arg Cys Phe Cys Thr Lys His Cys
         35                  40                  45

<210> SEQ ID NO 451
<211> LENGTH: 461
<212> TYPE: DNA
<213> ORGANISM: Arachis hypogaea
<220> FEATURE:
<221> NAME/KEY: CDS
<222> LOCATION: (44)...(271)
<220> FEATURE:
<221> NAME/KEY: mat_peptide
<222> LOCATION: (128)...(268)
<220> FEATURE:
<221> NAME/KEY: misc_feature
<222> LOCATION: 305, 319, 357, 372, 400, 406, 420, 443, 452, 455
<223> OTHER INFORMATION: n = A,T,C or G

<400> SEQUENCE: 451
gatatcaata tatctatata gctgtttact ttaatcataa gcc atg gcg ggg aaa    55
                                             Met Ala Gly Lys
                                              1
```

```
tct cta acc ggg ttt tgc ttc atc ctc ctc ctc gtt gtt gct cag      103
Ser Leu Thr Gly Phe Cys Phe Ile Leu Leu Leu Val Val Ala Gln
 5                  10                  15                  20 gaa atg gtg gtg caa agt gag gca gca acg tgt gag aac ctg gcg gat  151
Glu Met Val Val Gln Ser Glu Ala Ala Thr Cys Glu Asn Leu Ala Asp
                25                  30                  35 acc tac agg gga cca tgc ttc acc acc gga agc tgc gac gac cac tgc  199
Thr Tyr Arg Gly Pro Cys Phe Thr Thr Gly Ser Cys Asp Asp His Cys
                40                  45                  50 aag aac aag gag cac ctg ctc agc ggc cgc tgc cgc gac gat ttc cgc  247
Lys Asn Lys Glu His Leu Leu Ser Gly Arg Cys Arg Asp Asp Phe Arg
            55                  60                  65 tgt tgg tgc acc aga aac tgt taa attacgcatc atgagctacg tacgcagatc 301
Cys Trp Cys Thr Arg Asn Cys *
    70                  75 gatncaagat gctggatntg agctagctag ctaaggagca tatatataca taaatnatac 361 ttctaagcta ncactgcatt taaatatgtt accaaaaant tttgnaaggg tggaattgna 421 atgccctatt gcctaataca tnacgggcca nttntgttcg                      461

<210> SEQ ID NO 452
<211> LENGTH: 75
<212> TYPE: PRT
<213> ORGANISM: Arachis hypogaea

<400> SEQUENCE: 452

Met Ala Gly Lys Ser Leu Thr Gly Phe Cys Phe Ile Leu Leu Leu
 1               5                  10                  15

Val Val Ala Gln Glu Met Val Val Gln Ser Glu Ala Ala Thr Cys Glu
                20                  25                  30

Asn Leu Ala Asp Thr Tyr Arg Gly Pro Cys Phe Thr Thr Gly Ser Cys
            35                  40                  45

Asp Asp His Cys Lys Asn Lys Glu His Leu Leu Ser Gly Arg Cys Arg
        50                  55                  60

Asp Asp Phe Arg Cys Trp Cys Thr Arg Asn Cys
65                  70                  75

<210> SEQ ID NO 453
<211> LENGTH: 47
<212> TYPE: PRT
<213> ORGANISM: Arachis hypogaea

<400> SEQUENCE: 453

Ala Thr Cys Glu Asn Leu Ala Asp Thr Tyr Arg Gly Pro Cys Phe Thr
 1               5                  10                  15

Thr Gly Ser Cys Asp Asp His Cys Lys Asn Lys Glu His Leu Leu Ser
                20                  25                  30

Gly Arg Cys Arg Asp Asp Phe Arg Cys Trp Cys Thr Arg Asn Cys
            35                  40                  45

<210> SEQ ID NO 454
<211> LENGTH: 527
<212> TYPE: DNA
<213> ORGANISM: Brassica napus
<220> FEATURE:
<221> NAME/KEY: CDS
<222> LOCATION: (80)...(313)
<220> FEATURE:
<221> NAME/KEY: mat_peptide
<222> LOCATION: (170)...(310)
<220> FEATURE:
```

```
<221> NAME/KEY: misc_feature
<222> LOCATION: 525, 526, 527
<223> OTHER INFORMATION: n = A,T,C or G

<400> SEQUENCE: 454
ccacgcgtcc gcggacgcgt gggcggacgc gtgggttccg actctctctc tccctgaaag    60
tttctttctc tctctcaaa atg aag ctc tct atg cgt ttg atc tca gct gtt   112
                     Met Lys Leu Ser Met Arg Leu Ile Ser Ala Val
                      1               5                      10 ctc ctc ttg ttc atg ata ttc gtt gcc aca ggg atg ggt cca gtc aca    160
Leu Leu Leu Phe Met Ile Phe Val Ala Thr Gly Met Gly Pro Val Thr
            15                  20                  25 gtg gag gca cgc acg tgt gag tcg aag agc cat agg ttc aag ggt aca    208
Val Glu Ala Arg Thr Cys Glu Ser Lys Ser His Arg Phe Lys Gly Thr
        30                  35                  40 tgt gtg agc tca aca aac tgc gga aac gtg tgt cac aac gaa ggt ttt    256
Cys Val Ser Ser Thr Asn Cys Gly Asn Val Cys His Asn Glu Gly Phe
    45                  50                  55 ggc gga ggt aaa tgc cgt ggt ttc cgt cgt cgt tgc tac tgc acc aga    304
Gly Gly Gly Lys Cys Arg Gly Phe Arg Arg Arg Cys Tyr Cys Thr Arg
60                  65                  70                  75 cat tgc tga tctatcgatc gattctcata actcaaatct accatatcca            353
His Cys * tcgtctggtg ttgttccttt ctatctaata ttccgtacaa caccatgtcg taccgtacat   413
gtgtgtgtaa tatgttttcg aataagtctc tgtttgtgtg ttttgttttt tttttttgtaa   473 cgcaagtgtt ttcagttcat gtaatgttat atcagtttta tcgttttctt tnnn        527

<210> SEQ ID NO 455
<211> LENGTH: 77
<212> TYPE: PRT
<213> ORGANISM: Brassica napus

<400> SEQUENCE: 455

Met Lys Leu Ser Met Arg Leu Ile Ser Ala Val Leu Leu Leu Phe Met
 1               5                  10                  15

Ile Phe Val Ala Thr Gly Met Gly Pro Val Thr Val Glu Ala Arg Thr
            20                  25                  30

Cys Glu Ser Lys Ser His Arg Phe Lys Gly Thr Cys Val Ser Ser Thr
        35                  40                  45

Asn Cys Gly Asn Val Cys His Asn Glu Gly Phe Gly Gly Gly Lys Cys
    50                  55                  60

Arg Gly Phe Arg Arg Arg Cys Tyr Cys Thr Arg His Cys
65                  70                  75

<210> SEQ ID NO 456
<211> LENGTH: 47
<212> TYPE: PRT
<213> ORGANISM: Brassica napus

<400> SEQUENCE: 456

Arg Thr Cys Glu Ser Lys Ser His Arg Phe Lys Gly Thr Cys Val Ser
 1               5                  10                  15

Ser Thr Asn Cys Gly Asn Val Cys His Asn Glu Gly Phe Gly Gly Gly
            20                  25                  30

Lys Cys Arg Gly Phe Arg Arg Arg Cys Tyr Cys Thr Arg His Cys
        35                  40                  45

<210> SEQ ID NO 457
```

```
<211> LENGTH: 547
<212> TYPE: DNA
<213> ORGANISM: Zea mays
<220> FEATURE:
<221> NAME/KEY: CDS
<222> LOCATION: (75)...(317)
<220> FEATURE:
<221> NAME/KEY: mat_peptide
<222> LOCATION: (165)...(311)

<400> SEQUENCE: 457
cagcattacg aggccaaaag taagctgctg ctgttcttcg acccgtcccg ttcgttcgat      60
tcgttctttc cgcc atg gag gct cgg agg aag ccc gcg gtg tgc tgt gcc      110
              Met Glu Ala Arg Arg Lys Pro Ala Val Cys Cys Ala
                1               5                   10 ctt ctt gtg ctg ctc atc gtc gcc tcc agc aca acg gtg tcg act gct      158
Leu Leu Val Leu Leu Ile Val Ala Ser Ser Thr Thr Val Ser Thr Ala
         15                  20                  25 cat gac gag agc tgc tgg aag gac gac gac cac cac cct atc tgc ttt      206
His Asp Glu Ser Cys Trp Lys Asp Asp Asp His His Pro Ile Cys Phe
     30                  35                  40 ccc gaa gac tgc gtg gcg acc tgc cag gat cac ggc cac gcg gac ggc      254
Pro Glu Asp Cys Val Ala Thr Cys Gln Asp His Gly His Ala Asp Gly
 45                  50                  55                  60 cgc tgc aac tgg gca tgg tcg tgg agg ccg tat tgc cag tgc ctg ttg      302
Arg Cys Asn Trp Ala Trp Ser Trp Arg Pro Tyr Cys Gln Cys Leu Leu
                 65                  70                  75 gcg gac tgc caa tag gcgcgaacag ctgcgtcgca tggcgtcctg gctgcctcgc      357
Ala Asp Cys Gln  *
             80 cggccgatga aggatgaacg gttgcggccg atgatcgatg tcgacgatgt gtgcgttggc      417 gtgtcgatca ctcattgaac ccctctaat cctgtgcggt attattttca tggcacctgt      477 ggccattaaa gatccatgga cacgtacagt accaagaatt ttcattccga tacaaaaaaa      537 aaaaaaaaaa                                                            547

<210> SEQ ID NO 458
<211> LENGTH: 80
<212> TYPE: PRT
<213> ORGANISM: Zea mays

<400> SEQUENCE: 458

Met Glu Ala Arg Arg Lys Pro Ala Val Cys Cys Ala Leu Leu Val Leu
  1               5                  10                  15

Leu Ile Val Ala Ser Ser Thr Thr Val Ser Thr Ala His Asp Glu Ser
             20                  25                  30

Cys Trp Lys Asp Asp His His Pro Ile Cys Phe Pro Glu Asp Cys
         35                  40                  45

Val Ala Thr Cys Gln Asp His Gly His Ala Asp Gly Arg Cys Asn Trp
     50                  55                  60

Ala Trp Ser Trp Arg Pro Tyr Cys Gln Cys Leu Leu Ala Asp Cys Gln
 65                  70                  75                  80

<210> SEQ ID NO 459
<211> LENGTH: 49
<212> TYPE: PRT
<213> ORGANISM: Zea mays

<400> SEQUENCE: 459

Glu Ser Cys Trp Lys Asp Asp His His Pro Ile Cys Phe Pro Glu
  1               5                  10                  15
```

```
Asp Cys Val Ala Thr Cys Gln Asp His Gly His Ala Asp Gly Arg Cys
            20                  25                  30

Asn Trp Ala Trp Ser Trp Arg Pro Tyr Cys Gln Cys Leu Leu Ala Asp
            35                  40                  45

Cys

<210> SEQ ID NO 460
<211> LENGTH: 556
<212> TYPE: DNA
<213> ORGANISM: Zea mays
<220> FEATURE:
<221> NAME/KEY: CDS
<222> LOCATION: (63)...(365)
<220> FEATURE:
<221> NAME/KEY: mat_peptide
<222> LOCATION: (150)...(299)

<400> SEQUENCE: 460
cagcatccca ttcttaccaa ataaacaac ggcaatacct attatattaa taatataagc        60 ca atg aag cct ttc atc tgc agc agc cat ttc gtc gtt ctc gtt ctg        107
   Met Lys Pro Phe Ile Cys Ser Ser His Phe Val Val Leu Val Leu
     1               5                  10                  15 tcc atc gcc atc gcc gcc gag atg gcg tcc gtc gag gca ggt gat gac        155
Ser Ile Ala Ile Ala Ala Glu Met Ala Ser Val Glu Ala Gly Asp Asp
                20                  25                  30 tgc tac cac ctg agc gca aag ttc aag ggg tgg tgc ttg tac ccg gac        203
Cys Tyr His Leu Ser Ala Lys Phe Lys Gly Trp Cys Leu Tyr Pro Asp
            35                  40                  45 cac tgc gcg gac gtg tgc tcc act gag agc gac aac aac ctt ggc ggc        251
His Cys Ala Asp Val Cys Ser Thr Glu Ser Asp Asn Asn Leu Gly Gly
        50                  55                  60 acg tgc cgc ggc ttc ccg tct cgt tgc tac tgc agg gca tta ttc tgc        299
Thr Cys Arg Gly Phe Pro Ser Arg Cys Tyr Cys Arg Ala Leu Phe Cys
    65                  70                  75 ccg cag ggg cca aag gct gct cct agc act att gct gct gct agg tct        347
Pro Gln Gly Pro Lys Ala Ala Pro Ser Thr Ile Ala Ala Ala Arg Ser
 80                  85                  90                  95 cct cca acc att gga tga gccctgccct gattttttgc ctggttccgg                395
Pro Pro Thr Ile Gly *
                100 tcggtagcct cgtagtagta atgtttgtgg ttggtgagga agatcagttc gtgacaatgt       455 attgctgcgc ttcgatcagc atcagaataa aaaaacaaa gacatgtttg gctgcaaaaa        515 aaaaaaaaaa aaaaaaaaa aaaaaaaaa aaaaaaaaa a                              556

<210> SEQ ID NO 461
<211> LENGTH: 100
<212> TYPE: PRT
<213> ORGANISM: Zea mays

<400> SEQUENCE: 461

Met Lys Pro Phe Ile Cys Ser Ser His Phe Val Val Leu Val Leu Ser
  1               5                  10                  15

Ile Ala Ile Ala Ala Glu Met Ala Ser Val Glu Ala Gly Asp Asp Cys
             20                  25                  30

Tyr His Leu Ser Ala Lys Phe Lys Gly Trp Cys Leu Tyr Pro Asp His
         35                  40                  45

Cys Ala Asp Val Cys Ser Thr Glu Ser Asp Asn Asn Leu Gly Gly Thr
     50                  55                  60
```

```
Cys Arg Gly Phe Pro Ser Arg Cys Tyr Cys Arg Ala Leu Phe Cys Pro
 65                  70                  75                  80

Gln Gly Pro Lys Ala Ala Pro Ser Thr Ile Ala Ala Arg Ser Pro
                 85                  90                  95

Pro Thr Ile Gly
            100

<210> SEQ ID NO 462
<211> LENGTH: 50
<212> TYPE: PRT
<213> ORGANISM: Zea mays

<400> SEQUENCE: 462

Asp Asp Cys Tyr His Leu Ser Ala Lys Phe Lys Gly Trp Cys Leu Tyr
  1               5                  10                  15

Pro Asp His Cys Ala Asp Val Cys Ser Thr Glu Ser Asp Asn Asn Leu
                 20                  25                  30

Gly Gly Thr Cys Arg Gly Phe Pro Ser Arg Cys Tyr Cys Arg Ala Leu
             35                  40                  45

Phe Cys
    50

<210> SEQ ID NO 463
<211> LENGTH: 514
<212> TYPE: DNA
<213> ORGANISM: Zea mays
<220> FEATURE:
<221> NAME/KEY: CDS
<222> LOCATION: (56)...(304)

<400> SEQUENCE: 463
cgcgcgtctc cggtcccgtc cgtaataaca ctgatccgat ccacgccggc cggcg atg      58
                                                               Met
                                                                 1 gag ctc atc aag tcc agg gcg acc gtg tgc gcg ctc ctc ctg gcg ctg     106
Glu Leu Ile Lys Ser Arg Ala Thr Val Cys Ala Leu Leu Leu Ala Leu
              5                  10                  15 ctc ctg ctc tca cac tac gac ggc ggg acg acg acg acg atg gtg gcg     154
Leu Leu Leu Ser His Tyr Asp Gly Gly Thr Thr Thr Thr Met Val Ala
         20                  25                  30 gag gcc cgg gtg tgc atg ggc aag agc cag cac cac tcg ttc ccc tgc     202
Glu Ala Arg Val Cys Met Gly Lys Ser Gln His His Ser Phe Pro Cys
 35                  40                  45 atc tcc gac cgc ctc tgc agc aac gag tgc gtc aag gag gac ggc ggg     250
Ile Ser Asp Arg Leu Cys Ser Asn Glu Cys Val Lys Glu Asp Gly Gly
 50                  55                  60                  65 tgg acc gcc ggc tac tgc cac ctc cgc tac tgc agg tgc cag aag gcg     298
Trp Thr Ala Gly Tyr Cys His Leu Arg Tyr Cys Arg Cys Gln Lys Ala
                 70                  75                  80 tgc taa gcaaagctct tgaaacaccc ttggcttgcc agaactgaac tgtggtagta      354
Cys * ctaagtaaca cccttggcta gctgtgcaca acctacgtac cgtgcatgca tgtaatgtgg    414
tgtcatgtaa cgtgacagca ataaatatta ataacaataa taacacggca tgtagccttt    474
gcatgcttct agcagcaaaa aaaaaaaaaa aaaaaaaaa                           514

<210> SEQ ID NO 464
<211> LENGTH: 82
<212> TYPE: PRT
<213> ORGANISM: Zea mays
```

```
<400> SEQUENCE: 464

Met Glu Leu Ile Lys Ser Arg Ala Thr Val Cys Ala Leu Leu Leu Ala
1               5                   10                  15

Leu Leu Leu Leu Ser His Tyr Asp Gly Gly Thr Thr Thr Thr Met Val
            20                  25                  30

Ala Glu Ala Arg Val Cys Met Gly Lys Ser Gln His His Ser Phe Pro
        35                  40                  45

Cys Ile Ser Asp Arg Leu Cys Ser Asn Glu Cys Val Lys Glu Asp Gly
    50                  55                  60

Gly Trp Thr Ala Gly Tyr Cys His Leu Arg Tyr Cys Arg Cys Gln Lys
65                  70                  75                  80

Ala Cys

<210> SEQ ID NO 465
<211> LENGTH: 516
<212> TYPE: DNA
<213> ORGANISM: Zea mays
<220> FEATURE:
<221> NAME/KEY: CDS
<222> LOCATION: (50)...(325)

<400> SEQUENCE: 465 atttccttg gattggatcg tcggcgccaa acgaataat aatccggca atg gag tct       58
                                                   Met Glu Ser
                                                   1 tca cga ggg aag ctg tct gcc gcc ggc gtc ctc ctg cta atg acg ctc      106
Ser Arg Gly Lys Leu Ser Ala Ala Gly Val Leu Leu Leu Met Thr Leu
    5                   10                  15 ctc atg gtg gcc gcc atg cgg gcg gtt gag gca cga gac tgc ctg acg      154
Leu Met Val Ala Ala Met Arg Ala Val Glu Ala Arg Asp Cys Leu Thr
20                  25                  30                  35 cag agt acc cgg tta ccg ggg cat ctg tgc gtg cgg tcg gac tac tgc      202
Gln Ser Thr Arg Leu Pro Gly His Leu Cys Val Arg Ser Asp Tyr Cys
                40                  45                  50 gcg atc ggg tgc agg gcg gag ggc aag ggc tac acg ggc ggc agg tgc      250
Ala Ile Gly Cys Arg Ala Glu Gly Lys Gly Tyr Thr Gly Gly Arg Cys
            55                  60                  65 ctt atc tct ccc atc ccg ctc gac ggg att ctc tgc tac tgc gtc aag      298
Leu Ile Ser Pro Ile Pro Leu Asp Gly Ile Leu Cys Tyr Cys Val Lys
        70                  75                  80 cct tgc aca tcc acc acg aca aaa tga tgagacaaga caagagcggt            345
Pro Cys Thr Ser Thr Thr Thr Lys *
    85                  90 gggtgcaatg caggctgacc gggggttatc agttatatat ggacatccta ccgtgtctgt    405
taataacttg taaatgtctt gggaaagttt gtggtgataa gttttaaatg tcttggaata    465
aagtgggttc tatacagact tctactcgtt aaaaaaaaaa aaaaaaaaa a              516

<210> SEQ ID NO 466
<211> LENGTH: 91
<212> TYPE: PRT
<213> ORGANISM: Zea mays

<400> SEQUENCE: 466

Met Glu Ser Ser Arg Gly Lys Leu Ser Ala Ala Gly Val Leu Leu Leu
1               5                   10                  15

Met Thr Leu Leu Met Val Ala Ala Met Arg Ala Val Glu Ala Arg Asp
            20                  25                  30

Cys Leu Thr Gln Ser Thr Arg Leu Pro Gly His Leu Cys Val Arg Ser
```

```
                35                  40                  45
Asp Tyr Cys Ala Ile Gly Cys Arg Ala Glu Gly Lys Gly Tyr Thr Gly
 50                  55                  60

Gly Arg Cys Leu Ile Ser Pro Ile Pro Leu Asp Gly Ile Leu Cys Tyr
 65                  70                  75                  80

Cys Val Lys Pro Cys Thr Ser Thr Thr Lys
                 85                  90

<210> SEQ ID NO 467
<211> LENGTH: 517
<212> TYPE: DNA
<213> ORGANISM: Zea mays
<220> FEATURE:
<221> NAME/KEY: CDS
<222> LOCATION: (50)...(289)

<400> SEQUENCE: 467
atcccacatc agtagtcgac caagcacaag cagcagagcc ggccggaat atg tgg acg        58
                                                     Met Trp Thr
                                                      1 atc agg aag gtg gcg acg ccg cag gtg gcc gtc ctc ctg ctc ctc            106
Ile Arg Lys Val Ala Thr Pro Gln Val Ala Val Leu Leu Leu Leu
  5                  10                  15 atc gtc gtt gcg cag gag gcg gcg ccg ttg gcg gag gcg cgc gtg tgc        154
Ile Val Val Ala Gln Glu Ala Ala Pro Leu Ala Glu Ala Arg Val Cys
 20                  25                  30                  35 cgg cgc cgg agc gcg ggc ttc aag ggg gtc tgc atg tcc gac cac aac        202
Arg Arg Arg Ser Ala Gly Phe Lys Gly Val Cys Met Ser Asp His Asn
                 40                  45                  50 tgc gcg cag gtg tgc ttg cag gag ggc tac ggc ggc ggc aac tgc gac        250
Cys Ala Gln Val Cys Leu Gln Glu Gly Tyr Gly Gly Gly Asn Cys Asp
                 55                  60                  65 ggc atc atg cgc cag tgc aag tgc atc agg gag tgc tag ctagctaggc        299
Gly Ile Met Arg Gln Cys Lys Cys Ile Arg Glu Cys  *
                 70                  75 tctaggatct agcaagctag ctatatcggc ctttaattaa attaataagg atcgacgtcg      359
tggccggtcg ctaaatatgt actactatac gtctacacta catgcaataa tgcaccacat      419
gtacgcgtac gcgcgccgag ctgtgtggac gccgccgctt aaaaaaaaaa aaaaaaaaa       479 aaaaaaaaaa aaaaaaaaa aaaaaaaaaa aaaaaaaa                               517

<210> SEQ ID NO 468
<211> LENGTH: 79
<212> TYPE: PRT
<213> ORGANISM: Zea mays

<400> SEQUENCE: 468

Met Trp Thr Ile Arg Lys Val Ala Thr Pro Gln Val Ala Val Leu Leu
  1               5                  10                  15

Leu Leu Leu Ile Val Val Ala Gln Glu Ala Ala Pro Leu Ala Glu Ala
                 20                  25                  30

Arg Val Cys Arg Arg Arg Ser Ala Gly Phe Lys Gly Val Cys Met Ser
             35                  40                  45

Asp His Asn Cys Ala Gln Val Cys Leu Gln Glu Gly Tyr Gly Gly Gly
         50                  55                  60

Asn Cys Asp Gly Ile Met Arg Gln Cys Lys Cys Ile Arg Glu Cys
 65                  70                  75

<210> SEQ ID NO 469
```

```
-continued
<211> LENGTH: 181
<212> TYPE: DNA
<213> ORGANISM: Artificial Sequence
<220> FEATURE:
<223> OTHER INFORMATION: Consensus sequence for the Zm-PDF family

<400> SEQUENCE: 469
atgagtctcc gcagtccgcc gcctcctcct gctctctgct ggacgaccgg tggcgtggcg        60
gagcgagggt gccggcagag ccagcgttcg ggcgctgcat gccacaactg cgccaacgtg       120
tgcgacggag ggcttcccgg cggcagtgca acccgccccg catgcatctg caaaggtgct       180
a                                                                      181
```